(12) United States Patent
Sefton et al.

(10) Patent No.: US 8,076,375 B2
(45) Date of Patent: Dec. 13, 2011

(54) METHODS OF INHIBITING POXVIRUS GROWTH

(75) Inventors: Bartholomew M. Sefton, La Jolla, CA (US); Roberta J. Schulte, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 667 days.

(21) Appl. No.: 12/090,081

(22) PCT Filed: Oct. 10, 2006

(86) PCT No.: PCT/US2006/039836
§ 371 (c)(1),
(2), (4) Date: Apr. 11, 2008

(87) PCT Pub. No.: WO2007/047339
PCT Pub. Date: Apr. 26, 2007

(65) Prior Publication Data
US 2008/0306031 A1   Dec. 11, 2008

Related U.S. Application Data

(60) Provisional application No. 60/727,001, filed on Oct. 13, 2005.

(51) Int. Cl.
*A61K 31/19* (2006.01)
(52) U.S. Cl. .................................................... 514/569
(58) Field of Classification Search .................... 514/569
See application file for complete search history.

(56) References Cited

U.S. PATENT DOCUMENTS

| | | |
|---|---|---|
| 4,073,904 A | 2/1978 | Fleming et al. |
| 4,082,550 A | 4/1978 | Yoerger |
| 4,801,593 A | 1/1989 | Hodson et al. |
| 5,521,184 A | 5/1996 | Zimmermann |
| 5,977,061 A | 11/1999 | Holy et al. |

FOREIGN PATENT DOCUMENTS
WO   WO 2005/048928 A2   6/2005

OTHER PUBLICATIONS

Austin et al., "NIH Molecular Libraries Initiative," *Science* 306:1138-1139, 2004.
Boyle and Traktman, "Members of a Novel Family of Mammalian Protein Kinases Complement the DNA-Negative Phenotype of a Vaccinia Virus *ts* Mutant Defective in the B1 Kinase," *J Virol.* 78:1992-2005, 2004.
Gubser et al., "Poxvirus Genomes: a Phylogenetic Analysis," *J. Gen. Virol.* 85:105-117, 2004.
Harrison et al., "Discovery of Antivirals Against Smallpox," *PNAS* 101:11178-11192, 2004.

(Continued)

*Primary Examiner* — Shengjun Wang
(74) *Attorney, Agent, or Firm* — Klarquist Sparkman, LLP

(57) ABSTRACT

This disclosure ascribes new functions to derivatives of tetralin, anthraquinone, naphthylamine, tri-amino-pyrimidine, xanthen-3-one, and/or cinnamic acid (including, for example, NSC270718R, NSC117285R, NSC170008Y, NSC306711P, NSC119913X, NSC119915Z, NSC119911V, NSC119910U, NSC128437O, NSC125908P, NSC9600Q, or NSC13778J, each obtained from the Structure Diversity Set, National Institutes of Health, National Cancer Institute, Developmental Therapeutics Program). These compounds are shown to be effective inhibitors of viral essential protein kinases (such as poxvirus B1 and/or F10 protein kinases). Exemplary chemical structures for viral protein kinase (VPK) inhibitors are provided, as are methods of using such compounds, for instance, to inhibit VPK activity and/or poxvirus growth, and/or for the treatment of poxvirus infection. Also provided are pharmaceutical compositions including disclosed VPK inhibitors.

25 Claims, 14 Drawing Sheets

OTHER PUBLICATIONS

Herget et al., "Novel Chemical Class of pUL97 Protein Kinase-Specific Inhibitors with Strong Anticytomegaloviral Activity," *Antimicrob. Agents Chemother.* 48:4154-4162, 2004.

McFadden, "Poxvirus Tropism," *Nat. Rev. Microbiol.* 3:201-213, 2005.

Szajner et al., "Evidence for an Essential Catalytic Role of the F10 Protein Kinase in Vaccinia Virus Morphogenesis," *J. Virol.* 78:257-265, 2004.

Yang et al.., Antiviral Chemotherapy Facilitates Control of Poxvirus Infections Through Inhibition of Cellular Signal Transduction, *J. Clin. Invest.* 115:379-387, 2005.

FIG. 3

```
            1
Vaccinia F10  MGVANDSSPEYQWMSPHRLSDTVILGDCLYFNNIMSQLDLHQNWAPSVRL
Variola F10   MGVANDSSPEYQWMSPHRLSDTVILGDCLYFNNIMSQLDLHQNWAPSVRL LNYFKNFNRETLLKIEENDYINSSFFQQKDKRFYPINDDFYHISTGGYGI
              LNYFKNFNRETLLKIEENDYINSSFFQQKDKRFYPINDDFYHISTGGYGI

*
              VFKIDNYVVKFVFEATKLYSPMETTAEFTVPKFLYNNLKGDEKKLIVCAW
              VFKIDNYVVKFVFEATKLYSPMETTAEFTVPKFLYNNLKGDEKKLIVCAL

*
              AMGLNYKLTFLHTLYKRVLHMLLLLIQTMDGQELSLRYSSKVFLKAFNER
              AMGLNYKLTFLHTLYKRVLNMLLLLIQTMDGQELSLRYSSKVFLKAFNER

KDSIKFVKLLSHFYPAVINSNINVINYFNRMFHFFEHEKRTNYEYERGNI
              KDSIKFVKLLSHFYPAVINSNINVINYFNRMFHFFEHEKRTNYEYERGNI

IIFPLALYSADKVDTELAIKLGFKSLVQYIKFIFLQMALLYIKIYELPCC
              IIFPLALYSADKVDTELAIKLGFKSLVQYIKFIFLQMALLYIKIYELPCC

DNFLHADLKPDNILLFDSNEPIIIHLKDKKFVFNERIKSALNDFDFSQVA
              DNFLHADLKPDNILLFDSNEPIIIHLKDKKFVFNERIKSALNDFDFSQVA

*
              GIINKKIKNNFKVKHNWYYDFHFFVHTLLKTYPEIEKDIEFSTALEEFIM
              GIINKKIKNNFKVEHNWYYDFHFFVHTLLKTYPEIEKDIEFSTALEEFIM

*
              CTKTDCDKYRLKVSILHPISFLEKFIMRDIFSDWINGGN
              CTKTDCDKYRLKVSILHPISFLEKFIMRDIFSDWINGRN
                                                    439
```

FIG. 4

```
vaccinia (Copenhagen)    MNFQGLVLTDNCKNQWVVGPLIGKGGFGSIYTTNDNNYVVKIEPKANGSLFTEQAFYTRV 60
variola major            MNFQGLVLTDNCKNQWVVGPLIGKGGFGSIYTTNDNNYVVKIEPKANGSLFTEQAFYTRV 60
                         ************************************************************ vaccinia (Copenhagen)    LKPSVIEEWKKSHNIKHVGLITCKAFGLYKSINVEYRFLVINRLGVDLDAVIRANNNRLP 120
variola major            LKPSVIEEWKKSHHISHVGVITCKAFGLYKSINTEYRFLVINRLGVDLDAVIRANNNRLP 120
                         *************:*.*:*********.************************ vaccinia (Copenhagen)    KRSVMLIGIEILNTIQFMHEQGYSHGDIKASNIVLDQIDKNKLYLVDYGLVSKFMSNGEH 180
variola major            KRSVMLVGIEILNTIQFMHEQGYSHGNIKASNIVLDQMDKNKLYLVDYGLVSKFMSNGEH 180
                         ****:***************:******:******************** vaccinia (Copenhagen)    VPFIRNPNKMDNGTLEFTPIDSHKGYVVSRRGDLETLGYCMIRWLGGILPWTKISETKNC 240
variola major            VPFIRNPNKMDNGTLEFTPIDSHKGYVVSRRGDLETLGYCMIRWLGGILPWTKIAETKNC 240
                         ***************************************************:**** vaccinia (Copenhagen)    ALVSATKQKYVNNTATLLMTSLQYAPRELLQYITMVNSLTYFEEPNYDEFRHILMQGVYY 300
variola major            ALVSATKQKYVNNTTTLLMTSLQYAPRELLQYITMVNSLTYFEEPNYDKFRHILMQGAYY 300
                         **************.********************************:********.**
```

FIG. 5

```
Vaccinia       MGVANDSSPEYQWMSPHRLSDTVILGDCLYFNNIMSQLDLHQNWAPSVRLLNYFKNFNRE 60
Rabbitpox      MGVANDSSPEYQWMSPHRLSDTVILGDCLYFNNIMSQLDLHQNWAPSVRLLNYFKNFNKE 60
Cowpox         MGVANDSSPEYQWMSPHRLSDTVILGDCLYFNNIMSQLDLHQNWAPSVRLLNYFKNFNKE 60
Monkeypox      MGVANDSSPEYQWMSPHRLSDTVILGDCLYFNNIMSQLDLHQNWAPSVRLLNYFKNFNKE 60
Ectromelia     MGVANDSSPEYQWMSPHRLSDTVILGDCLYFNNIMSQLDLHQNWAPSVRLLNYFKNFNRE 60
Camelpox       MGVANDSSPEYQWMSPHRLSDTVILGDCLYFNNIMSQLDLHQNWAPSVRLLNYFKNFNRE 60
Variola_major  MGVANDSSPEYQWMSPHRLSDTVILGDCLYFNNIMSQLDLHQNWAPSVRLLNYFKNFNRE 60
Variola_minor  MGVANNSSPEYQWMSPHRLSDTVILGDCLYFNNIMSQLDLHQNWAPSVRLLNYFKNFNRE 60
               ****:*******************************************************:*

Vaccinia       TLLKIEENDYINSSFFQQKDKRFYPINDDFYHISTGGYGIVFKIDNYVVKFVFEATKLYS 120
Rabbitpox      TLLKIEENDYINSSFFQQKDKRFYPINDDFYHISTGGYGIVFKIDNYVVKFVFEATKLYS 120
Cowpox         TLLKIEENDYINSSFFQQKDKRFYPINDDFYHISTGGYGIVFKIDNYVVKFVFEATKLYS 120
Monkeypox      TLLKIEENDYINSSFFQQKDKRFYPINDDFYHISTGGYGIVFKIDNYVVKFVFEATKLYS 120
Ectromelia     TLLKIEENDYINSSFFQQKDKRFYPINDDFYHISTGGYGIVFKIDNYVVKFVFEATKLYS 120
Camelpox       TLLKIEENDYINSSFFQQKDKRFYPINDDFYHISTGGYGIVFKIDNYVVKFVFEATKLYS 120
Variola_major  TLLKIEENDYINSSFFQQKDKRFYPINDDFYHISTGGYGIVFKIDNYVVKFVFEATKLYS 120
Variola_minor  TLLKIEENDYINSSFFQQKDKRFYPINDDFYHISTGGYGIVFKIDNYVVKFVFEATKLYS 120
               ************************************************************

Vaccinia       PMETTAEFTVPKFLYNNLKGDEKKLIVCAWAMGLNYKLTFLHTLYKRVLHMLLLLIQTMD 180
Rabbitpox      PMETTAEFTVPKFLYNNLKGDEKKLIVCAWAMGLNYKLTFLHTLYKRVLHMLLLLIQTMD 180
Cowpox         PMETTAEFTVPKFLYNNLKGDEKKLIVCAWAMGLNYKLTFLHTLYKRVLHMLLLLIQTMD 180
Monkeypox      PMETTAEFTVPKFLYNNLKGDEKKLIVCAWAMGLNYKLTFLHTLYKRVLHMLLLLIQTMD 180
Ectromelia     PMETTAEFTVPKFLYNNLKGDEKKLIVCAWAMGLNYKLTFLHTLYKRVLNMLLLLIQTMD 180
Camelpox       PMETTAEFTVPKFLYNNLKGDEKKLIVCAWAMGLNYKLTFLHTLYKRVLNMLLLLIQTMD 180
Variola_major  PMETTAEFTVPKFLYNNLKGDEKKLIVCALAMGLNYKLTFLHTLYKRVLNMLLLLIQTMD 180
Variola_minor  PMETTAEFTVPKFLYNNLKGDEKKLIVCALVMGLNYKLTFLHTLYKRVLNMLLLLIQTMD 180
               ****************************. .*******************:*********

Vaccinia       GQELSLRYSSKVFLKAFNERKDSIKFVKLLSHFYPAVINSNINVINYFNRMFHFFEHEKR 240
Rabbitpox      GQELSLRYSSKVFLKAFNERKDSIKFVKLLSHFYPAVINSNINVINYFNRMFHFFEHEKR 240
Cowpox         GQELSLRYSSKVFLKAFNERKDSIKFVKLLSHFYPAVINSNINVINYFNRMFHFFEHEKR 240
Monkeypox      GQELSLRYSSKVFLKAFNERKDSIKFVKLLSHFYPAVINSNINVINYFNRMFHFFEHEKR 240
Ectromelia     GQELSLRYSSKVFLKAFNERKDSIKFVKLLSHFYPAVINSNINVINYFNRMFHFFEHEKR 240
Camelpox       GQELSLRYSSKVFLKAFNERKDSIKFVKLLSHFYPAVINSNINVINYFNRMFHFFEHEKR 240
Variola_major  GQELSLRYSSKVFLKAFNERKDSIKFVKLLSHFYPAVINSNINVINYFNRMFHFFEHEKR 240
Variola_minor  GQELSLRYSSKVFLKAFNERKDSIKFVKLLSHFYPAVINSNINVINYFNRMFHFFEHEKR 240
               ************************************************************

Vaccinia       TNYEYERGNIIIFPLALYSADKVDTELAIKLGFKSLVQYIKFIFLQMALLYIKIYELPCC 300
Rabbitpox      TNYEYERGNIIIFPLALYSADKVDTELAIKLGFKSLVQYIKFIFLQMALLYIKIYELPCC 300
Cowpox         TNYEYERGNIIIFPLALYSADKVDTELAIKLGFKSLVQYIKFIFLQMALLYIKIYELPCC 300
Monkeypox      TNYEYERGNIIIFPLALYSADKVDTELAIKLGFKSLVQYIKFIFLQMSLLYIKIYELPCC 300
Ectromelia     TNYEYERGNIIIFPLALYSADKVDTELAIKLGFKSLVQYIKFIFLQMSLLYIKIYELPCC 300
Camelpox       TNYEYERGNIIIFPLALYSADKVDTELAIKLGFKSLVQYIKFIFLQMALLYIKIYELPCC 300
Variola_major  TNYEYERGNIIIFPLALYSADKVDTELAIKLGFKSLVQYIKFIFLQMALLYIKIYELPCC 300
Variola_minor  TNYEYERGNIIIFPLALYSADKVDTELAIKLGFKSLVQYIKFIFLQMALLYIKIYELPSC 300
               ***********************************************:*********.*

Vaccinia       DNFLHADLKPDNILLFDSNEPIIIHLKDKKFVFNERIKSALNDFDFSQVAGIINKKIKNN 360
Rabbitpox      DNFLHADLKPDNILLFDSNEPIIIHLKDKKFVFNERIKSALNDFDFSQVAGIINKKIKNN 360
Cowpox         DNFLHADLKPDNILLFDSNEPIIIHLKDKKFVFNERIKSALNDFDFSQVAGIVNKKIKNN 360
Monkeypox      DNFLHADLKPDNILLFDSNEPIIIHLKNKKFVFNERIKSALNDFDFSQVAGIINKKIKNN 360
Ectromelia     DNFLHADLKPDNILLFDSNEPIIIHLKDKKFVFNERIKSALNDFDFSQVAGIINKKIKTN 360
Camelpox       DNFLHADLKPDNILLFDSNEPIIIHLNDKTFVFNERIKSALNDFDFSQVAGIINKKIKNN 360
Variola_major  DNFLHADLKPDNILLFDSNEPIIIHLKDKKFVFNERIKSALNDFDFSQVAGIINKKIKNN 360
Variola_minor  DNFLHADLKPDNILLFDSNEPIIIHLKDKKFVFNERIKSALNDFDFSQVAGIINKKIKNN 360
               **************************::*.*********************:*****.*
```

FIG. 5 (cont.)

```
Vaccinia        FKVKHNWYYDFHFFVHTLLKTYPEIEKDIEFSTALEEFIMCTKTDCDKYRLKVSILHPIS 420
Rabbitpox       FKVKHNWYYDFHFFVHTLLKTYPEIEKDIEFSTALEEFIMCTKTDCDKYRLKVSILHPIS 420
Cowpox          FKVEHNWYYDFHFFVHTLLKTYPEIEKDIEFSTALEEFIMCTKTDCDKYRLKVSILHPIS 420
Monkeypox       FKVEHNWYYDFHFFVHTLLKTYPEIEKDIEFSTALEEFIMCTKTDCDKYRLKVSILHPIS 420
Ectromelia      FKVEHNWYYDFHFFVHTLLKTYPEIEKDIEFSTALEEFIMCTKTDCDKYRLKVSILHPIS 420
Camelpox        FKVEHNWYYDFHFFVHTLLKTYPEIEKDIEFSTALEEFIMCTKTDCDKYRLKVSILHPIS 420
Variola_major   FKVEHNWYYDFHFFVHTLLKTYPEIEKDIEFSTALEEFIMCTKTDCDKYRLKVSILHPIS 420
Variola_minor   FKVEHNWYYDFHFFVHTLLKTYPEIEKDIEFSTALEEFIMCTKTDCDKYRLKVSILHPIS 420
                ***:********************************************************

Vaccinia        FLEKFIMRDIFSDWINGGN 439
Rabbitpox       FLEKFIMRDIFSDWINGGN 439
Cowpox          FLEKFIMRDIFSDWINGGN 439
Monkeypox       FLEKFIMRDIFSDWINGGN 439
Ectromelia      FLEKFIMRDIFSDWINGGN 439
Camelpox        FLEKFIMRDIFSDWINGGN 439
Variola_major   FLEKFIMRDIFSDWINGRN 439
Variola_minor   FLEKFIMRDIFSDWINGRN 439
                ***************** *
```

FIG. 6

```
Vaccinia                    ------------------------------------------MGVANDSS   8
Rabbitpox                   ------------------------------------------MGVANDSS   8
Cowpox                      ------------------------------------------MGVANDSS   8
Ectromelia                  ------------------------------------------MGVANDSS   8
Monkeypox                   ------------------------------------------MGVANDSS   8
Camelpox                    ------------------------------------------MGVANDSS   8
Variola_major               ------------------------------------------MGVANDSS   8
Variola_minor               ------------------------------------------MGVANNSS   8
Mule_deer_pox               ------------------------------------------MRIMNEDS   8
Yaba_monkey_tumor           ------------------------------------------MGVKTDNS   8
Yaba_like_disease           ------------------------------------------MGVKTDNS   8
Swinepox                    ---------------------------------------------MKEIN   5
Lumpy_skin_disease          ------------------------------------------MVIMEIDD   8
Sheeppox                    -----------------------------------------------MEIDY 5
Rabbit_fibroma              ------------------------------------------MGIMEDIN   8
Myxoma                      ------------------------------------------MGIMEDVE   8
Molluscum_contagiosum       ------------------------------------------MAFSDSAS   8
Orf_virus                   MILARAGGRPRTPAAAAAAAEDGEHSDRRKRKRKTPNCEDADNSDDELAQ  50
Bovine_papular_stomatitis   -------------MSPPGAED---KKPRRARRKTPDCADDEAAALD-AQ  32
Fowlpox                     ---------------------------------------------MEFPD   5
Canarypox                   ---------------------------------------------MEFTD   5

Vaccinia                    --PEYQWM--SPHR--LSDTVILGDCLYFNNIMSQLDLH-QNWAPSVRLL  51
Rabbitpox                   --PEYQWM--SPHR--LSDTVILGDCLYFNNIMSQLDLH-QNWAPSVRLL  51
Cowpox                      --PEYQWM--SPHR--LSDTVILGDCLYFNNIMSQLDLH-QNWAPSVRLL  51
Ectromelia                  --PEYQWM--SPHR--LSDTVILGDCLYFNNIMSQLDLH-QNWAPSVRLL  51
Monkeypox                   --PEYQWM--SPHR--LSDTVILGDCLYFNNIMSQLDLH-QNWAPSVRLL  51
Camelpox                    --PEYQWM--SPHR--LSDTVILGDCLYFNNIMSQLDLH-QNWAPSVRLL  51
Variola_major               --PEYQWM--SPHR--LSDTVILGDCLYFNNIMSQLDLH-QNWAPSVRLL  51
Variola_minor               --PEYQWM--SPHR--LSDTVILGDCLYFNNIMSQLDLH-QNWAPSVRLL  51
Mule_deer_pox               --PECQWE--YKDDI-ENTTTILGDDIYFDYIISQLDIN-QSWSPNSKLI  52
Yaba_monkey_tumor           --LECQWE--LKNDE-RIETTILGDDIYFDYVISQIDTH-QSWSPSIRLV  52
Yaba_like_disease           --LECQWD--LQDDK-KLETTILGDDIYFDYVFSQIDVN-QNWSPSIRLI  52
Swinepox                    -SLECQWE--SIDD--NNDTTILGDDIYFDYIISQLDIH-QNWSPDIRLI  49
Lumpy_skin_disease          NSLECQWD--NDED--IKSTTVLGDDIYFDYVISQLDIY-QSWSPNVRLI  53
Sheeppox                    NSLECQWD--NNED--IKSTTVLGDDIYFDYVISQLDIY-QSWSPNVRLI  50
Rabbit_fibroma              -SLEGQWE--PVDN--EDDTTVLGDDIYFDYVISQLDTH-KSWSPSVKLV  52
Myxoma                      NSLEGQWE--RGET--EDDTTVLGDDIYFDYVISQLDTH-KSWSPSVK-V  52
Molluscum_contagiosum       --ADAPWS--AVPAPRRDETTVLGDEIYFNYVYGQLELS-DSWIPHVRML  53
Orf_virus                   TPCDREWPDCRASSITSSDSVSLGDEIYLRYVASQVDFA-QTWAPPVRLL  99
Bovine_papular_stomatitis   VPCDREWADCRSSALTGPDSVSLGDEIYLRYVASQVDFA-QTWAPPVRLL  81
Fowlpox                     IHAYNSTK--YLED---GDTTILGDTIQFQFIYENIDNKEHISLPKIKIF  50
Canarypox                   LYYSDSNN--YAKD---DKTIILGDTIQFQFIYEHIGN--YQQLPKIKIS  48
                                 :  ***  :  :  :  ::         *    :

Vaccinia                    NYFKN-FNRETLLKIEENDYINSSFFQQKDKRFYPINDDFYHISTGGYGI 100
Rabbitpox                   NYFKN-FNKETLLKIEENDYINSSFFQQKDKRFYPINDDFYHISTGGYGI 100
Cowpox                      NYFKN-FNKETLLKIEENDYINSSFFQQKDKRFYPINDDFYHISTGGYGI 100
Ectromelia                  NYFKN-FNRETLLKIEENDYINSSFFQQKDKRFYPINDDFYHISTGGYGI 100
Monkeypox                   NYFKN-FNKETLLKIEENDYINSSFFQQKDKRFYPINDDFYHISTGGYGI 100
Camelpox                    NYFKN-FNRETLLKIEENDYINSSFFQQKDKRFYPINDDFYHISTGGYGI 100
Variola_major               NYFKN-FNRETLLKIEENDYINSSFFQQKDKRFYPINDDFYHISTGGYGI 100
Variola_minor               NYFKN-FNRETLLKIEENDYINSSFFQQKDKRFYPINDDFYHISTGGYGI 100
Mule_deer_pox               SYFKN-FNRETLNKIINEDYVNPSFFQQKDKRFYPMNDDFYHISTGGYGI 101
Yaba_monkey_tumor           KYFKN-FNKELLETIASNEYVNPSFFQQKDKRFYPVNDDFYHISTGGYGI 101
Yaba_like_disease           KYFKN-FNKELLDTIASKEYVNPSFFQQKDKRFYPINDDFYHLSTGGYGI 101
Swinepox                    RYFRK-FNKESFDKISDTEYINPSFFQQRDKRFYPLNDDFYHISTGGYGI  98
Lumpy_skin_disease          RYFKK-FTKETLNKIAENEYINPSFFQQKDKRFYPINDDFYHISTGGYGI 102
Sheeppox                    RYFKK-FTKETLNKIAENEYINPSFFQQKDKRFYPINDDFYHISTGGYGI  99
Rabbit_fibroma              RYFKN-FNKTALDKIANEEYINPSFFQQKDDRFYPANDDFYHISTGGYGI 101
Myxoma                      RYFKN-FNKSAFDKIANEEYINPSFFQQKDDRFYPTNDDFYHISTGGYGI 101
Molluscum_contagiosum       RYFRN-FSRAALLRIASTEYVNPSYFQQKDKRFAPVNNDFYHLSTGGYGI 102
```

FIG. 6 (cont.)

```
Orf_virus                  RFFGN-FSKETLNRMSRRGYVNRSYFQMAHARFSPTNDDMYHMATGGYGI 148
Bovine_papular_stomatitis  RFFGN-FSKDTLDRMSKRGYVNRSYYQMAHARFSPTNDDMYHMATGGYGI 130
Fowlpox                    KYFRDKISFETLDRIIKNDYINPSYFQLKDKKFCAHNRDFYHLSTGGYGI 100
Canarypox                  KYFKEKISLDTLKRIAKNDSIDPSYYQLKDKHFIPLNNVFYHLSTGGYGI 98
                            :* . :.    :     :   :: *::*   .:* . *  :**:;******

Vaccinia                   VFKIDNYVVKFVFEA-TKLYSPMETTAEFTVPKFLYNNLKGDEKKLIVCA 149
Rabbitpox                  VFKIDNYVVKFVFEA-TKLYSPMETTAEFTVPKFLYNNLKGDEKKLIVCA 149
Cowpox                     VFKIDNYVVKFVFEA-TKLYSPMETTAEFTVPKFLYNNLKGDEKKLIVCA 149
Ectromelia                 VFKIDNYVVKFVFEA-TKLYSPMETTAEFTVPKFLYNNLKGDEKKLIVCA 149
Monkeypox                  VFKIDNYVVKFVFEA-TKLYSPMETTAEFTVPKFLYNNLKGDEKKLIVCA 149
Camelpox                   VFKIDNYVVKFVFEA-TKLYSPMETTAEFTVPKFLYNNLKGDEKKLIVCA 149
Variola_major              VFKIDNYVVKFVFEA-TKLYSPMETTAEFTVPKFLYNNLKGDEKKLIVCA 149
Variola_minor              VFKIDNYVVKFVFEA-TKLYSPMETTAEFTVPKFLYNNLKGDEKKLIVCA 149
Mule_deer_pox              VFKIDKYVVKFVYEP-NKQYSPIETTAEYTIPKFLYNNLKGDEKKLIVCA 150
Yaba_monkey_tumor          VFKIDKYVVKFVYEP-NKSYSPIDTTAEYTIPKFLYINLKGDEKKLIVCA 150
Yaba_like_disease          VFKIDKYVVKFVYEP-NKNYSPIDTTAEYTIPKFLYLNLKGDEKKLIVCA 150
Swinepox                   VFKMDKYVVKFVYEP-NKQYSPIDTTAEYTIPKFLYNNLKGDEKKLIVCA 147
Lumpy_skin_disease         VFKIDKYVVKFVYEP-NKQYSPIETTAEYTIPKFLFNNLKGDEKKLIVCA 151
Sheeppox                   VFKIDKYVVKFVYEP-NKNYSPIETTAEYTIPKFLFNNLKGDEKKLIVCA 148
Rabbit_fibroma             VFKIDKYVVKFVYEP-NKNYTPIDTTAEYTIPKFLYNNLKGDEKKLIVCA 150
Myxoma                     VFKIDKYVVKFVYEP-NKNYTPIDATAEYTIPKFLYNNLKGDEKKLIVCA 150
Molluscum_contagiosum      VFRVEEYVVKFVFEP-GSQFHPMDLTSEYTVPRFLYNNLRGDERLLVVRA 151
Orf_virus                  VFRFDRYVVKYVFEH-RNGMSEMDASTEYTVPRFLRNNLKGDEREFVVCA 197
Bovine_papular_stomatitis  VCRFDRYVVKFVFEH-RNGMSEIDASTEYTVPRFLRSNLKGDEREFVVCA 179
Fowlpox                    IFRMEKYVVKFVFEDGSKKYKPMEVTSEFTIPRFLYNNLKGDERKFIVCA 150
Canarypox                  VFKIGKYVVKFVFEDTSKKYDPMEVTSEFTVPRFLYNNLKGDERKLIVCA 148
                            : :. .****:*:*         :: ::*:*;*:**  **:***: ::* *

Vaccinia                   WAMGLNYKLTFLHTLYKRVLHMLLLLIQTMDGQELSLR-YSSKVFLKAFN 198
Rabbitpox                  WAMGLNYKLTFLHTLYKRVLHMLLLLIQTMDGQELSLR-YSSKVFLKAFN 198
Cowpox                     WAMGLNYKLTFLHTLYKRVLHMLLLLIQTMDGQELSLR-YSSKVFLKAFN 198
Ectromelia                 WAMGLNYKLTFLHTLYKRVLNMLLLLIQTMDGQELSLR-YSSKVFLKAFN 198
Monkeypox                  WAMGLNYKLTFLHTLYKRVLHMLLLLIQTMDGQELSLR-YSSKVFLKAFN 198
Camelpox                   WAMGLNYKLTFLHTLYKRVLNMLLLLIQTMDGQELSLR-YSSKVFLKAFN 198
Variola_major              LAMGLNYKLTFLHTLYKRVLNMLLLLIQTMDGQELSLR-YSSKVFLKAFN 198
Variola_minor              LVMGLNYKLTFLHTLYKRVLNMLLLLIQTMDGQELSLR-YSSKVFLKAFN 198
Mule_deer_pox              WAMGLNYRLTFLYNLYKRVLYILLLLLQTIDNQQLNLHHFSHKYFLKSFN 200
Yaba_monkey_tumor          WAMGLNYRLTFLHDLYKRVLYMLILLIQIMDGEKLNLNNFSHKQFLKSFN 200
Yaba_like_disease          WAMGLNYKLTFLYDLYKRVLYMLILLLQIMDGEKLDLHNFSHKHFLKSFN 200
Swinepox                   WAMGLNYKLTFLHRLYKRVLYMLLLIIQTIDNQRLNIHHFSHKYFLKSFN 197
Lumpy_skin_disease         WAMGVNFKLTFLYNLYKRVLYMILLLIQTMDDQKLSISNFSHKYFLKSFN 201
Sheeppox                   WAMGVNFKLTFLYNLYKRVLYMILLLIQTMDDQKLSISNFSHKYFLKSFN 198
Rabbit_fibroma             WAMGVNYNLSFLYNLYKRVLYMLLLIVQILDEQPLNLTHFSHKYFLKSFN 200
Myxoma                     WAMGVNYNLSFLYNLYKRVLYMLLLIVQILDEQPLNLTHFSHKYFLKSFN 200
Molluscum_contagiosum      LAMGLNYKIGFLYTLYKRVLHMVLLLARILDGQPLSLA-YSRRQVAKLFA 200
Orf_virus                  LAMGLNYRLGFLHSLYRRVLHTLLLLMRVEEGQRPSVE-MSKKPLLRWFE 246
Bovine_papular_stomatitis  LAMGLNYRLGFLHSLYRRVLHTLLLLMRAEEGQRPSVE-MAKKPLLRWFE 228
Fowlpox                    IAMGINFKIDFLRTIYYNTMSLMSALFNIMEGEPLENK-YSHRKVLRYFA 199
Canarypox                  IAMGLNFKINFLRTIYYNTINLLSALFSILEREPIKEK-YSHKKVLSYFS 197
                            .**:*:.: **  :*  ..:  :  :   :  . :  : .  *

Vaccinia                   ERKDSIKFVKLLSHFYPAVINSNINVINYFNRMFHFFEHEKRTNYEYERG 248
Rabbitpox                  ERKDSIKFVKLLSHFYPAVINSNINVINYFNRMFHFFEHEKRTNYEYERG 248
Cowpox                     ERKDSIKFVKLLSHFYPAVINSNINVINYFNRMFHFFEHEKRTNYEYERG 248
Ectromelia                 ERKDSIKFVKLLSHFYPAVINSNINVINYFNRMFHFFEHEKRTNYEYERG 248
Monkeypox                  BRKDSIKFVKLLSHFYPAVINSNINVINYFNRMFHFFEHEKRTNYEYERG 248
Camelpox                   ERKDSIKFVKLLSHFYPAVINSNINVINYFNRMFHFFEHEKRTNYEYERG 248
Variola_major              ERKDSIKFVKLLSHFYPAVINSNINVINYFNRMFHFFEHEKRTNYEYERG 248
Variola_minor              ERKDSIKFVKLLSHFYPAVINSNINVINYFNRMFHFFEHEKRTNYEYERG 248
Mule_deer_pox              EKKGDIKFVKLLSYFYPLLVQSNINVINYFTHMFHFFEHEKRSNYLYDRG 250
Yaba_monkey_tumor          DKKDDIKFVRLISYFYPIVIQSNINVINYFSYMFHFFEHEKRSDYLYERG 250
Yaba_like_disease          DKKDDIKFVKLISYFYPIVIQSNINVINYFSYMFHFFEHEKRSDYLYERG 250
Swinepox                   EKKSDIKFVKLLSYFYPIVVQSNINVINYFTHMFHFFEHEKRANYLYDRG 247
Lumpy_skin_disease         EKKGDVKFVKLLSYFYPIVIQSNVNVINYFTHMFHFFEHEKRSNYLYDRG 251
```

FIG. 6 (cont.)

```
Sheeppox                EKKGDVKFVKLLSYFYPIVIQSNVNVINYFTHMFHFFEHEKRSNYLYDRG 248
Rabbit_fibroma          EKKGDVKFVKLLSYFYPIVVQSNINVINYFTHMFYFFEHEKRSNYAYDKG 250
Myxoma                  EKKGDVKFVKLLSYFYPIVVQSNINVINYFTHMFYFFEHEKRSNYSYDKG 250
Molluscum_contagiosum   ERKDSAKFVRLLSYFYPAVIKSNLNVINHFGHMIHPFEHEKRANYTYDRG 250
Orf_virus               ARKDSESFVRLISYFYPSAVQSNVNLINNFHHLVHPFEHEKRARYVFDRG 296
Bovine_papular_stomatitis SRKDSESFVRLVSYFYPSAVQSNVNLVNNFPHLVHPFEHEKRARYVFDRG 278
Fowlpox                 KYKQSNDFVKLISQFYPYVVNSNINVINNFNYLINFFERSRRSNGYFNRG 249
Canarypox               KYKNTKDFVKIISQFYPFVVSNNINIINNFNYLINFFESTKRANGYFERG 247
                          *  .**::* ***  :..*:*::* *  :. ***  :*:   ::*

Vaccinia                NIIIFPLALYSADKVDTELAIKLGFKSLVQYIKFIFLQMALLYIKIYELP 298
Rabbitpox               NIIIFPLALYSADKVDTELAIKLGFKSLVQYIKFIFLQMALLYIKIYELP 298
Cowpox                  NIIIFPLALYSADKVDTELAIKLGFKSLVQYIKFIFLQMALLYIKIYELP 298
Ectromelia              NIIIFPLALYSADKVDTELAIKLGFKSLVQYIKFIFLQMSLLYIKIYELP 298
Monkeypox               NIIIFPLALYSADKVDTELAIKLGFKSLVQYIKFIFLQMSLLYIKIYELP 298
Camelpox                NIIIFPLALYSADKVDTELAIKLGFKSLVQYIKFIFLQMALLYIKIYELP 298
Variola_major           NIIIFPLALYSADKVDTELAIKLGFKSLVQYIKFIFLQMALLYIKIYELP 298
Variola_minor           NIIIFPLALYSADKVDTELAIKLGFKSLVQYIKFIFLQMALLYIKIYELP 298
Mule_deer_pox           NIIVFPLARCSADKITEKMALEFGFSSLVNYIKFLFLQIALLYIKIYELP 300
Yaba_monkey_tumor       NIIIFPLARCSADKVTEKMAKKLGFSSLVSYIKFLFLQMSLLYIKIYELP 300
Yaba_like_disease       NIIIFPLARCSADKVTEKMARKLGFCSLVDYIKFLFLQMALLYIKIYELP 300
Swinepox                NIIIFPLARFSSDKVTEQMAIELGFKSIVQYVKFIFLQISLLYIKIYELP 297
Lumpy_skin_disease      NIIIFPLAKFSSDKVSEKMAIELGFKSLVEYIKFIFLQMALLYVKIYELP 301
Sheeppox                NIIIFPLAKFSSDKVNEKMAIELGFKSLVEYIKFIFLQMALLYVKIYELP 298
Rabbit_fibroma          NIIVFPLAKCSADKITGKVITRFGFKSLTDYVKFLFLQIALLYVKIYELP 300
Myxoma                  NIIVFPLAKCSADKITGKVAERFGFKSLTEYVKFLFLQIALLYVKIYELP 300
Molluscum_contagiosum   NIIVFPLARCSAEKVTAANCAEFGFASVVHYVKFLFLQMALLYIKIYELS 300
Orf_virus               AVIVFPLARGSADSISPEAAAALGFAPHSEFLKFVFLQIALLYLKIYELP 346
Bovine_papular_stomatitis AVIVFPLARGSADSVSAEAALGLGFSSHAEFLKFVFLQIALLYLKIYEMP 328
Fowlpox                 NIIIFPLAKCSAEKITPDNYAQYGFSSIVEYTKFMFLQIALLYIKIYELP 299
Canarypox               NIIIFPLAKFSAEKITPSNCTKYGFVDIVEYTKFMFLQIALLYIKIYELP 297
                        :*:****  *::.:          **     : **:***::***:****:.

Vaccinia                CCDNFLHADLKPDNILLFDSNEPIIIHLKDKKFVFNERIKSALNDFDFSQ 348
Rabbitpox               CCDNFLHADLKPDNILLFDSNEPIIIHLKDKKFVFNERIKSALNDFDFSQ 348
Cowpox                  CCDNFLHADLKPDNILLFDSNEPIIIHLKDKKFVFNERIKSALNDFDFSQ 348
Ectromelia              CCDNFLHADLKPDNILLFDSNEPIIIHLKDKKFVFNERIKSALNDFDFSQ 348
Monkeypox               CCDNFLHADLKPDNILLFDSNEPIIIHLKNKKFVFNERIKSALNDFDFSQ 348
Camelpox                CCDNFLHADLKPDNILLFDSNEPIIIHLNDKTPVFNERIKSALNDFDFSQ 348
Variola_major           CCDNFLHADLKPDNILLFDSNEPIIIHLKDKKFVFNERIKSALNDFDFSQ 348
Variola_minor           SCDNFLHADLKPDNILLFDSNEPIIIHLKDKKFVFNERIKSALNDFDFSQ 348
Mule_deer_pox           CCNNFLHVDLKPDNILLFDSNKPIKIKFKEMSYIFNEPIKACLNDFDFSQ 350
Yaba_monkey_tumor       CCDNFLHVDLKPDNILLFDSDEKLQIKFNNNLYVFNEKVKSCLNDFDFSQ 350
Yaba_like_disease       CCDNFLHVDLKPDNILLFDSDEEICISFNNNVVYVFKEKIKSCLNDFDFSQ 350
Swinepox                CCDNFLHVDLKPDNILIFNSDCPITIKFKKYTYVFNEPIKACLNDFDFSQ 347
Lumpy_skin_disease      CCNNFLHVDLKPDNILIFDSDESIKISLNENTYIFNEPIKACLNDFDFSQ 351
Sheeppox                CCNNFLHVDLKPDNILIFDSDESIKISLNENIYIFNEPIKACLNDFDFSQ 348
Rabbit_fibroma          CCNNFVHVDLKPDNILVFDSPTPLSITFKHNTYVFNEPIKACLNDFDFSQ 350
Myxoma                  CCNNFVHVDLKPDNLLIFDSPTPLRITFKHNTYVFNEPIKVCLNDFDFSQ 350
Molluscum_contagiosum   -CHNFIHVDLKPDNILLFDSEREMRIHVGERSYVFREPVRSALNDFDFSQ 349
Orf_virus               VCTNFLHVDLKPDNVLIFDSARALSVTAAGATPRFEEPVRAALNDFDFAR 396
Bovine_papular_stomatitis GCANFLHVDLKPDNILFDSSRALSVEAAGATPRFEEPVRAALNDFDFAR 378
Fowlpox                 -CSNFVHLDLKPDNILIFDSKEPINIYVGDMHYVFKEPIRCTLNDFDFSQ 348
Canarypox               -CNNFVHLDLKPDNILIFDSKDTINIYVGNTHYVFNEPIRCTLNDFDFSQ 346
                          * **:* ******:*:*:*    ;  ;      : *.*  ::   ******::

Vaccinia                VAGII-NKKIKNNFKVKHNWYYDFHFFVHTLLKTYPEIEK-DIEFSTALE 396
Rabbitpox               VAGII-NKKIKNNFKVKHNWYYDFHFFVHTLLKTYPEIEK-DIEFSTALE 396
Cowpox                  VAGIV-NKKIKNNFKVEHNWYYDFHFFVHTLLKTYPEIEK-DIEFSTALE 396
Ectromelia              VAGII-NKKIKTNFKVEHNWYYDFHFFVHTLLKTYPEIEK-DIEFSTALE 396
Monkeypox               VAGII-NKKIKNNFKVEHNWYYDFHFFVHTLLKTYPEIEK-DIEFSTALE 396
Camelpox                VAGII-NKKIKNNFKVEHNWYYDFHFFVHTLLKTYPEIEK-DIEFSTALE 396
Variola_major           VAGII-NKKIKNNFKVEHNWYYDFHFFVHTLLKTYPEIEK-DIEFSTALE 396
Variola_minor           VAGII-NKKIKNNFKVEHNWYYDFHFFVHTLLKTYPEIEK-DIEFSTALE 396
Mule_deer_pox           VASIV-NKKIKNSLKVEHNWYYDFHFFIHTLLRTYPEIEK-DVEFNNALE 398
```

FIG. 6 (cont.)

```
Yaba_monkey_tumor        VANIT-NKKIKNSLKVEHNWYYDFHFFTHTLLKTYPEIKN-DAEFNNSLE 398
Yaba_like_disease        VANIT-NKKIKNSLKVEHNWYYDFHFFTHTLLKTYPEIKN-DVIFNSALE 398
Swinepox                 VANIL-NKKIKNSLKIEHNWYYDFHFFIHTLLRTYPEIES-DKEFSDSLE 395
Lumpy_skin_disease       VANII-NKKIKNNIKVEHNWYYDFHFFIHTLLKTYPEIET-DKEFYNTLE 399
Sheeppox                 VANII-NKKIKNNIKVEHNWYYDFHFFIHTLLKTYPEIET-DKEFYNTLE 396
Rabbit_fibroma           VASIT-NKKIKNSLKVEHNWYYDFHFFTHTLFRTYPEIET-DKEFTKALS 398
Myxoma                   VASIM-NKKIKNSLKVEHNWYYDFHFFTHTLFRTYPEIET-DKEFTKALS 398
Molluscum_contagiosum    VSEIP-NKKITASLRVEQNWFYDFHFFVHTLLKVYPELER-DAAWSKALG 397
Orf_virus                VATIE-NRKISGSVRVPQNWYYDFHFFAHTLLRAYPHIAAEDPGFHALLS 445
Bovine_papular_stomatitis VANIE-NRKIAGSIRVPQNWYYDFHFFAHTLLRAYPNIAAEDPAFHSVLS 427
Fowlpox                  ISEIIPNKKAVTAINKEQNWYYDFHFFSHVLFKVYPEISK-DEDFTSLLN 397
Canarypox                ISEILPNRKTVTAIHREQNWYYDFHFFSHVLFKVYPEINK-DSEFTSVLH 395
                         ::  *  *;*      ..  :**:****** *.*::.**.:  *  :  *

Vaccinia                 EFIMCT-KTDCDKYRLKVSILHPISFLEKFIM-RDIFSDWIN--GGN--- 439
Rabbitpox                EFIMCT-KTDCDKYRLKVSILHPISFLEKFIM-RDIFSDWIN--GGN--- 439
Cowpox                   EFIMCT-KTDCDKYRLKVSILHPISFLEKFIM-RDIFSDWIN--GGN--- 439
Ectromelia               EFIMCT-KTDCDKYRLKVSILHPISFLEKFIM-RDIFSDWIN--GGN--- 439
Monkeypox                EFIMCT-KTDCDKYRLKVSILHPISFLEKFIM-RDIFSDWIN--GGN--- 439
Camelpox                 EFIMCT-KTDCDKYRLKVSILHPISFLEKFIM-RDIFSDWIN--GGN--- 439
Variola_major            EFIMCT-KTDCDKYRLKVSILHPISFLEKFIM-RDIFSDWIN--GRN--- 439
Variola_minor            EFIMCT-KTDCDKYRLKVSILHPISFLEKFIM-RDIFSDWIN--GRN--- 439
Mule_deer_pox            EFIICCSKNTCDKFRLKVSILHPITFLEKFVS-KNIFSPWIN--GGEPS- 444
Yaba_monkey_tumor        ELIMCCNKSICDKFRLKVSILHPISFLEKFVT-RDIFSEWIN--GRDTES 445
Yaba_like_disease        ELIMCCNKSTCDKFRLKVSILHPISFLEKFVT-RDIFSTWIN--DGNTTG 445
Swinepox                 DFIMCCTKNTCEKFRLKVSILHPISFLENLIT-KNIFSNWIN--GESC-- 440
Lumpy_skin_disease       EFIICCNKNTCDKFRLKISILHPISFLEKIISKKNIFSTWIN--GKPLSS 447
Sheeppox                 EFIICCNKNTCDKFRLKISILHPISFLEKIISKKNIFSTWIN--GKPLSS 444
Rabbit_fibroma           EFIMCCTKTTCDKFRLKTSILHPISFLEKFIT-KNIFSNWIN--GTRCTT 445
Myxoma                   EFIMCCTKTTCDKFRLKTSILHPISFLEKFIT-KNIFSNWIN--GTHGAA 445
Molluscum_contagiosum    EFLVCCNRNTCEKFRLRVRRLHPISFLVRFVA-RDLFSDWIN--GERRP- 443
Orf_virus                ELTVSCSRGTCDRFRLRVSSPHPIEHLARLVR-RDVFSRWINAAADAPDA 494
Bovine_papular_stomatitis ELTISCSRSTCDRFRLRVSSTHPIEHLARIVR-RDLFSRWINAATDAPDP 476
Fowlpox                  EFTICD-KYICENFRLQVNKLPSISFLINIVS-RDIFSKWI--DGKSTSH 443
Canarypox                EFIVCN-KSICENFRLQVNRLPSISFLTNIVS-RSIFSKWISKDGKQSSS 443
                         ::  :.   :  *:.:**:      .*  .*  .::   :.:** **

Vaccinia                 ----
Rabbitpox                ----
Cowpox                   ----
Ectromelia               ----
Monkeypox                ----
Camelpox                 ----
Variola_major            ----
Variola_minor            ----
Mule_deer_pox            ----
Yaba_monkey_tumor        ----
Yaba_like_disease        ----
Swinepox                 ----
Lumpy_skin_disease       ----
Sheeppox                 ----
Rabbit_fibroma           ----
Myxoma                   ----
Molluscum_contagiosum    ----
Orf_virus                AALS 498
Bovine_papular_stomatitis AAA- 479
Fowlpox                  Q--- 444
Canarypox                E--- 444
```

FIG. 7

```
Vaccinia_Copenhagen   MNFQGLVLTDNCKNQWVVGPLIGKGGFGSIYTTNDNNYVVKIEPKANGSLFTEQAFYTRV 60
Vaccinia_WR           MNFQGLVLTDNCKNQWVVGPLIGKGGFGSIYTTNDNNYVVKIEPKANGSLFTEQAFYTRV 60
Vaccinia_Ankara       MNFQGLVLTDNCKNQWVVGPLIGKGGFGSIYTTNDNNYVVKIEPKANGSLFTEQAFYTRV 60
Vaccinia_Acambis      MNFQGLVLTDNCKNQWVVGPLIGKGGFGSIYTTNDNNYVVKIEPKANGSLFTEQAFYTRV 60
Vaccinia_TT           MNFQGLVLTDNCKNQWVVGPLIGKGGFGSIYTTNDNNYVVKIEPKANGSLFTEQAFYTRV 60
Vaccinia_LC16mO       MNFQGLVLTDNCKNQWVVGPLIGKGGFGSIYTTNDNNYVVKIEPKANGSLFTEQAFYTRV 60
Vaccinia_LC16m8       MNFQGLVLTDNCKNQWVVGPLIGKGGFGSIYTTNDNNYVVKIEPKANGSLFTEQAFYTRV 60
Variola_maj_India     MNFQGLVLTDNCKNQWVVGPLIGKGGFGSIYTTNDNNYVVKIEPKANGSLFTEQAFYTRV 60
Variola_maj_BD        MNFQGLVLTDNCKNQWVVGPLIGKGGFGSIYTTNDNNYVVKIEPKANGSLFTEQAFYTRV 60
Variola_min_Garcia    MNFQGLVLTDNCKNQWVVGPLIGKGGFGSIYTTNDNNYVVKIEPKANGSLFTEQAFYTRV 60
Cowpox_GRI90          MNFQGLVLTDNCKNQWVVGPLIGKGGFGSIYTTNDNNYVVKIEPKANGSLFTEQAFYTRV 60
Cowpox_BR             MNFQGLVLTDNCKNQWVVGPLIGKGGFGSIYTTNDNNYVVKIEPKANGSLFTEQAFYTRV 60
Rabbitpox             MNFQGLVLTDNCKNQWVVGPLIGKGGFGSIYTTNDNNYVVKIEPKANGSLFTEQAFYTRV 60
Camelpox_M96          MNFQGLVLTDNCKNQWVVGPLIGKGGFGSIYTTNDNNYVVKIEPKANGSLFTEQAFYTRV 60
Camelpox_CMS          MNFQGLVLTDNCKNQWVVGPLIGKGGFGSIYTTNDNNYVVKIEPKANGSLFTEQAFYTRV 60
Ectromelia_Moscow     MNFQGLVLTDNCKNQWVVGPLIGKGGFGSIYTTNDNNYVVKIEPKANGSLFTEQAFYTRV 60
Monkeypox_MPXV        MKFQGLVLTDNCKNQWVVGPLIGKGGFGSIYTTNDNNYVVKIEPKANGSLFTEQAFYTRV 60
Monkeypox_Zaire       MKFQGLVLIDNCKNQWVVGPLIGKGGFGSIYTTNDNNYVVKIEPKANGSLFTEQAFYTRV 60
                      *:****** ***************************************************

Vaccinia_Copenhagen   LKPSVIEEWKKSHNIKHVGLITCKAFGLYKSINVEYRFLVINRLGVDLDAVIRANNNRLP 120
Vaccinia_WR           LKPSVIEEWKKSHNIKHVGLITCKAFGLYKSINVEYRFLVINRLGADLDAVIRANNNRLP 120
Vaccinia_Ankara       LKPSVIEEWKKSHNIKHVGLITCKAFGLYKSINVEYRFLVINRLGADLDAVIRANNNRLP 120
Vaccinia_Acambis      LKPSVIEEWKKSHNIKHVGLITCKAFGLYKSINVEYRFLVINRLGADLDAVIRANNNRLP 120
Vaccinia_TT           LKPSVIEEWKKSHNIKHVGLITCKAFGLYKSINVEYRFLVINRLGADLDAVIRANNNRLP 120
Vaccinia_LC16mO       LKPSVIEEWKKSHNIKHVGLITCKAFGLYKSINVEYRFLVINRLGADLDAVIRANNNRLP 120
Vaccinia_LC16m8       LKPSVIEEWKKSHNIKHVGLITCKAFGLYKSINVEYRFLVINRLGADLDAVIRANNNRLP 120
Variola_maj_India     LKPSVIEEWKKSHHISHVGVITCKAFGLYKSINTEYRFLVINRLGVDLDAVIRANNNRLP 120
Variola_maj_BD        LKPSVIEEWKKSHHISHVGVITCKAFGLYKSINTEYRFLVINRLGVDLDAVIRANNNRLP 120
Variola_min_Garcia    LKPSVIEEWKKSHHISHVGVITCKAFGLYKSINTEYRFLVINRLGADLDAVIRANNNRLP 120
Cowpox_GRI90          LKPSVIEEWKKSHNIKHVGLITCKAFGLYKSINVEYRFLVINRLGADLDAVIRANNNRLP 120
Cowpox_BR             LKPSVIEEWKKTRHIKHVGLITCKAFGLYKSINVEYRFLVINRLGADLDAVIRANNNRLP 120
Rabbitpox             LKPSVIEEWKKSHNIKHVGLITCKAFGLYKSINVEYRFLVINRLGADLDAVIRANNNRLP 120
Camelpox_M96          LKPSVIEEWKKYHHISHVGVITCKAFGLYKSINAEYRFLVINRLGVDLDAVIRANNNRLP 120
Camelpox_CMS          LKPSVIEEWKKYHHISHVGVITCKAFGLYKSINAEYRFLVINRLGVDLDAVIRANNNRLP 120
Ectromelia_Moscow     LKPSVIEEWKKSHNIKHVGLITCTAFGLYKSINVEYRFLVINRLGADLDAVIRANNNRLP 120
Monkeypox_MPXV        LKPSVIEEWKKSHNIKHVGLITCKAFGLYKSINVEYRFLVINRLGADLDAVIRANNNRLP 120
Monkeypox_Zaire       LKPSVIEEWKKSHNIKHVGLITCKAFGLYKSINVEYRFLVINRLGADLDAVIRANNNRLP 120
                      ***********::*.***:***.*********.***********.**************

Vaccinia_Copenhagen   KRSVMLIGIEILNTIQFMHEQGYSHGDIKASNIVLDQIDKNKLYLVDYGLVSKFMSNGEH 180
Vaccinia_WR           KRSVMLIGIEILNTIQFMHEQGYSHGDIKASNIVLDQIDKNKLYLVDYGLVSKFMSNGEH 180
Vaccinia_Ankara       KRSVMLIGIEILNTIQFMHEQGYSHGDIKASNIVLDQIDKNKLYLVDYGLVSKFMSNGEH 180
Vaccinia_Acambis      KRSVMLIGIEILNTIQFMHEQGYSHGDIKASNIVLDQIDKNKLYLVDYGLVSKFMSNGEH 180
Vaccinia_TT           KRSVMLIGIEILNTIQFMHEQGYSHGDIKASNIVLDQIDKNKLYLVDYGLVSKFMSNGEH 180
Vaccinia_LC16mO       KRSVMLIGIEILNTIQFMHEQGYSHGDIKASNIVLDQIDKNKLYLVDYGLVSKFMSNGEH 180
Vaccinia_LC16m8       KRSVMLIGIEILNTIQFMHEQGYSHGDIKASNIVLDQIDKNKLYLVDYGLVSKFMSNGEH 180
Variola_maj_India     KRSVMLVGIEILNTIQFMHEQGYSHGNIKASNIVLDQMDKNKLYLVDYGLVSKFMSNGEH 180
Variola_maj_BD        KRSVMLVGIEILNTIQFMHEQGYSHGDIKASNIVLDQMDKNKLYLVDYGLVSKFMYNGEH 180
Variola_min_Garcia    KRSVMLVGIEILNTIQFMHEQGYSHGDIKASNIVLDQMDKNKLYLVDYGLVSKFMSNGEH 180
Cowpox_GRI90          KRSVMLIGIEILNTIQFMHEQGYSHGDIKASNIVLDQIDKNKLYLVDYGLVSKFMSNGEH 180
Cowpox_BR             KRSVMLVGIEILNTIQFMHEQGYSHGDIKASNIVLDQMDKNKLYLVDYGLVSKFMSNGEH 180
Rabbitpox             KRSVMLIGIEILNTIQFMHEQGYSHGDIKASNIVLDQIDKNKLYLVDYGLVSKFMSNGEH 180
Camelpox_M96          KRSVMLVGIEILNTIQFMHEQGYSHGDIKASNIVLDQMDKNKLYLVDYGLVSKFMSNGEH 180
Camelpox_CMS          KRSVMLVGIEILNTIQFMHEQGYSHGDIKASNIVLDQMDKNKLYLVDYGLVSKFMSNGEH 180
Ectromelia_Moscow     KRSVMLIGIEILNTIQFMHEQGYSHGDIKASNIVLDQMDKNKLYLVDYGLVSKFMSNGEH 180
Monkeypox_MPXV        ERSVMLIGIEILNTIQFMHEQGYSHGDIKASNIVLDQIDKNKLYLVDYGLVSKFMSNGEH 180
Monkeypox_Zaire       ERSVMLIGIEILNTIQFMHEQGYSHGDIKASNIVLDQIDKNKLYLVDYGLVSKFMSNGEH 180
                      :****:********************:*********:********************* ****
```

FIG. 7 (cont.)

```
Vaccinia_Copenhagen   VPFIRNPNKMDNGTLEFTPIDSHKGYVVSRRGDLETLGYCMIRWLGGILPWTKISETKNC 240
Vaccinia_WR           VPFIRNPNKMDNGTLEFTPIDSHKGYVVSRRGDLETLGYCMIRWLGGILPWTKISETKNC 240
Vaccinia_Ankara       VPFIRNPNKMDNGTLEFTPIDSHKGYVVSRRGDLETLGYCMIRWLGGILPWTKISETKNC 240
Vaccinia_Acambis      VPFIRNPNKMDNGTLEFTPIDSHKGYVVSRRGDLETLGYCMIRWLGGILPWTKISETKNC 240
Vaccinia_TT           VPFIRNPNKMDNGTLEFTPIDSHKGYVVSRRGDLETLGYCMIRWLGGILPWTKISETKNC 240
Vaccinia_LC16mO       VPFIRNPNKMDNGTLEFTPIDSHKGYVVSRRGDLETLGYCMIRWLGGILPWTKISETKNC 240
Vaccinia_LC16m8       VPFIRNPNKMDNGTLEFTPIDSHKGYVVSRRGDLETLGYCMIRWLGGILPWTKISETKNC 240
Variola_maj_India     VPFIRNPNKMDNGTLEFTPIDSHKGYVVSRRGDLETLGYCMIRWLGGILPWTKIAETKNC 240
Variola_maj_BD        VPFIRNPNKMDNGTLEFTPIDSHKGYVVSRRGDLETLGYCMIRWLGGILPWTKIAETKNC 240
Variola_min_Garcia    VPFIRNPNKMDNGTLEFTPIDSHKGYVVSRRGDLETLGYCMIRWLGGILPWTKIAETKNC 240
Cowpox_GRI90          VPFIRNPNKMDNGTLEFTPIDSHKGYVVSRRGDLETLGYCMIRWLGGILPWTKISETKNC 240
Cowpox_BR             VPFIRNPNRMDNGTLEFTPIDSHKGYVVSRRGDLETLGYCMIRWLGGILPWTKISETKNC 240
Rabbitpox             VPFIRNPNKMDNGTLEFTPIDSHKGYVVSRRGDLETLGYCMIRWLGGILPWTKISETKNC 240
Camelpox_M96          VPFIRNPNKMDNGTLEFTPIDSHKGYVVSRRGDLETLGYCMIRWLGGILPWTKIAETKNC 240
Camelpox_CMS          VPFIRNPNKMDNGTLEFTPIDSHKGYVVSRRGDLETLGYCMIRWLGGILPWTKIAETKNC 240
Ectromelia_Moscow     VPFIRNPNKMDNGTLEFTPIDSHKGYVVSRRGDLETLGYCMIRWLGGILPWTKMSETKNC 240
Monkeypox_MPXV        VPFIRNPNKMDNGTLEFTPIDSHKGYVVSRRGDLETLGYCMIRWLGGILPWTKISETKNS 240
Monkeypox_Zaire       VPFIRNPNKMDNGTLEFTPIDSHKGYVVSRRGDLETLGYCMIRWLGGILPWTKISETKNS 240
                      ********:***************************************:****.

Vaccinia_Copenhagen   ALVSATKQKYVNNTATLLMTSLQYAPRELLQYITMVNSLTYFEEPNYDEFRHILMQGVYY 300
Vaccinia_WR           ALVSATKQKYVNNTATLLMTSLQYAPRELLQYITMVNSLTYFEEPNYDEFRHILMQGVYY 300
Vaccinia_Ankara       ALVSATKQKYVNNTATLLMTSLQYAPRELLQYITMVNSLTYFEEPNYDKFRHILMQGVYY 300
Vaccinia_Acambis      ALVSATKQKYVNNTATLLMTSLQYAPRELLQYITMVNSLTYFEEPNYDKFRHILMQGVYY 300
Vaccinia_TT           ALVSATKQKYVNNTATLLMTSLQYAPRELLQYITMVNSLTYFEEPNYDEFRHILMQGVYY 300
Vaccinia_LC16mO       ALVSATKQKYVNNTATLLMTSLQYEPRELLQYITMVNSLTYFEEPNYDKFRHILMQGVYY 300
Vaccinia_LC16m8       ALVSATKQKYVNNTATLLMTSLQYEPRELLQYITMVNSLTYFEEPNYDKFRHILMQGVYY 300
Variola_maj_India     ALVSATKQKYVNNTTTLLMTSLQYAPRELLQYITMVNSLTYFEEPNYDKFRHILMQGAYY 300
Variola_maj_BD        ALVSATKQKYVNNTTTLLMTSLQYAPRELLQYITMVNSLTYFEEPNYDKFRHILMQGAYY 300
Variola_min_Garcia    ALVSATKQKYVNNTATLLMTSLQYAPRELLQYITMVNSLTYFEEPNYDKFRHILMQGAYY 300
Cowpox_GRI90          ALVSATKQKYVNNTATLLMTSLQYAPRELLQYITMVNSLTYFEEPNYDEFRHILMQGVYY 300
Cowpox_BR             ALVSATKQKYVNNTATLLMTSLQYAPRELLQYITMVNSLTYFEEPNYDEFRRVLMNGVM- 299
Rabbitpox             ALVSATKQKYVNNTATLLMTSLQYAPRELLQYITMVNSLTYFEEPNYDEFRHILMQGVYY 300
Camelpox_M96          ALVSATKQKYVNNTATLLMTSLQYAPRELLQYITMVNSLTYFEEPNYDEFRRILMQGVYY 300
Camelpox_CMS          ALVSATKQKYVNNTATLLMTSLQYAPRELLQYITMVNSLTYFEEPNYDEFRRILMQGVYY 300
Ectromelia_Moscow     ALVSATKQKYVNNTATLLMTSLQYAPKELLQYITMVNSLTYFEEPNYDEFRRVLMNGVM- 299
Monkeypox_MPXV        ALVSAAKQKYVNNTATLLMTSLQYAPRELLQYITMVNSLTYFEEPNYDEFRRVLMNGVMK 300
Monkeypox_Zaire       ALVSAAKQKYVNNTATLLMTSLQYAPRELLQYITMVNSLTYFEEPNYDEFRRVLMNGVM- 299
                     *****:********:********* *:*******************:**:.**:*.

Vaccinia_Copenhagen   ---
Vaccinia_WR           ---
Vaccinia_Ankara       ---
Vaccinia_Acambis      ---
Vaccinia_TT           ---
Vaccinia_LC16mO       ---
Vaccinia_LC16m8       ---
Variola_maj_India     ---
Variola_maj_BD        ---
Variola_min_Garcia    ---
Cowpox_GRI90          ---
Cowpox_BR             ---
Rabbitpox             ---
Camelpox_M96          ---
Camelpox_CMS          ---
Ectromelia_Moscow     ---
Monkeypox_MPXV        NFC 303
Monkeypox_Zaire       ---
```

FIG. 8

```
Lumpy_skin        -MPKR-NINVFEEGDVLVDSVKKEWRLGKIIGQGGFGFIFLAYS-------QNNEEYVVK 51
Sheeppox          -MPKP-NINVFEEGDVLVDSLKKEWKLGKIIGQGGFGFIFLAYS-------QNNEEYVVK 51
Mule_deer_pox     -MPKKINNEMFDEGETLTDNTGRRWKLGNIIGKGGFGFIYLSFLYIDDTHIDTEERYVIK 59
Myxoma            -MSKR---NEIEPGDVLIDASKREWVLGDILGKGGFGYIYTARLCSE--EEF--DKYVIK 52
Rabbit_fibroma    -MLKR---NGIEPGDALTDSSKREWILGDVLGKGGFGYIYTARLCSE--EER--DKYVIK 52
Swinepox          -MSGRG--NMFNEGEILIDTKRRSWKLGTLIGKGGFGCIYTASIHGK--EDVSETQYAIK 55
Yaba_monkey       -MSKN---QELKEGEILIDSTKTKWKLGQIVGKGGFGYIYFAVKDCD---KYSDFTHVIK 53
Yaba_like_disease -MSKN---QELKEGEVLTDTTKTKWKIGKIVGKGGFGFIYFAVKDSE---KNKDFTHVVK 53
Variola_major     ---------MNFQGLVLTDNCKNQWVVGPLIGKGGFGSIYTTND----------NNYVVK 41
Variola_minor     ---------MNFQGLVLTDNCKNQWVVGPLIGKGGFGSIYTTND----------NNYVVK 41
Camelpox          ---------MNFQGLVLTDNCKNQWVVGPLIGKGGFGSIYTTND----------NNYVVK 41
Cowpox            ---------MNFQGLVLTDNCKNQWVVGPLIGKGGFGSIYTTND----------NNYVVK 41
Rabbitpox         ---------MNFQGLVLTDNCKNQWVVGPLIGKGGFGSIYTTND----------NNYVVK 41
Vaccinia          ---------MNFQGLVLTDNCKNQWVVGPLIGKGGFGSIYTTND----------NNYVVK 41
Ectromelia        ---------MNFQGLVLTDNCKNQWVVGPLIGKGGFGSIYTTND----------NNYVVK 41
Monkeypox         ---------MKFQGLVLTDNCKNQWVVGPLIGKGGFGSIYTTND----------NNYVVK 41
Fowlpox           MPQNKVLSFPLPEGTLLEDITKNKWILGKQLGSGGFGLVYQVS------CKSKEIDCVAK 54
Canarypox         MALINKKVLPLPSGTVLTDLAKRRWVLEKQIGCGGFGLVYDVYPE----NDNTNMRYIAK 56
                           * * *    *   :* ****  ::                         *

Lumpy_skin        IEPKSNGPLFVEQVFYQRIGK-RDMITLWSKNNHIDHLGIPVFYGFGFHKKNGIDYRFII 110
Sheeppox          IEPKSNGPLFVEQVFYQRIGK-RDMITLWSKKNHIDHLGIPVFYGFGFHKKNGIDYRFII 110
Mule_deer_pox     IEPKSNGPLFVEQIFYQRICK-KELIEKWLKENNIQYIGIPTFYGFGFCKKNKIEYRFII 118
Myxoma            IEPKSNGPLFVEQVFYQRVGK-TDMVTDWCKKNNLPYLGIPSFHGFGFYTKNKKDYRFII 111
Rabbit_fibroma    IEPKSNGPLFVEQVFYQRVGK-VDMIADWCKKHNLTYLGIPSFHGFGFCTKNKKDYRFII 111
Swinepox          IEPKSNGPLFVEQVFYQRIGK-WDMIDSWKKSNGINHLGIPNFYGFGFYTKNKKEYRFII 114
Yaba_monkey       VEPKSNGPLFVEQVFYQRTGK-KEIIDNWMLENNVSHLGIPKCYGFGFHKNGNNEYRFII 112
Yaba_like_disease VEPKSNGPLFVEQIFYQRIGK-KEIINNWMLTNNVSYLGIPKCYGFGFHKSDKNDYRFII 112
Variola_major     IEPKANGSLFTEQAFYTRVLK-PSVIEEWKKSHHISHVGVITCKAFGLYKSINTEYRFLV 100
Variola_minor     IEPKANGSLFTEQAFYTRVLK-PSVIEEWKKSHHISHVGVITCKAFGLYKSINTEYRFLV 100
Camelpox          IEPKANGSLFTEQAFYTRVLK-PSVIEEWKKYHHISHVGVITCKAFGLYKSINAEYRFLV 100
Cowpox            IEPKANGSLFTEQAFYTRVLK-PSVIEEWKKSHNIKHVGLITCKAFGLYKSINVEYRFLV 100
Rabbitpox         IEPKANGSLFTEQAFYTRVLK-PSVIEEWKKSHNIKHVGLITCKAFGLYKSINVEYRFLV 100
Vaccinia          IEPKANGSLFTEQAFYTRVLK-PSVIEEWKKSHNIKHVGLITCKAFGLYKSINVEYRFLV 100
Ectromelia        IEPKANGSLFTEQAFYTRVLK-PSVIEEWKKSHNIKHVGLITCTAFGLYKSINVEYRFLV 100
Monkeypox         IEPKANGSLFTEQAFYTRVLK-PSVIEEWKKSHNIKHVGLITCKAFGLYKSINVEYRFLV 100
Fowlpox           IELKESGGLFCEINFYNRVMKNKTSLDTWMKEQKIDYIGIPSFHGFGITIYKNVEYRFAI 114
Canarypox         LEHKDSGGLFCEINPYIRVMRNNYFVDEWKKNNLISHLGIPKYHGSGISMYNGKEYRFLI 116
                  :* * .* ** * **  *   :    *    : ::*:  . *:     :*** :

Lumpy_skin        INRLGCDLNKIIQCNNNKLPERSVFLIASKIIMILKYLHENGYTHSDIKASNIAIDINNK 170
Sheeppox          ISRLGCDLNKIIQCNNNKLPERSVFLIASKIIMILKYLHENGYTHSDIKASNIAIDINNK 170
Mule_deer_pox     IDRLGCDLNKIISVNNNKLPVRSVFLIAINIINTLKYLHNNGYTHSDIKSSNIAIGLHDK 178
Myxoma            IDRLGCDLYNILQYNNYTLPLKTVCLIAIKIIVVLKYLHEHGYAHSDIKASNIAIGARDK 171
Rabbit_fibroma    IDRLGCDLYNILQHNNYTLPLRTVCLIAVRIIIILKYLHEHGYTHSDIKASNIAIDVRDK 171
Swinepox          VDRLGCDLNKIIQNNNNKLPQSTVFKIADRIITVLRYIHDHGYTHGDIKASNIAIDYYDK 174
Yaba_monkey       IDRLGCDLQRIIQANDNKLPKKTVLKIGAVVLVILKFIHDNGYTHSDIKASNIALNKDDK 172
Yaba_like_disease IDRLGCDLQRIIQANDNKLPKKTVLKIGAIILVILKFIHDNGYVHSDIKASNIALDKNDK 172
Variola_major     INRLGVDLDAVIRANNNRLPKRSVMLVGIEILNTIQFMHEQGYSHGDIKASNIVLDQMDK 160
Variola_minor     INRLGADLDAVIRANNNRLPKRSVMLVGIEILNTIQFMHEQGYSHGDIKASNIVLDQMDK 160
Camelpox          INRLGVDLDAVIRANNNRLPKRSVMLVGIEILNTIQFMHEQGYSHGDIKASNIVLDQMDK 160
Cowpox            INRLGADLDAVIRANNNRLPKRSVMLIGIEILNTIQFMHEQGYSHGDIKASNIVLDQIDK 160
Rabbitpox         INRLGADLDAVIRANNNRLPKRSVMLIGIEILNTIQFMHEQGYSHGDIKASNIVLDQIDK 160
Vaccinia          INRLGVDLDAVIRANNNRLPKRSVMLIGIEILNTIQFMHEQGYSHGDIKASNIVLDQIDK 160
Ectromelia        INRLGADLDAVIRANNNRLPKRSVMLIGIEILNTIQFMHEQGYSHGDIKASNIVLDQMDK 160
Monkeypox         INRLGADLDAVIRANNNRLPERSVMLIGIEILNTIQFMHEQGYSHGDIKASNIVLDQIDK 160
Fowlpox           IQRLGRDLENILS-EKEKFNITVIKKLAIKILDILKFIHSKEFSHGDIKAGNILFGKDD- 172
Canarypox         IEKLGSDIHRLLV-DRKKFNISGVKTLATNILTILEFIHDKGYSHGDIKSENILLGLRD- 174
                  :.:** *:  ::    :   :    :  ::  :..::*.:  : *.:**: ** :.  :
```

FIG. 8 (cont.)

```
Lumpy_skin         NKIYLLDYGLSYRFMINGNHVEYKRDPKKMHNGTIEYTSIDMHKGVSPSRRGDLEILGYC 230
Sheeppox           NKIYLLDYGLSYRFMINGNHVEYKRDPKKMHNGTIEYTSIDMHNGVSPSRRGDLEILGYC 230
Mule_deer_pox      NKIYLLDYGLSYRYMINGKHVEYKRDPKKMHNGTIEFTSIDMHRGACPSRRGDLEILGYC 238
Myxoma             NKIYLLDYGLSYRFMVDGRHVLYKRDPKKMHNGTIEFTSTDMHNGACPSRRGDLETLGYC 231
Rabbit_fibroma     NKIYLLDYGLSYRFMVDGRHVLYKRDPKKMHNGTIEFTSTDMHNGACPSRRGDLEILGYC 231
Swinepox           NKIYLIDYGLSHRYKVNDVHIQYKRDPKKMHNGTIEFTSIDMHNGASITRRGDLEILGYC 234
Yaba_monkey        NKIYLIDYGLAFRFMVNGKHVDFKKDPKRMHNGTVEFTSIDAHCGAYPSRRGDLEILGYC 232
Yaba_like_disease  NKLYLIDYGLAFRFMVNDIHVEFKKDPKRMHNGTIEFTSIDAHCGAYPSRRGDLEILGYC 232
Variola_major      NKLYLVDYGLVSKFMSNGEHVPFIRNPNKMDNGTLEFTPIDSHKGYVVSRRGDLETLGYC 220
Variola_minor      NKLYLVDYGLVSKFMSNGEHVPFIRNPNKMDNGTLEFTPIDSHKGYVVSRRGDLETLGYC 220
Camelpox           NKLYLVDYGLVSKFMSNGEHVPFIRNPNKMDNGTLEFTPIDSHKGYVVSRRGDLETLGYC 220
Cowpox             NKLYLVDYGLVSKFMSNGEHVPFIRNPNKMDNGTLEFTPIDSHKGYVVSRRGDLETLGYC 220
Rabbitpox          NKLYLVDYGLVSKFMSNGEHVPFIRNPNKMDNGTLEFTPIDSHKGYVVSRRGDLETLGYC 220
Vaccinia           NKLYLVDYGLVSKFMSNGEHVPFIRNPNKMDNGTLEFTPIDSHKGYVVSRRGDLETLGYC 220
Ectromelia         NKLYLVDYGLVSKFMSNGEHVPFIRNPNKMDNGTLEFTPIDSHKGYVVSRRGDLETLGYC 220
Monkeypox          NKLYLVDYGLVSKFMSNGEHVPFIRNPNKMDNGTLEFTPIDSHKGYVVSRRGDLETLGYC 220
Fowlpox            DKVYLVDYGLATKYSSNGKHKEYTINPKNRHNGTMAFTSIDAHKGVTVSRRGDLESLGFC 232
Canarypox          NRIYLVDYGLSAKFLQGKEHRPYFRDPKARHNGTLLFASIDAHNGVVVSRKGDLESLGYC 234
                   :::**:****  ::  . *  : :*: ,***:  ::.  * *    :*:**** **:*

Lumpy_skin         IIKWLGGKLPWEN--DLKNCKYVMESKIKYMNDIGNLMTDSLGS-NYPEKILKYFNYIKT 287
Sheeppox           IIKWLGGKLPWEN--DLKNCKYVMESKIKYMNDIGNLMTDSLGS-NYPEKILKYFNYIKT 287
Mule_deer_pox      MITWLGGKLPWED--NLKNCNYVMNSKVDHLKDVRLFIEKCLGD-NYPKKLLDYFIYINS 295
Myxoma             LIKWLGGTLPWED--NLKNCKYVMESKIKFLNDIKQGIETSLS--ACVEPLRRYFLYVKS 287
Rabbit_fibroma     LIKWLGGTLPWED--NLKNCKYVMESKIKFLNDIKQGIEASLS--ACVEPLRRYFLYVKS 287
Swinepox           MVKWLGGILPWEN--DLKNRKYVMEQKIRCIGDIHNFLTESLG--RYPVELYNYFIYISS 290
Yaba_monkey        MIKWMSGKLPWED--NLKNKEYVKSSKIKYMNNLKLLMNECFKDGSDFTELEKYMNIVKS 290
Yaba_like_disease  MIKWMSGKLPWED--DLKNKEYVKMSKIKYMNDVNLLMKECFNDSKEFLELEKYMNAVKL 290
Variola_major      MIRWLGGILPWTKIAETKNCALVSATKQKYVNNTTTLLMTSLQY--APRELLQYITMVNS 278
Variola_minor      MIRWLGGILPWTKIAETKNCALVSATKQKYVNNTATLLMTSLQY--APRELLQYITMVNS 278
Camelpox           MIRWLGGILPWTKIAETKNCALVSATKQKYVNNTATLLMTSLQY--APRELLQYITMVNS 278
Cowpox             MIRWLGGILPWTKISETKNCALVSATKQKYVNNTATLLMTSLQY--APRELLQYITMVNS 278
Rabbitpox          MIRWLGGILPWTKISETKNCALVSATKQKYVNNTATLLMTSLQY--APRELLQYITMVNS 278
Vaccinia           MIRWLGGILPWTKISETKNCALVSATKQKYVNNTATLLMTSLQY--APRELLQYITMVNS 278
Ectromelia         MIRWLGGILPWTKMSETKNCALVSATKQKYVNNTATLLMTSLQY--APKELLQYITMVNS 278
Monkeypox          MIRWLGGILPWTKISETKNSALVSAAKQKYVNNTATLLMTSLQY--APRELLQYITMVNS 278
Fowlpox            MLKWYSGKLPWEK--YEKEPENVQGMKEAFVNNISKKTIPFKN----AGIIYNYIKVVTK 286
Canarypox          MIKWLVGRLPWEG--YEKDPDSVQNMKEKFIENITKKYVIEKD----IDIIYNYIKTVSS 288
                   :: *  * ***    *:    *     *   : :             : *:  :.

Lumpy_skin         LQYDSIPDYEKIMSFFLL------- 305
Sheeppox           LQYDSIPDYEKIMSSFLL------- 305
Mule_deer_pox      LEYDSTPDYKKLISFLSVKT----- 315
Myxoma             LAYEQRPDYDLLIQLLTKA------ 306
Rabbit_fibroma     LSYEQCPDYDLLIQLLKKT------ 306
Swinepox           LKYDECPDYNLITRMINKT------ 309
Yaba_monkey        LNYDSLPNYVELISVLDGF------ 309
Yaba_like_disease  LNYDSLPNYTELISILNHF------ 309
Variola_major      LTYFEEPNYDKFRHILMQGAYY--- 300
Variola_minor      LTYFEEPNYDKFRHILMQGAYY--- 300
Camelpox           LTYFEEPNYDEFRRILMQGVYY--- 300
Cowpox             LTYFEEPNYDEFRHILMQGVYY--- 300
Rabbitpox          LTYFEEPNYDEFRHILMQGVYY--- 300
Vaccinia           LTYFEEPNYDEFRHILMQGVYY--- 300
Ectromelia         LTYFEEPNYDEFRRVLMNGVM---- 299
Monkeypox          LTYFEEPNYDEFRRVLMNGVMKNFC 303
Fowlpox            LEYEEAPNYESLKQMFL-------- 303
Canarypox          LDYSENPDYDHLKKMFL-------- 305
                   * *  . *:*  :    :
```

METHODS OF INHIBITING POXVIRUS GROWTH

CROSS REFERENCE TO RELATED APPLICATIONS

This is the U.S. National Stage of International Application No. PCT/US2006/039836, filed Oct. 10, 2006 (published in English under PCT Article 21(2)), which claims the benefit of U.S. Provisional Application No. 60/727,001, filed Oct. 13, 2005, both of which applications are incorporated herein in their entirety.

STATEMENT OF GOVERNMENT SUPPORT

This invention was made with United States government support pursuant to grant no. R01 CA 42350 from the National Institutes of Health; the United States government has certain rights in the invention.

FIELD

This disclosure concerns the use of derivatives, of tetralin, anthraquinone, naphthylamine, tri-amino-pyrimidine, xanthen-3-one, and/or cinnamic acid to inhibit viral protein kinases and poxvirus growth, and to treat poxvirus infection.

BACKGROUND

Poxviruses are the largest known animal viruses with approximately 200 distinct genes (Moss, In: *Fields Virology*, ed. by Knipe and Howley, Philadelphia: Lippincott Williams & Wilkins, 2001, pp. 2849-2883). They are DNA viruses that replicate entirely in the cytoplasm. Thus, a subset of their gene products carries out the functions that are essential for the viruses to be independent of the host-cell nucleus. The other viral gene products use or modulate a wide array of host-cell and immune-system processes.

Poxviruses infect most vertebrates and invertebrates causing a variety of diseases of veterinary and medical importance. The Poxviridae family has two main subfamilies, the chordopoxvirinae, which infect vertebrates, and the entomopoxvirinae, which infect insects. The chordopoxviruses include the genera *Orthopoxvirus, Parapoxvirus, Avipoxvirus, Capripoxvirus, Leporipoxvirus, Suipoxvirus, Molluscipoxvirus*, and *Yatapoxvirus*. Each of the chordopoxviruses has a restricted and specific host array. Humans are the sole hosts of two poxviruses, variola virus (smallpox virus) and molluscum contagiosum virus; however many members of *Orthopoxvirus, Parapoxvirus*, and *Yatapoxvirus* are zoonotic, i.e., can infect both animals and humans. Vaccinia virus is the virus used in the variola virus vaccine, and it is widely used as a model poxvirus in the laboratory. Variola virus and vaccinia virus are members of the *Orthopoxvirus* genus.

Smallpox virus (variola major) has the potential to be used as a weapon. The virus is contagious, easy to store, and infection is fatal in 30-40% of unimmunized individuals (Davis et al., *Microbiology*, Hagerstown, Md.: Harper & Row, 1980, pp. 1077-1093; Harrison et al., *Proc. Natl. Acad. Sci. USA*, 101(31): 11178-11192, 2004). Importantly, more than half the world's population has never been vaccinated against this virus and essentially no one has been re-immunized for at least 20 years. Efforts to resume immunization and re-immunization have foundered. A drug that inhibited the growth of variola should prevent and cure acute smallpox infection even in unimmunized individuals. To this end, efforts have been made to develop nucleoside analogs as anti-poxvirus drugs (Bray et al., *J. Infect. Dis.*, 181: 10-19, 2000; De Clercq, *Clin. Microbiol. Rev.*, 14: 382-397, 2001; Keith et al., *Antimicrob. Agents Chemother.*, 47: 2193-2198, 2003). One promising drug currently available is Cidofovir, a cytosine analog (Keith et al., *Antimicrob. Agents Chemother.*, 47: 2193-2198, 2003). It shows considerable anti-poxvirus activity in animals but cannot be administered orally.

The poxviruses, including variola and vaccinia viruses, encode two protein kinases, B1 and F10 (Lin and Broyles, *Proc. Natl. Acad. Sci. USA*, 91: 7653-7657, 1994; Lin et al., *J. Virol.*, 66: 2717-2723, 1992; Traktman et al., *J. Biol. Chem.*, 264: 21458-21461, 1989). Both kinases are essential for vaccinia virus growth. Temperature-sensitive mutations in either the B1 or F10 genes prevent vaccinia virus multiplication at the non-permissive temperature (Lin and Broyles, *Proc. Natl. Acad. Sci. USA*, 91: 7653-7657, 1994; Traktman et al., *J. Biol. Chem.*, 264: 21458-21461, 1989). Additionally, vaccinia virus F10 catalytic activity has been shown to be required for virus growth (Szajner et al., *J. Virol.*, 78: 257-265, 2004). Substances that inhibit the enzymatic activity of either or both poxvirus protein kinases are needed to increase and diversify the arsenal of anti-poxviral drugs.

One consideration in the discovery of viral protein kinase inhibitors is cross-reactivity with protein kinases normally expressed in host cells. Human cells, for example, express hundreds of protein kinases that often have important functions in the regulation of cell growth and metabolism. An anti-viral drug that coincidentally inhibits important cellular protein kinases may have adverse side effects for the host cell and/or organism; however, this is certainly not always the case. Several high-affinity inhibitors of cellular protein kinases have proved to be both useful in treatment of a number of human malignancies and to exhibit acceptable toxicity. Gleevec (Novartis), an inhibitor of Abl, the platelet-derived growth factor receptor, and the Kit receptor is efficacious in chronic myeloid leukemia (Druker et al., *N. Engl. J. Med.*, 344: 1031-1037, 2001; Joensuu et al., *N. Engl. J. Med.*, 344: 1052-1056, 2001), gastrointestinal stromal tumor (Joensuu et al., *N. Engl. J. Med.*, 344: 1052-1056, 2001), and hypereosinophilia syndrome (Schaller and Burkland, *Med. Gen. Med.*, 3: 9, 2001). Iressa (AstraZeneca), an inhibitor of the epidermal growth factor receptor, is valuable in treatment of a subset of small cell lung tumors (Han et al., *J. Clin. Oncol.*, 23: 2493-2501, 2005; Mitsudomi et al., *J. Clin. Oncol.*, 23: 2513-2520, 2005). The foregoing drugs are tolerated well even when used chronically.

Advantageously, a poxvirus protein kinase inhibitor would only need to be used acutely to treat or prevent variola infection. The virus life cycle is less than 24 hours and infection with smallpox virus lasts approximately two weeks in humans (Davis et al., *Microbiology*, Hagerstown, Md.: Harper & Row, 1980, pp. 1077-1093). Therefore, even if a viral protein kinase inhibitor cross-reacted to some extent with host cell protein kinases, any side effects of the inhibitor may be short lived and clinically acceptable.

New drugs are needed to combat the multitude of diseases caused by poxviruses, especially those poxviruses that could be used as bioterrorism agents, such as variola virus.

SUMMARY

This disclosure concerns the discovery that poxvirus protein kinases (such as the B1 and/or F10 kinases) and poxvirus growth are inhibited by certain derivatives of tetralin, anthraquinone, xanthen-3-one, naphthylamine, cinnamic acid, and/or tri-amino-pyrimidine. This important discovery enables, for instance, methods of inhibiting poxvirus protein kinases and poxvirus growth, and methods of treating poxvirus infection.

Exemplary viral protein kinase inhibitors are provided throughout the disclosure and, by way of example, include compounds having one of the following general structures:

Formula I

Formula II

Formula III

Formula IV

Formula V

Formula VI

Other exemplary viral protein kinase inhibitors include compounds, such as NSC270718R; NSC117285R (2-hydroxy-4-(2,4,6-triaminopyrimidin-5-yl)diazenyl-benzoic acid); NSC170008Y (2-acetyl-7,8-bis(dihydroxymethylidene)-3-ethyl-9-hydroxy-anthracene-1,4,6,10-tetrone); NSC306711P; NSC119913X (7-methyl-6-(4,5,6,-trihydroxy-3-oxo-xanthen-9-yl)-bicyclo[2.2.1]hetp-2-ene-5-carboxylic acid); NSC119915Z (3-(4,5,6-trihydroxy-3-oxo-xanthen-9-yl)propanoic acid); NSC119911V (3-(4,5,6-trihydroxy-3-oxo-xanthen-9-yl)prop-2-enoic acid); NSC119910U (2-(4,5,6-trihydroxy-3-oxo-xanthen-9-yl)cyclohexane-1-carboxylic acid); NSC128437O (4-(4-cyclohexylamino-9,10-dioxo-anthracen-1-yl)aminobenzenesulfonic acid); NSC125908P (3-(9,10-dioxo-2-sulfoanthracen-1-yl)diazenyl-2-hydroxy-benzoic acid); NSC9600Q (4-[N'-(2-hydroxynaphthalen-1-yl)-N'-sulfo-hydrazino]benzenesulfonic acid); or NSC13778J (3-(3-stibonophenyl)prop-2-enoic acid).

Advantageously, poxvirus F10 and B1 protein kinases are involved in poxvirus growth; thus, poxvirus growth can be inhibited by interfering with the function of such kinases. Moreover, the F10 and B1 kinases have no, or only distantly related, homologs in the human genome; thus, inhibitors of such kinases are less likely to interfere with the functions of cellular kinases in the host cell or organism.

The foregoing and other features and advantages will become more apparent from the following detailed description of several embodiments, which proceeds with reference to the accompanying figures.

BRIEF DESCRIPTION OF THE FIGURES

FIG. 3 is an alignment of the amino acid sequences of the F10 kinases from vaccinia (SEQ ID NO: 4) and variola major (SEQ ID NO: 12) viruses.

FIG. 4 is an alignment of the amino acid sequences of the B1 kinases from vaccinia (SEQ ID NO: 2) and variola major (SEQ ID NO: 8) viruses.

FIG. 5 is an alignment of F10 kinase homologs from the indicated Orthopoxviruses. The alignment was generated with CLUSTALW (publicly available at the website ebi.ac.uk/clustalw) using default parameters. An asterisk (*) indicates identity among the residues at the indicated location, a colon (:) indicates conservative substitutions among the residues at the indicated location, and a period (.) indicates semi-conservative substitutions among the residues at the indicated location. SEQ ID NOs: 4, 18, 20, 22, 24, 26, 28 and 30 from the top to bottom.

FIG. 6 is an alignment of F10 kinase homologs from the indicated poxviruses (Lumpy_skin=lumpy skin disease virus, Mule_deer_pox=mule deer poxvirus, Yaba_monkey=Yaba monkey tumor virus, Yaba_like_disease=Yaba-like disease virus). The alignment was generated with CLUSTALW (publicly available at the website ebi.ac.uk/clustalw) using default parameters. An asterisk (*) indicates identity among the residues at the indicated location, a colon (:) indicates conservative substitutions among the residues at the indicated location, and a period (.) indicates semi-conservative substitutions among the residues at the indicated location. SEQ ID NOs: 4, 18, 20, 22, 24, 26, 28, 30, 32, 34, 36, 38, 40, 42, 44, 46, 48, 50, 52, 54, and 56 from the top to bottom.

FIG. 7 is an alignment of B1 kinase homologs from the indicated Orthopoxviruses. The particular viral strain or isolate is shown after the virus name (WR=Western Reserve, Acambis=Acambis 3000 Modified Virus Ankara (MVA), TT=Tian Tan, Variola_maj_India=Variola major (India-1967, isolate=Ind3), Variola_maj_BD=Variola major (Bangladesh-1975), Variola_min_Garcia=Variola minor (Garcia-1966), BR=Brighton Red, MPXV=MPXV-WRAIR7-61; Walter Reed 267). The alignment was generated with CLUSTALW (publicly available at the website ebi.ac.uk/clustalw) using default parameters. An asterisk (*) indicates identity among the residues at the indicated location, a colon (:) indicates conservative substitutions among the residues at the indicated location, and a period (.) indicates semi-conservative substitutions among the residues at the indicated location. SEQ ID NOs: 2, 58, 60, 62, 64, 66, 68, 8, 70, 72, 74, 76, 78, 80, 82, 84, 86, and 88 from top to bottom.

FIG. 8 is an alignment of B1 kinase homologs from the indicated poxviruses (Lumpy_skin=lumpy skin disease virus, Mule_deer_pox=mule deer poxvirus, Yaba_monkey=Yaba monkey tumor virus, Yaba_like_disease=Yaba-like disease virus). The alignment was generated with CLUSTALW (publicly available at the website ebi.ac.uk/clustalw) using default parameters. An asterisk (*) indicates identity among the residues at the indicated location, a colon (:) indicates conservative substitutions among the residues at the indicated location, and a period (.) indicates semi-conservative substitutions among the residues at the indicated location. SEQ ID NOs: 90, 92, 94, 102, 104, 100, 96, 98, 8, 72, 80, 74, 78, 2, 84, 86, 106, and 108 from top to bottom.

SEQUENCE LISTING

Figure 1:
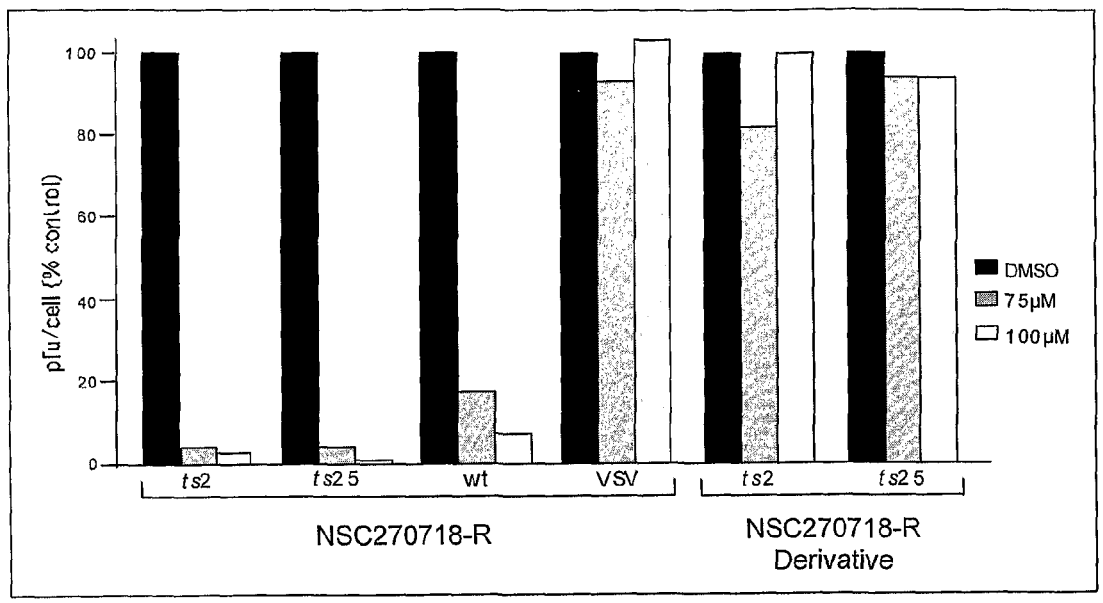
FIG. 1 is a series of bar graphs showing virus yield (plaque-forming units per infected cell) of ts2, ts25, or wild-type (wt) vaccinia virus, or vesicular stomatitis virus (VSV) grown in HeLa cells in the presence of 1% DMSO (control) or 75 μM or 100 μM NSC270718-R or its "2"-methyl derivative. NSC270718-R inhibited the growth of each vaccinia virus, but not the growth of VSV. The NSC270718-R derivative did not inhibit the growth of ts2 or ts25 vaccinia virus at the permissive temperature.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. All sequence database accession numbers referenced herein are understood to refer to the version of the sequence identified by that accession number as it was available on the filing date of U.S. Provisional Application No. 60/727,001. In the accompanying sequence listing:

SEQ ID NO: 1 is a nucleic acid sequence encoding vaccinia virus (Copenhagen strain) B1 kinase (see also, GenBank Accession No. M35027, B1R gene, CDS=162884 . . . 163786; or GenBank Accession No. NC_001559, CDS=162884 . . . 163786).

SEQ ID NO: 2 is an amino acid sequence of vaccinia virus (Copenhagen strain) B1 kinase (see also, GenBank Accession No. AAA48194 or NP_063857).

SEQ ID NO: 3 is a nucleic acid sequence encoding vaccinia virus (Copenhagen strain) F10 kinase (see also, GenBank Accession No. M35027, F10L gene, CDS=complement (39563 . . . 40882); or GenBank Accession No. NC_001559, CDS=complement (39563 . . . 40882)).

SEQ ID NO: 4 is an amino acid sequence of vaccinia virus (Copenhagen strain) F10 kinase (see also, GenBank Accession No. AAA48026 or NP_063689).

SEQ ID NO: 5 is a nucleic acid sequence encoding vaccinia virus (Ankara strain) F10 kinase (see also, GenBank Accession No. U94848, MVA039L gene, CDS=complement (31416 . . . 32735)).

SEQ ID NO: 6 is an amino acid sequence of vaccinia virus (Ankara strain) F10 kinase (see also, GenBank Accession No. AAB96420).

SEQ ID NO: 7 is a nucleic acid sequence encoding variola major virus (India-1967, ssp. major strain, isolate Ind3) B1 kinase (see also, GenBank Accession No. NC_001611, B1R gene, CDS=152700 . . . 153602; or GenBank Accession No. X69198, BIR gene, CDS=152700 . . . 153602).

SEQ ID NO: 8 is an amino acid sequence of variola major (India-1967, ssp. major strain, isolate Ind3) B1 kinase (see also, GenBank Accession No. NP_042213 or CAA491110).

SEQ ID NO: 9 is a nucleic acid sequence encoding variola major virus (India-1967, ssp. major strain, isolate Ind3) F10 kinase (see also, GenBank Accession No. NC_001611, C14L gene, CDS=complement (27297 . . . 28616)).

SEQ ID NO: 10 is an amino acid sequence of variola major virus (India-1967, ssp. major strain, isolate Ind3) F10 kinase (see also, GenBank Accession No. NP_042078).

SEQ ID NO: 11 is a nucleic acid sequence encoding variola major virus (strain Congo-1965) F10 kinase (see also, GenBank Accession No. U18337, C14L gene, CDS=complement (27303 . . . 28622)).

SEQ ID NO: 12 is an amino acid sequence of variola major virus (strain Congo-1965) F10 kinase (see also, GenBank Accession No. AAA69339).

SEQ ID NOs: 13 and 14 are a primer pair useful, at least, for amplifying the gene encoding vaccinia virus B1 kinase. Such primers also will amplify genes encoding B1 kinase homologs from at least some of the respective viral genomes (in particular, those B1-encoding homologs having a relatively high percentage of sequence identity (e.g., at least about 70%, at least about 80%, at least about 90%, at least about 95%, or at least about 98% sequence identity) to the vaccinia virus B1-encoding gene, such as variola virus and others).

SEQ ID NOs: 15 and 16 are a primer pair useful, at least, for amplifying the gene encoding vaccinia virus F10 kinase. Such primers also will amplify at least some of the genes encoding F10 kinase homologs from the respective viral genomes (in particular, those F10-encoding homologs having a relatively high percentage of sequence identity (e.g., at least about 70%, at least about 80%, at least about 90%, at least about 95%, or at least about 98% sequence identity) to the vaccinia virus F10-encoding gene, such as variola virus and others).

SEQ ID NOs: 17-56 are nucleic acid and corresponding amino acid sequences of exemplary F10 VPK homologs (see, e.g., FIGS. 5 and 6).

SEQ ID NOs: 57-108 are nucleic acid and corresponding amino acid sequences of exemplary B1 kinases or B1 VPK homologs (see, e.g., FIGS. 7 and 8).

DETAILED DESCRIPTION

I. Abbreviations and Terms

| PK | protein kinase |
|---|---|
| PFU | plaque forming unit |
| PVT | polyvinyl toluene |
| SPA | scintillation proximity assay |
| VPK | viral protein kinase |
| VSV | vesicular stomatitis virus |

Unless otherwise noted, technical terms are used according to conventional usage. Definitions of common terms in chemistry may be found in *The McGraw-Hill Dictionary of Chemical Terms*, Second Edition, New York: McGraw-Hill, 2003, and Dean, *Lange's Handbook of Chemistry*, Fifteen Edition, New York: McGraw-Hill, 1999. The singular terms "a," "an," and "the" include plural referents unless context clearly indicates otherwise. "Comprising" means "including"; hence, "comprising A or B" means "including A or B" or "including A and B."

In order to facilitate review of the various embodiments of the invention, the following explanations of specific terms are provided:

"Acyl" refers to a group having the structure —C(O)R, where R may be alkyl, or substituted alkyl. "Lower acyl" groups are those that contain from 1 to 10 (such as from 1 to 6) carbon atoms.

"Acyloxy" refers to a group having the structure RCOO—, where R may be alkyl or substituted alkyl. "Lower acyloxy" groups contain from 1 to 10 (such as from 1 to 6) carbon atoms.

The term "aliphatic" refers to a straight-chain, branched-chain, or cyclic alkane, alkene, or alkyne. In some examples, an aliphatic group contains from 1 to 25 carbon atoms; for example, from 1 to 15, from 1 to 10, or from 1 to 6 carbon atoms. An aliphatic group having 10 or fewer carbon atoms (such as from 1 to 10 or from 1 to 6 carbon atoms) may be referred to as a "lower aliphatic" group. Unless expressly referred to as an "unsubstituted aliphatic," aliphatic groups can either be unsubstituted or substituted. An aliphatic group can be substituted with one or more substituents (for instance, up to two substituents for each methylene carbon in an aliphatic chain, or up to one substituent for each carbon of a —C=C— double bond in an aliphatic chain, or up to one substituent for a carbon of a terminal methine group). Exemplary aliphatic substituents include, for instance, amine, amide, sulfonamide, halogen, cyano, carboxy, hydroxy, mercapto, trifluoromethyl, alkyl, alkoxy, alkylthio, thioalkoxy, arylalkyl, heteroaryl, alkylamino, dialkylamino, other functionality known to those of skill in the art and combinations thereof.

The term "alkoxy" refers to a group having the formula —OR, wherein R is an alkyl group. "Lower alkoxy" refers to an —OR group in which the R group has from 1 to 10 carbon atoms, such as from 1 to 6 carbon atoms. Examples of lower alkoxy groups include, but are not limited to, methoxy, ethoxy, n-propoxy, isopropoxy and butoxy groups.

"Alkenyl" refers to a straight-chain, branched-chain, or cyclic hydrocarbon group including one or more double bonds that may or may not be conjugated with each other. Alkenyl groups may be unsubstituted or substituted, so the term "alkenyl" is to be understood to include both unsubstituted alkenyl groups and substituted alkenyl groups unless clearly indicated otherwise. In some examples, an alkenyl group has from 2 to 25 carbon atoms. "Lower alkenyl" groups contain from 2 to 10 (such as from 2 to 6) carbon atoms.

The term "alkyl" refers to a straight-chain, branched-chain, or cyclic hydrocarbon, which is saturated. This term is further exemplified by groups such as methyl, ethyl, n-propyl, iso-propyl, isobutyl, t-butyl, pentyl, pivalyl, heptyl, adamantyl, and cyclopentyl. Alkyl groups can either be unsubstituted or substituted with one or more substituents, e.g., halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

In some examples, an alkyl group contains from 1 to 25 carbon atoms, unless a different number of carbon atoms is expressly stated. The term "lower alkyl" refers to an alkyl group having from 1 to 10 carbon atoms (such as from 1 to 6 carbon atoms). This term is further exemplified by such radicals as methyl, ethyl, n-propyl, i-propyl, n-butyl, t-butyl, i-butyl (or 2-methylpropyl), cyclopropylmethyl, i-amyl, and n-amyl. Lower alkyl groups can also be unsubstituted or substituted, where a specific example of a substituted alkyl is 1,1-dimethyl propyl. Particular examples of lower alkyls are methyl, butyl and propyl (including isopropyl).

The term "alkylthio" refers to a group having the structure —SR, where R is alkyl.

"Alkynyl" refers to a straight-chain, branched-chain, or cyclic hydrocarbon group including one or more triple bonds. Alkynyl groups may be unsubstituted or substituted, so the term "alkynyl" is to be understood to include both unsubstituted and substituted alkynyl groups unless clearly indicated otherwise. In some examples, an alkynyl group contains from 2 to 25 carbon atoms. "Lower alkynyl" groups are those that contain from 2 to 10 (such as from 2 to 6) carbon atoms.

The term "amino" refers to a substituent having the structure —NRR', wherein R and R' each are independently hydrogen, substituted or unsubstituted alkyl, substituted or unsubstituted aryl, or substituted or unsubstituted alkoxy or thioalkoxy groups. Particular examples of amino groups include "alkylamino" groups (—NHR, where R is alkyl), "dialkylamino" groups (—NRR', where R and R' are both alkyl), and "arylamino groups (—NHR, where R is aryl, e.g., substituted or unsubstituted phenyl). Where used alone in reference to a specific compound (such as in the name of a compound or a particular substituent at a particular position in a structure) the term "amino" refers to the group —NH$_2$.

The term "amino-substituted alkyl" refers to an alkyl group substituted with at least one amino group.

"Animal" refers to living multi-cellular vertebrate organisms, a category that includes, for example, mammals and birds. The term mammal includes both human and non-human mammals. Similarly, the term "subject" includes all animals, including humans, simians, dogs, cats, horses, cows, rodents, etc. Likewise, the term "mammal" includes both human and non-human mammals.

The term "aryl" refers to a polyunsaturated, aromatic moiety that can be a single ring or multiple rings (for example, from 1 to 3 rings), which are fused together or linked covalently. Aryl groups can be unsubstituted or substituted.

The term "aryl" also includes "heteroaryl" groups (or rings) that contain at least one heteroatom (such as from 1 to 4) independently selected from N, O, and S, wherein the nitrogen and sulfur atoms are optionally oxidized, and the nitrogen atom(s) are optionally quaternized. A heteroaryl group can be attached to the remainder of the molecule through a heteroatom. Aryl and heteroaryl groups also can be fused to a ring of a molecule, typically at adjacent atoms in the ring of the molecule. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl, and 6-quinolyl.

"Azo" refers to a substituent having the structure —N=N—R where R is hydrogen, substituted or unsubstituted alkyl, substituted or unsubstituted aryl (such as substitute or unsubstituted phenyl), or substituted or unsubstituted alkoxy or thioalkoxy groups.

"Carbocycle" (or "carbocyclic") means a saturated or unsaturated cyclic radical of 3 to 8 ring atoms in which each of the ring atoms are carbon. The carbocyclic ring may be optionally substituted independently with one, two or three substituents selected from alkyl, heteroalkyl, haloalkyl, cycloalkyl, cycloalkylalkyl, aliphatic, heteroaliphatic, aryl, aralkyl, heteroaryl, heteroaralkyl, halo, cyano, acyl, acylamino, amino, monosubstituted amino, disubstituted amino, —COOR (where R is hydrogen or alkyl), —XR (where X is O or $S(O)_n$, where n is an integer from 0 to 2, and R is hydrogen, alkyl, haloalkyl, cycloalkyl, aralkyl, aryl, heteroaryl or heteroaralkyl), and —C(O)N(R')R" (where R' and R" are independently selected from hydrogen and alkyl). Representative examples include, but are not limited to, cyclopentyl, cyclohexyl, cycloheptyl, cycloheptenyl, or cycloheptyl-2, 3, or 4-one, and the like.

"Carbonyl-containing" refers to any substituent containing a carbon-oxygen double bond (C=O), including substituents based on —COR or —RCHO where R is an aliphatic, heteroaliphatic, alkyl, heteroalkyl, hydroxyl, or a secondary, tertiary, or quaternary amine. Carbonyl-containing groups include, for example, aldehydes, ketones, carboxylic acids, and esters. Alternatively, "carbonyl-containing group" refers to —RC(O)R' groups wherein R and R' are independently aliphatic, heteroaliphatic, alkyl, heteroalkyl, hydroxyl, or secondary, tertiary, or quaternary amine. Examples include —COOH, —CH$_2$COOH, —CH$_2$COOCH$_3$, —CH$_2$CONH$_2$, —CH$_2$CON(CH$_3$)$_2$.

"Carboxyl" refers to —COOH substituent or its conjugate base —COO$^-$.

"Carboxylate" refers to any salt, ester, or conjugate base of a carboxylic acid.

A "derivative" is a chemical substance that differs from another chemical substance by one or more functional groups. Preferably, a derivative retains a biological activity of a molecule from which it was derived (such as B1 and/or F10 protein kinase inhibitory activity or poxvirus growth inhibitory activity).

The term "diamine" refers to a substituent having the structure $—NR'—(CH_2)_n—NR''R'''$, wherein n=1-5 and R', R", and R''' each are independently hydrogen, substituted or unsubstituted alkyl, substituted or unsubstituted aryl, or substituted or unsubstituted alkoxy or thioalkoxy groups, for example, each are independently H or substituted or unsubstituted alkyl, such as each being independently H or unsubstituted or substituted lower alkyl. A diamine group can be further substituted, for example, with additional lower alkyl groups.

The term "halogen" refers to fluoro, bromo, chloro, and iodo substituents.

Hybridization: Nucleic acid sequences (such as, oligonucleotides and their analogs) hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide (or other nucleic acid sequence) can be complementary to a VPK-encoding nucleic acid.

"Specifically hybridizable" and "specifically complementary" are terms that indicate a sufficient degree of complementarity such that stable and specific binding occurs between a nucleic acid sequence (such as, an oligonucleotide) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. Exemplary hybridization conditions are provided elsewhere in this specification.

The term "nitro" refers to a substituent having the structure —NO$_2$.

Nucleic acid molecule: This term refers to a polymeric form of nucleotides, which may include both sense and antisense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.). The term "nucleic acid molecule" also includes any topological conformation, including single-stranded, double-stranded, partially duplexed, triplexed, hairpinned, circular and padlocked conformations.

The term "phosphonate" refers to phosphonates of the formula —PO$_3$R wherein R represents hydrogen, a cationic counterion, or an aliphatic (such as a lower aliphatic or an alkyl, e.g., lower alkyl) or aromatic moiety.

A "poxvirus" is any virus belonging to the family Poxyiridae. Poxyiridae are characterized by, at least, a relatively large, double-stranded DNA genome (ranging from approximately 130 to 400 kbp). Virions are enveloped, slightly pleomorphic, ovoid, or brick shaped (approximately 140-260 nm in diameter and 220-450 nm long). Virions are composed of an external coat containing lipid and tubular or globular protein structures enclosing one or two lateral bodies and a core, which contains the genome. Particular poxviruses may belong to the chordopoxvirinae or entomopoxvirinae subfamily, which infect vertebrate or insect hosts, respectively. A poxvirus of the chordopoxvirinae subfamily may further belong to the genus *Orthopoxvirus* (including, e.g., monkeypox virus, vaccinia virus, buffalopoxvirus, camelpox virus, cowpox virus, elephantpox virus, variola virus (such as variola major and/or variola minor viruses), volepox virus, ectromelia virus, raccoonpox virus, skunkpox virus, or taterapox virus), *Parapoxvirus* (including, e.g., bovine papular stomatitis virus, Orf virus, psuedocowpox virus, sealpox virus, or Auzduk disease virus), *Avipoxvirus* (including, e.g., fowlpox virus), *Capripoxvirus* (including, e.g., sheeppox virus, lumpy skin disease virus, or goatpox virus), *Leporipoxvirus* (including, e.g., myxoma virus, or Shope fibroma virus), *Suipoxvirus* (including, e.g., swinepox virus), *Molluscipoxvirus* (including, e.g., molluscum contagiosum virus), or *Yatapoxvirus* (including, e.g., tanapox virus or Yaba monkey tumor virus). Viruses of the *Othropoxvirus* and *Parapoxvirus* genera can be further characterized as zoonotic (including, e.g., monkeypox virus, vaccinia virus, buffalopoxvirus, camelpox virus, cowpox virus, elephantpox virus, bovine papular stomatitis virus, Orf virus, psuedocowpox virus, or sealpox virus) or nonzoonotic (including, e.g., variola virus, volepox virus, ectromelia virus, raccoonpox virus, skunkpox virus, taterapox virus, or Auzduk disease virus). Zoonotic viruses can infect multiple species of hosts (e.g., humans and animals), while nonzoonotic viruses are believed to infect only a single host species (e.g., humans, fowl, or monkey, etc.). In some examples, a poxvirus is an *Orthopoxvirus*. In more specific examples, a poxvirus is vaccinia virus or variola virus. The complete genomes (including cross-references to individual genes included therein and proteins encoded thereby) of over 25 poxviruses are known and publicly available (see, for instance, GenBank Accession Nos. M35027, U94848, AF095689, L22579, X69198, Y16780, AF380138, AF012825, AY009089, AF438165, AF482758, AF170726, AF170722, AF198100, AF325528, AY077835, AY077836, AY077832, AY077833, AY077834, AF410153, U60315, AJ293568, AF063866, and/or AF250284).

The term "purified" does not require absolute or even substantial purity; rather, it is intended as a relative term. Thus, for example, a purified preparation is one in which a desired component (e.g., VPK inhibitor or VPK) is more enriched than it was in a preceding environment (e.g., when in a laboratory production vessel). A desired component (e.g., VPK inhibitor or VPK) is purified, for example, when at least about 0.5%, 1%, 2%, 5%, 10%, 15%, 20%, 30%, 40%, 50%, 60%, 70%, 80%, 85%, 90%, 92%, 95%, 98%, or 99% of a sample by weight is composed of the desired component. Purity of a compound may be determined, for example, by high pressure liquid chromatography (HPLC) or other conventional methods.

Compounds described herein may be obtained in a purified form or purified by any of the means known in the art, including silica gel and/or alumina chromatography. See, e.g., *Introduction to Modern Liquid Chromatography*, 2nd Edition, ed. by Snyder and Kirkland, New York: John Wiley and Sons, 1979; and *Thin Layer Chromatography*, ed. by Stahl, New York: Springer-Verlag, 1969.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2: 482, 1981; Needleman and Wunsch, *J. Mol. Biol.* 48: 443, 1970; Pearson and Lipman, *Proc. Natl. Acad. Sci. USA* 85: 2444, 1988; Higgins and Sharp, *Gene* 73: 237-244, 1988; Higgins and Sharp, *CABIOS* 5: 151-153, 1989; Corpet et al., *Nucleic Acids Research* 16: 10881-10890, 1988; Huang, et al., *Computer Applications in the Biosciences* 8: 155-165, 1992; Pearson et al., *Methods in Molecular Biology* 24: 307-331, 1994; Tatiana et al., (1999), *FEMS Microbiol. Lett.*, 174: 247-250, 1999. Altschul et al. present a detailed consideration of sequence-alignment methods and homology calculations (*J. Mol. Biol.* 215: 403-410, 1990).

The National Center for Biotechnology Information (NCBI) Basic Local Alignment Search Tool (BLAST, Altschul et al., *J. Mol. Biol.* 215: 403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST.

For comparisons of amino acid sequences of greater than about 30 amino acids, the "Blast 2 sequences" function of the BLAST (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties).

For comparisons of nucleic acid sequences, the "Blast 2 sequences" function of the BLAST (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions. (V) [default=100]; number of alignments to show (B) [default=100]).

A "sulfonate" is a salt, ester, or anion of a sulfonic acid ($RSO_2OH$).

The term "sulfonyl" refers to a substituent including the bivalent group —$SO_2$— or, more typically, —$SO_2R$, where R is substituted or unsubstituted alkyl, substituted or unsubstituted aryl, or substituted or unsubstituted alkoxy or thioalkoxy. Sulfonyl groups include "alkylsulfonyl" groups having the structure —$SO_2R$, where R is unsubstituted or substituted alkyl. Similarly, "lower alkylsulfonyl" refers to —$SO_2R$, wherein R is unsubstituted or substituted lower alkyl. "Arylsulfonyl" refers to groups having the structure —$SO_2R$, where R is unsubstituted or substituted aryl (such as phenyl). A sulfonyl group optionally can be substituted with a variety of substituents to form different sulfonyl groups, including, for example, sulfonic acids, sulfonamides, sulfonate esters and sulfones.

Treating or treatment: With respect to disease (such as smallpox), either term includes (i) preventing the disease, e.g., causing the clinical symptoms of the disease not to develop in a subject that may be exposed to or predisposed to the disease but does not yet experience or display symptoms of the disease, (ii) inhibiting the disease, e.g., arresting the development of the disease or its clinical symptoms, or (iii) relieving the disease, e.g., causing regression of the disease or its clinical symptoms.

A "viral protein kinase" is a protein kinase encoded by a viral nucleic acid (such as a viral genome or a gene isolated from a viral genome). In particular examples, a viral protein kinase is expressed by a poxvirus genome (such as an *Orthopoxvirus*, like variola virus or vaccinia virus). As is commonly known, a protein kinase is an enzyme that modifies (e.g., phosphorylates) a target protein (also referred to as a substrate) by chemically adding one or more phosphate groups to the target protein. The chemical activity of a kinase involves removing a phosphate group from ATP and covalently attaching the phosphate group to free hydroxyl groups of serine(s), threonine(s) and/or tyrosine(s) present in the target protein. Kinases that phosphorylate both serine and threonine are referred to as "serine/threonine protein kinases"; other kinases act on tyrosine and are referred to as "tyrosine kinases." Some kinases can phosphorylate serine, threonine and tyrosine (on the same or different substrates) and are referred to as "dual-specificity kinases." Certain examples herein involve dual-specificity kinases viral protein kinases (such as, B1 kinase and/or F10 kinase and/or variants (such as homologs) of either). In particular examples (e.g., with particular substrates), a viral protein kinase (such as, B1 kinase and/or F10 kinase and/or variants (such as homologs) of either) can act as either a serine/threonine kinase or a tyrosine kinase. Kinase-dependent phosphorylation often results in a functional change of the target protein, for example, by changing enzyme activity, cellular location or association with other proteins.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture."

The compounds described herein may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., March, *Advanced Organic Chemistry*, 4th edition, New York: John Wiley and Sons, 1992, Chapter 4). The symbol " ⫻ " in a chemical structure represents a double bond having either a cis or trans orientation.

Some exemplary compounds described herein can be obtained from the chemical repository of the National Institutes of Health, National Cancer Institute, Developmental Therapeutics Program, Structural Diversity Set. The compounds in the Structural Diversity Set are each assigned an identifier of 3 to 7 numbers and a letter, all of which is sometimes preceded by "NSC"; thus, compounds herein named NSC#####A, NSC####-A, ####A, or ####-A (where "####" can be from 3 to 7 numbers and "A" is any letter) should be understood to be compounds from the Structural Diversity Set.

It is further to be understood that any molecular weight or molecular mass values are approximate and are provided only for description. All publications, patent applications, patents, and other references mentioned herein are incorporated by reference in their entirety. In case of conflict, the present specification, including explanations of terms, will control.

Except as otherwise noted, the methods and techniques of the present invention are generally performed according to conventional methods well known in the art and as described in various general and more specific references that are cited and discussed throughout the present specification. See, e.g., Loudon, *Organic Chemistry*, Fourth Edition, New York: Oxford University Press, 2002, pp. 360-361, 1084-1085;

Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978.

II. Viral Protein Kinases

Virus genomes range in size from approximately 3.2 kilobase pairs (kbp) to approximately 800 kbp. The larger viral genomes encode a multiplicity of viral proteins. Some such proteins are essential for viral replication and, therefore, provide useful targets for identification and/or design of antiviral drugs.

Protein kinases are among the proteins encoded by some viruses, such as poxviruses, herpes viruses (e.g., cytomegalovirus), or baculoviruses. As a class of proteins, protein kinases often have profound functional effects, and viral protein kinases are no exception. Normal viral function is dependent upon the activity(ies) of various viral protein kinases (see, e.g., Prichard et al., *J. Virol.*, 73: 5663-5670, 1999; Lin and Broyles, *Proc. Natl. Acad. Sci. USA*, 91(16): 7653-7657, 1994; Rempel et al., *J. Virol.*, 64(2): 574-583, 1990). For example, poxviruses have two essential protein kinases, which are most studied in vaccinia virus (an *Orthopoxvirus*). The vaccinia virus F10L kinase (an exemplary F10 kinase) is encapsidated in the virion and plays an important role in virion morphogenesis (Traktman et al., *J. Virol.*, 69: 6581-6587, 1995; Wang and Shuman, *J. Virol.*, 69: 6376-6388, 1995). The vaccinia virus B1R protein kinase (an exemplary B1 kinase) is expressed early in infection, is found in the virosomes, and is also packaged into virions. Temperature-sensitive mutations that map to the B1R gene produce virus that cannot replicate its DNA at the restrictive temperature (Rempel and Traktman, *J. Virol.*, 66: 4413-4426, 1992).

An exemplary B1 kinase, the vaccinia virus B1R gene product, phosphorylates casein and histones in vitro (Banham and Smith, *Virol.*, 191: 803-812, 1992; Lin et al., *J. Virol.*, 66: 2717-2723, 1992; Rempel and Traktman, *J. Virol.*, 66: 4413-4426, 1992), ribosomal proteins Sa and S2 in vivo and in vitro (Banham et al., *FEBS Lett.*, 321: 27-31, 1993), and vaccinia virus protein H5R in vivo and in vitro (Beaud et al., *J. Virol.*, 69: 1819-1826, 1995). Typically, the foregoing phosphorylations are on serine and/or threonine. Casein and histones are readily available commercially and, at least for that reason, are advantageous substrates for use in in vitro kinase activity assays. The phosphorylation of the ribosomal proteins and H5R has been implicated in normal poxvirus (e.g., vaccinia virus) growth and/or infectivity (Punjabi and Traktman, *J. Virol.*, 79: 2171-2190, 2005).

An exemplary F10 kinase, the vaccinia virus F10 kinase, phosphorylates casein, phosvitin and myelin basic protein in vitro (Lin and Broyles, *Proc. Natl. Acad. Sci. USA*, 91: 7653-7657, 1994). Due to the commercial availability of these substrates, they are advantageous substrates for use in in vitro kinase activity assays. An exemplary vaccinia F10 kinase also phosphorylates vaccinia proteins A30 (in infected cells and in vitro) and G7 (in infected cells) (Mercer and Traktman, *J. Virol.*, 79: 7146-7161, 2005). Phosphorylations of casein, phosvitin, myelin basic protein, A30 and G7 substrates by a F10 kinase, typically, are on serine and threonine. As an example, a vaccinia virus F10 kinase also phosphorylates vaccinia protein A17 on tyrosine, at least, during infection in cells (Derrien et al., *J. Virol.*, 73: 7287-7296, 1999). Phosphorylation of A17 has been implicated in normal poxvirus (e.g., vaccinia virus) growth.

The disclosure herein of small molecules that inhibit B1 and/or F10 kinases makes possible, for example, methods of inhibiting viral protein kinases (including, B1 and/or F10 kinases and/or homologs and/or variants of either) and methods of inhibiting the growth of viruses expressing such viral protein kinases (including, poxviruses, like variola virus).

A. VPK Variants and Homologs

This disclosure provides methods of inhibiting viral protein kinases (VPKs), including variants (such as homologs) of a B1 protein kinase or a F10 protein kinase. Amino acid sequences of representative B1 and F10 protein kinases are shown in SEQ ID NO: 2 and 8 (also in FIGS. 7 and 8), and SEQ ID NOs: 4, 6, and 10 (also in FIGS. 5 and 6), respectively. Variants of a B1 protein kinase or a F10 protein kinase include polypeptides that differ in amino acid sequence from described (or otherwise publicly known) B1 or F10 protein kinase sequences, but that substantially retain a wild-type function of a prototypical B1 or F10 kinase.

VPK variants (including VPK homologs) contemplated by this disclosure have at least one function of a prototypical B1 kinase or F10 kinase. For example, a VPK variant will phosphorylate (e.g., serine and threonine and/or tyrosine residues of) a target protein (such as, casein, histones, ribosomal proteins Sa or S2, vaccinia virus protein H5R, phosvitin, myelin basic protein, and/or vaccinia proteins A30 or G7) under conditions well known in the art or such as those described in Example 1. A virus having a knock-out or knock-down mutation of a VPK (e.g., B1 or F10 kinase) variant will not replicate as efficiently as a virus carrying a non-mutated form of the VPK variant; provided that the viral genome does not also include one or more genes having redundant VPK (e.g., B1 and/or F10 kinase) function(s). In some examples, a B1 kinase variant will have the ability to in vivo phosphorylate (e.g., serine or threonine residues of) at least one of ribosomal proteins Sa or S2 and/or vaccinia virus protein H5R. In other examples, a F10 kinase variant will have the ability to in vivo phosphorylate (e.g., serine or threonine residues of) at least one of vaccinia proteins A30 or G7; and/or the ability to in vivo phosphorylate vaccinia virus protein A17 (e.g., on a tyrosine residue). Functional assays useful for characterizing a VPK (such as B1 or F10 kinase) variant are provided below.

FIGS. 5, 6, 7 and 8 provide structural information from which functional correlates can be derived. FIG. 5 is an alignment of F10 kinases and its homologs from a variety of Orthopoxviruses. As shown in FIG. 5, Orthopoxvirus F10 homologs are highly conserved and are likely to have similar function and be similarly inhibited by disclosed VPK inhibitors. FIG. 6 is an alignment of F10 kinases and its homologs from a variety of poxviruses. This alignment teaches that F10 kinases and its homologs are also conserved across poxviruses. Moreover, FIG. 6 shows identical (*) and conservatively substituted (:) residues across the range of poxvirus species presented. Modification of residues that are conserved or conservatively substituted across related species has a higher probability of adversely affecting a function of the protein; hence, in the making of functional F10 variants, such residues indicated in FIG. 6 are preferably avoided. FIGS. 6 and 7 teach analogous information with respect to B1 kinase and its homologs (and variants).

In some embodiments, VPK (such as B1 or F10 kinase) variants include polypeptides that share at least 40% amino acid sequence identity with a B1 or F10 kinase polypeptide sequence provided herein (e.g., SEQ ID NO: 2, 4, 6, 8, or 10); for example, some VPK (such as B1 or F10 kinase) variants will share at least 40%, at least 50%, at least 60%, at least 75%, at least 80%, at least 85%, at least 90%, at least 95%, or at least 98% amino acid sequence identity with a sequence set forth in SEQ ID NO: 2, 4, 6, 8, or 10.

With the description herein of prototypical B1 and F10 kinase amino acid sequences and corresponding nucleic acid sequences, VPK (e.g., B1 or F10 kinase) variants are easily obtained by conventional molecular methods. VPK (e.g., B1 or F10 kinase) variants can be naturally occurring (e.g., homologs) or produced by any method known in the art for making polypeptide variants. In some embodiments, a VPK (e.g., B1 or F10 kinase) variant is produced by manipulation of a described (or other publicly available) VPK-encoding nucleotide sequence (e.g., SEQ ID NOs: 1, 3, 5, 7, or 9) using standard procedures, including without limitation the commonly known techniques of site-directed mutagenesis or PCR. Naturally occurring VPK (e.g., B1 or F10 kinase) variants can be isolated using any of a myriad of protein purification techniques known in the art (for example, Scopes, *Protein Purification. Principles and Practice,* 3rd Edition, New York: Springer-Verlag, 1994; *Protein Purification Techniques,* 2nd Edition, ed. by Simon Roe, New York: Oxford University Press, 2001; *Membrane Protein Purification and Crystallization,* 2nd Edition, ed. by Hunte et al., San Diego: Academic Press, 2003). A nucleic acid sequence that encodes all or part of a VPK (e.g., B1 or F10 kinase) variant can be readily determined simply by applying a genetic code (such as a poxvirus genetic code) to the respective portion of the variant's amino acid sequence.

In some embodiments, VPK (e.g., B1 or F10 kinase) variants involve the substitution of one or several amino acids for amino acids having similar biochemical properties (so-called conservative substitutions). Conservative amino acid substitutions are likely to have minimal impact on the activity of the resultant protein. Further information about conservative substitutions can be found, for instance, in Ben Bassat et al. (*J. Bacteriol.,* 169: 751-757, 1987), O'Regan et al. (*Gene,* 77: 237-251, 1989), Sahin-Toth et al. (*Protein Sci.,* 3: 240-247, 1994), Hochuli et al. (*Bio/Technology,* 6: 1321-1325, 1988) and in widely used textbooks of genetics and molecular biology. In some examples, VPK (e.g., B1 or F10 kinase) variants can have no more than 3, 5, 10, 15, 20, 25, 30, 40, or 50 conservative amino acid changes compared to SEQ ID NO: 2, 4, 6, 8, or 10, as applicable. The following table shows exemplary conservative amino acid substitutions:

| Original Residue | Conservative Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Nucleotide sequences encoding VPK (e.g., B1 or F10 kinase) variants are comprehended by this disclosure; for example, to express a corresponding variant for use in a disclosed method. Such nucleotide variants may be naturally occurring (such as orthologs from other organism) or produced using commonly known techniques, including without limitation site-directed mutagenesis. Standard techniques for DNA mutagenesis are provided, for instance, in Sambrook et al. (*Molecular Cloning: A Laboratory Manual,* New York: Cold Spring Harbor Laboratory Press, 1989, Ch. 15). In addition, numerous commercially available kits are available to perform DNA mutagenesis (see, for example, Quikchange™ Site-Directed Mutagenesis Kit (Stratagene), GeneTailor™ Site-Directed Mutagenesis System (Invitrogen); GPS™-M Mutagenesis System (New England Biolabs, Diversify™ PCR Random Mutagenesis Kit (BD Biosciences Clontech); Mutation Generation System (MJ Research); Exsite™ PCR-Based Site-Directed Mutagenesis Kit (Stratagene); GeneMorph™ PCR Mutagenesis Kit (Stratagene); or LA PCR Mutagenesis Kit (Takara Mirus Bio)).

Other conventional methods for isolating a nucleic acid sequence encoding a VPK (e.g., B1 or F10 kinase) variant include library screening (including nucleic acid libraries or expression libraries) or PCR. Direct PCR amplification may be performed on genomic libraries prepared from a virus having a B1 or F10 kinase homolog (such as a poxvirus, an *Orthopoxvirus,* or other vaccinia or variola virus strains), or RT-PCR may be performed using RNA extracted from cells infected with such viruses using standard methods. Conventional hybridization techniques (like nucleic acid library screening) involve the use of a labeled probe derived from a B1 kinase- or F10 kinase-encoding nucleic acid sequence, which probe is hybridized to a nucleic acid (e.g., genomic DNA) library prepared using a virus having a B1 or F10 kinase homolog. A hybridizing colony or plaque (depending on the type of library used) is purified and the cloned sequence contained in that colony or plaque isolated and characterized.

In some embodiments, a nucleotide sequence encoding a VPK (e.g., B1 or F10 kinase) variant (including VPK homologs) shares at least 40%, at least 50%, at least 60%, at least 70%, at least 75%, at least 80%, at least 85%, at least 90%, at least 95%, or at least 98% nucleotide sequence identity with a described (or otherwise publicly available) VPK-encoding (e.g., B1 kinase- or F10 kinase-encoding) nucleic acid sequence (including SEQ ID NO: 1, 3, 5, 7, or 9). Alternatively, related nucleic acid molecules can have no more than 3, 5, 10, 20, 50, 75, or 100 nucleic acid changes compared to SEQ ID NO: 1, 3, 5, 7, or 9.

In one embodiment, VPK (e.g., B1 or F10 kinase) nucleic acid variants may differ from the disclosed sequences by alteration of the coding region to fit the codon usage bias of a particular organism, for example, an organism into which the nucleic acid molecule is to be introduced. In other embodiments, VPK (e.g., B1 or F10 kinase) variants are derived by taking advantage of the degeneracy of the genetic code to alter the VPK (e.g., B1 kinase or F10 kinase) coding sequence. In these embodiments, the variant nucleotide sequence may be substantially different from a prototypic B1 kinase- or F10 kinase-encoding nucleic acid sequence (e.g., SEQ ID NO: 1, 3, 5, 7, or 9) and, nevertheless, encode a protein having an amino acid sequence substantially similar (if not identical) to a disclosed B1 kinase or F10 kinase. For example, because of redundancy in the genetic code, any one of four nucleotide codons encode alanine (i.e., GCT, GCG, GCC or GCA); accordingly, the sequence encoding any alanine residue within a VPK (e.g., B1 or F10 kinase) polypeptide could be changed to any of these alternative codons without affecting the amino acid composition or characteristics of the encoded protein. Analogous redundancies are well known for each amino acid. The genetic codes for a variety of organisms are publicly available on the National Center for Biotechnology Information (NCBI) Taxonomy website.

An alternative indication that two nucleic acid molecules are closely related is that the two molecules hybridize to each other. In certain embodiments, VPK (e.g., B1 or F10 kinase) nucleic acid variants hybridize to a disclosed VPK (e.g., B1 or F10 kinase) nucleic acid sequence (or fragments thereof), for example, under low stringency, high stringency, or very high stringency conditions. Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, although wash times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11.

The following are representative hybridization conditions and are not meant to be limiting.

| Very High Stringency (detects sequences that share about 90% sequence identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |
| High Stringency (detects sequences that share about 80% sequence identity or greater) | |
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |
| Low Stringency (detects sequences that share greater than about 50% sequence identity) | |
| Hybridization: | 6x SSC at RT to 55° C. for 16-20 hours |
| Wash at least twice: | 2x-3x SSC at RT to 55° C. for 20-30 minutes each. |

The nucleic acid sequence of a variant, then, can be isolated using conventional methods, such as library screening (including nucleic acid libraries or expression libraries) or PCR. Direct PCR amplification may be performed on cDNA or genomic libraries prepared from a virus having a B1 or F10 kinase homolog (such as a poxvirus, an Orthopoxvirus, or other vaccinia or variola virus strains), or RT-PCR may be performed using RNA extracted from cells infected with such viruses using standard methods. For conventional hybridization techniques, a labeled probe derived from a B1 kinase- or F10 kinase-encoding nucleic acid sequence may be hybridized to a cDNA or genomic library prepared from a virus having a B1 or F10 kinase homolog. The hybridization probe is preferably conjugated with a detectable label such as a radioactive label. A hybridization signal may be detected using methods known in the art. The hybridizing colony or plaque (depending on the type of library used) is purified and the cloned sequence contained in that colony or plaque isolated and characterized.

B. B1 Viral Protein Kinase

The amino acid sequences of prototypical B1 (or B1-like) VPKs and the nucleic acid sequences encoding the same are well known. Exemplary sequences for vaccinia virus (Copenhagen strain) B1 kinase are provided in SEQ ID NOs: 1 (nucleic acid sequence) and 2 (amino acid sequence). Exemplary sequences for variola major virus (India-1967 strain) B1 kinase are provided in SEQ ID NOs: 7 (nucleic acid sequence) and 8 (amino acid sequence). Routine comparison (e.g., using BLASTP software, for amino acid sequence, or BLASTN software, for nucleic acid sequences) of these (or other) prototypical B1 (or B1-like) sequences against publicly available databases (such as GenBank non-redundant and/or patent databases) reveals numerous B1 protein kinase homologs. Several exemplary B1 protein kinase homologs and information for obtaining the known sequences are provided in the following table:

TABLE 1

| B1 Protein Kinase Homologs[1] | |
|---|---|
| Source | GenBank Accession No. (Protein Name; Viral Strain (as applicable)) |
| Vaccinia virus | NP_063857.1 (B1R; strain Copenhagen; SEQ ID NO: 2), AAA48194.1 (B1R; strain Copenhagen), AAA47963.1 (B1 30 kDa protein; strain Western Reserve; SEQ ID NO: 58); AAB96545.1 (protein kinase, similar to vaccinia Copenhagen B1R; strain Ankara; SEQ ID NO: 60); AAT10565.1 (serine/threonine kinase, similar to Vaccinia Copenhagen B1R; strain Acambis 3000 Modified Virus Ankara (MVA); SEQ ID NO: 62); AAF34067.1 (TB1R; strain Tian Tan; SEQ ID NO: 64); AAO89462.1 (ser/thr kinase, similar to VACCP-B1R; strain Western Reserve); BAA00519.1 (B1R; strain Western Reserve); BAA01831.1 (34.2K protein; strain Western Reserve); AAW23907.1 (putative ser/thr protein kinase; strain LC16mO; SEQ ID NO: 66); AAW23625.1 (putative ser/thr protein kinase; strain LC16m8; SEQ ID NO: 68) |
| Variola major virus | NP_042213.1 (B1R; SEQ ID NO: 8); CAA49110.1 (B1R), AAA60910.1 (homolog of vaccinia virus CDS B1R; SEQ ID NO: 70) |
| Variola minor virus | CAB54770.1 (H1R protein; SEQ ID NO: 72); H72171 (H1R protein - strain Garcia-1966); |
| Cowpox virus | CAD90727.1 (B1R protein; SEQ ID NO: 74); AAM13635.1 (CPXV196 protein; SEQ ID NO: 76); NP_619977.1 (CPXV196 protein) |
| Rabbitpox virus | AAS49878.1(RPXV165; SEQ ID NO: 78) |
| Camelpox virus | AAL73885.1 (CMLV178; SEQ ID NO: 80); AAG37677.1 (CMP175R; SEQ ID NO: 82); NP_570568.1 (CMLV178) |
| Ectromelia virus | AAM92457.1 (EVM152; SEQ ID NO: 84); NP_671671.1 (EVM152); AAC99565.1 (C6R); NP_671679.1 (C6R) |
| Monkeypox virus | AAU01366.1 (MPXV-WRAIR156; SEQ ID NO: 86); NP_536591.1 (B3R; SEQ ID NO: 88); AAL40622.1 (B3R) |
| lumpy skin disease virus | AAN02707.1 (SEQ ID NO: 90); AAK85100.1 (LSDV139); NP_150573.1 (LSDV139); AAN02865.1 (putative Ser/Thr protein kinase) |
| Sheeppox virus | NP_659709.1 (SEQ ID NO: 92) |
| Mule deer poxvirus | YP_227529.1 (SEQ ID NO: 94) |

TABLE 1-continued

B1 Protein Kinase Homologs[1]

| Source | GenBank Accession No. (Protein Name; Viral Strain (as applicable)) |
|---|---|
| Yaba monkey tumor virus | AAR07494.1 (142R; SEQ ID NO: 96); NP_938393.1 (142R) |
| Yaba-like disease virus | CAC21380.1 (142R protein; SEQ ID NO: 98); NP_073527.1 (142R protein) |
| Swinepox virus | AAL69876.1 (SPV137; SEQ ID NO: 100); NP_570297.1 (SPV137) |
| Myxoma virus | AAF15030.1 (m142R; SEQ ID NO: 102); NP_051856.1 (m142R) |
| Rabbit fibroma virus | AAF18022.1 (gp142R; SEQ ID NO: 104); NP_052028.1 (gp142R) |
| Fowlpox virus | CAE52750.1 (B1R-like protein; SEQ ID NO: 106); AAF44556.1 (FPV212); NP_039175.1 (FPV212); CAE52761.1 (B1R-like protein); AAF44570.1 (FPV226); NP_039189.1 (FPV226) |
| Canarypox virus | NP_955309.1 (CNPV286; SEQ ID NO: 108); AAR83632.1 (CNPV286); NP_955322.1 (CNPV299); AAR83645.1 (CNPV299) |
| *Mus musculus* | AAH16676.1 (Vaccinia related kinase 1, isoform c); NP_001025015.1 (vaccinia related kinase 1 isoform c); NP_035835.1 (vaccinia related kinase 1 isoform a); NP_001025014.1 (vaccinia related kinase 1 isoform b); AAC29496.1 (serine/threonine protein kinase 51PK(S)); CAI52021.1 (vaccinia related kinase 2); AAN64922.1 (VRK2); NP_081536.1 (vaccinia related kinase 2) |
| *Gallus gallus* | NP_001006485.1 (vaccinia related kinase 1) |
| *Rattus norvegicus* | XP_576097.1 (vaccinia related kinase 1 (predicted)); NP_001012194.1 (vaccinia related kinase 1 (predicted)) |
| *Homo sapiens* | NP_003375.1 (vaccinia related kinase 1); AAH36434.1 (VRK2 protein); NP_006287.2 (vaccinia related kinase 2); AAO73052.1 (vaccinia related kinase 2 isoform 6); CAD54446.2 (vaccinia-related kinase 2); AAO73048.1 (Vaccinia related kinase 2 isoform 2); AAH27854.1 (Vaccinia related kinase 2); AAO73047.1 (vaccinia related kinase 2 isoform 1); AAO73049.1 (vaccinia related kinase 2 isoform 3) |
| *Pan troglodytes* | XP_510157.1 (Vaccinia-related kinase-1) |

[1]Results are selected from "Sequences producing significant alignments" obtained by BLASTP 2.2.12 (Altschul et al., Nucleic Acids Res., 25: 3389-3402, 1997) search of GenBank non-redundant database using default parameters and the amino acid sequence of vaccinia virus (Copenhagen strain) B1 kinase as set forth in SEQ ID NO: 2. A nucleic acid sequence corresponding to any of the amino acid sequences referenced above can be obtained by following the "CDS" link provided in each of the amino acid sequence records.

C. F10 Viral Protein Kinase

The amino acid sequences of prototypical F10 (or F10-like) VPKs and the nucleic acid sequences encoding the same are well known. Exemplary sequences for vaccinia virus (Copenhagen and Ankara strains) F10 kinase are provided in SEQ ID NOs: 3 and 5 (nucleic acid sequence) and SEQ ID NOs: 4 and 6 (amino acid sequence). Exemplary sequences for variola major virus (India-1967 strain) F10 kinase are provided in SEQ ID NO: 9 (nucleic acid sequence) and 10 (amino acid sequence). Routine comparison (e.g., using BLASTP software, for amino acid sequence, or BLASTN software, for nucleic acid sequences) of these (or other) prototypical F10 (or F10-like) sequences against publicly available databases (such as GenBank non-redundant and/or patent databases) reveals numerous F10 protein kinase homologs. Several exemplary F10 kinase homologs and information for obtaining the known sequences are provided in the following table:

TABLE 2

| F10 Viral Protein Kinase Homologs[1] | |
|---|---|
| Source | GenBank Accession No. (Protein Name; Viral Strain (as applicable)) |
| Vaccinia virus | NP_063689.1 (putative ser/thr protein kinase; strain Copenhagen; SEQ ID NO: 4); AAA48026.1 (F10L; putative; strain Copenhagen); AAB96420.1 (serine/threonine protein kinase 2; strain Ankara); AAT10437.1 (serine/threonine kinase; strain Acambis 3000 Modified Virus Ankara (MVA)); AAW23730.1 (putative ser/thr protein kinase; strain LC16mO); AAW23448.1 (putative ser/thr protein kinase; strain LC16m8); AAO89328.1 (ser/thr kinase; strain Western Reserve); AAA83263.1 (protein kinase 2; strain Western Reserve); AAA48288.1 (F8; strain LIVP); AAF33901.1 (TF10L; strain Tian Tan) |
| Rabbitpox virus | AAS49751.1 (RPXV038; SEQ ID NO: 18) |
| Cowpox virus | CAD90598.1 (G10L protein; SEQ ID NO: 20); AAM13503.1 (CPXV057 protein); NP_619845.1 (CPXV057 protein) |

TABLE 2-continued

F10 Viral Protein Kinase Homologs[1]

| Source | GenBank Accession No. (Protein Name; Viral Strain (as applicable)) |
| --- | --- |
| Ectromelia virus | AAM92337.1 (EVM033; SEQ ID NO: 24); NP_671551.1 (EVM033) |
| Monkeypox virus | AAU01246.1 (MPXV-WRAIR036; SEQ ID NO: 22); NP_536469.1 (C16L); AAL40500.1 (C16L) |
| Camelpox virus | AAL73752.1 (CMLV045; SEQ ID NO: 26); AAG37505.1 (CMP45L); NP_570435.1 (CMLV045) |
| Variola major virus | AAA69445.1 (C14L; SEQ ID NO: 28); AAA69339.1 (C14L); AAA60782.1 (homolog of vaccinia virus CDS F10L); NP_042078.1 (C14L); CAA48975.1 (C14L); AAB29628.1 (C14L product; variola virus VAR, India-1967) |
| Variola minor virus | CAB54634.1 (E10L protein; SEQ ID NO: 30); AAA69380.1 (E10L) |
| Mule deer poxvirus | YP_227408.1 (Serine/threonine protein kinase; SEQ ID NO: 32) |
| Yaba monkey tumor virus | AAR07382.1 (25L; SEQ ID NO: 34); NP_938281.1 (25L) |
| Yaba-like disease virus | CAC21263.1 (25L protein; SEQ ID NO: 36); NP_073410.1 (25L protein) |
| Swinepox virus | AAL69761.1 (SPV022 putative serine/threonine protein kinase; SEQ ID NO: 38); AAC37851.1 (C20L); NP_570182.1 (SPV022 putative serine/threonine protein kinase) |
| lumpy skin disease virus | AAN02750.1 (putative Ser/Thr protein kinase; SEQ ID NO: 40); AAN02592.1 putative Ser/Thr protein kinase; AAK84986.1 (LSDV025 putative ser/thr protein kinase; NP_150459.1 (LSDV025 putative ser/thr protein kinase); AAK43565.1 (protein kinase) |
| Sheeppox virus | NP_659598.1 (Ser/Thr protein kinase; SEQ ID NO: 42) |
| Rabbit fibroma virus | AAF17904.1 (gp020L; SEQ ID NO: 44); NP_051909.1 (gp020L) |
| Myxoma virus | AAF14908.1 (m20L; SEQ ID NO: 46); NP_051734.1 (m20L) |
| Molluscum contagiosum | AAC55145.1 (MC017L; SEQ ID NO: 48); AAB57937.1 (similar to variola C14L and vaccinia F10L); NP_043968.1 (MC017L); AAB49658.1 (similar to Vaccina virus protein kinase F10L); T30619 (probable serine/threonine-specific protein kinase 17L); AAA97934.1 (protein kinase 2 homolog) |
| Orf virus | AAR98225.1 (ORF130 putative serine/threonine protein kinase; SEQ ID NO: 50); AAO31700.1 (vaccinia virus F10L-like protein); NP_957907.1 (ORF130 putative serine/threonine protein kinase); AAR98355.1 (ORF130 putative serine/threonine protein kinase) |
| Bovine papular stomatitis virus | NP_958038.1 (ORF130 protein kinase; SEQ ID NO: 52); AAR98486.1 (ORF130 protein kinase); AAO31708.1 (vaccinia virus F10L-like protein) |
| Fowlpox virus | CAE52652.1 (virus assembly protein F10L orthologue; SEQ ID NO: 54); AAF44455.1 (ORF FPV111 Serine/threonine protein kinase); NP_039074.1 (ORF FPV111 Serine/threonine protein kinase) |
| Canarypox virus | NP_955161.1 (CNPV138 putative serine/threonine protein kinase; SEQ ID NO: 56); AAR83484.1 (CNPV138 putative serine/threonine protein kinase) |
| Vertebrates | No significant homology to protein sequences in GenBank non-redundant database. |

[1]Results selected from "Sequences producing significant alignments" obtained by BLASTP 2.2.12 (Altschul et al., Nucleic Acids Res., 25: 3389-3402, 1997) search of GenBank non-redundant database using default parameters and the amino acid sequence of vaccinia virus (Copenhagen strain) F10 kinase as set forth in SEQ ID NO: 4. A nucleic acid sequence corresponding to any of the amino acid sequences referenced above can be obtained by following the "CDS" link provided in each of the amino acid sequence records.

III. VPK Inhibitors

One aspect of the disclosure pertains to compounds that herein are identified as inhibitors of VPK activity and/or viral (e.g., poxvirus) growth. Among other things, these compounds can be used to treat viral (such as poxvirus) infection, such as smallpox and a variety of other human and veterinary diseases. Pharmaceutically acceptable salts and stereoisomers of the compounds also are contemplated in some embodiments.

In the structures that follow, all valency requirements are understood to be satisfied. Thus, for example, carbon atoms have four bonds to other atoms, even if all such bonds are not shown. Where all four bonds to a carbon atom are not shown, additional bonds to hydrogen atoms are implied.

Disclosed viral protein kinase inhibitors are derivatives of tetralin, anthraquinone, naphthylamine, tri-amino-pyrimidine, xanthen-3-one, and/or cinnamic acid. Exemplary compounds are provided throughout the disclosure. Some representative examples are shown in the following table.

| Structure | Name(s) |
|---|---|
| Exemplary B1 Inhibitors[1] | |
| (structure) | NSC270718R |
| (structure) | NSC117285R<br>IUPAC:<br>2-hydroxy-<br>4-(2,4,6-triaminopyrimidin-5-yl)-<br>diazenyl-benzoic acid |
| (structure) | NSC170008Y<br>IUPAC:<br>2-acetyl-<br>7,8-bis(dihydroxymethylidene)-<br>3-ethyl-9-hydroxy-anthracene-<br>1,4,6,10-tetrone<br>(Depositor-supplied Name:<br>7-acetyl-6-ethyl-9,10-dihydro-<br>3,5,8-trihydroxy-9,10-dioxo-<br>1,2-anthracenedicarboxylic acid) |
| (structure) | NSC306711P |
| (structure) | NSC119913X<br>IUPAC:<br>7-methyl-6-(4,5,6,-trihydroxy-<br>3-oxo-xanthen-9-yl)-<br>bicyclo[2.2.1]hetp-2-ene-<br>5-carboxylic acid<br>(Depositor-supplied name:<br>7-methyl-3-(4,5,6-trihydroxy-3-oxo-<br>3H-xanthen-9-yl)-<br>bicyclo[2.2.1]hept-5-ene-<br>2-carboxylic acid) |

| Structure | Name(s) |
|---|---|
| 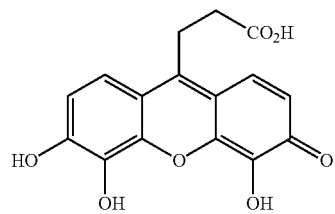 | NSC119915Z<br>IUPAC:<br>3-(4,5,6-trihydroxy-3-oxo-xanthen-9-yl)propanoic acid<br>(Depositor-supplied name:<br>4,5,6-trihydroxy-3-oxo-3H-xanthene-9-propanoic acid) |
| 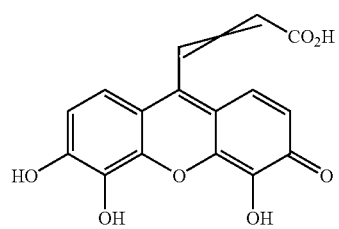 | NSC119911V<br>IUPAC:<br>3-(4,5,6-trihydroxy-3-oxo-xanthen-9-yl)prop-2-enoic acid |
| 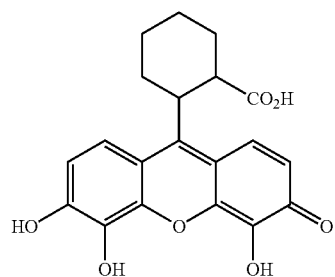 | NSC119910U<br>IUPAC:<br>2-(4,5,6-trihydroxy-3-oxo-xanthen-9-yl)cyclohexane-1-carboxylic acid<br>(Depositor-supplied name:<br>2-(4,5,6-trihydroxy-3-oxo-3H-xanthen-9-yl)-cyclohexanecarboxylic acid) |

Exemplary F10 Inhibitors:

| Structure | Name(s) |
|---|---|
| 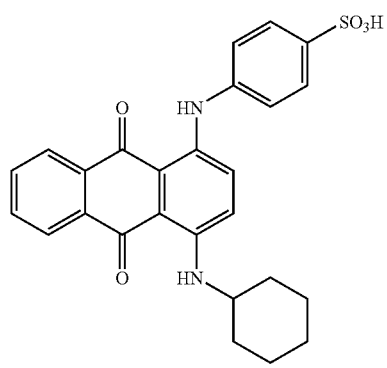 | NSC128437O<br>IUPAC:<br>4-(4-cyclohexylamino-9,10-dioxo-anthracen-1-yl)aminobenzene-sulfonic acid |
| 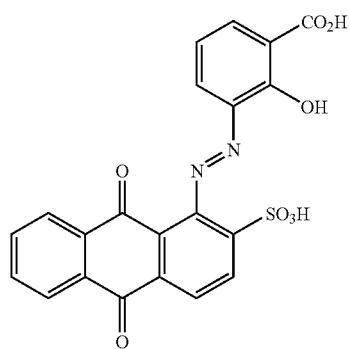 | NSC125908P<br>IUPAC:<br>3-(9,10-dioxo-2-sulfo-anthracen-1-yl)diazenyl-2-hydroxy-benzoic acid |

| Structure | Name(s) |
|---|---|
| 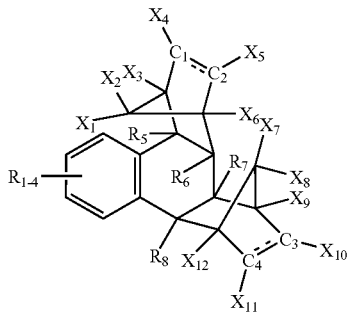 | NSC9600Q<br>IUPAC:<br>4-[N'-(2-hydroxynaphthalen-1-yl)-<br>N'-sulfo-hydrazino]benzenesulfonic<br>acid |
| | NSC13778J<br>IUPAC:<br>3-(3-stibonophenyl)prop-2-enoic<br>acid |

[1]NSC119110-U, NSC119111-V, NSC119913-X, NSC119915-Z, NSC170008-Y, and NSC306711-P also inhibited the F10 protein kinase by at least 88% (as compared to control).

A. Tetralin Derivatives

In some embodiments, a disclosed protein kinase inhibitor (such as a B1 and/or F10 protein kinase inhibitor) conforms to the chemical structure of Formula I:

Formula I wherein $R_{1-4}$ are independently hydrogen, aliphatic (such as lower aliphatic or alkyl (e.g., lower alkyl)), sulfonyl (such as sulfonic acid, alkylsulfonyl (e.g., lower alkylsulfonyl) or arylsulfonyl), alkoxy, nitro, phosphonate, or carbonyl-containing (such as acyl, acyloxy, carboxyl, or ester); $R_5$, $R_6$, $R_7$ and $R_8$ are independently hydrogen or aliphatic (such as lower aliphatic or alkyl (e.g., lower alkyl)); $X_1$-$X_{12}$ are independently hydrogen or halogen (such as chloro, or fluoro); and bonds between $C_1$-$C_2$ and $C_3$-$C_4$ are independently a single bond or a double bond. Typically, $X_4$ and $X_5$ and $X_{10}$ and $X_{11}$ are oriented cis relative to each other; however, the $C_1$-$C_2$ and $C_3$-$C_4$ double bonds can be trans. In some examples, at least two of $R_{1-4}$ are independently sulfonyl (such as sulfonic acid, alkylsulfonyl (e.g., lower alkylsulfonyl) or arylsulfonyl), nitro, phosphonate, or carbonyl-containing (such as acyl, acyloxy, carboxyl, or ester).

In other embodiments, exemplified by Formula IA (below), $R_{1-4}$ and $C_1$-$C_2$ and $C_3$-$C_4$ are as described for Formula I, and X is a halogen, such as chloro or fluoro. In particular examples, X is chloro. In other examples, X is fluoro.

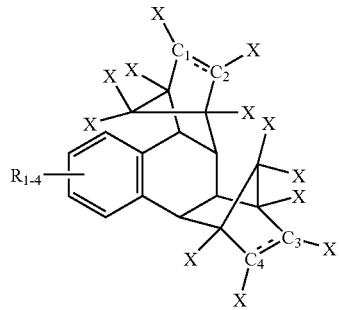

Formula IA

In some embodiments, exemplified by Formula IB (below), $C_1$-$C_2$ and $C_3$-$C_4$ and X are as described for Formula IA, and $R_1$ and $R_2$ are independently aliphatic (such as lower aliphatic or alkyl (e.g., lower alkyl)), sulfonyl (such as sulfonic acid, alkylsulfonyl (e.g., lower alkylsulfonyl) or arylsulfonyl), alkoxy, nitro, phosphonate, or carbonyl-containing (such as acyl, acyloxy, carboxyl, or ester).

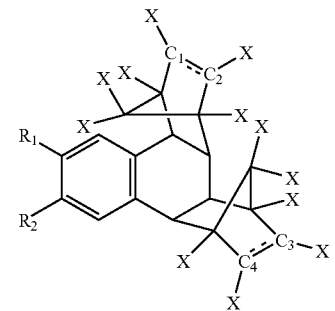

Formula IB

In other examples, $R_1$ and/or $R_2$ comprise an anionic group or an ester thereof, such as a carboxylate, phosphonate, sulfonate, or the like.

In more particular examples, $R_1$ and $R_2$ are independently sulfonyl (such as sulfonic acid, alkylsulfonyl (e.g., lower alkylsulfonyl) or arylsulfonyl), alkoxy, nitro, phosphonate, or carbonyl-containing (such as acyl, acyloxy, carboxyl, or ester). In other examples, $R_1$ and $R_2$ are independently sulfonyl (such as sulfonic acid, alkylsulfonyl (e.g., lower alkylsulfonyl) or arylsulfonyl) or carbonyl-containing (such as acyl, acyloxy, carboxyl, or ester). In still other particular examples, $R_1$ is carbonyl-containing (such as acyl, acyloxy, carboxyl, or ester) and $R_2$ is sulfonyl (such as sulfonic acid, alkylsulfonyl (e.g., lower alkylsulfonyl) or arylsulfonyl). In other examples, $R_1$ and $R_2$ are independently —COOH (or its conjugate base), —COOR, or —SO$_3$H (or its conjugate base).

Particular embodiments of compounds having the structure of Formula IB include compounds exemplified by Formula IB1:

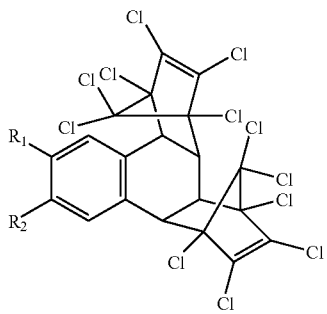

Formula IB1 wherein $R_1$ and $R_2$ are as described for Formula IB.

Even more particular embodiments include compounds exemplified by Formula IB2:

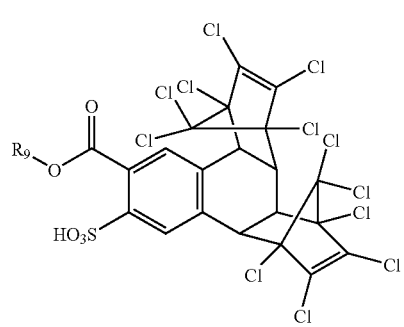

Formula IB2 wherein $R_9$ is hydrogen or aliphatic (such as lower aliphatic or alkyl (e.g., lower alkyl)). With continued reference to Formula IB2, particular examples of $R_9$ groups include, without limitation, hydrogen, methyl, ethyl and benzyl. Throughout this disclosure, unless otherwise expressly mentioned, embodiments including —SO$_3$H substituents implicitly include the corresponding conjugate base (—SO$_3^-$), carboxylic acid groups (—COOH) implicitly include the corresponding conjugate base (—COO$^-$), and —PO$_3$H$_2$ substituents implicitly include the corresponding conjugate bases (—PO$_3$H$^-$ and —PO$_3^{-2}$).

Other representative VPK inhibitors are provided in the following table:

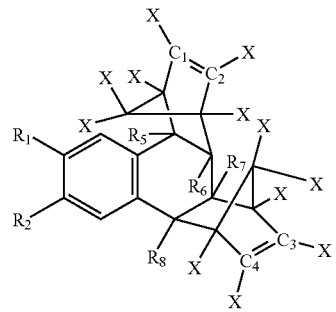

| $R_1$ | $R_2$ | X | $R_{5-8}$ | $C_1$—$C_2$ and $C_3$—$C_4$ |
|---|---|---|---|---|
| —COOR (where R = lower alkyl), —COOH, —COO$^-$, —SO$_3$H, —SO$_3^-$, —NO$_2$, —PO$_3^{-2}$, —R—SO$_3$H (where R = lower alkyl), —R—SO$_3^-$ (where R = lower alkyl) | —COOR (where R = lower alkyl), —COOH, —COO$^-$, —SO$_3$H, —SO$_3^-$, —NO$_2$, —PO$_3^{-2}$, —R—SO$_3$H (where R = lower alkyl), —R—SO$_3^-$ (where R = lower alkyl) | Cl or F | H or lower alkyl | independently a double bond or a single bond |
| same as above | same as above | Cl | same as above | same as above |
| same as above | same as above | F | same as above | same as above |
| same as above | same as above | Cl or F | H | same as above |
| same as above | same as above | Cl or F | lower alkyl | same as above |
| same as above | same as above | Cl or F | H or lower alkyl | each a double bond |
| same as above | same as above | Cl or F | H or lower alkyl | each a single bond |
| same as above | same as above | Cl or F | H or lower alkyl | C1-C2 a double bond and C3-C4 a single bond |

-continued

| $R_1$ | $R_2$ | X | $R_{5-8}$ | $C_1$—$C_2$ and $C_3$—$C_4$ |
|---|---|---|---|---|
| same as above | same as above | Cl or F | H or lower alkyl | C1-C2 a single bond and C3-C4 a double bond |
| same as above | same as above | Cl | H | each a double bond |
| same as above | —$SO_3H$, —$SO_3^-$, —R—$SO_3H$ (where R = lower alkyl), —R—$SO_3^-$ (where R = lower alkyl) | Cl | H | each a double bond |
| —COOR (where R = lower alkyl), —COOH, —COO$^-$ | —COOR (where R = lower alkyl), —COOH, —COO$^-$, —$SO_3H$, —$SO_3^-$, —$NO_2$, —$PO_3^{-2}$, —R—$SO_3H$ (where R = lower alkyl), —R—$SO_3^-$ (where R = lower alkyl) | Cl | H | each a double bond |
| —COOR (where R = lower alkyl), —COOH, —COO$^-$ | —$SO_3H$, —$SO_3^-$, —R—$SO_3H$ (where R = lower alkyl), —R—$SO_3^-$ (where R = lower alkyl) | Cl | H | each a double bond |
| —COOR (where R = lower alkyl), —COOH, —COO$^-$ | —$SO_3H$, —$SO_3^-$, —R—$SO_3H$ (where R = lower alkyl), —R—$SO_3^-$ (where R = lower alkyl) | Cl or F | H or lower alkyl | independently a double bond or a single bond |
| —COOR (where R = lower alkyl), —COOH, —COO$^-$ | —$SO_3H$, —$SO_3^-$, —R—$SO_3H$ (where R = lower alkyl), —R—$SO_3^-$ (where R = lower alkyl) | Cl or F | H | each a double bond |

Disclosed tetralin derivatives inhibit, at least, (i) an activity (e.g., kinase activity) of a B1 kinase and/or a F10 kinase, and/or a homolog or variant of either, and/or (ii) viral (e.g., poxvirus) growth. In particular examples, a disclosed tetralin derivative (such as a compound exemplified by Formula I, Formula IA, Formula IB, Formula IB1, or Formula IB2) inhibits a B1 kinase and/or a homolog or variant thereof (such as a vaccinia virus and/or variola virus B1 kinase). In other examples, a disclosed tetralin derivative (such as a compound exemplified by Formula I, Formula IA, Formula IB, Formula IB1, or Formula IB2) inhibits virus growth (such as poxvirus growth, for example, chordopoxvirus growth or *Orthopoxvirus* growth, each including vaccinia virus and/or variola virus growth).

B. Derivatives of Anthraquinone

In some embodiments, disclosed protein kinase inhibitors (such as a B1 and/or F10 protein kinase inhibitor) conform to the chemical structure of Formula II:

Formula II wherein $Y_1$ and $Y_2$ are independently O, S, or N—R (where R is hydrogen or aliphatic, such as lower aliphatic or alkyl (e.g., lower alkyl)); $R_1$ is hydroxyl, alkoxy (such as lower alkoxy, e.g., methoxy), amino (such as arylamino) or azo; $R_2$ is hydrogen, aliphatic (such as lower aliphatic or alkyl (e.g., lower alkyl)), or sulfonyl (such as sulfonic acid, alkylsulfonyl (e.g., lower alkylsulfonyl) or arylsulfonyl); $R_3$ is hydrogen, aliphatic (such as lower aliphatic or alkyl (e.g., lower alkyl)), or carbonyl-containing (such as acyl, lower acyl, acyloxy, carboxyl, or ester); $R_4$ is hydrogen, aliphatic (such as lower aliphatic or alkyl (e.g., lower alkyl)), hydroxyl, alkoxy (such as lower alkoxy), or amino (such as alkylamino); $R_5$, $R_6$ and $R_7$ are independently hydrogen, hydroxyl, alkoxy, carbonyl-containing, sulfonyl, or phosphonate; and $R_8$ is hydrogen or aliphatic (such as lower aliphatic or alkyl (e.g., lower alkyl)).

Other exemplary VPK inhibitors, which are derived from anthraquinone, have the following structure:

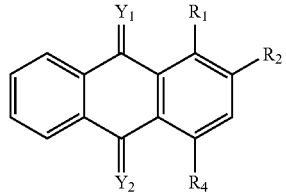

Formula IIA wherein $Y_1$ and $Y_2$, and $R_1$, $R_2$, and $R_4$ are as described for compounds having the structure of Formula II. In more particular embodiments, $Y_1$ and $Y_2$ are O; $R_1$ is amino (such as arylamino) or azo; $R_2$ is hydrogen, aliphatic (such as lower aliphatic or alkyl (e.g., lower alkyl)), or sulfonyl (such as sulfonic acid, alkylsulfonyl (e.g., lower alkylsulfonyl) or arylsulfonyl); and $R_4$ is hydrogen, lower alkyl, or amino (such as alkylamino).

Particular embodiments of compounds having the structure of Formula IIA include compounds exemplified by Formula IIA1:

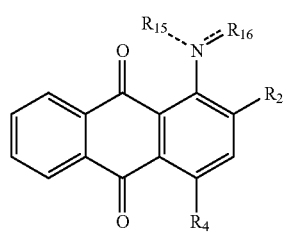

Formula IIA1 wherein $R_2$ and $R_4$ are as described for compounds having the structure of Formula II; $R_{15}$ is hydrogen or lower alkyl; and $R_{16}$ is substituted or unsubstituted aryl (such as substituted or unsubstituted phenyl). In another embodiment, $R_2$ and $R_4$ are as described for compounds having the structure of Formula II; $R_{15}$ is absent; and $R_{16}$ has the structure =N—R, where R is substituted or unsubstituted aryl (such as substituted or unsubstituted phenyl, or —N—$R_{20}$ (as described below)).

Further examples include compounds having one of the following structures:

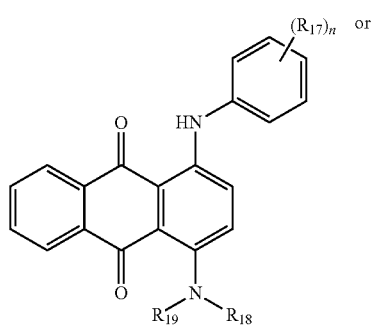

Formula IIA1a or

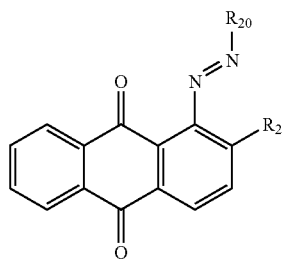

Formula IIA1b

With regard to exemplary compounds having the structure of Formula IIA1a, $(R_{17})_n$ represents five substituents independently selected from hydrogen, carbonyl-containing, phosphonate, and sulfonyl; and $R_{18}$ and $R_{19}$ are independently hydrogen, or aliphatic (for example, lower aliphatic or alkyl (such as lower alkyl or carbocylic (for instance, cyclohexane))). In more particular examples, $(R_{17})_n$ represents five substituents wherein four substituents are hydrogen and the fifth substituent is sulfonyl (such as —$SO_3H$ or $SO_3^-$); $R_{18}$ is hydrogen or lower alkyl; and $R_{19}$ is alkyl (such as lower alkyl or carbocylic (for instance, cyclohexane)).

With regard to exemplary compounds having the structure of Formula IIA1b, $R_2$ is hydrogen, aliphatic (such as lower aliphatic or alkyl (e.g., lower alkyl)), or sulfonyl (such as sulfonic acid, alkylsulfonyl (e.g., lower alkylsulfonyl) or arylsulfonyl); and $R_{20}$ is aliphatic (such as lower aliphatic or alkyl (e.g., lower alkyl)), or aryl (such as substituted or unsubstituted phenyl). In more particular examples, $R_2$ is sulfonyl (such as sulfonic acid, alkylsulfonyl (e.g., lower alkylsulfonyl) or arylsulfonyl) and $R_{20}$ is a di-substituted phenyl; for example, independently substituted with carboxyl and/or hydroxyl groups.

Other exemplary VPK inhibitors derived from anthraquinone have the following structure:

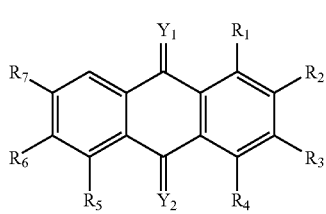

Formula IIB wherein $Y_1$ and $Y_2$ are independently O, S, or N—R (where R is hydrogen or aliphatic (such as lower aliphatic or alkyl (e.g., lower alkyl))); $R_1$, $R_4$, and $R_7$ are independently hydroxyl or alkoxy (such as lower alkoxy, e.g., methoxy); $R_2$ is hydrogen or aliphatic (such as lower aliphatic or alkyl (e.g., lower alkyl)); $R_3$ is carbonyl-containing (such as acyl, lower acyl, acyloxy, carboxyl, or ester); $R_4$ is hydrogen, aliphatic (such as lower aliphatic or alkyl (e.g., lower alkyl)), hydroxyl, alkoxy (such as lower alkoxy); and $R_5$, and $R_6$ are independently carbonyl-containing, sulfonyl, or phosphonate. In more particular embodiments, $Y_1$ and $Y_2$ are O; and $R_1$-$R_7$ are as previously described in this paragraph.

Particular embodiments of compounds having the structure of Formula IIB include compounds exemplified by Formula IIB1:

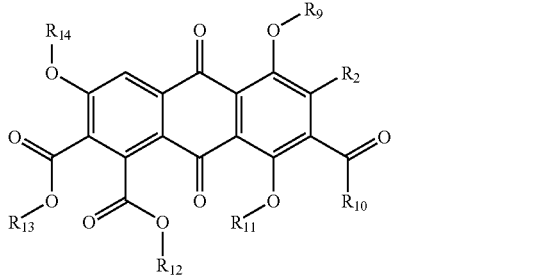

Formula IIB1 wherein $R_2$ and $R_9$-$R_{14}$ are independently hydrogen or aliphatic (such as lower aliphatic or alkyl (e.g., lower alkyl)). In some examples, $R_2$ and $R_9$-$R_{14}$ are independently hydrogen or lower alkyl (such as methyl, ethyl, propyl, i-propyl, butyl or i-butyl). In other examples, $R_2$ and $R_{10}$ are independently lower alkyl (such as methyl, ethyl, propyl, i-propyl, butyl or i-butyl); and $R_9$ and $R_{11}$-$R_{14}$ are hydrogen.

Disclosed derivatives of anthraquinone inhibit, at least, (i) an activity (e.g., kinase activity) of a B1 kinase and/or a F10 kinase, and/or a homolog or variant of either, and/or (ii) viral (e.g., poxvirus) growth. In particular examples, disclosed anthraquinone derivatives (such as a compound exemplified by Formula II, Formula IIB or Formula IIB1) inhibit a B1 kinase and/or a homolog or variant thereof (such as a vaccinia virus and/or variola virus B1 kinase). In other examples, a disclosed anthraquinone derivative (such as a compound exemplified by Formula II, Formula IIA, Formula IIA1, Formula IIA1a, or Formula IIA1b) inhibits a F10 kinase and/or a homolog or variant thereof (such as a vaccinia virus and/or variola virus B1 kinase). In still other examples, a disclosed anthraquinone derivative (such as a compound exemplified by Formula II, Formula IIA, Formula IIA1, Formula IIA1a, Formula IIA1b, Formula IIB or Formula IIB1) inhibits virus growth (such as poxvirus growth, for example, chordopoxvirus growth or *Orthopoxvirus* growth, each including vaccinia virus and/or variola virus growth).

C. Xanthen-3-One Derivatives

In some embodiments, disclosed protein kinase inhibitors (such as a B1 and/or F10 protein kinase inhibitor) conform to the chemical structure of Formula III:

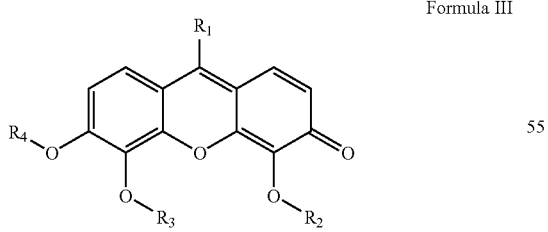

Formula III wherein $R_1$ is aliphatic (for example, alkyl (e.g., carbocyclic, carbobicyclic) or alkene) substituted with one or more (such as one, two, three, four, five or six) carbonyl-containing and/or sulfonyl groups; and $R_2$-$R_4$ are independently hydrogen or aliphatic, for example, lower alkyl (such as methyl, ethyl, propyl, i-propyl, butyl or i-butyl). In some examples, $R_1$ is a substituted aliphatic group; for example, substituted with a carboxylic acid or carboxylic ester moiety (such as a straight-chain or branched-chain, saturated or unsaturated carboxylic acid; or a saturated or partially unsaturated carbocyclic group substituted with a carboxylic acid); and $R_2$-$R_4$ are independently hydrogen, lower alkyl (such as methyl, ethyl, propyl, i-propyl, butyl or i-butyl), or acyl. In other examples, $R_1$ is a lower alkyl carboxylic acid (such as —$(CH_2)_n$—$CO_2R$, e.g., —$CH_2$—$CH_2$—COOH), a lower alkenyl carboxylic acid (such as —CH═CH—$CO_2R$, e.g., —CH═CH—COOH), a carbocycle (such as a cyclohexyl moiety) substituted with a carboxylic acid, or a bicyclic, unsaturated carbocycle (such as a bicycloheptenyl moiety) substituted with a carboxylic acid; and $R_2$-$R_4$ are independently hydrogen, lower alkyl (such as methyl, ethyl, propyl, i-propyl, butyl or i-butyl) or acyl, such as —C(O)R, wherein R represents a lower alkyl group.

Disclosed xanthen-3-one derivatives inhibit, at least, (i) an activity (e.g., kinase activity) of a B1 kinase and/or a F10 kinase, and/or a homolog or variant of either, and/or (ii) viral (e.g., poxvirus) growth. In particular examples, a disclosed xanthen-3-one derivative (such as a compound exemplified by Formula III) inhibits a B1 kinase and/or a homolog or variant thereof (such as a vaccinia virus and/or variola virus B1 kinase). In other examples, a disclosed xanthen-3-one derivative (such as a compound exemplified by Formula III) inhibits a F10 kinase and/or a homolog or variant thereof (such as a vaccinia virus and/or variola virus B1 kinase). In still other examples, a disclosed xanthen-3-one derivative (such as a compound exemplified by Formula III) inhibits virus growth (such as poxvirus growth, for example, chordopoxvirus growth or *Orthopoxvirus* growth, each including vaccinia virus and/or variola virus growth).

D. Naphthylamine Derivatives

In some embodiments, a disclosed protein kinase inhibitor (such as a B1 and/or F10 protein kinase inhibitor) conforms to the chemical structure of Formula IV:

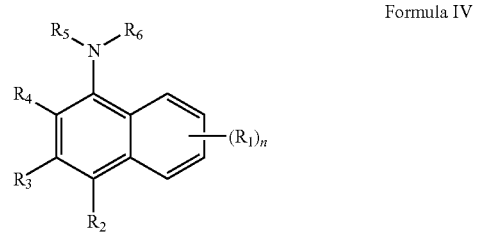

Formula IV wherein $(R_1)_n$ represents four substituents independently selected from hydrogen, aliphatic (such as lower aliphatic or alkyl (e.g., lower alkyl)), or aryl; $R_2$, $R_4$, and $R_5$ are independently hydrogen, aliphatic (for example, lower aliphatic or alkyl (such as lower alkyl)), sulfonyl (such as sulfonic acid, alkylsulfonyl (e.g., lower alkylsulfonyl) or arylsulfonyl), hydroxyl, alkoxy, nitro, phosphonate, or carbonyl-containing (such as acyl, acyloxy, carboxyl, or ester); $R_3$ is hydrogen or aliphatic (such as lower aliphatic or alkyl (e.g., lower alkyl)); and $R_6$ is hydrogen or amino (such as substituted or unsubstituted arylamino).

More particular examples include compounds conforming to the following structure:

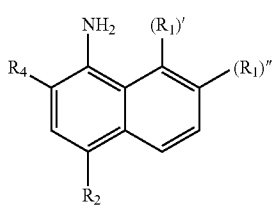

Formula IVA wherein $R_2$ and $R_4$ are independently sulfonyl (such as sulfonic acid, alkylsulfonyl (e.g., lower alkylsulfonyl) or arylsulfonyl), hydroxyl, alkoxy, nitro, phosphonate, or carbonyl-containing (such as acyl, acyloxy, carboxyl, or ester); and $(R_1)'$ and $(R_1)''$ form a polycyclic ring system having the following structure:

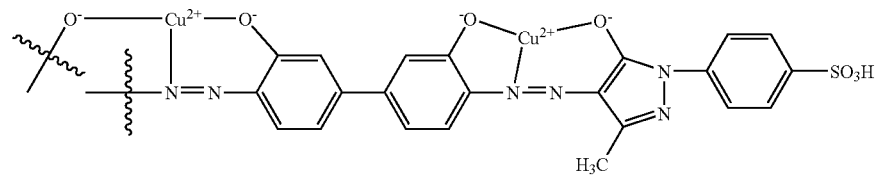

In even more particular examples, $(R_1)'$ and $(R_1)''$ form the immediately preceding polycyclic ring system; and $R_2$ and $R_4$ are independently sulfonyl (such as sulfonic acid, alkylsulfonyl (e.g., lower alkylsulfonyl) or arylsulfonyl), or carbonyl-containing (such as acyl, acyloxy, carboxyl, or ester).

Other embodiments of compounds having the structure of Formula IV include compounds exemplified by Formula IVB:

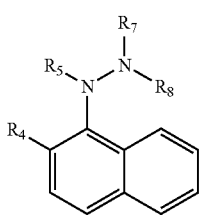

Formula IVB wherein $R_4$ is hydroxyl or alkoxy (such as methoxy or ethoxy); $R_5$ is sulfonyl (such as sulfonic acid, alkylsulfonyl (e.g., lower alkylsulfonyl) or arylsulfonyl), nitro, phosphonate, or carbonyl-containing (such as acyl, acyloxy, carboxyl, or ester); $R_7$ is hydrogen or aliphatic (such as lower aliphatic or alkyl (e.g., lower alkyl)); and $R_8$ is aryl (such as substituted or unsubstituted phenyl). In more particular embodiments, $R_4$ is hydroxyl or alkoxy (such as methoxy or ethoxy); $R_5$ is sulfonyl (such as sulfonic acid, alkylsulfonyl (e.g., lower alkylsulfonyl) or arylsulfonyl); $R_7$ is hydrogen or lower alkyl (such as methyl, ethyl, propyl, i-propyl, butyl or i-butyl); and $R_8$ is substituted phenyl.

Some specific examples conform to the structure shown below in Formula IVB1:

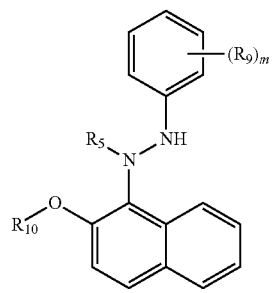

Formula IVB1 wherein $R_5$ is sulfonyl (such as sulfonic acid, alkylsulfonyl (e.g., lower alkylsulfonyl) or arylsulfonyl), nitro, phosphonate, or carbonyl-containing (such as acyl, acyloxy, carboxyl, or ester); $(R_9)_m$ represents five substituents independently selected from hydrogen, sulfonyl (such as sulfonic acid, alkylsulfonyl (e.g., lower alkylsulfonyl) or arylsulfonyl), nitro, phosphonate, and carbonyl-containing (such as acyl, acyloxy, carboxyl, or ester); and $R_{10}$ is hydrogen or lower alkyl (such as methyl, ethyl, propyl, i-propyl, butyl or i-butyl). In other examples conforming to Formula IVB1, $R_5$ is sulfonyl (such as sulfonic acid, alkylsulfonyl (e.g., lower alkylsulfonyl) or arylsulfonyl); $(R_9)_m$ represents five substituents independently selected from hydrogen and sulfonyl (such as sulfonic acid, alkylsulfonyl (e.g., lower alkylsulfonyl) or arylsulfonyl); and $R_{10}$ is hydrogen or lower alkyl (such as methyl, ethyl, propyl, i-propyl, butyl or i-butyl). In still other examples conforming to Formula IVB1, $R_5$ is sulfonyl (such as sulfonic acid, alkylsulfonyl (e.g., lower alkylsulfonyl) or arylsulfonyl); $(R_9)_m$ represents five substituents wherein four substituents are hydrogen and one substituent is sulfonyl (such as sulfonic acid, alkylsulfonyl (e.g., lower alkylsulfonyl) or arylsulfonyl); and $R_{10}$ is hydrogen or lower alkyl (such as methyl, ethyl, propyl, i-propyl, butyl or i-butyl).

Disclosed naphthylamine derivatives inhibit, at least, (i) an activity (e.g., kinase activity) of a B1 kinase and/or a F10 kinase, and/or a homolog or variant of either, and/or (ii) viral (e.g., poxvirus) growth. In particular examples, disclosed naphthylamine derivatives (such as a compound exemplified by Formula IV or Formula IVA) inhibit a B1 kinase and/or a homolog or variant thereof (such as a vaccinia virus and/or variola virus B1 kinase). In other examples, a disclosed naphthylamine derivative (such as a compound exemplified by Formula IV, Formula IVA, Formula IVB or Formula IVB1) inhibits a F10 kinase and/or a homolog or variant thereof (such as a vaccinia virus and/or variola virus B1 kinase). In still other examples, a disclosed naphthylamine derivative (such as a compound exemplified by Formula IV, Formula IVA, Formula IVB or Formula IVB1) inhibits virus growth

E. Cinnamic Acid Derivatives

In some embodiments, a disclosed protein kinase inhibitor (such as a B1 and/or F10 protein kinase inhibitor) conforms to the chemical structure of Formula V:

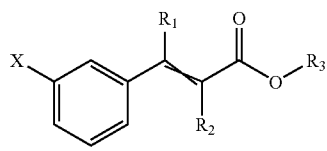

Formula V wherein X is sulfonyl (such as sulfonic acid, alkylsulfonyl (e.g., lower alkylsulfonyl) or arylsulfonyl), phosphonate (such as —P(O)(OH)$_2$ or its conjugate base), carbonyl-containing (such as acyl, acyloxy, carboxyl, or ester), or —Sb(O)(OH)$_2$ (or its conjugate base); and R$_1$, R$_2$ and R$_3$ are independently hydrogen or aliphatic (such as lower aliphatic or alkyl (e.g., lower alkyl)). As indicated in Formula V, substituents around the double bond in the side chain may be oriented in cis or trans. In particular examples, X is —SO$_3$H (or its conjugate base, SO3$^-$), —PO$_3$H$_2$ or its conjugate base), —COOH (or its conjugate base), —COOR (wherein R is lower alkyl), or —Sb(O)(OH)$_2$ (or its conjugate base); and R$_1$, R$_2$ and R$_3$ are independently hydrogen or lower alkyl (such as methyl, ethyl, propyl, i-propyl, butyl or i-butyl). In other particular examples, X is —Sb(O)(OH)$_2$ (or its conjugate base); and R$_1$, R$_2$ and R$_3$ are independently hydrogen or lower alkyl (such as methyl, ethyl, propyl, i-propyl, butyl or i-butyl).

Disclosed cinnamic acid derivatives inhibit, at least, (i) an activity (e.g., kinase activity) of a B1 kinase and/or a F10 kinase, and/or a homolog or variant of either, and/or (ii) viral (e.g., poxvirus) growth. In particular examples, disclosed cinnamic acid derivatives (such as a compound exemplified by Formula V) inhibit a F10 kinase and/or a homolog or variant thereof (such as a vaccinia virus and/or variola virus F10 kinase). In other examples, a disclosed cinnamic acid derivative (such as a compound exemplified by Formula V) inhibits virus growth (such as poxvirus growth, for example, chordopoxvirus growth or *Orthopoxvirus* growth, each including vaccinia virus and/or variola virus growth).

F. Tri-Amino-Pyrimidine Derivatives

In some embodiments, a disclosed protein kinase inhibitor (such as a B1 and/or F10 protein kinase inhibitor) conforms to the chemical structure of Formula VI:

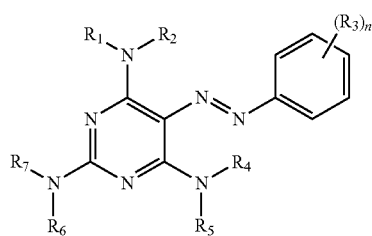

Formula VI wherein R$_1$, R$_2$, and R$_4$-R$_7$ are independently hydrogen or aliphatic (such as lower aliphatic or alkyl (e.g., lower alkyl); and (R$_3$)$_n$ represents five substituents independently selected from hydrogen, aliphatic (such as lower aliphatic or alkyl (e.g., lower alkyl)), carbonyl-containing (such as acyl, acyloxy, carboxyl, or ester), sulfonyl (such as sulfonic acid, alkylsulfonyl (e.g., lower alkylsulfonyl) or arylsulfonyl), phosphonate, hydroxyl, and alkoxy. In particular examples, two of the (R$_3$)$_n$ substituents are independently carbonyl-containing (such as acyl, acyloxy, carboxyl, or ester), sulfonyl (such as sulfonic acid, alkylsulfonyl (e.g., lower alkylsulfonyl) or arylsulfonyl), phosphonate, hydroxyl, or alkoxy, and the other three (R$_3$)$_n$ substituents are independently hydrogen or aliphatic (such as lower aliphatic or alkyl (e.g., lower alkyl).

In other compound embodiments having the structure of Formula IV, R$_1$, R$_2$, and R$_4$-R$_7$ are independently hydrogen or lower alkyl (such as methyl, ethyl, propyl, i-propyl, butyl or i-butyl); and (R$_3$)$_n$ represents five substituents, three of which are independently hydrogen, or lower alkyl (such as methyl, ethyl, propyl, i-propyl, butyl or i-butyl), and two of which are independently carboxyl (such as —COOH or —COOR, where R is lower alkyl), —SO$_3$H (or its conjugate base, SO3$^-$), —PO$_3$H$_2$ or its conjugate base), hydroxyl, or alkoxy (such as methoxy or ethoxy).

Some specific examples conform to the structure shown below in Formula VIA:

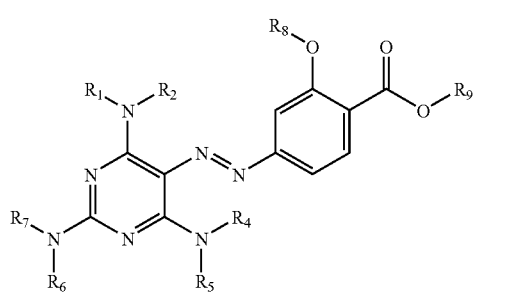

Formula VIA wherein R$_1$, R$_2$, and R$_4$-9 are independently hydrogen or aliphatic (such as lower aliphatic or alkyl (e.g., lower alkyl). In particular examples, R$_1$, R$_2$, and R$_4$-9 are independently hydrogen or lower alkyl (such as methyl, ethyl, propyl, i-propyl, butyl or i-butyl).

Disclosed tri-amino-pyrimidine derivatives inhibit, at least, (i) an activity (e.g., kinase activity) of a B1 kinase and/or a F10 kinase, and/or a homolog or variant of either, and/or (ii) viral (e.g., poxvirus) growth. In particular examples, disclosed tri-amino-pyrimidine derivatives (such as a compound exemplified by Formula VI or Formula VIA) inhibit a B1 kinase and/or a homolog or variant thereof (such as a vaccinia virus and/or variola virus B1 kinase). In other examples, a disclosed tri-amino-pyrimidine derivative (such as a compound exemplified by Formula VI, Formula VIA) inhibits virus growth (such as poxvirus growth, for example, chordopoxvirus growth or *Orthopoxvirus* growth, each including vaccinia virus and/or variola virus growth).

G. Considerations for Viral Protein Kinase Inhibitors

Prodrug derivatives of disclosed VPK inhibitors can be prepared. In one example, a prodrug derivative includes one or more substituents that are converted in vivo into one or more different substituents. In several instances, the prodrugs also fall within the scope of the range of compounds described above. For example, prodrugs can be prepared by reacting a compound with an acylating or carbamylating agent, such as 1,1-acyloxyalkylcarbonochloridate, p-nitrophenyl carbonate or the like, as is known to those of skill in the art of medicinal chemistry. Further examples of methods suitable for preparing prodrug derivatives of viral protein kinase inhibitors are described by Saulnier et al., *Biorg Med. Chem. Lett.*, 4: 1985, 1994.

Protected derivatives of the viral protein kinase inhibitors disclosed herein also can be made. Exemplary techniques for preparing such derivatives are provided by Greene, *Protecting Groups in Organic Synthesis*, 3rd Edition, New York: John Wiley & Sons, Inc., 1999.

In some embodiments a disclosed viral protein kinase inhibitor is included in a pharmaceutical composition and/or administered to a subject for the treatment of poxvirus (such as variola virus) infection. Accordingly, it is advantageous for some VPK inhibitor embodiments to have characteristics suitable for in vivo administration. One rule of thumb for drug design is Lipinski's "Rule of 5" (Lipinski et al., *Adv. Drug Deliv. Rev.*, 23(1-3): 3-25, 1997), which suggests that absorption and permeation of a drug candidate (which is not a biological transporter substrate) is likely to be increased if at least three of the following parameters are satisfied: (i) there are no more than about 5 H-bond donors (expressed as the sum of hydroxyl and amine groups); (ii) the molecular weight is not substantially greater than 500 g/mole (but can be anything less); (iii) the logP (logarithm of the octanol-water partition coefficient of the drug candidate) is no more than about 5; and (iv) there are no more than about 10 H-bond acceptors (the sum of nitrogens and oxygens). Some VPK inhibitor embodiments may satisfy one, two, three or all four Rule of 5 parameters.

H. Obtaining VPK Inhibitors

Certain of the disclosed VPK inhibitors are available from the Developmental Therapeutics Program, National Cancer Institutes, National Institutes of Health, Bethesda, Md., U.S.A. Other disclosed VPK inhibitors are structurally related to the publicly available compounds and can be synthesized from such compounds using syntheses commonly known in the art. Many general references providing commonly known chemical synthetic schemes and conditions useful for synthesizing the disclosed compounds are available (see, e.g., Smith and March, *March's Advanced Organic Chemistry Reactions, Mechanisms, and Structure*, Fifth Edition, Wiley-Interscience, 2001; Vogel, *A Textbook of Practical Organic Chemistry, Including Qualitative Organic Analysis*, Fourth Edition, New York: Longman, 1978; or Loudon, Organic Chemistry, Fourth Edition, New York: Oxford University Press, 2002).

I. Functional Assays for VPK Inhibitors

The disclosed VPK inhibitors are useful, at least, in the treatment of poxvirus infection (such as smallpox) and to inhibit virus (such as poxvirus growth). Such VPK inhibitors are believed to exert an inhibitory effect on poxviruses (and thereby treat poxvirus-related disease) by interfering with the activity of one or more essential protein kinases (such as the B1 and/or F10 kinase). Accordingly, if it is desirable to do so, non-limiting methods useful to functionally characterize VPK inhibitors are (i) in vitro protein kinase assays, and (ii) virus growth assays (e.g., plaque formation assays in cultured cells and/or virus growth assays in cultured cells. A disclosed VPK inhibitor is expected to reduce viral protein kinase activity and/or virus growth as compared to such activity or growth measured in the absence of such inhibitor. Numerous assays suitable for the measurement of viral protein kinase activity and/or virus (such as poxvirus) growth in the presence and absence of disclosed VPK inhibitors are known (see, e.g., *Protein Kinase Protocols*, First Edition, ed. by A. Reith, New York: Humana Press, 2001; *Methods in Enzymology*, Volume 200, "Protein Phosphorylation, Part A: Protein Kinases: Assays, Purification, Antibodies, Functional Analysis, Cloning, and Expression," ed. by Hunter and Sefton, New York: Academic Press, 1991; Methods in Enzymology, Volume 201, "Protein Phosphorylation, Part B: Analysis of Protein Phosphorylation, Protein Kinase Inhibitors, and Protein Phosphatases," ed. by Hunter and Sefton, New York: Academic Press, 1991; *Vaccinia Virus and Poxyirology: Methods and Protocols*, ed. by Issacs, Clifton, N.J.: Humana Press, 2004). Exemplary methods are provided below and in the Examples.

1. Viral Protein Kinase Assays

A traditional method for assaying the activity of protein kinase inhibitors is a radiometric assay in which the gamma phosphate of ATP is labeled with either $^{32}P$ or $^{33}P$. When a viral protein kinase (such as a B1 or F10 kinase), a protein substrate (such as casein) and labeled ATP are mixed under suitable conditions (see, e.g., Example 1), the VPK transfers the gamma phosphate to a hydroxyl (e.g., serine and/or threonine) of the protein substrate. As a result, the substrate protein (i.e., target) becomes covalently labeled with the radioisotope. The target protein is removed from the free radiolabeled ATP (for example, by immunoprecipitation) and the amount of radioactive protein is determined. In the presence of a VPK inhibitor, the amount of radioactive target protein will be reduced as compared to control.

An alternative radiometric assay, which is more amenable to higher throughput, is the SPA or scintillation proximity assay (see e.g., Hart et al., *Mol. Immunol.,* 16: 265, 1979; and U.S. Pat. Nos. 4,271,139; 4,382,074; and 4,568,649). In this assay, a target protein (such as casein) is directly or indirectly immobilized on scintillant-impregnated beads. The VPK, target protein, and radioactive ATP are placed in a reaction mixture as described above. Radio-labeled target protein is captured on the scintillant-impregnated beads, which causes the scintillant to emit light. The amount of emitted light is proportional to the amount of phosphorylation of the target protein (and, hence, to the activity of the VPK). A decrease in the amount of emitted light in the presence of a compound identifies that compound as a VPK inhibitor.

Protein kinase activity (and inhibition thereof) can also be determined using fluorescence polarization techniques. In these assays, the enzyme transfers the gamma phosphate of ATP to a protein or peptide substrate. This activity is monitored by detecting the phosphor-peptide by such means as an antibody specific for the phosphorylated protein. The binding of the antibody to the phosphor-peptide will slow the free rotation of the peptide in solution and, therefore, a polarization signal from the product of the catalytic reaction can be detected (see, e.g., U.S. Pat. App. Pub. No. 2001/0004522; Turek et al., *Anal. Biochem.,* 299(1): 25-53, 2001). A VPK inhibitor will affect the amount of polarization signal measured in the reaction.

As yet another alternative, protein kinase activity can be assayed using the Alphascreen™ technique (PerkinElmer). This assay involves a phospho-specific antibody that recognizes the phosphorylated substrate of the kinase in question. A biotinylated substrate peptide is bound to streptavidin-coated "donor" beads. The kinase reaction is carried out in the presence of "acceptor" beads to which the phospho-specific antibody is bound. Laser excitation causes the "donor" beads to release singlet state oxygen. When released in close proximity to the "acceptor" bead, the singlet state oxygen generates a chemiluminescent signal that is then amplified. Light emission is proportional to substrate phosphorylation.

The fluorescence resonance energy transfer (FRET)-based Z'-Lyte™ technique (PanVera/Invitrogen) also can be used to measure protein kinase activity. This assay measures FRET in a protein kinase substrate peptide labeled at either end with coumarin and fluorescein. A high level of FRET occurs in the intact peptide. The assay measures the protease sensitivity of the peptide. Once cleaved by a protease, FRET no longer occurs. The peptide is designed so that the site phosphorylation by the kinase of interest is within the protease cleavage site. Phosphorylation inhibits cleavage and therefore prevents the inhibition of FRET by proteolytic degradation. A high level of residual FRET is indicative of protein kinase activity and, consequently, a protein kinase inhibitor would decrease the FRET.

2. Virus Growth Assays

Virus growth assays detect, for example, to what extent (or whether) a putative VPK inhibitor can slow virus growth. Two exemplary virus growth assays are in vitro cell culture assays and plaque reduction assays.

In a representative in vitro cell culture assay (see, e.g., Example 1), cultured cells susceptible to infection by the virus of interest (such as a poxvirus, like vaccinia virus) are grown to a desired cell density (such as $4\times10^5$ cells per well in a 12-well plate) under culture conditions (e.g., 37° C., 95% $O_2$, 5% $CO_2$ and 98% relative humidity) suitable to the particular cell type. The cultured cells, then, are infected (either with a single or multiple inoculum(s)) with a known amount of virus (such as, about 0.03 plaque-forming units per cell). The virus inoculum remains in contact with the cells for a sufficient time (such as 30 minutes) to permit virus to adsorb to the cells. Unbound virus is removed and medium containing inhibitor or vehicle (control) is then added. Infection is permitted to proceed for a sufficient time (e.g., about 18-24 hours) for the virus to replicate (at least under control conditions) to a comfortably measurable level. Virus is harvested, for example, by removal of the medium (e.g., for viruses that shed from the cells) and/or by collection of infected cells and isolation of virus from such cells.

Virus can be isolated from infected cells by any method known in the art. In one exemplary method, cells are disrupted (e.g., by cycles of freezing and thawing and/or shearing with a syringe needle (such as 1.5 inch 22 gauge needle)), and debris is removed by centrifugation (e.g., 750×g for 1 minute). Virus are collected in the supernatant, which, optionally, is mixed with protease (e.g., 0.25% trypsin for 30 minutes at 37° C.). Debris, again, can be removed by centrifugation (e.g., 750×g for 1 minute). Then, supernatant containing virus is serially diluted for plaque assay.

In the plaque assay, cultured cells (e.g., in a series of culture dishes) are contacted with virus (e.g., serial dilutions) for a sufficient time to permit virus to adsorb to the cells. The infected monolayers of cells, then, are overlaid with medium containing agarose (and no inhibitor). Incubation of the cells is continued for a period of time (e.g., from about 18 to about 40 hours), after which time, the number of plaques are counted (e.g., by staining cells with 1% crystal violet in 20% ethanol). A VPK inhibitor would be expected to reduce the number of plaques relative to control.

A plaque reduction assay also is useful to determine the ability of a compound (such as a VPK inhibitor) to inhibit virus growth (such as, poxvirus growth). In this assay, monolayers of cultured cells susceptible to infection by the virus of interest (e.g., poxvirus, such as vaccinia virus) are exposed to a viral inoculum. After a period of time for adsorption of the viral particles to the cells, the culture medium is removed and replaced with a nutrient agarose containing the test compound (e.g., putative VPK inhibitor). After a period of incubation (e.g., several days), plaques, which are areas where cells have died as a result of viral infection, are counted. In the case of vaccinia virus, plaques can be recognized after about 48 hours by staining with crystal violet or neutral red. An effective VPK inhibitor would be expected to reduce the number of plaques as compared to control. Particular conditions for an exemplary plaque reduction assay are described, for instance, in Landry et al. (*Antimicrob. Agents Chemother.*, 44(3): 688-692, 2000).

IV. Methods of Use

The present disclosure includes methods of inhibiting a viral protein kinase (such as, a B1 kinase, a F10 kinase or a variant (including homologs) thereof), and methods of treating poxvirus infection and/or inhibiting poxvirus growth.

In some examples, a viral protein kinase or a virus recited in a disclosed method is (or is from) a poxvirus, such as a chordopoxvirus (for example an *Orthopoxvirus, Parapoxvirus, Avipoxvirus, Capripoxvirus, Leporipoxvirus, Suipoxvirus, Molluscipoxvirus*, or *Yatapoxvirus*, or a combination thereof). Specific method embodiments involve *Orthopoxviruses* (or VPKs therefrom), including without limitation variola virus, vaccinia virus, monkeypox virus, buffalopox virus, camelpox virus, elephantpox virus, volepox virus, ectromelia virus, raccoonpox viruse, skunkpox viruse, Uasin Gishu disease virus, or taterapox virus, or a combination thereof. Some method embodiments involve the treatment or growth inhibition of variola virus (such as variola major or variola minor virus), or inhibition of variola virus VPKs. Other method embodiments involve poxviruses capable of infecting human hosts (such as monkeypox virus, vaccinia virus, buffalopox virus, cowpox virus, elephantpox virus, variola virus, bovine papular stomatitis virus, orf virus, pseudocowpox virus, sealpox virus, tanapox virus, or Yaba monkey tumor virus, or combinations thereof), or inhibition of VPKs from such human pathogens. Some methods of treatment involve the treatment of smallpox, human monkeypox, parapoxvirus infection, molluscum contagiosum virus infection, or human cowpox.

A. Treatment Methods

Disclosed methods of treating a poxvirus infection or an associated disease include administering a disclosed VPK inhibitor (and, optionally, one or more other pharmaceutical agents) to a subject in a pharmaceutically acceptable carrier and in an amount effective to treat poxvirus (such as variola virus) infection or an associated disease (such as smallpox). The treatment can be used prophylactically in any subject in a demographic group at substantial risk for such diseases; for example, children in Central Africa (who are at particular risk for monkeypox infection), or persons who have not previously been immunized with a vaccine against poxvirus infection (such as the smallpox vaccine). Alternatively, subjects can be selected using more specific criteria, such as a probable or definitive diagnosis of poxvirus infection or smallpox or other poxvirus-based disease based on, for example, clinical signs and symptoms and/or laboratory evidence of poxvirus infection. For example, smallpox (or variola virus infection) may present clinically with abrupt onset of fever and prostration with a macular rash (on the head, limbs, hands (including palms) and feet (including soles) and inside the mouth), which rash progresses to vesicles which become pustular, ulcerated, scabbed, and healed with scarring; provided that the subject recovers in the face of an approximately 40% mortality rate. Other poxvirus infections may be clinically identified based on localised pustules with scar formation (e.g., vaccinia virus), ulcerative lesions (sometimes called "milkers nodules"; e.g., cowpox); non-ulcerative milker's nodules (e.g., pseudocowpox virus); single painless, papulo-vesicular lesion on the hand, forearm or face (e.g., ORF virus); or other known symptoms of poxvirus infection.

Laboratory tests useful for identifying poxvirus infection include histological examination of a curetted or biopsied lesion, electron microscopy, immunohistochemistry using antibodies specific for poxvirus proteins, in situ hybridization or PCR using poxvirus-specific nucleic acid probes or primers, respectively, antigen detecting agar gel immune precipitation test, or other commonly known diagnostic tests (see, e.g., Mangana-Vougiouka et al., *Mol. Cell. Probes*, 14(5): 305-10, 2000).

Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described elsewhere herein.

An effective amount of a VPK inhibitor will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated. For example, this may be the amount of a VPK inhibitor necessary to prevent, inhibit, reduce or relieve poxvirus infection and/or one or more symptoms of poxvirus-related disease (such as smallpox) in a subject, preferably without causing a substantial cytotoxic effect on host cells. It is anticipated that disclosed VPK inhibitors will be well tolerated in mammalian subjects (such as humans) because the toxicity of some VPK inhibitors (for instance, NSC270718-R, NSC306711-P, NSC119913-X, NSC119915-Z, NSC119911-V, and NSC119910-U) have been tested in mammals and no toxic effects were observed at the tested doses (information available at the website dtp.nci.nih.gov/dtpstandard/servlet/InvivoScreen?testshortname=Tumor+PS+%28ip%29+in+06&sear chtype=NSC&searchlist=#####, where "#####" are the numbers only from the NSC identifier for the compound).

Therapeutically effective doses (or growth inhibitory amounts) of a disclosed VPK inhibitor or pharmaceutical composition can be determined by one of skill in the art, with a goal of achieving local (e.g., tissue) concentrations that are at least as high as the $IC_{50}$ of the applicable compound disclosed in the examples herein. An example of a dosage range is from about 0.1 to about 200 mg/kg body weight orally in single or divided doses (such as from about 5 mg/kg to about 200 mg/kg). In particular examples, a dosage range is from about 1.0 to about 100 mg/kg body weight orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated. In one exemplar oral dosage regimen, a tablet containing from about 500 mg to about 1000 mg active ingredient is administered once (e.g., a loading dose) followed by administration of ½ dosage tablets (e.g., from about 250 to about 500 mg) each 6 to 24 hours for at least 3 days.

The specific dose level and frequency of dosage for any particular subject may be varied and will depend upon a variety of factors, including the activity of the specific VPK inhibitor, the metabolic stability and length of action of that compound, the age, body weight, general health, sex and diet of the subject, mode and time of administration, rate of excretion, drug combination, and severity of the condition of the host undergoing therapy.

The present disclosure also contemplates combinations of one or more disclosed VPK inhibitors with one or more other agents or therapies useful in the treatment of poxvirus infection or poxvirus-related disease. For example, one or more disclosed VPK inhibitors may be administered in combination with effective doses of other medicinal and pharmaceutical agents, or in combination other non-medicinal therapies, such as hormone or radiation therapy. The term "administration in combination with" refers to both concurrent and sequential administration of the active agents. In some examples, the one or more other anti-viral agents or therapies include cidofovir, hexadecyloxypropyll-cidofovir, and the diacetate ester prodrug of 2-amino-7-[(1,3-dihydroxy-2-propoxy)methyl]purine (HOE961) (Smee et al., *Int. J. Antimicrobial Agents,* 23: 430-437, 2004).

B. Methods of Inhibiting Virus Growth

Other disclosed methods involve inhibiting the growth of a virus (such as a poxvirus, like variola virus) by contacting the virus with a growth inhibitory amount of a disclosed VPK inhibitor. The phrase "inhibiting virus growth" (and analogous phrases, such as inhibition of virus growth) conveys a wide-range of inhibitory effects that an agent (e.g., VPK inhibitors) may have on the normal (i.e., control) rate of virus growth. The terms "virus growth," "virus multiplication," and "virus replication" are intended to be synonymous. In some instances, duplication of a viral genome could be used as a measure of virus replication; however, duplication of a viral genome is only one possible (and optional) indicator of viral growth.

The phrase "inhibiting virus growth" (or like terminology) may be considered relative to the normal (i.e., uninhibited or control) rate of growth of a particular virus or viruses of interest (e.g., poxvirus, such as variola virus or vaccinia virus). Thus, inhibiting virus growth includes situations wherein the normal growth rate of a virus has slowed (i.e., virus number (or plaque-forming units (pfus)) increases over time, but not as rapidly as control), equals zero (i.e., there is substantially no change in virus number (or pfus) in the population over time, e.g., virus growth is approximately equal to inhibition of virus growth), or becomes negative (i.e., virus number (or pfus) decrease over time). A negative rate of virus growth can (but need not) result in clearance of substantially all viruses from a host cell or organism. In particular instances, a VPK inhibitor can reduce virus growth by at least about 60% (as compared to untreated control); for example, by at least about 70%, by at least about 75%, by at least about 80%, by at least about 85%, by at least about 90%, or even up to by about 95% or nearly 100%.

Contact between a VPK inhibitor and a poxvirus may occur in vitro (such as in culture conditions) or in vivo (such as in a subject infected with at least one poxvirus). In certain method embodiments, growth inhibitory amounts include amounts described in the Examples (for example, $IC_{50}$ concentrations). In some examples, a growth inhibitory amount is from about 10 nm to about 1 μM, from about 0.1 μM to about 10 μM, from about 1 μM to about 100 μM, from about 2.5 μM to about 250 μM, or from about 10 μM to about 500 μM (such as from about 25 μM to about 400 μM, from about 50 μM to about 300 μM, or from about 100 μM to about 250 μM).

Methods for determining inhibition of viral growth are provided in Example 1 and elsewhere in this specification.

C. Methods of Inhibiting VPK Activity

Disclosed herein are methods of inhibiting an activity of a viral protein kinase by contacting a viral protein kinase with an inhibitory amount of a disclosed VPK inhibitor. Contact between a VPK inhibitor and a viral protein kinase may occur in vitro (such as in a reaction vessel, or in a cell culture) or in vivo (such as in a subject infected with a virus (e.g., poxvirus) that expresses a viral protein kinase). Viral protein kinases have been described in detail elsewhere in this specification, but, by way of example, include the B1 kinase, F10 kinase and/or variants (such as homologs thereof) thereof. An activity of a viral protein kinase that can be inhibited by a disclosed VPK inhibitor includes kinase activity (e.g., the ability to transfer a γ-phosphate group from ATP to a substrate protein), and/or ATP and/or protein substrate affinities. Exemplary assays for measuring kinase activity (and inhibition thereof) have been provided elsewhere herein. Assays for determining substrate (e.g., ATP and/or protein substrate) binding affinities are well known in the art; for example, the reaction rate can be measured at varying concentrations of substrate, either ATP and/or peptide/protein, and substrate affinities calculated by plotting reaction rates according to Lineweaver-Burk (as described in biochemistry textbooks).

An inhibitory amount can be any amount that reduces an activity of a viral protein kinase (such as, B1 kinase and/or F10 kinase or a variant thereof). In particular instances, a VPK inhibitor can reduce an activity (such as, kinase activity) of a viral protein kinase by at least about 60% (as compared to untreated control); for example, by at least about 70%, by at least about 75%, by at least about 80%, by at least about 85%, by at least about 90%, or even up to by about 95% or nearly 100%. In certain method embodiments, inhibitory amounts include amounts described in the Examples (for example, $IC_{50}$ concentrations). In other embodiments, an inhibitory amount is from about 10 nM to about 25 µM of a disclosed VPK inhibitor (such as from about 50 nM to about 15 µM, from about 0.1 µM to about 10 µM, from about 0.5 µM to about 7 µM, or from about 1 µM to about 5 µM).

V. Pharmaceutical Compositions

The disclosed VPK inhibitors are useful, at least, for the treatment of poxvirus infection inhibiting the growth of viruses, such as poxviruses. Accordingly, pharmaceutical compositions comprising at least one disclosed VPK inhibitor are also described herein.

Formulations for pharmaceutical compositions are well known in the art. For example, *Remington's Pharmaceutical Sciences*, by E. W. Martin, Mack Publishing Co., Easton, Pa., 15th Edition, 1975, describes exemplary formulations (and components thereof) suitable for pharmaceutical delivery of disclosed VPK inhibitors. Pharmaceutical compositions comprising at least one of the disclosed VPK inhibitors can be formulated for use in human or veterinary medicine. Particular formulations of a disclosed pharmaceutical composition may depend, for example, on the mode of administration (e.g., oral or parenteral) and/or on the location of the infection to be treated. In some embodiments, formulations include a pharmaceutically acceptable carrier in addition to at least one active ingredient, such as a VPK inhibitor. In other embodiments, other medicinal or pharmaceutical agents, for example, with similar, related or complementary effects on the affliction being treated (such as poxvirus infection or smallpox), can also be included as active ingredients in a pharmaceutical composition.

Pharmaceutically acceptable carriers useful for the disclosed methods and compositions are conventional in the art.

The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

The disclosed pharmaceutical compositions may be formulated as a pharmaceutically acceptable salt of a disclosed VPK inhibitor. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydriodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in *Remington's Pharmaceutical Sciences*, 17th Edition, Mack Publishing Company, Easton, Pa., 1985. A pharmaceutically acceptable salt may also serve to adjust the osmotic pressure of the composition.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a disclosed VPK inhibitor may be formulated in unit dosage form suitable for individual administration of precise dosages. The amount of active ingredient (e.g., VPK inhibitor) administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

EXAMPLES

The following examples are provided to illustrate certain particular features and/or embodiments. These examples should not be construed to limit the invention to the particular features or embodiments described.

Example 1

Representative Materials and Methods

This Example describes materials and methods used in the following Examples 2-7.

A. Chemicals

Nineteen commercially available protein kinase inhibitors were tested for activity against poxvirus B1 or F10 kinase. ML-7, Emodin, H-89, Indirubin-3'-monoxime-5-sulphonic acid, 5-iodo-indirubin-3'-monoxime, staurosporine, KT 5720, and Ro-31-8220 were obtained from Calbiochem. Y-27632, Indirubin-3'-monoxime, SP600125, and bisindolylmaleimides I, IV and V were obtained from Alexis. IC261 was from VWR. CKI-7 was from United States Biological Corp. Epigallocatechin and apigenin were from Sigma. Gleevec/STI571 can be obtained from Novartis.

Naphthalene-bis(hexachlorocyclopentadiene) adduct, 2-nitronaphthalene-bis(hexachlorocyclopentadiene) adduct, and 3-nitro-2-naphthoic acid-bis(hexachlorocyclopentadiene) adduct were obtained from Fisher. 2-methyl-naphthalene-bis(hexachlorocyclopentadiene) adduct and 2-bromonaphthalene-bis(hexachlorocyclopentadiene) adduct were obtained from Aldrich. The foregoing chemical names are those provided by the respective supplier.

B. Viruses

Wild-type vaccinia virus and Condit's ts2 and ts25 (Condit and Motyczka, *Virology,* 113: 224-241, 1981; Traktman et al., *J. Biol. Chem.,* 264: 21458-21461, 1989) mutants of vaccinia encoding temperature-sensitive B1 protein kinase were obtained from Paula Traktman. Wild-type vaccinia virus also is commercially available from American Type Culture Collection.

C. Protein Purification

DNA sequences encoding the B1 and F10 kinases of vaccinia virus were isolated by PCR using vaccinia VTF7-3 virus (Fuerst et al., *Proc. Natl. Acad. Sci. USA,* 83: 8122-8126, 1986) as a template. The B1-encoding nucleotide sequence was amplified with the primers:

```
                                    (SEQ ID NO: 13)
5'-ATAGAATTCACATTATGAACTTTCAAGGACTT-3';
and
                                    (SEQ ID NO: 14)
5'-TATCTCGAGCACCACACTTAATAATATACACC-3'.
```

The F10-encoding nucleotide sequence was amplified using the primers:

```
5'-ATACTCGAGGAAATGGGTGTTGCCAAT-3'; (SEQ ID NO: 15)
and

5'-GCGAAGCTTTTAGTTTCCGCCATTTAT-3'. (SEQ ID NO: 16)
```

The amplified sequences were ligated into pGEX-KG (Amersham Pharmacia) to create GST fusion proteins (see, e.g., Guan and Dixon, *Anal. Biochem.,* 192: 262-267, 1991). Four mutations (changing Trp150 to Leu, His170 to Asn, Lys 364 to Glu, and Gly438 to Arg) were introduced into the gene encoding vaccinia F10 by PCR-mediated mutagenesis to convert it to a gene encoding variola F10. *E. coli* strain BL21 (DE3)pLysS (Invitrogen) was transformed with plasmids encoding GST-fusion proteins containing vaccinia B1 or variola F10. To isolate the kinases, the transformed bacteria were grown to an $OD_{600}$ of 0.6 at 37° C. and placed on ice for 30 minutes. Ethanol was added to a concentration of 2% and isopropylthiogalactoside was added to a concentration of 500 μM. Cultures were then incubated for 48 hours at 18° C. with shaking (Derrien et al., *J. Virol.,* 73: 7287-7296, 1999). Bacteria were lysed in 20 mM Tris-HCl, pH 8.4, 150 mM NaCl, 2 mM EDTA, 50 mM NaF, 0.2% lysozyme with freeze-thawing and sonication. GST-proteins were isolated with glutathione-Sepharose (Amersham).

D. Scintillation Proximity Assay

The Structural Diversity Set of compounds from the Developmental Therapeutics Program at NCI/NIH was screened to identify small molecules exhibiting inhibitory activity toward vaccinia virus B1 or variola F10 using a scintillation proximity assay (SPA). Briefly, this method involves the capture of a $^{33}P$-labeled peptide or protein onto streptavidin-coated polyvinyl toluene (PVT) SPA beads. β-particles emitted from the captured $^{33}P$-labeled substrate in close proximity to the beads are able to excite the scintillant, resulting in the generation of light which can be quantified. To efficiently harvest the greater energy associated with $^{33}P$ and to reduce non-specific signal resulting from free [$^{33}P$]ATP in solution, the beads are settled or centrifuged before counting.

The assays were carried out in 96 well Corning 3600 plates. Each reaction contained either 50 ng of GST-B1 or 150 ng of GST F10, 250 ng biotinylated casein, 0.5 μCi [γ-$^{33}P$]ATP (PerkinElmer), inhibitor (10 μM in DMSO) or DMSO in 100 μl of 10 mM sodium PIPES, pH 7.0, 5 mM $MgCl_2$, 5 mM $MnCl_2$, 1 mM dithiothreitol. EDTA (5 mM) was used as a positive control inhibitor in each dish. The reaction was allowed to proceed for 30 minutes at room temperature and was terminated by the addition of 150 μl of 5 mM EDTA, 0.1% Triton X-100 containing 200-300 ng of SPA streptavidin-coated PVT beads (Amersham). The plates were incubated for 15 minutes at room temperature, centrifuged at 1700×g for 15 minutes and then counted in a Packard Top Count microplate scintillation counter. To exclude the possibility of inhibition due to interference with the scintillant, all colored candidate inhibitors were re-analyzed by SPA following aspiration of the supernatant. Additionally, if a colored compound showed inhibitory activity, the pellet of SPA beads was dissolved in SDS polyacrylamide gel electrophoresis sample buffer and the phosphorylation of biotinylated casein was quantified by SDS polyacrylamide gel electrophoresis and PhosphorImaging.

E. In Vitro Protein Kinase Assays

SPA (described above) and gel electrophoresis were used to quantify inhibitor activity with B1 and F10. B1 and F10 kinase reactions for analysis by SDS polyacrylamide gel electrophoresis were carried out in 100 μl of a buffer containing 10 mM sodium PIPES, pH 7.0, 5 mM $MnCl_2$, 5 mM $MgCl_2$, 1 mM dithiothreitol, 50 ng of kinase, 500 ng of casein, 2.5 μCi/ml of [γ-$^{32}P$]ATP (Amersham), and 1% DMSO or 10 mM inhibitor in DMSO, as appropriate. The reaction was carried out for 30 minutes at room temperature and was terminated by the addition of 25 μl of five-fold concentrated Tris-buffered SDS sample buffer. To assay Lck, the activated F505 form of Lck was obtained from transiently transfected human 293 cells by immunoprecipitation as described by Hurley and Sefton (*Oncogene,* 4: 265-272, 1989). Lck autophosphorylation kinase assays were carried out as described above except that the reactions were terminated by the addition of 0.5 ml of 150 mM NaCl, 50 mM Tris-HCl, pH 7.2, 0.01% Triton X-100. The immunoprecipitated Lck was recovered by centrifugation and resuspended in SDS gel sample buffer. The immunoprecipitates were subjected to SDS polyacrylamide gel electrophoresis and incorporation of $^{32}P$ into casein or into Lck was quantified by PhosphorImaging using a Molecular Dynamics Typhoon 8600™ variable mode imager.

F. Virus Growth

HeLa cells were seeded at a density of $4\times10^5$ cells per well in a 12 well plate (Corning) in Dulbecco-Vogt-modified Eagle Medium (DMEM) containing 10% bovine calf serum 18-24 hours prior to use. Infection was with a multiplicity of infection of 0.03 plaque-forming units per cell. The virus inoculum was allowed to adsorb for 30 minutes in a volume of 0.075 ml. Unbound virus was removed and medium containing inhibitor or vehicle (DMSO) was then added. The infection was allowed to proceed at 37° C. for 18 hours, in the case of vesicular stomatitis virus (VSV), or 24 hours, in the case of wild-type vaccinia virus. In most examples, the medium contained 10% serum. Example 7 describes results obtained using medium containing 2% serum. Growth of ts2 or ts25 was for 24 hours at 32° C. VSV was harvested by removal of the medium. To harvest vaccinia virus, the cells were scraped off the dish into their growth medium and collected by centrifugation at 1000×g for 5 minutes. The cells were washed once in phosphate-buffered physiological saline, resuspended in DMEM containing 2.5% bovine fetal calf serum and then subjected to three cycles of freezing and thawing. Finally, the virus preparation was subjected to 6 rounds of shearing with a 1.5 inch 22 gauge syringe needle. Debris was removed by centrifugation at 750×g for 1 minute. For analysis, virus was mixed with an equal volume of 0.25% trypsin (Difco) and incubated for 30 minutes at 37° C. Debris was removed by centrifugation at 750×g for 1 minute and the virus was diluted in growth medium containing 10% bovine calf serum.

G. Plaque Assays

BSC-1 cells were seeded at a density of $5\times10^5$ cells per well in a 6 well plate (Corning) in DMEM supplemented with 10% bovine calf serum 18-24 hours prior to use. For the plaque assays, the medium was aspirated and diluted virus in 0.2 ml was allowed to adsorb for 30 minutes at 37° C., or 32° C. in the case of temperature-sensitive mutants. Following adsorption, 3 ml of medium was added to each culture. For assays of VSV, the infected monolayers were overlaid with 3.0 ml of medium containing 0.4% agarose. The dishes were incubated at 32° C. or 37° C. as appropriate. Cell monolayers were stained 18 to 40 hours later with 1% crystal violet in 20% ethanol.

Example 2

Twelve Inhibitors of Poxvirus B1 and/or F10 Protein Kinases Identified in Screening Assay Nineteen commercially available protein kinase inhibitors with diverse specificities (see Example 1) were tested for their abilities to inhibit poxvirus B1 or F10 in vitro. Of these, only staurosporine, a microbial alkaloid, inhibited B1 or F10 kinase. Because of its toxicity (Bertrand et al., *Exp. Cell Res.*, 211: 314-321, 1994), staurosporine was not consider an optimum candidate for an anti-poxvirus drug and was not further examined.

A scintillation proximity assay was then used to screen the Structural Diversity Set of compounds from the Developmental Therapeutics Program of NIH/NCI (information located at the website, dtp.nci.nih.gov/branches/dscb/diversity_explanation.html). The screen was carried out in a 96-well format, and each reaction contained GST-B1 or GST-F10, biotinylated casein (as a substrate), and $[\gamma\text{-}^{33}P]ATP$. The compound being tested was present at a concentration of 10 µM. Nineteen hundred and ninety compounds were screened with each kinase.

As shown in Table 3, eight compounds (117285-R, 119110-U, 119111-V, 119913-X, 119915-Z, 170008-Y, 270718-R, and 306711-P) inhibited GST-B1 by at least 87% of the control value. Seven of the 8 compounds identified as B1 inhibitors (119110-U, 119111-V, 119913-X, 119915-Z, 170008-Y, 270718-R, and 306711-P) also inhibited F10 by at least 81% (as compared to control). An additional four compounds (9600-Q, 13778-J, 125908-P, and 128437-O) specifically inhibited GST-F10. Two of the F10 inhibitors (9600-Q and 13778-J) exhibited considerable specificity, inhibiting B1 almost not at all at a concentration of 10 µM. In fact, 13778-J stimulated B1 in vitro.

TABLE 3

Inhibition of B1 or F10 kinase activity by 10 µM inhibitor.

| Compound | Percent activity remaining at 10 µM | |
|---|---|---|
| | B1 | F10 |
| 117285-R | 4 ± 2 | 48 ± 20 |
| 119910-U | 0 | 6 |
| 119911-V | 0 | 2 |
| 119913-X | 1 | 2 |
| 119915-Z | 1 | 4 |
| 170008-Y | 12 | 2 |
| 270718-R | 12 ± 14 | 19 ± 18 |
| 306711-P | 6 | 4 |
| 9600-Q | 93 ± 2 | 8 ± 5 |
| 13778-J | 152 ± 11 | 4 ± 4 |
| 125908-P | 23 | 8 |
| 128437-O | 47 | 12 |

Four of the B1 inhibitors, 119110-U, 119111-V, 119913-X, and 119915-Z, had similar structures (derivatives of xanthen-3-one) and were related in structure to flourescein.

The potency of each inhibitory compound was measured in vitro. As shown in Table 4, 117285-R, a derivative of 2,6-diaminopurine, was the most potent inhibitor of B1, reducing the activity of the kinase by 50% at a concentration ($IC_{50}$) of 1 µM. 13778-J, a compound containing pentavalent antimony, was the most potent inhibitor of F10, exhibiting an $IC_{50}$ of 0.3 µM.

TABLE 4

Concentrations of inhibitors required for 50% inhibition of kinase activity.

| Compound | |
|---|---|
| | $IC_{50}$ (µM) for B1 |
| 117285-R | 1.0 |
| 119910-U | 3.5 |
| 119911-V | 3.0 |
| 119913-X | 2.5 |
| 119915-Z | 3.0 |
| 170008-Y | 2.5 |
| 270718-R | 2.5 |
| 306711-P | 2.5 |
| | $IC_{50}$ (µM) for F10 |
| 9600-Q | 4.0 |
| 13778-J | 0.3 |
| 125908-P | 1.0 |
| 128437-O | 1.0 |

Example 3

Poxvirus Protein Kinase Inhibitors do not Inhibit a Cellular Protein Kinase

This Example demonstrates that the VPK inhibitors identified in Example 2 do not inhibit a cellular tyrosine protein kinase (Lck) that is expressed in a variety of vertebrate species, including humans. This result indicates that the disclosed VPK inhibitors may not coincidentally inhibit protein kinases of the host cell or organism and, therefore, may be well tolerated when administered to a subject.

Table 5 shows that five of the VPK inhibitors (119910-U, 119913-X, 306711-P, 9600-Q, and 125908-P) minimally inhibited Lck when used at a concentration of 10 μM. The other seven compounds had little effect on the activity of Lck at this concentration.

TABLE 5

Inhibition of Lck kinase activity by 10 μM inhibitor.

| Compound | Percent Lck activity remaining |
|---|---|
| 117285-R | 76 ± 25 |
| 119910-U | 59 |
| 119911-V | 70 |
| 119913-X | 56 |
| 119915-Z | 78 |
| 170008-Y | 81 |
| 270718-R | 86 ± 46 |
| 306711-P | 45 |
| 9600-Q | 53 ± 18 |
| 13778-J | 79 ± 9 |
| 125908-P | 53 |
| 128437-O | 88 |

Example 4

VPK Inhibitors Also Inhibit Poxvirus Growth In Vivo

This Example demonstrates that several of the VPK inhibitors identified in Example 2 can also inhibit poxvirus replication in living human cells. In particular, two B1 inhibitors (270718-R and 119913-X) and two F10 inhibitors (13778-J and 128437-O) inhibited the growth of wild-type vaccinia virus and, in the case of the B1 inhibitors, two vaccinia virus mutants (ts2 and ts25) in a human (HeLa) cell culture system containing 10% bovine calf serum.

The ts2 and ts25 vaccinia virus mutants each encode a temperature-sensitive B1 kinase (e.g., Rempel and Traktman, *J. Virol.*, 66: 4413-4426, 1992). It was reasoned that the level of enzymatically active viral kinase in cells infected with the mutant viruses might be limiting, even at the permissive temperature. If so, inhibition of the less active mutant kinase by a compound should be reflected in a measurable reduction in virus yield. Accordingly, the B1 inhibitors were first tested against HeLa cells infected with the ts2 and ts25 mutants. Compounds 270718-R (see FIG. 1) and 119913-X reproducibly inhibited the growth of both the ts2 and ts25 mutant viruses in HeLa cells. Compound 270718-R had the greatest effect. It reduced virus yield by an average of 86%±13% (in seven experiments) at a concentration of 100 μM (FIG. 1 shows a single experiment where 99% inhibition was observed). Compound 119913-X reduced virus yield approximately 84%±5% at a concentration of 200 μM.

The virus growth inhibitory activity of compound 270718-R was also apparent when it was tested with HeLa cells infected with wild-type vaccinia virus. Compound 270718-R inhibited wild-type vaccinia virus by 84%±15% at a concentration of 100 μM. FIG. 1 shows an example where compound 270718-R inhibited the growth of wild-type vaccinia virus by 93% at a concentration of 100 μM.

The other B1 and/or F10 inhibitors from Example 2 (117285-R, 119110-U, 119111-V, 119915-Z, 170008-Y, 306711-P, 9600-Q, and 125908-P) had no apparent effect on virus growth in HeLa cell culture. The low activity of these particular VPK inhibitors in this system may be due to an inability of the compounds to enter the cells. Accordingly, modifying such compounds to enhance cell permeability (e.g., by making the compounds more lipophilic) may markedly improve the abilities of these compounds to inhibit poxvirus growth in vivo.

For safety reasons, vaccinia viruses were used in this Example. Nonetheless, the result presented here are equally applicable to variola virus and other poxviruses. The B1 and F10 protein kinases from smallpox virus are almost identical in sequence to those in vaccinia virus. F10 differs at 4 positions out of 400 (see FIG. 3), B1 differs at 11 positions out of 300 (see FIG. 4). The number of positions that differ will vary slightly depending upon the particular vaccinia virus and variola virus strains from which the respective B1- or F10-encoding sequences are obtained. The high degree of conservation suggests that the two protein kinases are essential for smallpox virus as well as for vaccinia virus. Additionally, the Example 2 screen for F10 inhibitors was performed with variola F10; thus, it is evident that the identified compounds have activity against the smallpox virus protein kinase. It is equally straightforward to mutate vaccinia B1 to smallpox virus B1 using commonly known techniques (e.g., site-directed or PCR-based mutagenesis) to test the B1 inhibitors against the variola B1 kinase homolog.

Example 5

The 270718-R PVK Inhibitor is Non-Toxic to Human Cells

This Example demonstrates that the inhibition of vaccinia virus growth by 270718-R was specific to viruses expressing a protein kinase and was not the result of host cell toxicity.

Figure 2:
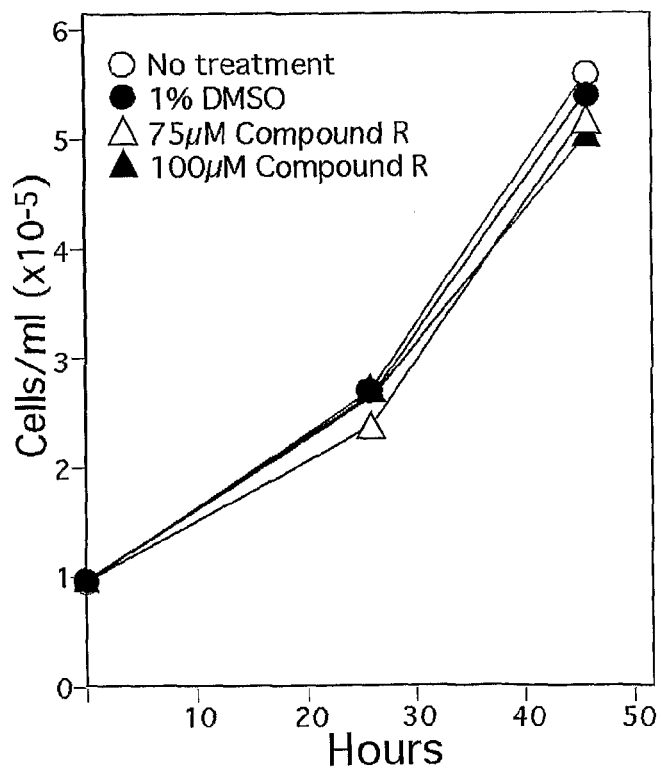
FIG. 2 shows a time course of human Ramos B cell growth in the absence (no treatment) or presence of 1% DMSO, 50 μM NSC270718-R, or 100 μM NSC270718-R. The cells were counted with a hemacytometer after growth for 24 and 48 hours at 37° C. NSC270718-R had no effect on the growth of this human cell line.
Figure 9:
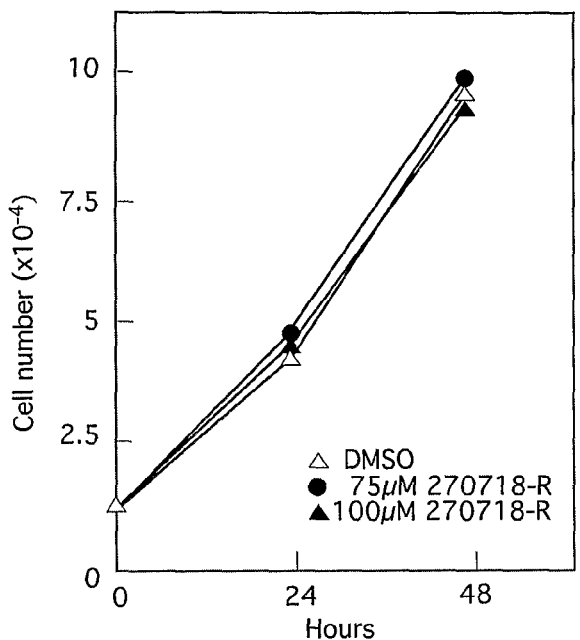
FIG. 9 is a graph illustrating that compound 270718-R does not inhibit the growth of human HeLa cells. HeLa cells were seeded at a density of $1.5 \times 10^4$ cells per well in a 48 well dish and allowed to adhere and grow for 18 hours. The growth medium was then replaced with medium containing 0.5% DMSO, or medium containing 0.5% DMSO and either 75 µM 270718-R or 100 µM 270718-R. The cells were counted with a Coulter counter 24 and 48 hours after addition of the drug. Each point represents the average of the three wells counted at each time point. The data are from a single representative experiment.

Using methods analogous to those described in Example 4, the ability of 270718-R to inhibit the growth of vesicular stomatitis virus (VSV), a rhabdovirus that does not encode a protein kinase, was tested. As shown in FIG. 1, compound 270718-R had no effect on the growth of VSV in HeLa cells, even when used at a concentration of 200 μM. Moreover, up to 100 μM 270718-R had no effect on the growth of human Ramos B cells (see FIG. 2) or HeLa cells (see FIG. 9) over a period of 48 hours.

This and the preceding Examples illustrate that the inhibition of poxvirus growth by 270718-R is due to inhibition of the viral protein kinases, rather than to some non-specific effect. At a concentration of 100 μM, 270718-R had no effect on the growth of human Ramos B cells over 48 hours. At this same concentration, 270718-R inhibited the growth of vaccinia virus over 24 hours by 86-99%. Additionally, even when used at a concentration of 200 μM, 270718-R had essentially no effect on the growth of vesicular stomatitis virus, an unrelated virus that does not encode a protein kinase. Additionally, the toxicity of this compound has been studied previously at NCI/NIH in three cell-based assays (information available at the website, dtp.nci.nih.gov/dtpstandard/servlet/dwindex?searchtype=NSC&chemnameboolean=and&outputform at=html&searchlist=270718&Submit=Submit). No growth inhibition was observed in any of the NCI/NIH-conducted cell assay when the drug was used at a concentration of 50 μM. Finally, 270718-R has been administered to mice (information available at the website, dtp.nci.nih.gov/dtp-standard/servlet/InvivoScreen?testshortname=Tumor+PS+%28ip%29+in+06&sear chtype=NSC&searchlist=270718). No toxicity in mice was noted when the compound was injected at a concentration of 200 mg/kg body weight.

Example 6

Negatively Charged Substituents May Enhance PKV Inhibitor Activity

Compound 270718-R is a tetralin (1,2,3,4-tetrahydronaphthalene) derivative having the structure:

[Chemical structure]

Commercial suppliers name compound 270718-R a "3-sulfo-2-naphthoic acid-bis(hexachlorocyclopentadiene) adduct." This nomenclature (including the numbering of the substituents) may not correspond with formal naming conventions; however, the locations of the "3" (sulfonyl group) and "2" (carboxyl group) positions in accordance with the suppliers' nomenclature can be inferred from the above structure. Several related compounds (having the same substituent numbering conventions) are commercially available, including naphthalene-bis(hexachlorocyclopentadiene) adduct, 2-methylnaphthalene-bis(hexachlorocyclopentadiene) adduct, 2-bromonaphthalene-bis(hexachlorocyclopentadiene) adduct, and 2-nitronaphthalene-bis(hexachlorocyclopentadiene) adduct. The substituents at positions "2" and "3" in each of these 270718-R-related compounds are shown in the following table:

| Compound | Substituent Position "2" | Substituent Position "3" |
|---|---|---|
| naphthalene-bis(hexachlorocyclopentadiene) adduct | —H | —H |
| 2-methylnaphthalene-bis(hexachlorocyclopentadiene) adduct | —CH$_3$ | —H |
| 2-bromonaphthalene-bis(hexachlorocyclopentadiene) adduct | —Br | —H |
| 2-nitronaphthalene-bis(hexachlorocyclopentadiene) adduct | —NO$_2$ | —H |

Using methods analogous to those described in Examples 1 and 2, none of the above-listed related compounds inhibited poxvirus B1 protein kinase activity in vitro. In addition, as shown in FIG. 1, 2-methylnaphthalene-bis(hexachlorocyclopentadiene) adduct had no effect on the growth of ts2 or ts25 vaccinia virus in HeLa cells at a concentration of 100 μM. At this same concentration, 270718-R reduced the growth of both ts2 and ts25 in HeLa cells by 99% (see Example 4).

This Example suggests that (i) substituents that are negatively charged under physiological conditions (such as carbonate, carboxylate, sulfonate, phosphonate, alkoxycarbonyl, acyloxy, alkoxy, or acyl) at the "2" and/or "3" positions, or (ii) a non-hydrogen substituent at position "3" are likely to facilitate the activity of 270718-R as a protein kinase inhibitor in vitro and poxvirus growth inhibitor in vivo.

Example 7

The Effective Concentration of 270718-R IS Reduced by Serum

The results described in Example 4 were obtained under conditions including 10% bovine calf serum. To test whether serum reduced the effective concentration of 270718-R, the potency of the compound in medium containing only 2% bovine calf serum was determined. Wild-type vaccinia virus and VSV were grown in HeLa cells in medium containing 2% bovine calf serum, 0.5% DMSO, and 10 μM, 25 μM or 50 μM 270718-R. Virus was harvested and assayed as described in Example 1.

Figure 10:
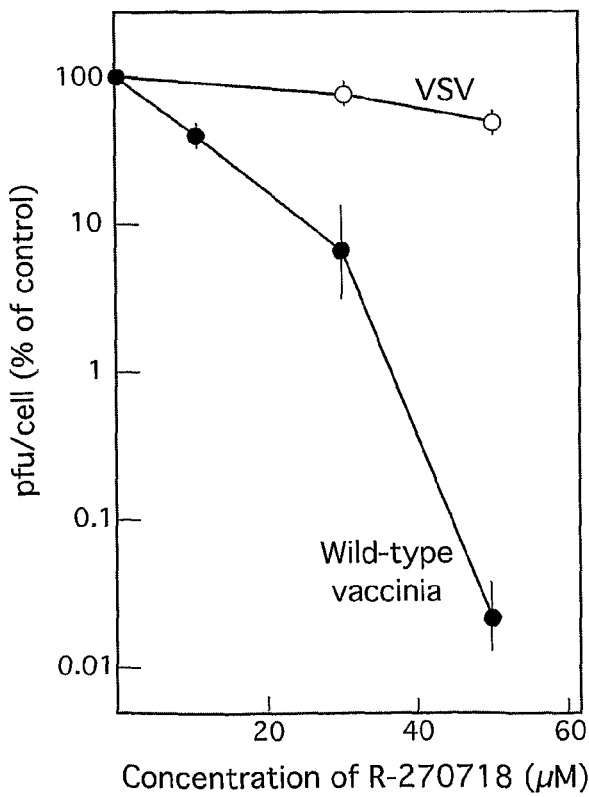
FIG. 10 shows virus yields (pfu/cell) from HeLa cells grown in 2% bovine calf serum and the indicated concentrations of 270718-R. Values are shown as a percentage of the yield from HeLa cells grown in the same medium containing vehicle (0.5% DMSO) only. The data represent the averages of three experiments. The error bars indicate the standard deviations of the data.

As shown in FIG. 10, 270718-R was approximately four-fold more active under reduced-serum conditions. The compound inhibited the growth of wild-type vaccinia virus by 90% at a concentration of approximately 25 μM and by 99% at a concentration of approximately 35 μM. The inhibition of the growth of VSV was slight under these conditions (see FIG. 10). Reduced serum did not increase the activity of the other compounds examined in the foregoing Examples.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims:

The invention claimed is:

1. A method of inhibiting a poxviral protein kinase comprising contacting the poxviral protein kinase with an inhibitory amount of at least one compound having the formula:

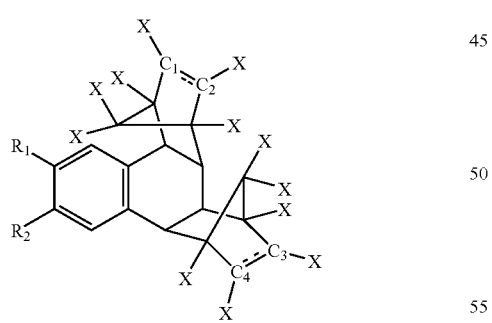

wherein $R_1$ and $R_2$ are independently sulfonyl or carbonyl-containing; X is chloro or fluoro; and $C_1$-$C_2$ and $C_3$-$C_4$ are independently a single bond or a double bond.

2. The method of claim 1, wherein the poxviral protein kinase is a B1 protein kinase or F10 protein kinase or a variant of either.

3. The method of claim 1, wherein sulfonyl is sulfonic acid, alkylsulfonyl, or arylsulfonyl; and carbonyl-containing is carboxylic acid or carboxylic acid ester.

4. The method of claim 1, wherein the at least one compound is a 3-sulfo-2-napthoic acid-bis(hexachlorocyclopentadiene) adduct.

5. The method of claim 1, wherein X is chloro.

6. The method of claim 1, wherein the at least one compound is NSC270718R.

7. A method of inhibiting poxvirus growth comprising contacting the poxvirus with a growth inhibitory amount of at least one compound having the formula:

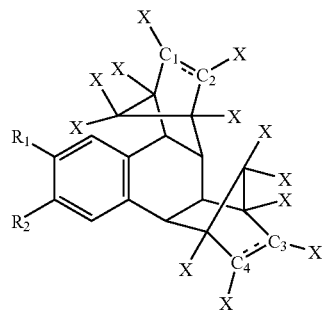

wherein $R_1$ and $R_2$ are independently sulfonyl or carbonyl-containing; X is chloro or fluoro; and $C_1$-$C_2$ and $C_3$-$C_4$ are independently a single bond or a double bond.

8. The method of claim 7, wherein the poxvirus is a member of the chordopoxvirinae subfamily.

9. The method of claim 7, wherein sulfonyl is sulfonic acid, alkylsulfonyl, or arylsulfonyl; and carbonyl-containing is carboxylic acid or carboxylic acid ester.

10. The method of claim 7, wherein the at least one compound is a 3-sulfo-2-napthoic acid-bis(hexachlorocyclopentadiene) adduct.

11. The method of claim 7, wherein the poxvirus is variola virus or vaccinia virus.

12. The method of claim 7, wherein the growth inhibitory amount is no more than about 250 µM.

13. The method of claim 7, wherein the at least one compound is NSC270718R.

14. The method of claim 7, wherein the poxvirus of the poxvirus is a vaccinia virus, variola virus, monkeypox virus, buffalopox virus, cowpox virus, elephantpox virus, bovine papular stomatitis virus, orf virus, pseudocowpox virus, sealpox virus, tanapox virus, or Yaba monkey tumor virus, or combinations thereof.

15. The method of claim 8, wherein the member of the chordopoxvirinae subfamily is an *Orthopoxvirus, Parapoxvirus, Avipoxvirus, Capripoxvirus, Leporipoxvirus, Suipoxvirus, Molluscisposvirus,* or *Yatapoxvirus*.

16. A method for treating poxvirus infection in a subject, comprising administering to a subject a therapeutically effective amount of at least one compound having the formula:

wherein $R_1$ and $R_2$ are independently sulfonyl or carbonyl-containing; X is chloro or fluoro; and $C_1$-$C_2$ and $C_3$-$C_4$ are independently a single bond or a double bond; and wherein administering the at least one compound treats poxvirus infection in the subject.

17. The method of claim 16, wherein the poxvirus of the poxvirus infection is vaccinia virus, variola virus, monkeypox virus, buffalopox virus, cowpox virus, elephantpox virus, bovine papular stomatitis virus, orf virus, pseudocowpox virus, sealpox virus, tanapox virus, or Yaba monkey tumor virus, or combinations thereof.

18. The method of claim 16, wherein sulfonyl is sulfonic acid, alkylsulfonyl, or arylsulfonyl; and carbonyl-containing is carboxylic acid or carboxylic acid ester.

19. The method of claim 16, wherein the at least one compound is a 3-sulfo-2-napthoic acid-bis(hexachlorocyclopentadiene) adduct.

20. The method of claim 16, wherein the poxvirus is a member of the chordopoxvirinae subfamily.

21. The method of claim 16, wherein the poxvirus is vaccinia virus or variola virus.

22. The method of claim 16, wherein the subject is a human.

23. The method of claim 16, wherein the therapeutically effective amount is from about 5 mg/kg to about 200 mg/kg per day.

24. The method of claim 16, wherein the at least one compound is NSC270718R.

25. The method of claim 20, wherein the member of the chordopoxvirinae subfamily is an *Orthopoxvirus, Parapoxvirus, Avipoxvirus, Capripoxvirus, Leporipoxvirus, Suipoxvirus, Molluscisposvirus,* or *Yatapoxvirus*

* * * * *

UNITED STATES PATENT AND TRADEMARK OFFICE
CERTIFICATE OF CORRECTION

| | | |
|---|---|---|
| PATENT NO. | : 8,076,375 B2 | Page 1 of 1 |
| APPLICATION NO. | : 12/090081 | |
| DATED | : December 13, 2011 | |
| INVENTOR(S) | : Sefton and Schulte | |

It is certified that error appears in the above-identified patent and that said Letters Patent is hereby corrected as shown below:

In the Specification:

Column 43, line 22, "5H-bond donors" should be --5 H-bond donors--.

Column 43, line 27, "10H-bond" should be --10 H-bond--.

Column 43, line 59, "cells. A" should be --cells). A--.

Column 48, line 12, "in combination other" should be --in combination with other--.

Column 53, line 58, "not consider an" should be --not considered an--.

Column 56, line 67, "putform at" should be --putformat--.

In the Claims:

Column 299, lines 13-14, claim 14, "wherein the poxvirus of the poxvirus is a" should be --wherein the poxvirus is a--.

Signed and Sealed this
Fifteenth Day of May, 2012

David J. Kappos
*Director of the United States Patent and Trademark Office*

SEQUENCE LISTING

<160> NUMBER OF SEQ ID NOS: 108

<210> SEQ ID NO 1
<211> LENGTH: 903
<212> TYPE: DNA

<213> ORGANISM: Vaccinia Virus (Copenhagen Strain)
<220> FEATURE:
<221> NAME/KEY: CDS
<222> LOCATION: (1)..(903)

<400> SEQUENCE: 1

| | | | | | | | | | | | | | | | | |
|---|---|---|---|---|---|---|---|---|---|---|---|---|---|---|---|---|
| atg | aac | ttt | caa | gga | ctt | gtg | tta | act | gac | aat | tgc | aaa | aat | caa | tgg | 48 |
| Met | Asn | Phe | Gln | Gly | Leu | Val | Leu | Thr | Asp | Asn | Cys | Lys | Asn | Gln | Trp | |
| 1 | | | | 5 | | | | | 10 | | | | | 15 | | |
| gtc | gtt | gga | cca | tta | ata | gga | aaa | ggt | gga | ttt | ggt | agt | att | tat | act | 96 |
| Val | Val | Gly | Pro | Leu | Ile | Gly | Lys | Gly | Gly | Phe | Gly | Ser | Ile | Tyr | Thr | |
| | | | 20 | | | | | 25 | | | | | 30 | | | |
| act | aat | gac | aat | aat | tat | gta | gta | aaa | ata | gag | ccc | aaa | gct | aac | gga | 144 |
| Thr | Asn | Asp | Asn | Asn | Tyr | Val | Val | Lys | Ile | Glu | Pro | Lys | Ala | Asn | Gly | |
| | | 35 | | | | | 40 | | | | | 45 | | | | |
| tca | tta | ttt | acc | gaa | cag | gca | ttt | tat | act | aga | gta | ctt | aaa | cca | tcc | 192 |
| Ser | Leu | Phe | Thr | Glu | Gln | Ala | Phe | Tyr | Thr | Arg | Val | Leu | Lys | Pro | Ser | |
| 50 | | | | | 55 | | | | | 60 | | | | | | |
| gtt | atc | gaa | gaa | tgg | aaa | aaa | tct | cac | aat | ata | aag | cac | gta | ggt | ctt | 240 |
| Val | Ile | Glu | Glu | Trp | Lys | Lys | Ser | His | Asn | Ile | Lys | His | Val | Gly | Leu | |
| 65 | | | | | 70 | | | | | 75 | | | | | 80 | |
| atc | acg | tgc | aag | gca | ttt | ggt | cta | tac | aaa | tcc | att | aat | gtg | gaa | tat | 288 |
| Ile | Thr | Cys | Lys | Ala | Phe | Gly | Leu | Tyr | Lys | Ser | Ile | Asn | Val | Glu | Tyr | |
| | | | | 85 | | | | | 90 | | | | | 95 | | |
| aga | ttc | ttg | gta | att | aat | aga | tta | ggt | gta | gat | cta | gat | gcg | gtg | atc | 336 |
| Arg | Phe | Leu | Val | Ile | Asn | Arg | Leu | Gly | Val | Asp | Leu | Asp | Ala | Val | Ile | |
| | | | | 100 | | | | | 105 | | | | | 110 | | |
| aga | gcc | aat | aat | aat | aga | tta | cca | aaa | agg | tcg | gtg | atg | tta | atc | gga | 384 |
| Arg | Ala | Asn | Asn | Asn | Arg | Leu | Pro | Lys | Arg | Ser | Val | Met | Leu | Ile | Gly | |
| | | | 115 | | | | | 120 | | | | | 125 | | | |
| atc | gaa | atc | tta | aat | acc | ata | caa | ttt | atg | cac | gag | caa | gga | tat | tct | 432 |
| Ile | Glu | Ile | Leu | Asn | Thr | Ile | Gln | Phe | Met | His | Glu | Gln | Gly | Tyr | Ser | |
| | | 130 | | | | | 135 | | | | | 140 | | | | |
| cac | gga | gat | att | aaa | gcg | agt | aat | ata | gtc | ttg | gat | caa | ata | gat | aag | 480 |
| His | Gly | Asp | Ile | Lys | Ala | Ser | Asn | Ile | Val | Leu | Asp | Gln | Ile | Asp | Lys | |
| 145 | | | | | 150 | | | | | 155 | | | | | 160 | |
| aat | aaa | tta | tat | cta | gtg | gat | tac | gga | ttg | gtt | tct | aaa | ttc | atg | tct | 528 |
| Asn | Lys | Leu | Tyr | Leu | Val | Asp | Tyr | Gly | Leu | Val | Ser | Lys | Phe | Met | Ser | |
| | | | 165 | | | | | 170 | | | | | 175 | | | |
| aat | ggc | gaa | cat | gtt | cca | ttt | ata | aga | aat | cca | aat | aaa | atg | gat | aac | 576 |
| Asn | Gly | Glu | His | Val | Pro | Phe | Ile | Arg | Asn | Pro | Asn | Lys | Met | Asp | Asn | |
| | | | 180 | | | | | 185 | | | | | 190 | | | |
| ggt | act | cta | gaa | ttt | aca | cct | ata | gat | tcg | cat | aaa | gga | tac | gtt | gta | 624 |
| Gly | Thr | Leu | Glu | Phe | Thr | Pro | Ile | Asp | Ser | His | Lys | Gly | Tyr | Val | Val | |
| | | 195 | | | | | 200 | | | | | 205 | | | | |
| tct | aga | cgt | gga | gat | cta | gaa | aca | ctt | gga | tat | tgt | atg | att | aga | tgg | 672 |
| Ser | Arg | Arg | Gly | Asp | Leu | Glu | Thr | Leu | Gly | Tyr | Cys | Met | Ile | Arg | Trp | |
| | 210 | | | | | 215 | | | | | 220 | | | | | |
| ttg | gga | ggt | atc | ttg | cca | tgg | act | aag | ata | tct | gaa | aca | aag | aat | tgt | 720 |
| Leu | Gly | Gly | Ile | Leu | Pro | Trp | Thr | Lys | Ile | Ser | Glu | Thr | Lys | Asn | Cys | |
| 225 | | | | | 230 | | | | | 235 | | | | | 240 | |
| gca | tta | gta | agt | gcc | aca | aaa | cag | aaa | tat | gtt | aac | aat | act | gcg | act | 768 |
| Ala | Leu | Val | Ser | Ala | Thr | Lys | Gln | Lys | Tyr | Val | Asn | Asn | Thr | Ala | Thr | |
| | | | | 245 | | | | | 250 | | | | | 255 | | |
| ttg | tta | atg | acc | agt | ttg | caa | tat | gca | cct | aga | gaa | ttg | ctg | caa | tat | 816 |
| Leu | Leu | Met | Thr | Ser | Leu | Gln | Tyr | Ala | Pro | Arg | Glu | Leu | Leu | Gln | Tyr | |
| | | | 260 | | | | | 265 | | | | | 270 | | | |
| att | acc | atg | gta | aac | tct | ttg | aca | tat | ttt | gag | gaa | ccc | aat | tac | gac | 864 |
| Ile | Thr | Met | Val | Asn | Ser | Leu | Thr | Tyr | Phe | Glu | Glu | Pro | Asn | Tyr | Asp | |
| | | 275 | | | | | 280 | | | | | 285 | | | | |
| gag | ttt | cgg | cac | ata | tta | atg | cag | ggt | gta | tat | tat | taa | | | | 903 |

```
Glu Phe Arg His Ile Leu Met Gln Gly Val Tyr Tyr
    290                 295                 300

<210> SEQ ID NO 2
<211> LENGTH: 300
<212> TYPE: PRT
<213> ORGANISM: Vaccinia Virus (Copenhagen Strain)

<400> SEQUENCE: 2

Met Asn Phe Gln Gly Leu Val Leu Thr Asp Asn Cys Lys Asn Gln Trp
  1               5                  10                  15

Val Val Gly Pro Leu Ile Gly Lys Gly Phe Gly Ser Ile Tyr Thr
             20                  25                  30

Thr Asn Asp Asn Asn Tyr Val Val Lys Ile Glu Pro Lys Ala Asn Gly
             35                  40                  45

Ser Leu Phe Thr Glu Gln Ala Phe Tyr Thr Arg Val Leu Lys Pro Ser
 50                  55                  60

Val Ile Glu Glu Trp Lys Lys Ser His Asn Ile Lys Val Gly Leu
 65                  70                  75                  80

Ile Thr Cys Lys Ala Phe Gly Leu Tyr Lys Ser Ile Asn Val Glu Tyr
                 85                  90                  95

Arg Phe Leu Val Ile Asn Arg Leu Gly Val Asp Leu Asp Ala Val Ile
                100                 105                 110

Arg Ala Asn Asn Asn Arg Leu Pro Lys Arg Ser Val Met Leu Ile Gly
                115                 120                 125

Ile Glu Ile Leu Asn Thr Ile Gln Phe Met His Glu Gln Gly Tyr Ser
            130                 135                 140

His Gly Asp Ile Lys Ala Ser Asn Ile Val Leu Asp Gln Ile Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
                180                 185                 190

Gly Thr Leu Glu Phe Thr Pro Ile Asp Ser His Lys Gly Tyr Val Val
            195                 200                 205

Ser Arg Arg Gly Asp Leu Glu Thr Leu Gly Tyr Cys Met Ile Arg Trp
210                 215                 220

Leu Gly Gly Ile Leu Pro Trp Thr Lys Ile Ser Glu Thr Lys Asn Cys
225                 230                 235                 240

Ala Leu Val Ser Ala Thr Lys Gln Lys Tyr Val Asn Asn Thr Ala Thr
                245                 250                 255

Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
        275                 280                 285

Glu Phe Arg His Ile Leu Met Gln Gly Val Tyr Tyr
    290                 295                 300

<210> SEQ ID NO 3
<211> LENGTH: 1320
<212> TYPE: DNA
<213> ORGANISM: Vaccinia Virus (Copenhagen Strain)
<220> FEATURE:
<221> NAME/KEY: CDS
<222> LOCATION: (1)..(1320)

<400> SEQUENCE: 3 atg ggt gtt gcc aat gat tca tcc cct gaa tat caa tgg atg tct ccc         48
```

```
                                              -continued

Met Gly Val Ala Asn Asp Ser Ser Pro Glu Tyr Gln Trp Met Ser Pro
1               5                   10                  15 cat aga tta tca gat act gtt ata tta gga gac tgt tta tat ttt aac           96
His Arg Leu Ser Asp Thr Val Ile Leu Gly Asp Cys Leu Tyr Phe Asn
             20              25                  30 aac ata atg tcc caa tta gat tta cac caa aat tgg gct ccg tca gtt          144
Asn Ile Met Ser Gln Leu Asp Leu His Gln Asn Trp Ala Pro Ser Val
         35              40                  45 aga ttg tta aat tat ttt aag aat ttt aat agg gaa aca cta cta aag          192
Arg Leu Leu Asn Tyr Phe Lys Asn Phe Asn Arg Glu Thr Leu Leu Lys
     50              55                  60 ata gaa gag aat gat tac att aat tca tca ttt ttc caa caa aag gat          240
Ile Glu Glu Asn Asp Tyr Ile Asn Ser Ser Phe Phe Gln Gln Lys Asp
65              70                  75                  80 aaa cga ttt tat cct ata aac gac gat ttt tat cac ata tct aca gga          288
Lys Arg Phe Tyr Pro Ile Asn Asp Asp Phe Tyr His Ile Ser Thr Gly
                 85                  90                  95 gga tat ggt ata gtt ttt aag ata gat aac tat gta gta aaa ttt gta          336
Gly Tyr Gly Ile Val Phe Lys Ile Asp Asn Tyr Val Val Lys Phe Val
            100                 105                 110 ttc gag gcc aca aaa tta tat agt ccc atg gaa act acg gcg gag ttc          384
Phe Glu Ala Thr Lys Leu Tyr Ser Pro Met Glu Thr Thr Ala Glu Phe
        115                 120                 125 aca gta ccc aaa ttt cta tac aac aat cta aag gga gat gaa aaa aaa          432
Thr Val Pro Lys Phe Leu Tyr Asn Asn Leu Lys Gly Asp Glu Lys Lys
    130                 135                 140 tta atc gtg tgt gcg tgg gcc atg gga tta aac tat aaa tta aca ttt          480
Leu Ile Val Cys Ala Trp Ala Met Gly Leu Asn Tyr Lys Leu Thr Phe
145                 150                 155                 160 tta cat act ctg tat aaa cgt gtt ctt cat atg ttg cta tta ttg ata          528
Leu His Thr Leu Tyr Lys Arg Val Leu His Met Leu Leu Leu Leu Ile
                165                 170                 175 caa act atg gat ggt cag gaa ctc tca ttg aga tat tct tct aaa gtt          576
Gln Thr Met Asp Gly Gln Glu Leu Ser Leu Arg Tyr Ser Ser Lys Val
            180                 185                 190 ttt cta aag gcg ttt aac gag aga aag gac agt atc aaa ttc gtg aaa          624
Phe Leu Lys Ala Phe Asn Glu Arg Lys Asp Ser Ile Lys Phe Val Lys
        195                 200                 205 tta cta tcc cac ttt tac ccg gca gtt att aac agt aat att aat gtt          672
Leu Leu Ser His Phe Tyr Pro Ala Val Ile Asn Ser Asn Ile Asn Val
    210                 215                 220 ata aac tat ttt aac cgc atg ttt cac ttt ttc gaa cat gaa aag aga          720
Ile Asn Tyr Phe Asn Arg Met Phe His Phe Phe Glu His Glu Lys Arg
225                 230                 235                 240 act aac tac gaa tat gaa aga gga aac att ata att ttt ccc cta gca          768
Thr Asn Tyr Glu Tyr Glu Arg Gly Asn Ile Ile Ile Phe Pro Leu Ala
                245                 250                 255 ctg tat tcg gca gat aaa gta gat acc gag tta gct atc aaa tta gga          816
Leu Tyr Ser Ala Asp Lys Val Asp Thr Glu Leu Ala Ile Lys Leu Gly
            260                 265                 270 ttt aaa tct ttg gta caa tac ata aag ttt atc ttt tta cag atg gct          864
Phe Lys Ser Leu Val Gln Tyr Ile Lys Phe Ile Phe Leu Gln Met Ala
        275                 280                 285 ctg tta tac att aaa atc tac gaa cta cca tgc tgc gac aac ttt tta          912
Leu Leu Tyr Ile Lys Ile Tyr Glu Leu Pro Cys Cys Asp Asn Phe Leu
    290                 295                 300 cac gca gat ctt aaa ccc gat aat atc tta ctt ttt gat tcc aat gaa          960
His Ala Asp Leu Lys Pro Asp Asn Ile Leu Leu Phe Asp Ser Asn Glu
305                 310                 315                 320 cca ata ata att cat cta aag gat aaa aag ttt gtt ttt aat gaa cgt         1008
```

```
                Pro Ile Ile Ile His Leu Lys Asp Lys Lys Phe Val Phe Asn Glu Arg
                                325                 330                 335 att aaa tcg gca tta aac gac ttt gac ttt tcc caa gtg gct gga atc          1056
Ile Lys Ser Ala Leu Asn Asp Phe Asp Phe Ser Gln Val Ala Gly Ile
            340                 345                 350 att aac aag aaa ata aaa aac aat ttc aaa gtt aaa cat aac tgg tat          1104
Ile Asn Lys Lys Ile Lys Asn Asn Phe Lys Val Lys His Asn Trp Tyr
            355                 360                 365 tac gat ttc cat ttc ttt gtt cat act tta tta aaa aca tat cca gaa          1152
Tyr Asp Phe His Phe Phe Val His Thr Leu Leu Lys Thr Tyr Pro Glu
        370                 375                 380 atc gaa aaa gat atc gaa ttt agt acg gca ttg gaa gaa ttc atc atg          1200
Ile Glu Lys Asp Ile Glu Phe Ser Thr Ala Leu Glu Glu Phe Ile Met
385                 390                 395                 400 tgt acc aaa aca gac tgt gat aaa tat aga tta aag gtt tcc att ctt          1248
Cys Thr Lys Thr Asp Cys Asp Lys Tyr Arg Leu Lys Val Ser Ile Leu
                405                 410                 415 cac cca att agt ttc ttg gaa aaa ttt att atg aga gac att ttc tca          1296
His Pro Ile Ser Phe Leu Glu Lys Phe Ile Met Arg Asp Ile Phe Ser
            420                 425                 430 gac tgg ata aat ggc gga aac taa                                           1320
Asp Trp Ile Asn Gly Gly Asn
            435

<210> SEQ ID NO 4
<211> LENGTH: 439
<212> TYPE: PRT
<213> ORGANISM: Vaccinia Virus (Copenhagen Strain)

<400> SEQUENCE: 4

Met Gly Val Ala Asn Asp Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Arg Glu Thr Leu Leu Lys
    50                  55                  60

Ile Glu Glu Asn Asp Tyr Ile Asn Ser Ser Phe Phe Gln Gln Lys Asp
65                  70                  75                  80

Lys Arg Phe Tyr Pro Ile Asn Asp Asp Phe Tyr His Ile Ser Thr Gly
                85                  90                  95

Gly Tyr Gly Ile Val Phe Lys Ile Asp Asn Tyr Val Val Lys Phe Val
            100                 105                 110

Phe Glu Ala Thr Lys Leu Tyr Ser Pro Met Glu Thr Thr Ala Glu Phe
        115                 120                 125

Thr Val Pro Lys Phe Leu Tyr Asn Asn Leu Lys Gly Asp Glu Lys Lys
    130                 135                 140

Leu Ile Val Cys Ala Trp Ala Met Gly Leu Asn Tyr Lys Leu Thr Phe
145                 150                 155                 160

Leu His Thr Leu Tyr Lys Arg Val Leu His Met Leu Leu Leu Leu Ile
                165                 170                 175

Gln Thr Met Asp Gly Gln Glu Leu Ser Leu Arg Tyr Ser Ser Lys Val
            180                 185                 190

Phe Leu Lys Ala Phe Asn Glu Arg Lys Asp Ser Ile Lys Phe Val Lys
        195                 200                 205

Leu Leu Ser His Phe Tyr Pro Ala Val Ile Asn Ser Asn Ile Asn Val
    210                 215                 220
```

```
Ile Asn Tyr Phe Asn Arg Met Phe His Phe Glu His Glu Lys Arg
225                 230                 235                 240

Thr Asn Tyr Glu Tyr Glu Arg Gly Asn Ile Ile Ile Phe Pro Leu Ala
            245                 250                 255

Leu Tyr Ser Ala Asp Lys Val Asp Thr Glu Leu Ala Ile Lys Leu Gly
        260                 265                 270

Phe Lys Ser Leu Val Gln Tyr Ile Lys Phe Ile Phe Leu Gln Met Ala
    275                 280                 285

Leu Leu Tyr Ile Lys Ile Tyr Glu Leu Pro Cys Cys Asp Asn Phe Leu
290                 295                 300

His Ala Asp Leu Lys Pro Asp Asn Ile Leu Leu Phe Asp Ser Asn Glu
305                 310                 315                 320

Pro Ile Ile Ile His Leu Lys Asp Lys Lys Phe Val Phe Asn Glu Arg
                325                 330                 335

Ile Lys Ser Ala Leu Asn Asp Phe Asp Phe Ser Gln Val Ala Gly Ile
            340                 345                 350

Ile Asn Lys Lys Ile Lys Asn Phe Lys Val Lys His Asn Trp Tyr
        355                 360                 365

Tyr Asp Phe His Phe Phe Val His Thr Leu Leu Lys Thr Tyr Pro Glu
    370                 375                 380

Ile Glu Lys Asp Ile Glu Phe Ser Thr Ala Leu Glu Glu Phe Ile Met
385                 390                 395                 400

Cys Thr Lys Thr Asp Cys Asp Lys Tyr Arg Leu Lys Val Ser Ile Leu
                405                 410                 415

His Pro Ile Ser Phe Leu Glu Lys Phe Ile Met Arg Asp Ile Phe Ser
            420                 425                 430

Asp Trp Ile Asn Gly Gly Asn
        435

<210> SEQ ID NO 5
<211> LENGTH: 1320
<212> TYPE: DNA
<213> ORGANISM: Vaccinia Virus (Ankara Strain)
<220> FEATURE:
<221> NAME/KEY: CDS
<222> LOCATION: (1)..(1320)

<400> SEQUENCE: 5 atg ggt gtt gcc aat gat tca tcc cct gaa tat caa tgg atg tct ccc     48
Met Gly Val Ala Asn Asp Ser Ser Pro Glu Tyr Gln Trp Met Ser Pro
1               5                   10                  15 cat aga tta tca gat act gtt ata tta gga gac tgt ttg tat ttt aac     96
His Arg Leu Ser Asp Thr Val Ile Leu Gly Asp Cys Leu Tyr Phe Asn
                20                  25                  30 aat ata atg tcc caa tta gat tta cac caa aat tgg gct cca tca gtt    144
Asn Ile Met Ser Gln Leu Asp Leu His Gln Asn Trp Ala Pro Ser Val
            35                  40                  45 aga ttg tta aat tat ttt aag aat ttt aat aag gaa aca cta cta aag    192
Arg Leu Leu Asn Tyr Phe Lys Asn Phe Asn Lys Glu Thr Leu Leu Lys
        50                  55                  60 ata gaa gag aat gat tac att aat tca tcc ttt ttc caa caa aag gat    240
Ile Glu Glu Asn Asp Tyr Ile Asn Ser Ser Phe Phe Gln Gln Lys Asp
65                  70                  75                  80 aaa cga ttt tat cct ata aac gac gat ttt tat cac ata tct aca gga    288
Lys Arg Phe Tyr Pro Ile Asn Asp Asp Phe Tyr His Ile Ser Thr Gly
                85                  90                  95 gga tat ggt ata gtc ttt aag ata gat aac tat gta gta aaa ttt gta    336
Gly Tyr Gly Ile Val Phe Lys Ile Asp Asn Tyr Val Val Lys Phe Val
```

```
                100                 105                 110
ttc gag gcc aca aaa tta tat agt ccc atg gaa act acg gcg gag ttc      384
Phe Glu Ala Thr Lys Leu Tyr Ser Pro Met Glu Thr Thr Ala Glu Phe
            115                 120                 125 aca gta ccc aaa ttt cta tac aac aat cta aag gga gat gaa aaa aaa      432
Thr Val Pro Lys Phe Leu Tyr Asn Asn Leu Lys Gly Asp Glu Lys Lys
        130                 135                 140 tta atc gtg tgt gcg tgg gcc atg gga tta aac tat aaa tta aca ttt      480
Leu Ile Val Cys Ala Trp Ala Met Gly Leu Asn Tyr Lys Leu Thr Phe
145                 150                 155                 160 tta cat act ctg tat aaa cgt gtt ctt cat atg ttg cta tta ttg ata      528
Leu His Thr Leu Tyr Lys Arg Val Leu His Met Leu Leu Leu Leu Ile
                165                 170                 175 caa act atg gat ggt cag gaa cta tca ttg aga tat tct tct aaa gtt      576
Gln Thr Met Asp Gly Gln Glu Leu Ser Leu Arg Tyr Ser Ser Lys Val
            180                 185                 190 ttt tta aag gcg ttt aac gag aga aag gac agt atc aaa ttc gtg aaa      624
Phe Leu Lys Ala Phe Asn Glu Arg Lys Asp Ser Ile Lys Phe Val Lys
        195                 200                 205 tta cta tcc cac ttt tat ccg gca gtt att aac agt aat att aat gtt      672
Leu Leu Ser His Phe Tyr Pro Ala Val Ile Asn Ser Asn Ile Asn Val
210                 215                 220 ata aac tat ttt aac cgc atg ttt cac ttt ttc gaa cat gaa aag aga      720
Ile Asn Tyr Phe Asn Arg Met Phe His Phe Phe Glu His Glu Lys Arg
225                 230                 235                 240 act aac tac gaa tac gaa aga gga aat att ata att ttt ccc cta gca      768
Thr Asn Tyr Glu Tyr Glu Arg Gly Asn Ile Ile Ile Phe Pro Leu Ala
                245                 250                 255 ctg tat tcg gca gat aaa gta gat acc gag cta gct atc aaa tta gga      816
Leu Tyr Ser Ala Asp Lys Val Asp Thr Glu Leu Ala Ile Lys Leu Gly
            260                 265                 270 ttt aaa tct ttg gta caa tac ata aag ttt atc ttt tta cag atg gct      864
Phe Lys Ser Leu Val Gln Tyr Ile Lys Phe Ile Phe Leu Gln Met Ala
        275                 280                 285 ctg tta tac att aaa att tac gaa cta cca tgc tgc gac aac ttt tta      912
Leu Leu Tyr Ile Lys Ile Tyr Glu Leu Pro Cys Cys Asp Asn Phe Leu
290                 295                 300 cac gca gat ctt aaa ccc gat aat atc tta ctt ttt gat tcc aat gaa      960
His Ala Asp Leu Lys Pro Asp Asn Ile Leu Leu Phe Asp Ser Asn Glu
305                 310                 315                 320 cca ata ata att cat cta aag gat aaa aag ttt gtt ttt aat gaa cgt     1008
Pro Ile Ile Ile His Leu Lys Asp Lys Lys Phe Val Phe Asn Glu Arg
                325                 330                 335 att aaa tcg gca tta aac gac ttt gac ttt tcc caa gtg gct gga atc     1056
Ile Lys Ser Ala Leu Asn Asp Phe Asp Phe Ser Gln Val Ala Gly Ile
            340                 345                 350 att aac aag aaa ata aaa aac aat ttc aaa gtt aaa cat aac tgg tat     1104
Ile Asn Lys Lys Ile Lys Asn Asn Phe Lys Val Lys His Asn Trp Tyr
        355                 360                 365 tac gat ttc cat ttc ttt gtt cat act tta tta aaa aca tat cca gaa     1152
Tyr Asp Phe His Phe Phe Val His Thr Leu Leu Lys Thr Tyr Pro Glu
370                 375                 380 atc gaa aaa gat atc gaa ttt agt acg gca ttg gaa gaa ttc atc atg     1200
Ile Glu Lys Asp Ile Glu Phe Ser Thr Ala Leu Glu Glu Phe Ile Met
385                 390                 395                 400 tgt acc aaa aca gac tgt gat aaa tat aga tta aag gtt tcc att ctt     1248
Cys Thr Lys Thr Asp Cys Asp Lys Tyr Arg Leu Lys Val Ser Ile Leu
                405                 410                 415 cac cca att agt ttc ttg gaa aaa ttt att atg aga gac att ttc tca     1296
His Pro Ile Ser Phe Leu Glu Lys Phe Ile Met Arg Asp Ile Phe Ser
```

```
                420             425             430
gac tgg ata aat ggc gga aac taa                             1320
Asp Trp Ile Asn Gly Gly Asn
        435
```

<210> SEQ ID NO 6
<211> LENGTH: 439
<212> TYPE: PRT
<213> ORGANISM: Vaccinia Virus (Ankara Strain)

<400> SEQUENCE: 6

```
Met Gly Val Ala Asn Asp Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Lys Glu Thr Leu Leu Lys
    50                  55                  60

Ile Glu Glu Asn Asp Tyr Ile Asn Ser Ser Phe Phe Gln Gln Lys Asp
65                  70                  75                  80

Lys Arg Phe Tyr Pro Ile Asn Asp Asp Phe Tyr His Ile Ser Thr Gly
                85                  90                  95

Gly Tyr Gly Ile Val Phe Lys Ile Asp Asn Tyr Val Val Lys Phe Val
            100                 105                 110

Phe Glu Ala Thr Lys Leu Tyr Ser Pro Met Glu Thr Thr Ala Glu Phe
        115                 120                 125

Thr Val Pro Lys Phe Leu Tyr Asn Asn Leu Lys Gly Asp Glu Lys Lys
    130                 135                 140

Leu Ile Val Cys Ala Trp Ala Met Gly Leu Asn Tyr Lys Leu Thr Phe
145                 150                 155                 160

Leu His Thr Leu Tyr Lys Arg Val Leu His Met Leu Leu Leu Leu Ile
                165                 170                 175

Gln Thr Met Asp Gly Gln Glu Leu Ser Leu Arg Tyr Ser Ser Lys Val
            180                 185                 190

Phe Leu Lys Ala Phe Asn Glu Arg Lys Asp Ser Ile Lys Phe Val Lys
        195                 200                 205

Leu Leu Ser His Phe Tyr Pro Ala Val Ile Asn Ser Asn Ile Asn Val
    210                 215                 220

Ile Asn Tyr Phe Asn Arg Met Phe His Phe Phe Glu His Glu Lys Arg
225                 230                 235                 240

Thr Asn Tyr Glu Tyr Glu Arg Gly Asn Ile Ile Ile Phe Pro Leu Ala
                245                 250                 255

Leu Tyr Ser Ala Asp Lys Val Asp Thr Glu Leu Ala Ile Lys Leu Gly
            260                 265                 270

Phe Lys Ser Leu Val Gln Tyr Ile Lys Phe Ile Phe Leu Gln Met Ala
        275                 280                 285

Leu Leu Tyr Ile Lys Ile Tyr Glu Leu Pro Cys Cys Asp Asn Phe Leu
    290                 295                 300

His Ala Asp Leu Lys Pro Asp Asn Ile Leu Leu Phe Asp Ser Asn Glu
305                 310                 315                 320

Pro Ile Ile Ile His Leu Lys Asp Lys Lys Phe Val Phe Asn Glu Arg
                325                 330                 335

Ile Lys Ser Ala Leu Asn Asp Phe Asp Phe Ser Gln Val Ala Gly Ile
            340                 345                 350
```

-continued

```
Ile Asn Lys Lys Ile Lys Asn Phe Lys Val Lys His Asn Trp Tyr
        355                 360                 365
Tyr Asp Phe His Phe Val His Thr Leu Leu Lys Thr Tyr Pro Glu
        370                 375                 380
Ile Glu Lys Asp Ile Glu Phe Ser Thr Ala Leu Glu Glu Phe Ile Met
385                 390                 395                 400
Cys Thr Lys Thr Asp Cys Asp Lys Tyr Arg Leu Lys Val Ser Ile Leu
                405                 410                 415
His Pro Ile Ser Phe Leu Glu Lys Phe Ile Met Arg Asp Ile Phe Ser
            420                 425                 430
Asp Trp Ile Asn Gly Gly Asn
            435

<210> SEQ ID NO 7
<211> LENGTH: 903
<212> TYPE: DNA
<213> ORGANISM: Variola Major Virus (India-1967 Strain)
<220> FEATURE:
<221> NAME/KEY: CDS
<222> LOCATION: (1)..(903)

<400> SEQUENCE: 7 atg aac ttt caa gga ctt gtc tta act gac aat tgc aaa aat caa tgg      48
Met Asn Phe Gln Gly Leu Val Leu Thr Asp Asn Cys Lys Asn Gln Trp
1               5                   10                  15 gtc gtt gga cca tta ata gga aaa ggt gga ttc ggt agt att tat act      96
Val Val Gly Pro Leu Ile Gly Lys Gly Gly Phe Gly Ser Ile Tyr Thr
            20                  25                  30 act aat gac aat aat tat gta gta aaa ata gag ccc aaa gct aac gga     144
Thr Asn Asp Asn Asn Tyr Val Val Lys Ile Glu Pro Lys Ala Asn Gly
        35                  40                  45 tca tta ttt act gaa cag gca ttt tat act aga gta ctt aaa cca tcc     192
Ser Leu Phe Thr Glu Gln Ala Phe Tyr Thr Arg Val Leu Lys Pro Ser
    50                  55                  60 gtt atc gaa gaa tgg aaa aaa tct cac cat ata agc cac gta gga gtt     240
Val Ile Glu Glu Trp Lys Lys Ser His His Ile Ser His Val Gly Val
65                  70                  75                  80 atc aca tgc aag gca ttt ggt cta tac aaa tcc att aat acg gaa tat     288
Ile Thr Cys Lys Ala Phe Gly Leu Tyr Lys Ser Ile Asn Thr Glu Tyr
                85                  90                  95 aga ttc ttg gta att aat aga ttg ggt gta gat cta gat gcg gtg atc     336
Arg Phe Leu Val Ile Asn Arg Leu Gly Val Asp Leu Asp Ala Val Ile
            100                 105                 110 agg gct aac aat aat aga cta ccg aaa aga tcg gtg atg tta gta gga     384
Arg Ala Asn Asn Asn Arg Leu Pro Lys Arg Ser Val Met Leu Val Gly
        115                 120                 125 ata gaa atc ttg aat acc ata caa ttt atg cac gag caa gga tat tct     432
Ile Glu Ile Leu Asn Thr Ile Gln Phe Met His Glu Gln Gly Tyr Ser
    130                 135                 140 cat gga aat att aaa gcg agc aat ata gtt ttg gat caa atg gat aag     480
His Gly Asn Ile Lys Ala Ser Asn Ile Val Leu Asp Gln Met Asp Lys
145                 150                 155                 160 aat aaa tta tat cta gtg gat tac gga ttg gtt tct aaa ttc atg tct     528
Asn Lys Leu Tyr Leu Val Asp Tyr Gly Leu Val Ser Lys Phe Met Ser
                165                 170                 175 aac ggc gaa cat gtt cca ttt ata aga aat cca aat aaa atg gat aat     576
Asn Gly Glu His Val Pro Phe Ile Arg Asn Pro Asn Lys Met Asp Asn
            180                 185                 190 ggt act cta gaa ttt aca cct ata gat tca cat aaa gga tac gtt gta     624
Gly Thr Leu Glu Phe Thr Pro Ile Asp Ser His Lys Gly Tyr Val Val
        195                 200                 205
```

```
tcg aga cgt gga gat cta gaa aca ctt gga tat tgt atg att aga tgg      672
Ser Arg Arg Gly Asp Leu Glu Thr Leu Gly Tyr Cys Met Ile Arg Trp
210                 215                 220 ttg gga ggt atc ttg cca tgg act aag ata gct gaa aca aag aat tgc      720
Leu Gly Gly Ile Leu Pro Trp Thr Lys Ile Ala Glu Thr Lys Asn Cys
225                 230                 235                 240 gca tta gta agt gct aca aaa cag aaa tat gtg aac aat act acg act      768
Ala Leu Val Ser Ala Thr Lys Gln Lys Tyr Val Asn Asn Thr Thr Thr
                245                 250                 255 ttg tta atg acc agt ttg caa tat gcg cct aga gaa ttg ctg caa tat      816
Leu Leu Met Thr Ser Leu Gln Tyr Ala Pro Arg Glu Leu Leu Gln Tyr
            260                 265                 270 att acc atg gta aac tct ttg aca tat ttt gag gaa ccc aat tac gat      864
Ile Thr Met Val Asn Ser Leu Thr Tyr Phe Glu Glu Pro Asn Tyr Asp
        275                 280                 285 aag ttt cgg cac ata tta atg cag ggt gca tat tat taa                  903
Lys Phe Arg His Ile Leu Met Gln Gly Ala Tyr Tyr
    290                 295                 300

<210> SEQ ID NO 8
<211> LENGTH: 300
<212> TYPE: PRT
<213> ORGANISM: Variola Major Virus (India-1967 Strain)

<400> SEQUENCE: 8

Met Asn Phe Gln Gly Leu Val Leu Thr Asp Asn Cys Lys Asn Gln Trp
1               5                   10                  15

Val Val Gly Pro Leu Ile Gly Lys Gly Phe Gly Ser Ile Tyr Thr
            20                  25                  30

Thr Asn Asp Asn Asn Tyr Val Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His His Ile Ser His Val Gly Val
65                  70                  75                  80

Ile Thr Cys Lys Ala Phe Gly Leu Tyr Lys Ser Ile Asn Thr Glu Tyr
                85                  90                  95

Arg Phe Leu Val Ile Asn Arg Leu Gly Val Asp Leu Asp Ala Val Ile
            100                 105                 110

Arg Ala Asn Asn Asn Arg Leu Pro Lys Arg Ser Val Met Leu Val Gly
        115                 120                 125

Ile Glu Ile Leu Asn Thr Ile Gln Phe Met His Gln Gly Tyr Ser
    130                 135                 140

His Gly Asn Ile Lys Ala Ser Asn Ile Val Leu Asp Gln Met Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
    210                 215                 220

Leu Gly Gly Ile Leu Pro Trp Thr Lys Ile Ala Glu Thr Lys Asn Cys
225                 230                 235                 240

Ala Leu Val Ser Ala Thr Lys Gln Lys Tyr Val Asn Asn Thr Thr Thr
                245                 250                 255
```

```
Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
        275                 280                 285

Lys Phe Arg His Ile Leu Met Gln Gly Ala Tyr Tyr
    290                 295                 300

<210> SEQ ID NO 9
<211> LENGTH: 1320
<212> TYPE: DNA
<213> ORGANISM: Variola Major Virus (India-1967 Strain)
<220> FEATURE:
<221> NAME/KEY: CDS
<222> LOCATION: (1)..(1320)

<400> SEQUENCE: 9 atg ggt gtt gcc aat gat tca tcc cct gaa tat caa tgg atg tct cca      48
Met Gly Val Ala Asn Asp Ser Ser Pro Glu Tyr Gln Trp Met Ser Pro
1               5                   10                  15 cat aga tta tct gat act gtt ata tta gga gac tgt tta tat ttt aac      96
His Arg Leu Ser Asp Thr Val Ile Leu Gly Asp Cys Leu Tyr Phe Asn
            20                  25                  30 aac ata atg tca caa tta gat tta cac caa aat tgg gct ccg tca gtt     144
Asn Ile Met Ser Gln Leu Asp Leu His Gln Asn Trp Ala Pro Ser Val
        35                  40                  45 aga ttg tta aat tat ttt aag aat ttt aat agg gaa aca cta cta aag     192
Arg Leu Leu Asn Tyr Phe Lys Asn Phe Asn Arg Glu Thr Leu Leu Lys
    50                  55                  60 ata gaa gag aat gat tac att aat tca tca ttt ttc caa caa aaa gat     240
Ile Glu Glu Asn Asp Tyr Ile Asn Ser Ser Phe Phe Gln Gln Lys Asp
65                  70                  75                  80 aaa cga ttt tat cct ata aac gac gat ttt tat cac ata tct aca gga     288
Lys Arg Phe Tyr Pro Ile Asn Asp Asp Phe Tyr His Ile Ser Thr Gly
                85                  90                  95 gga tat ggt ata gtc ttt aag ata gat aac tat gta gta aaa ttt gta     336
Gly Tyr Gly Ile Val Phe Lys Ile Asp Asn Tyr Val Val Lys Phe Val
            100                 105                 110 ttc gag gcc aca aaa tta tat agt ccc atg gaa act acg gcg gag ttc     384
Phe Glu Ala Thr Lys Leu Tyr Ser Pro Met Glu Thr Thr Ala Glu Phe
        115                 120                 125 acg gta cca aaa ttt cta tac aat aat cta aag gga gac gaa aaa aaa     432
Thr Val Pro Lys Phe Leu Tyr Asn Asn Leu Lys Gly Asp Glu Lys Lys
    130                 135                 140 tta atc gtg tgt gca ttg gcc atg gga tta aac tat aaa tta aca ttt     480
Leu Ile Val Cys Ala Leu Ala Met Gly Leu Asn Tyr Lys Leu Thr Phe
145                 150                 155                 160 tta cat aca ctg tat aaa cgg gtt ctt aat atg tta cta ttg ata         528
Leu His Thr Leu Tyr Lys Arg Val Leu Asn Met Leu Leu Leu Ile
                165                 170                 175 caa act atg gac ggt cag gaa ctc tca ttg aga tat tct tct aaa gtt     576
Gln Thr Met Asp Gly Gln Glu Leu Ser Leu Arg Tyr Ser Ser Lys Val
            180                 185                 190 ttt cta aag gcg ttt aac gag aga aag gac agt atc aaa ttc gtg aaa     624
Phe Leu Lys Ala Phe Asn Glu Arg Lys Asp Ser Ile Lys Phe Val Lys
        195                 200                 205 tta cta tcc cac ttt tat ccg gca gtt att aac agt aat att aat gtt     672
Leu Leu Ser His Phe Tyr Pro Ala Val Ile Asn Ser Asn Ile Asn Val
    210                 215                 220 ata aac tat ttt aac cgc atg ttt cac ttt ttc gaa cat gaa aag cga     720
Ile Asn Tyr Phe Asn Arg Met Phe His Phe Phe Glu His Glu Lys Arg
225                 230                 235                 240
```

```
act aac tac gaa tac gaa aga gga aat att ata att ttt ccc cta gca    768
Thr Asn Tyr Glu Tyr Glu Arg Gly Asn Ile Ile Ile Phe Pro Leu Ala
            245                 250                 255 ctg tat tcg gca gat aaa gta gat acc gag tta gct att aaa tta gga    816
Leu Tyr Ser Ala Asp Lys Val Asp Thr Glu Leu Ala Ile Lys Leu Gly
        260                 265                 270 ttt aaa tct ttg gta caa tac ata aag ttt atc ttt tta cag atg gct    864
Phe Lys Ser Leu Val Gln Tyr Ile Lys Phe Ile Phe Leu Gln Met Ala
    275                 280                 285 ctg tta tac att aaa atc tac gaa cta ccc cgt tgc gac aac ttt tta    912
Leu Leu Tyr Ile Lys Ile Tyr Glu Leu Pro Arg Cys Asp Asn Phe Leu
290                 295                 300 cac gca gat ctt aaa ccc gat aat atc tta ctt ttt gat tcc aat gaa    960
His Ala Asp Leu Lys Pro Asp Asn Ile Leu Leu Phe Asp Ser Asn Glu
305                 310                 315                 320 cca ata ata att cat cta aag gat aaa aag ttt gtt ttt aat gaa cgt   1008
Pro Ile Ile Ile His Leu Lys Asp Lys Lys Phe Val Phe Asn Glu Arg
                325                 330                 335 att aaa tcg gca tta aac gac ttt gac ttt tcc caa gtg gct gga atc   1056
Ile Lys Ser Ala Leu Asn Asp Phe Asp Phe Ser Gln Val Ala Gly Ile
            340                 345                 350 att aac aag aaa ata aaa aac aat ttc aaa gtt gaa cat aac tgg tat   1104
Ile Asn Lys Lys Ile Lys Asn Asn Phe Lys Val Glu His Asn Trp Tyr
        355                 360                 365 tac gat ttc cat ttc ttt gtt cat act tta tta aaa aca tat cca gaa   1152
Tyr Asp Phe His Phe Phe Val His Thr Leu Leu Lys Thr Tyr Pro Glu
    370                 375                 380 atc gaa aaa gat att gaa ttt agt aca gca tta gaa gaa ttc atc atg   1200
Ile Glu Lys Asp Ile Glu Phe Ser Thr Ala Leu Glu Glu Phe Ile Met
385                 390                 395                 400 tgt acc aaa aca gac tgt gat aaa tat aga tta aag gtt tcc att ctt   1248
Cys Thr Lys Thr Asp Cys Asp Lys Tyr Arg Leu Lys Val Ser Ile Leu
                405                 410                 415 cac cca att agt ttc ttg gaa aaa ttt att atg agg gac att ttc tca   1296
His Pro Ile Ser Phe Leu Glu Lys Phe Ile Met Arg Asp Ile Phe Ser
            420                 425                 430 gac tgg ata aat ggc aga aac taa                                   1320
Asp Trp Ile Asn Gly Arg Asn
        435

<210> SEQ ID NO 10
<211> LENGTH: 439
<212> TYPE: PRT
<213> ORGANISM: Variola Major Virus (India-1967 Strain)

<400> SEQUENCE: 10

Met Gly Val Ala Asn Asp Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Arg Glu Thr Leu Leu Lys
    50                  55                  60

Ile Glu Glu Asn Asp Tyr Ile Asn Ser Ser Phe Phe Gln Gln Lys Asp
65                  70                  75                  80

Lys Arg Phe Tyr Pro Ile Asn Asp Asp Phe Tyr His Ile Ser Thr Gly
                85                  90                  95

Gly Tyr Gly Ile Val Phe Lys Ile Asp Asn Tyr Val Val Lys Phe Val
```

```
                         100                 105                 110
Phe Glu Ala Thr Lys Leu Tyr Ser Pro Met Glu Thr Thr Ala Glu Phe
            115                 120                 125

Thr Val Pro Lys Phe Leu Tyr Asn Asn Leu Lys Gly Asp Glu Lys Lys
        130                 135                 140

Leu Ile Val Cys Ala Leu Ala Met Gly Leu Asn Tyr Lys Leu Thr Phe
145                 150                 155                 160

Leu His Thr Leu Tyr Lys Arg Val Leu Asn Met Leu Leu Leu Leu Ile
                165                 170                 175

Gln Thr Met Asp Gly Gln Glu Leu Ser Leu Arg Tyr Ser Ser Lys Val
            180                 185                 190

Phe Leu Lys Ala Phe Asn Glu Arg Lys Asp Ser Ile Lys Phe Val Lys
        195                 200                 205

Leu Leu Ser His Phe Tyr Pro Ala Val Ile Asn Ser Asn Ile Asn Val
210                 215                 220

Ile Asn Tyr Phe Asn Arg Met Phe His Phe Glu His Glu Lys Arg
225                 230                 235                 240

Thr Asn Tyr Glu Tyr Glu Arg Gly Asn Ile Ile Ile Phe Pro Leu Ala
            245                 250                 255

Leu Tyr Ser Ala Asp Lys Val Asp Thr Glu Leu Ala Ile Lys Leu Gly
        260                 265                 270

Phe Lys Ser Leu Val Gln Tyr Ile Lys Phe Ile Phe Leu Gln Met Ala
        275                 280                 285

Leu Leu Tyr Ile Lys Ile Tyr Glu Leu Pro Arg Cys Asp Asn Phe Leu
        290                 295                 300

His Ala Asp Leu Lys Pro Asp Asn Ile Leu Leu Phe Asp Ser Asn Glu
305                 310                 315                 320

Pro Ile Ile Ile His Leu Lys Asp Lys Lys Phe Val Phe Asn Glu Arg
                325                 330                 335

Ile Lys Ser Ala Leu Asn Asp Phe Asp Phe Ser Gln Val Ala Gly Ile
            340                 345                 350

Ile Asn Lys Lys Ile Lys Asn Asn Phe Lys Val Glu His Asn Trp Tyr
        355                 360                 365

Tyr Asp Phe His Phe Phe Val His Thr Leu Leu Lys Thr Tyr Pro Glu
        370                 375                 380

Ile Glu Lys Asp Ile Glu Phe Ser Thr Ala Leu Glu Glu Phe Ile Met
385                 390                 395                 400

Cys Thr Lys Thr Asp Cys Asp Lys Tyr Arg Leu Lys Val Ser Ile Leu
                405                 410                 415

His Pro Ile Ser Phe Leu Glu Lys Phe Ile Met Arg Asp Ile Phe Ser
            420                 425                 430

Asp Trp Ile Asn Gly Arg Asn
        435

<210> SEQ ID NO 11
<211> LENGTH: 1320
<212> TYPE: DNA
<213> ORGANISM: Variola Major Virus (Congo-1965 Strain)
<220> FEATURE:
<221> NAME/KEY: CDS
<222> LOCATION: (1)..(1320)

<400> SEQUENCE: 11 atg ggt gtt gcc aat gat tca tcc cct gaa tat caa tgg atg tct cca      48
Met Gly Val Ala Asn Asp Ser Ser Pro Glu Tyr Gln Trp Met Ser Pro
1               5                   10                  15
```

-continued

| | | |
|---|---|---|
| cat aga tta tct gat act gtt ata tta gga gac tgt tta tat ttt aac<br>His Arg Leu Ser Asp Thr Val Ile Leu Gly Asp Cys Leu Tyr Phe Asn<br>20 25 30 | | 96 |
| aac ata atg tca caa tta gat tta cac caa aat tgg gct ccg tca gtt<br>Asn Ile Met Ser Gln Leu Asp Leu His Gln Asn Trp Ala Pro Ser Val<br>35 40 45 | | 144 |
| aga ttg tta aat tat ttt aag aat ttt aat agg gaa aca cta cta aag<br>Arg Leu Leu Asn Tyr Phe Lys Asn Phe Asn Arg Glu Thr Leu Leu Lys<br>50 55 60 | | 192 |
| ata gaa gag aat gat tac att aat tca tca ttt ttc caa caa aaa gat<br>Ile Glu Glu Asn Asp Tyr Ile Asn Ser Ser Phe Phe Gln Gln Lys Asp<br>65 70 75 80 | | 240 |
| aaa cga ttt tat cct ata aac gac gat ttt tat cac ata tct aca gga<br>Lys Arg Phe Tyr Pro Ile Asn Asp Asp Phe Tyr His Ile Ser Thr Gly<br>85 90 95 | | 288 |
| gga tat ggt ata gtc ttt aag ata gat aac tat gta gta aaa ttt gta<br>Gly Tyr Gly Ile Val Phe Lys Ile Asp Asn Tyr Val Val Lys Phe Val<br>100 105 110 | | 336 |
| ttc gag gcc aca aaa tta tat agt ccc atg gaa act acg gcg gag ttc<br>Phe Glu Ala Thr Lys Leu Tyr Ser Pro Met Glu Thr Thr Ala Glu Phe<br>115 120 125 | | 384 |
| acg gta cca aaa ttt cta tac aac aat cta aag gga gac gaa aaa aaa<br>Thr Val Pro Lys Phe Leu Tyr Asn Asn Leu Lys Gly Asp Glu Lys Lys<br>130 135 140 | | 432 |
| tta atc gtg tgt gca ttg gcc atg gga tta aac tat aaa tta aca ttt<br>Leu Ile Val Cys Ala Leu Ala Met Gly Leu Asn Tyr Lys Leu Thr Phe<br>145 150 155 160 | | 480 |
| tta cat aca ctg tat aaa cgg gtt ctt aat atg tta cta tta ttg ata<br>Leu His Thr Leu Tyr Lys Arg Val Leu Asn Met Leu Leu Leu Leu Ile<br>165 170 175 | | 528 |
| caa act atg gac ggt cag gaa ctc tca ttg aga tat tct tct aaa gtt<br>Gln Thr Met Asp Gly Gln Glu Leu Ser Leu Arg Tyr Ser Ser Lys Val<br>180 185 190 | | 576 |
| ttt cta aag gcg ttt aac gag aga aag gac agt atc aaa ttc gtg aaa<br>Phe Leu Lys Ala Phe Asn Glu Arg Lys Asp Ser Ile Lys Phe Val Lys<br>195 200 205 | | 624 |
| tta cta tcc cac ttt tat ccg gca gtt att aac agt aat att aat gtt<br>Leu Leu Ser His Phe Tyr Pro Ala Val Ile Asn Ser Asn Ile Asn Val<br>210 215 220 | | 672 |
| ata aac tat ttt aac cgc atg ttt cac ttt ttc gaa cat gaa aag cga<br>Ile Asn Tyr Phe Asn Arg Met Phe His Phe Phe Glu His Glu Lys Arg<br>225 230 235 240 | | 720 |
| act aac tac gaa tac gaa aga gga aat att ata att ttt ccc cta gca<br>Thr Asn Tyr Glu Tyr Glu Arg Gly Asn Ile Ile Ile Phe Pro Leu Ala<br>245 250 255 | | 768 |
| ctg tat tcg gca gat aaa gta gat acc gag tta gct att aaa tta gga<br>Leu Tyr Ser Ala Asp Lys Val Asp Thr Glu Leu Ala Ile Lys Leu Gly<br>260 265 270 | | 816 |
| ttt aaa tct ttg gta caa tac ata aag ttt atc ttt tta cag atg gct<br>Phe Lys Ser Leu Val Gln Tyr Ile Lys Phe Ile Phe Leu Gln Met Ala<br>275 280 285 | | 864 |
| ctg tta tac att aaa atc tac gaa cta ccc tgt tgc gac aac ttt tta<br>Leu Leu Tyr Ile Lys Ile Tyr Glu Leu Pro Cys Cys Asp Asn Phe Leu<br>290 295 300 | | 912 |
| cac gca gat ctt aaa ccc gat aat atc tta ctt ttt gat tcc aat gaa<br>His Ala Asp Leu Lys Pro Asp Asn Ile Leu Leu Phe Asp Ser Asn Glu<br>305 310 315 320 | | 960 |
| cca ata ata att cat cta aag gat aaa aag ttt gtt ttt aat gaa cgt<br>Pro Ile Ile Ile His Leu Lys Asp Lys Lys Phe Val Phe Asn Glu Arg<br>325 330 335 | | 1008 |

```
att aaa tcg gca tta aac gac ttt gac ttt tcc caa gtg gct gga atc      1056
Ile Lys Ser Ala Leu Asn Asp Phe Asp Phe Ser Gln Val Ala Gly Ile
        340                 345                 350 att aac aag aaa ata aaa aac aat ttc aaa gtt gaa cat aac tgg tat      1104
Ile Asn Lys Lys Ile Lys Asn Asn Phe Lys Val Glu His Asn Trp Tyr
        355                 360                 365 tac gat ttc cat ttc ttt gtt cat act tta tta aaa aca tat cca gaa      1152
Tyr Asp Phe His Phe Phe Val His Thr Leu Leu Lys Thr Tyr Pro Glu
    370                 375                 380 atc gaa aaa gat att gaa ttt agt aca gca tta gaa gaa ttc atc atg      1200
Ile Glu Lys Asp Ile Glu Phe Ser Thr Ala Leu Glu Glu Phe Ile Met
385                 390                 395                 400 tgt acc aaa aca gac tgt gat aaa tat aga tta aag gtt tcc att ctt      1248
Cys Thr Lys Thr Asp Cys Asp Lys Tyr Arg Leu Lys Val Ser Ile Leu
                405                 410                 415 cac cca att agt ttc ttg gaa aaa ttt att atg agg gac att ttc tca      1296
His Pro Ile Ser Phe Leu Glu Lys Phe Ile Met Arg Asp Ile Phe Ser
            420                 425                 430 gac tgg ata aat ggc aga aac taa                                      1320
Asp Trp Ile Asn Gly Arg Asn
            435

<210> SEQ ID NO 12
<211> LENGTH: 439
<212> TYPE: PRT
<213> ORGANISM: Variola Major Virus (Congo-1965 Strain)

<400> SEQUENCE: 12

Met Gly Val Ala Asn Asp Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Arg Glu Thr Leu Leu Lys
    50                  55                  60

Ile Glu Glu Asn Asp Tyr Ile Asn Ser Ser Phe Phe Gln Gln Lys Asp
65                  70                  75                  80

Lys Arg Phe Tyr Pro Ile Asn Asp Asp Phe Tyr His Ile Ser Thr Gly
                85                  90                  95

Gly Tyr Gly Ile Val Phe Lys Ile Asp Asn Tyr Val Val Lys Phe Val
            100                 105                 110

Phe Glu Ala Thr Lys Leu Tyr Ser Pro Met Glu Thr Thr Ala Glu Phe
        115                 120                 125

Thr Val Pro Lys Phe Leu Tyr Asn Asn Leu Lys Gly Asp Glu Lys Lys
    130                 135                 140

Leu Ile Val Cys Ala Leu Ala Met Gly Leu Asn Tyr Lys Leu Thr Phe
145                 150                 155                 160

Leu His Thr Leu Tyr Lys Arg Val Leu Asn Met Leu Leu Leu Leu Ile
                165                 170                 175

Gln Thr Met Asp Gly Gln Glu Leu Ser Leu Arg Tyr Ser Ser Lys Val
            180                 185                 190

Phe Leu Lys Ala Phe Asn Glu Arg Lys Asp Ser Ile Lys Phe Val Lys
        195                 200                 205

Leu Leu Ser His Phe Tyr Pro Ala Val Ile Asn Ser Asn Ile Asn Val
    210                 215                 220

Ile Asn Tyr Phe Asn Arg Met Phe His Phe Phe Glu His Glu Lys Arg
225                 230                 235                 240
```

```
Thr Asn Tyr Glu Tyr Glu Arg Gly Asn Ile Ile Ile Phe Pro Leu Ala
                245                 250                 255

Leu Tyr Ser Ala Asp Lys Val Asp Thr Glu Leu Ala Ile Lys Leu Gly
            260                 265                 270

Phe Lys Ser Leu Val Gln Tyr Ile Lys Phe Ile Phe Leu Gln Met Ala
        275                 280                 285

Leu Leu Tyr Ile Lys Ile Tyr Glu Leu Pro Cys Cys Asp Asn Phe Leu
    290                 295                 300

His Ala Asp Leu Lys Pro Asp Asn Ile Leu Leu Phe Asp Ser Asn Glu
305                 310                 315                 320

Pro Ile Ile Ile His Leu Lys Asp Lys Lys Phe Val Phe Asn Glu Arg
                325                 330                 335

Ile Lys Ser Ala Leu Asn Asp Phe Asp Phe Ser Gln Val Ala Gly Ile
            340                 345                 350

Ile Asn Lys Lys Ile Lys Asn Asn Phe Lys Val Glu His Asn Trp Tyr
        355                 360                 365

Tyr Asp Phe His Phe Phe Val His Thr Leu Leu Lys Thr Tyr Pro Glu
    370                 375                 380

Ile Glu Lys Asp Ile Glu Phe Ser Thr Ala Leu Glu Glu Phe Ile Met
385                 390                 395                 400

Cys Thr Lys Thr Asp Cys Asp Lys Tyr Arg Leu Lys Val Ser Ile Leu
                405                 410                 415

His Pro Ile Ser Phe Leu Glu Lys Phe Ile Met Arg Asp Ile Phe Ser
            420                 425                 430

Asp Trp Ile Asn Gly Arg Asn
        435

<210> SEQ ID NO 13
<211> LENGTH: 32
<212> TYPE: DNA
<213> ORGANISM: Artificial
<220> FEATURE:
<223> OTHER INFORMATION: PCR Primer

<400> SEQUENCE: 13
atagaattca cattatgaac tttcaaggac tt                              32

<210> SEQ ID NO 14
<211> LENGTH: 32
<212> TYPE: DNA
<213> ORGANISM: Artificial
<220> FEATURE:
<223> OTHER INFORMATION: PCR Primer

<400> SEQUENCE: 14
tatctcgagc accacactta ataatataca cc                              32

<210> SEQ ID NO 15
<211> LENGTH: 27
<212> TYPE: DNA
<213> ORGANISM: Artificial
<220> FEATURE:
<223> OTHER INFORMATION: PCR Primer

<400> SEQUENCE: 15
atactcgagg aaatgggtgt tgccaat                                    27

<210> SEQ ID NO 16
<211> LENGTH: 27
<212> TYPE: DNA
```

<213> ORGANISM: Artificial
<220> FEATURE:
<223> OTHER INFORMATION: PCR Primer

<400> SEQUENCE: 16
gcgaagcttt tagtttccgc catttat                                              27

<210> SEQ ID NO 17
<211> LENGTH: 1320
<212> TYPE: DNA
<213> ORGANISM: Rabbitpox virus
<220> FEATURE:
<221> NAME/KEY: CDS
<222> LOCATION: (1)..(1320)

<400> SEQUENCE: 17

```
atg ggt gtt gcc aat gat tca tcc cct gaa tat caa tgg atg tct ccc        48
Met Gly Val Ala Asn Asp Ser Ser Pro Glu Tyr Gln Trp Met Ser Pro
 1               5                  10                  15 cat aga tta tca gat act gtt ata tta gga gac tgt ttg tat ttt aac        96
His Arg Leu Ser Asp Thr Val Ile Leu Gly Asp Cys Leu Tyr Phe Asn
                20                  25                  30 aat ata atg tcc caa tta gat tta cac caa aat tgg gct ccg tca gtt       144
Asn Ile Met Ser Gln Leu Asp Leu His Gln Asn Trp Ala Pro Ser Val
            35                  40                  45 aga ttg tta aat tat ttt aag aat ttt aat aag gaa aca cta cta aag       192
Arg Leu Leu Asn Tyr Phe Lys Asn Phe Asn Lys Glu Thr Leu Leu Lys
        50                  55                  60 ata gaa gag aat gat tac att aat tca tcc ttt ttc caa caa aag gat       240
Ile Glu Glu Asn Asp Tyr Ile Asn Ser Ser Phe Phe Gln Gln Lys Asp
 65                  70                  75                  80 aaa cga ttt tat cct ata aac gac gat ttt tat cac ata tct aca gga       288
Lys Arg Phe Tyr Pro Ile Asn Asp Asp Phe Tyr His Ile Ser Thr Gly
                 85                  90                  95 gga tat ggt ata gtt ttt aag ata gat aac tat gta gta aaa ttt gta       336
Gly Tyr Gly Ile Val Phe Lys Ile Asp Asn Tyr Val Val Lys Phe Val
            100                 105                 110 ttc gag gcc aca aaa tta tat agt ccc atg gaa act acg gcg gag ttc       384
Phe Glu Ala Thr Lys Leu Tyr Ser Pro Met Glu Thr Thr Ala Glu Phe
        115                 120                 125 aca gta ccc aaa ttt cta tac aac aat cta aag gga gat gaa aaa aaa       432
Thr Val Pro Lys Phe Leu Tyr Asn Asn Leu Lys Gly Asp Glu Lys Lys
    130                 135                 140 tta atc gtg tgt gcg tgg gcc atg gga tta aac tat aaa tta aca ttt       480
Leu Ile Val Cys Ala Trp Ala Met Gly Leu Asn Tyr Lys Leu Thr Phe
145                 150                 155                 160 tta cat act ctg tat aaa cgg gtt ctt cat atg ttg cta tta ttg ata       528
Leu His Thr Leu Tyr Lys Arg Val Leu His Met Leu Leu Leu Leu Ile
                165                 170                 175 caa act atg gat ggt cag gaa ctc tca ttg aga tat tct tct aaa gtt       576
Gln Thr Met Asp Gly Gln Glu Leu Ser Leu Arg Tyr Ser Ser Lys Val
            180                 185                 190 ttt tta aag gcg ttt aac gag aga aag gac agt atc aaa ttc gtg aaa       624
Phe Leu Lys Ala Phe Asn Glu Arg Lys Asp Ser Ile Lys Phe Val Lys
        195                 200                 205 tta cta tcc cac ttt tat ccg gca gtt att aac agt aat att aat gtt       672
Leu Leu Ser His Phe Tyr Pro Ala Val Ile Asn Ser Asn Ile Asn Val
    210                 215                 220 ata aac tat ttt aac cgc atg ttt cac ttt ttc gaa cat gaa aag aga       720
Ile Asn Tyr Phe Asn Arg Met Phe His Phe Phe Glu His Glu Lys Arg
225                 230                 235                 240 act aac tac gaa tac gaa aga gga aat att ata att ttt ccc cta gca       768
```

```
                Thr Asn Tyr Glu Tyr Glu Arg Gly Asn Ile Ile Ile Phe Pro Leu Ala
                                245                 250                 255 ctg tat tct gca gat aaa gta gat acc gag tta gct atc aaa tta gga        816
Leu Tyr Ser Ala Asp Lys Val Asp Thr Glu Leu Ala Ile Lys Leu Gly
            260                 265                 270 ttt aaa tct ttg gta caa tac ata aag ttt atc ttt tta cag atg gct        864
Phe Lys Ser Leu Val Gln Tyr Ile Lys Phe Ile Phe Leu Gln Met Ala
            275                 280                 285 ctg tta tac att aaa att tac gaa cta cca tgc tgc gac aac ttt tta        912
Leu Leu Tyr Ile Lys Ile Tyr Glu Leu Pro Cys Cys Asp Asn Phe Leu
            290                 295                 300 cac gca gat ctt aaa ccc gat aat atc tta ctt ttt gat tcc aat gaa        960
His Ala Asp Leu Lys Pro Asp Asn Ile Leu Leu Phe Asp Ser Asn Glu
305                 310                 315                 320 cca ata ata att cat cta aag gat aaa aag ttt gtt ttt aat gaa cgt       1008
Pro Ile Ile Ile His Leu Lys Asp Lys Lys Phe Val Phe Asn Glu Arg
                325                 330                 335 att aaa tcg gca tta aac gac ttt gac ttt tcc caa gtg gct gga atc       1056
Ile Lys Ser Ala Leu Asn Asp Phe Asp Phe Ser Gln Val Ala Gly Ile
            340                 345                 350 att aac aag aaa ata aaa aac aat ttc aaa gtt aaa cat aac tgg tat       1104
Ile Asn Lys Lys Ile Lys Asn Asn Phe Lys Val Lys His Asn Trp Tyr
            355                 360                 365 tac gat ttc cat ttc ttt gtt cat act tta tta aaa aca tat cca gaa       1152
Tyr Asp Phe His Phe Phe Val His Thr Leu Leu Lys Thr Tyr Pro Glu
370                 375                 380 atc gaa aaa gat atc gaa ttt agt acg gca tta gaa gaa ttc atc atg       1200
Ile Glu Lys Asp Ile Glu Phe Ser Thr Ala Leu Glu Glu Phe Ile Met
385                 390                 395                 400 tgt acc aaa aca gac tgt gat aaa tat aga tta aag gtt tcc att ctt       1248
Cys Thr Lys Thr Asp Cys Asp Lys Tyr Arg Leu Lys Val Ser Ile Leu
                405                 410                 415 cac cca att agt ttc ttg gaa aaa ttt att atg aga gac att ttc tca       1296
His Pro Ile Ser Phe Leu Glu Lys Phe Ile Met Arg Asp Ile Phe Ser
            420                 425                 430 gac tgg ata aat ggc gga aac taa                                       1320
Asp Trp Ile Asn Gly Gly Asn
            435

<210> SEQ ID NO 18
<211> LENGTH: 439
<212> TYPE: PRT
<213> ORGANISM: Rabbitpox virus

<400> SEQUENCE: 18

Met Gly Val Ala Asn Asp Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Lys Glu Thr Leu Leu Lys
    50                  55                  60

Ile Glu Glu Asn Asp Tyr Ile Asn Ser Ser Phe Phe Gln Gln Lys Asp
65                  70                  75                  80

Lys Arg Phe Tyr Pro Ile Asn Asp Asp Phe Tyr His Ile Ser Thr Gly
                85                  90                  95

Gly Tyr Gly Ile Val Phe Lys Ile Asp Asn Tyr Val Val Lys Phe Val
            100                 105                 110
```

```
Phe Glu Ala Thr Lys Leu Tyr Ser Pro Met Glu Thr Thr Ala Glu Phe
            115                 120                 125

Thr Val Pro Lys Phe Leu Tyr Asn Asn Leu Lys Gly Asp Glu Lys Lys
130                 135                 140

Leu Ile Val Cys Ala Trp Ala Met Gly Leu Asn Tyr Lys Leu Thr Phe
145                 150                 155                 160

Leu His Thr Leu Tyr Lys Arg Val Leu His Met Leu Leu Leu Leu Ile
                165                 170                 175

Gln Thr Met Asp Gly Gln Glu Leu Ser Leu Arg Tyr Ser Ser Lys Val
            180                 185                 190

Phe Leu Lys Ala Phe Asn Glu Arg Lys Asp Ser Ile Lys Phe Val Lys
        195                 200                 205

Leu Leu Ser His Phe Tyr Pro Ala Val Ile Asn Ser Asn Ile Asn Val
210                 215                 220

Ile Asn Tyr Phe Asn Arg Met Phe His Phe Glu His Glu Lys Arg
225                 230                 235                 240

Thr Asn Tyr Glu Tyr Glu Arg Gly Asn Ile Ile Ile Phe Pro Leu Ala
                245                 250                 255

Leu Tyr Ser Ala Asp Lys Val Asp Thr Glu Leu Ala Ile Lys Leu Gly
            260                 265                 270

Phe Lys Ser Leu Val Gln Tyr Ile Lys Phe Ile Phe Leu Gln Met Ala
        275                 280                 285

Leu Leu Tyr Ile Lys Ile Tyr Glu Leu Pro Cys Cys Asp Asn Phe Leu
290                 295                 300

His Ala Asp Leu Lys Pro Asp Asn Ile Leu Leu Phe Ser Asn Glu
305                 310                 315                 320

Pro Ile Ile Ile His Leu Lys Asp Lys Lys Phe Val Phe Asn Glu Arg
                325                 330                 335

Ile Lys Ser Ala Leu Asn Asp Phe Asp Phe Ser Gln Val Ala Gly Ile
            340                 345                 350

Ile Asn Lys Lys Ile Lys Asn Asn Phe Lys Val Lys His Asn Trp Tyr
        355                 360                 365

Tyr Asp Phe His Phe Phe Val His Thr Leu Leu Lys Thr Tyr Pro Glu
370                 375                 380

Ile Glu Lys Asp Ile Glu Phe Ser Thr Ala Leu Glu Glu Phe Ile Met
385                 390                 395                 400

Cys Thr Lys Thr Asp Cys Asp Lys Tyr Arg Leu Lys Val Ser Ile Leu
                405                 410                 415

His Pro Ile Ser Phe Leu Glu Lys Phe Ile Met Arg Asp Ile Phe Ser
            420                 425                 430

Asp Trp Ile Asn Gly Gly Asn
            435
```

<210> SEQ ID NO 19
<211> LENGTH: 1320
<212> TYPE: DNA
<213> ORGANISM: Cowpox virus
<220> FEATURE:
<221> NAME/KEY: CDS
<222> LOCATION: (1)..(1320)

<400> SEQUENCE: 19

```
atg ggt gtt gcc aat gat tca tcc cct gaa tat caa tgg atg tct ccc        48
Met Gly Val Ala Asn Asp Ser Ser Pro Glu Tyr Gln Trp Met Ser Pro
1               5                   10                  15 cat aga tta tca gat act gtt ata cta gga gac tgt tta tat ttt aac        96
His Arg Leu Ser Asp Thr Val Ile Leu Gly Asp Cys Leu Tyr Phe Asn
```

-continued

```
              20                  25                  30
aac ata atg tcc caa tta gat tta cac caa aat tgg gct ccg tca gtt     144
Asn Ile Met Ser Gln Leu Asp Leu His Gln Asn Trp Ala Pro Ser Val
         35                  40                  45 aga ttg tta aat tat ttt aag aat ttt aat aag gaa aca cta cta aag     192
Arg Leu Leu Asn Tyr Phe Lys Asn Phe Asn Lys Glu Thr Leu Leu Lys
 50                  55                  60 ata gaa gag aat gat tac att aat tca tcc ttt ttc caa caa aag gat     240
Ile Glu Glu Asn Asp Tyr Ile Asn Ser Ser Phe Phe Gln Gln Lys Asp
 65                  70                  75                  80 aaa cga ttt tat cct ata aac gac gat ttt tat cac ata tct aca gga     288
Lys Arg Phe Tyr Pro Ile Asn Asp Asp Phe Tyr His Ile Ser Thr Gly
                 85                  90                  95 gga tat ggt ata gtc ttt aag ata gat aac tat gta gta aaa ttt gta     336
Gly Tyr Gly Ile Val Phe Lys Ile Asp Asn Tyr Val Val Lys Phe Val
            100                 105                 110 ttc gag gcc aca aaa tta tat agt ccc atg gaa act acg gcg gag ttc     384
Phe Glu Ala Thr Lys Leu Tyr Ser Pro Met Glu Thr Thr Ala Glu Phe
        115                 120                 125 aca gta ccc aaa ttt cta tac aac aat cta aag gga gat gaa aaa aaa     432
Thr Val Pro Lys Phe Leu Tyr Asn Asn Leu Lys Gly Asp Glu Lys Lys
    130                 135                 140 tta atc gtg tgt gcg tgg gcc atg gga tta aac tat aaa tta aca ttt     480
Leu Ile Val Cys Ala Trp Ala Met Gly Leu Asn Tyr Lys Leu Thr Phe
145                 150                 155                 160 tta cat act ctg tat aaa cgg gtt ctt cat atg ttg cta tta ttg ata     528
Leu His Thr Leu Tyr Lys Arg Val Leu His Met Leu Leu Leu Leu Ile
                165                 170                 175 caa act atg gat ggt cag gaa ctc tca ttg aga tat tct tct aaa gtt     576
Gln Thr Met Asp Gly Gln Glu Leu Ser Leu Arg Tyr Ser Ser Lys Val
            180                 185                 190 ttt cta aag gcg ttt aac gag aga aag gac agt atc aaa ttc gtg aaa     624
Phe Leu Lys Ala Phe Asn Glu Arg Lys Asp Ser Ile Lys Phe Val Lys
        195                 200                 205 tta cta tcc cac ttt tat ccg gca gtt att aac agt aat att aat gtt     672
Leu Leu Ser His Phe Tyr Pro Ala Val Ile Asn Ser Asn Ile Asn Val
    210                 215                 220 ata aat tat ttt aac cgc atg ttt cac ttt ttc gaa cat gaa aag aga     720
Ile Asn Tyr Phe Asn Arg Met Phe His Phe Phe Glu His Glu Lys Arg
225                 230                 235                 240 act aac tac gaa tac gaa aga gga aat att ata att ttt ccc cta gca     768
Thr Asn Tyr Glu Tyr Glu Arg Gly Asn Ile Ile Ile Phe Pro Leu Ala
                245                 250                 255 ctg tat tcg gca gat aaa gta gat acc gag tta gct atc aaa tta gga     816
Leu Tyr Ser Ala Asp Lys Val Asp Thr Glu Leu Ala Ile Lys Leu Gly
            260                 265                 270 ttt aaa tct ttg gta caa tac ata aag ttt atc ttt tta cag atg gct     864
Phe Lys Ser Leu Val Gln Tyr Ile Lys Phe Ile Phe Leu Gln Met Ala
        275                 280                 285 ctg tta tac att aaa att tac gaa ctg cca tgc tgc gac aac ttt tta     912
Leu Leu Tyr Ile Lys Ile Tyr Glu Leu Pro Cys Cys Asp Asn Phe Leu
    290                 295                 300 cac gca gat ctt aaa ccc gat aat atc tta ctt ttt gat tcc aat gaa     960
His Ala Asp Leu Lys Pro Asp Asn Ile Leu Leu Phe Asp Ser Asn Glu
305                 310                 315                 320 cca ata ata att cat cta aag gat aaa aag ttt gtt ttt aat gaa cgt    1008
Pro Ile Ile Ile His Leu Lys Asp Lys Lys Phe Val Phe Asn Glu Arg
                325                 330                 335 att aaa tcg gca tta aac gac ttt gac ttt tcc caa gtg gct gga atc    1056
Ile Lys Ser Ala Leu Asn Asp Phe Asp Phe Ser Gln Val Ala Gly Ile
```

```
                340                 345                 350
gtc aac aag aaa ata aaa aac aat ttc aaa gtt gag cat aac tgg tat    1104
Val Asn Lys Lys Ile Lys Asn Asn Phe Lys Val Glu His Asn Trp Tyr
        355                 360                 365 tac gat ttc cat ttc ttt gtt cat act tta tta aaa aca tat cca gaa    1152
Tyr Asp Phe His Phe Phe Val His Thr Leu Leu Lys Thr Tyr Pro Glu
370                 375                 380 atc gaa aaa gat atc gaa ttt agt aca gca tta gaa gaa ttc atc atg    1200
Ile Glu Lys Asp Ile Glu Phe Ser Thr Ala Leu Glu Glu Phe Ile Met
385                 390                 395                 400 tgt acc aaa aca gac tgt gat aaa tat aga tta aag gtt tcc att ctt    1248
Cys Thr Lys Thr Asp Cys Asp Lys Tyr Arg Leu Lys Val Ser Ile Leu
            405                 410                 415 cac cca att agt ttc ttg gaa aaa ttt att atg aga gac att ttc tca    1296
His Pro Ile Ser Phe Leu Glu Lys Phe Ile Met Arg Asp Ile Phe Ser
            420                 425                 430 gac tgg ata aat ggc gga aac taa                                    1320
Asp Trp Ile Asn Gly Gly Asn
            435

<210> SEQ ID NO 20
<211> LENGTH: 439
<212> TYPE: PRT
<213> ORGANISM: Cowpox virus

<400> SEQUENCE: 20

Met Gly Val Ala Asn Asp Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Lys Glu Thr Leu Leu Lys
    50                  55                  60

Ile Glu Glu Asn Asp Tyr Ile Asn Ser Ser Phe Phe Gln Gln Lys Asp
65                  70                  75                  80

Lys Arg Phe Tyr Pro Ile Asn Asp Asp Phe Tyr His Ile Ser Thr Gly
                85                  90                  95

Gly Tyr Gly Ile Val Phe Lys Ile Asp Asn Tyr Val Lys Phe Val
            100                 105                 110

Phe Glu Ala Thr Lys Leu Tyr Ser Pro Met Glu Thr Thr Ala Glu Phe
        115                 120                 125

Thr Val Pro Lys Phe Leu Tyr Asn Asn Leu Lys Gly Asp Glu Lys Lys
    130                 135                 140

Leu Ile Val Cys Ala Trp Ala Met Gly Leu Asn Tyr Lys Leu Thr Phe
145                 150                 155                 160

Leu His Thr Leu Tyr Lys Arg Val Leu His Met Leu Leu Leu Ile
                165                 170                 175

Gln Thr Met Asp Gly Gln Glu Leu Ser Leu Arg Tyr Ser Ser Lys Val
            180                 185                 190

Phe Leu Lys Ala Phe Asn Glu Arg Lys Asp Ser Ile Lys Phe Val Lys
        195                 200                 205

Leu Leu Ser His Phe Tyr Pro Ala Val Ile Asn Ser Asn Ile Asn Val
    210                 215                 220

Ile Asn Tyr Phe Asn Arg Met Phe His Phe Glu His Glu Lys Arg
225                 230                 235                 240

Thr Asn Tyr Glu Tyr Glu Arg Gly Asn Ile Ile Ile Phe Pro Leu Ala
```

```
                    245                 250                 255
Leu Tyr Ser Ala Asp Lys Val Asp Thr Glu Leu Ala Ile Lys Leu Gly
            260                 265                 270

Phe Lys Ser Leu Val Gln Tyr Ile Lys Phe Ile Phe Leu Gln Met Ala
        275                 280                 285

Leu Leu Tyr Ile Lys Ile Tyr Glu Leu Pro Cys Cys Asp Asn Phe Leu
    290                 295                 300

His Ala Asp Leu Lys Pro Asp Asn Ile Leu Leu Phe Ser Asn Glu
305                 310                 315                 320

Pro Ile Ile Ile His Leu Lys Asp Lys Lys Phe Val Phe Asn Glu Arg
                325                 330                 335

Ile Lys Ser Ala Leu Asn Asp Phe Asp Phe Ser Gln Val Ala Gly Ile
            340                 345                 350

Val Asn Lys Lys Ile Lys Asn Asn Phe Lys Val Glu His Asn Trp Tyr
        355                 360                 365

Tyr Asp Phe His Phe Phe Val His Thr Leu Leu Lys Thr Tyr Pro Glu
    370                 375                 380

Ile Glu Lys Asp Ile Glu Phe Ser Thr Ala Leu Glu Glu Phe Ile Met
385                 390                 395                 400

Cys Thr Lys Thr Asp Cys Asp Lys Tyr Arg Leu Lys Val Ser Ile Leu
                405                 410                 415

His Pro Ile Ser Phe Leu Glu Lys Phe Ile Met Arg Asp Ile Phe Ser
            420                 425                 430

Asp Trp Ile Asn Gly Gly Asn
        435

<210> SEQ ID NO 21
<211> LENGTH: 1320
<212> TYPE: DNA
<213> ORGANISM: Ectromelia virus
<220> FEATURE:
<221> NAME/KEY: CDS
<222> LOCATION: (1)..(1320)

<400> SEQUENCE: 21 atg ggt gtt gcc aat gat

```
aca gta ccc aaa ttt cta tac aac aat cta aag gga gac gaa aaa aaa    432
Thr Val Pro Lys Phe Leu Tyr Asn Asn Leu Lys Gly Asp Glu Lys Lys
        130                 135                 140 tta atc gtg tgt gca tgg gcc atg gga tta aac tat aaa tta aca ttt    480
Leu Ile Val Cys Ala Trp Ala Met Gly Leu Asn Tyr Lys Leu Thr Phe
145                 150                 155                 160 tta cat act ctg tat aaa cgg gtt ctt aat atg ttg cta tta ttg ata    528
Leu His Thr Leu Tyr Lys Arg Val Leu Asn Met Leu Leu Leu Leu Ile
                165                 170                 175 caa act atg gat ggc cag gaa cta tca ttg aga tat tct tct aaa gtt    576
Gln Thr Met Asp Gly Gln Glu Leu Ser Leu Arg Tyr Ser Ser Lys Val
            180                 185                 190 ttt cta aag gcg ttt aac gag aga aag gac agt atc aaa ttc gtg aaa    624
Phe Leu Lys Ala Phe Asn Glu Arg Lys Asp Ser Ile Lys Phe Val Lys
        195                 200                 205 tta cta tcc cac ttt tat ccg gca gtt att aac agt aat att aat gtt    672
Leu Leu Ser His Phe Tyr Pro Ala Val Ile Asn Ser Asn Ile Asn Val
    210                 215                 220 ata aac tat ttt aac cgc atg ttt cac ttt ttc gaa cat gaa aag aga    720
Ile Asn Tyr Phe Asn Arg Met Phe His Phe Phe Glu His Glu Lys Arg
225                 230                 235                 240 act aac tac gaa tac gaa aga gga aac att ata att ttt ccc tta gcg    768
Thr Asn Tyr Glu Tyr Glu Arg Gly Asn Ile Ile Ile Phe Pro Leu Ala
                245                 250                 255 ctg tat tcg gca gat aaa gta gat acc gag tta gct atc aaa tta gga    816
Leu Tyr Ser Ala Asp Lys Val Asp Thr Glu Leu Ala Ile Lys Leu Gly
            260                 265                 270 ttt aaa tct ttg gta caa tac ata aag ttt atc ttt tta cag atg tct    864
Phe Lys Ser Leu Val Gln Tyr Ile Lys Phe Ile Phe Leu Gln Met Ser
        275                 280                 285 ctg tta tac att aaa att tac gaa ctg cca tgc tgt gac aac ttt tta    912
Leu Leu Tyr Ile Lys Ile Tyr Glu Leu Pro Cys Cys Asp Asn Phe Leu
    290                 295                 300 cac gca gat ctt aaa ccc gat aat atc tta ctt ttt gat tcc aat gaa    960
His Ala Asp Leu Lys Pro Asp Asn Ile Leu Leu Phe Asp Ser Asn Glu
305                 310                 315                 320 cca ata ata att cat cta aag gat aaa aag ttt gtt ttt aat gaa cgt   1008
Pro Ile Ile Ile His Leu Lys Asp Lys Lys Phe Val Phe Asn Glu Arg
                325                 330                 335 att aaa tcg gca tta aac gac ttt gac ttt tcc caa gtg gct gga atc   1056
Ile Lys Ser Ala Leu Asn Asp Phe Asp Phe Ser Gln Val Ala Gly Ile
            340                 345                 350 att aac aag aaa ata aaa acc aat ttc aaa gtt gaa cat aac tgg tat   1104
Ile Asn Lys Lys Ile Lys Thr Asn Phe Lys Val Glu His Asn Trp Tyr
        355                 360                 365 tac gat ttc cat ttc ttt gtt cat act tta tta aaa aca tat cca gaa   1152
Tyr Asp Phe His Phe Phe Val His Thr Leu Leu Lys Thr Tyr Pro Glu
    370                 375                 380 atc gaa aaa gat atc gaa ttt agt aca gca tta gaa gaa ttc atc atg   1200
Ile Glu Lys Asp Ile Glu Phe Ser Thr Ala Leu Glu Glu Phe Ile Met
385                 390                 395                 400 tgt acc aaa aca gac tgt gat aaa tat aga tta aag gtt tcc att ctt   1248
Cys Thr Lys Thr Asp Cys Asp Lys Tyr Arg Leu Lys Val Ser Ile Leu
                405                 410                 415 cac cca att agt ttc ttg gaa aaa ttt att atg aga gac att ttc tca   1296
His Pro Ile Ser Phe Leu Glu Lys Phe Ile Met Arg Asp Ile Phe Ser
            420                 425                 430 gac tgg ata aat ggc gga aac taa                                   1320
Asp Trp Ile Asn Gly Gly Asn
        435
```

<210> SEQ ID NO 22
<211> LENGTH: 439
<212> TYPE: PRT
<213> ORGANISM: Ectromelia virus

<400> SEQUENCE: 22

Met Gly Val Ala Asn Asp Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Arg Glu Thr Leu Leu Lys
    50                  55                  60

Ile Glu Glu Asn Asp Tyr Ile Asn Ser Ser Phe Phe Gln Gln Lys Asp
65                  70                  75                  80

Lys Arg Phe Tyr Pro Ile Asn Asp Asp Phe Tyr His Ile Ser Thr Gly
                85                  90                  95

Gly Tyr Gly Ile Val Phe Lys Ile Asp Asn Tyr Val Val Lys Phe Val
            100                 105                 110

Phe Glu Ala Thr Lys Leu Tyr Ser Pro Met Glu Thr Thr Ala Glu Phe
        115                 120                 125

Thr Val Pro Lys Phe Leu Tyr Asn Asn Leu Lys Gly Asp Glu Lys Lys
    130                 135                 140

Leu Ile Val Cys Ala Trp Ala Met Gly Leu Asn Tyr Lys Leu Thr Phe
145                 150                 155                 160

Leu His Thr Leu Tyr Lys Arg Val Leu Asn Met Leu Leu Leu Ile
                165                 170                 175

Gln Thr Met Asp Gly Gln Glu Leu Ser Leu Arg Tyr Ser Ser Lys Val
            180                 185                 190

Phe Leu Lys Ala Phe Asn Glu Arg Lys Asp Ser Ile Lys Phe Val Lys
        195                 200                 205

Leu Leu Ser His Phe Tyr Pro Ala Val Ile Asn Ser Asn Ile Asn Val
    210                 215                 220

Ile Asn Tyr Phe Asn Arg Met Phe His Phe Glu His Glu Lys Arg
225                 230                 235                 240

Thr Asn Tyr Glu Tyr Glu Arg Gly Asn Ile Ile Ile Phe Pro Leu Ala
                245                 250                 255

Leu Tyr Ser Ala Asp Lys Val Asp Thr Glu Leu Ala Ile Lys Leu Gly
            260                 265                 270

Phe Lys Ser Leu Val Gln Tyr Ile Lys Phe Ile Phe Leu Gln Met Ser
        275                 280                 285

Leu Leu Tyr Ile Lys Ile Tyr Glu Leu Pro Cys Cys Asp Asn Phe Leu
    290                 295                 300

His Ala Asp Leu Lys Pro Asp Asn Ile Leu Leu Phe Asp Ser Asn Glu
305                 310                 315                 320

Pro Ile Ile Ile His Leu Lys Asp Lys Lys Phe Val Phe Asn Glu Arg
                325                 330                 335

Ile Lys Ser Ala Leu Asn Asp Phe Asp Phe Ser Gln Val Ala Gly Ile
            340                 345                 350

Ile Asn Lys Lys Ile Lys Thr Asn Phe Lys Val Glu His Asn Trp Tyr
        355                 360                 365

Tyr Asp Phe His Phe Phe Val His Thr Leu Leu Lys Tyr Pro Glu
    370                 375                 380

```
Ile Glu Lys Asp Ile Glu Phe Ser Thr Ala Leu Glu Glu Phe Ile Met
385                 390                 395                 400

Cys Thr Lys Thr Asp Cys Asp Lys Tyr Arg Leu Lys Val Ser Ile Leu
                405                 410                 415

His Pro Ile Ser Phe Leu Glu Lys Phe Ile Met Arg Asp Ile Phe Ser
            420                 425                 430

Asp Trp Ile Asn Gly Gly Asn
        435

<210> SEQ ID NO 23
<211> LENGTH: 1320
<212> TYPE: DNA
<213> ORGANISM: Monkeypox virus
<220> FEATURE:
<221> NAME/KEY: CDS
<222> LOCATION: (1)..(1320)

<400> SEQUENCE: 23 atg ggt gtt gcc aat gat tca tcc cct gaa tat caa tgg atg tct ccc      48
Met Gly Val Ala Asn Asp Ser Ser Pro Glu Tyr Gln Trp Met Ser Pro
1               5                   10                  15 cat aga tta tca gat act gtt ata tta gga gac tgt tta tat ttt aac      96
His Arg Leu Ser Asp Thr Val Ile Leu Gly Asp Cys Leu Tyr Phe Asn
            20                  25                  30 aac ata atg tcc caa tta gat tta cac caa aat tgg gct cca tca gtt     144
Asn Ile Met Ser Gln Leu Asp Leu His Gln Asn Trp Ala Pro Ser Val
        35                  40                  45 aga ttg tta aat tat ttt aag aat ttt aat aag gaa aca cta cta aag     192
Arg Leu Leu Asn Tyr Phe Lys Asn Phe Asn Lys Glu Thr Leu Leu Lys
    50                  55                  60 ata gaa gag aat gat tac att aat tca tcc ttt ttc caa caa aaa gat     240
Ile Glu Glu Asn Asp Tyr Ile Asn Ser Ser Phe Phe Gln Gln Lys Asp
65                  70                  75                  80 aaa cga ttt tat cct ata aac gac gat ttt tat cac ata tct aca gga     288
Lys Arg Phe Tyr Pro Ile Asn Asp Asp Phe Tyr His Ile Ser Thr Gly
                85                  90                  95 gga tat ggt ata gtc ttt aag ata gat aac tat gta gta aaa ttt gta     336
Gly Tyr Gly Ile Val Phe Lys Ile Asp Asn Tyr Val Val Lys Phe Val
            100                 105                 110 ttc gag gcc aca aaa tta tat agt ccc atg gaa act acg gcg gag ttt     384
Phe Glu Ala Thr Lys Leu Tyr Ser Pro Met Glu Thr Thr Ala Glu Phe
        115                 120                 125 aca gta ccc aaa ttt cta tac aac aat cta aag gga gat gaa aaa aaa     432
Thr Val Pro Lys Phe Leu Tyr Asn Asn Leu Lys Gly Asp Glu Lys Lys
    130                 135                 140 tta atc gtg tgt gcg tgg gcc atg gga tta aac tat aaa tta aca ttt     480
Leu Ile Val Cys Ala Trp Ala Met Gly Leu Asn Tyr Lys Leu Thr Phe
145                 150                 155                 160 tta cat act ctg tat aag cgg gtt ctt cat atg ttg cta tta tgt ata     528
Leu His Thr Leu Tyr Lys Arg Val Leu His Met Leu Leu Leu Cys Ile
                165                 170                 175 caa act atg gat ggt cag gaa ctc tca ttg aga tat tct tct aaa gtt     576
Gln Thr Met Asp Gly Gln Glu Leu Ser Leu Arg Tyr Ser Ser Lys Val
            180                 185                 190 ttt cta aag gcg ttt aac gag aga aag gac agt atc aaa ttc gtg aaa     624
Phe Leu Lys Ala Phe Asn Glu Arg Lys Asp Ser Ile Lys Phe Val Lys
        195                 200                 205 tta cta tcc cac ttt tat ccg gca gtt att aac agt aat att aat gtt     672
Leu Leu Ser His Phe Tyr Pro Ala Val Ile Asn Ser Asn Ile Asn Val
    210                 215                 220
```

```
ata aac tat ttt aac cgc atg ttt cac ttt ttc gaa cat gaa aag aga      720
Ile Asn Tyr Phe Asn Arg Met Phe His Phe Phe Glu His Glu Lys Arg
225                 230                 235                 240 act aat tac gaa tac gaa aga gga aat att ata att ttt ccc cta gca      768
Thr Asn Tyr Glu Tyr Glu Arg Gly Asn Ile Ile Ile Phe Pro Leu Ala
            245                 250                 255 ctg tat tcg gca gat aaa gta gat acc gag tta gct atc aaa tta gga      816
Leu Tyr Ser Ala Asp Lys Val Asp Thr Glu Leu Ala Ile Lys Leu Gly
        260                 265                 270 ttt aaa tct ttg gta caa tac ata aag ttt atc ttt tta cag atg tct      864
Phe Lys Ser Leu Val Gln Tyr Ile Lys Phe Ile Phe Leu Gln Met Ser
    275                 280                 285 ctg tta tac att aaa atc tac gaa cta ccc tgt tgt gac aac ttt tta      912
Leu Leu Tyr Ile Lys Ile Tyr Glu Leu Pro Cys Cys Asp Asn Phe Leu
290                 295                 300 cat gca gat ctt aaa ccc gat aat atc tta ctt ttt gat tcc aat gaa      960
His Ala Asp Leu Lys Pro Asp Asn Ile Leu Leu Phe Asp Ser Asn Glu
305                 310                 315                 320 cca ata ata att cat cta aag aat aaa aag ttt gtt ttt aat gaa cgt     1008
Pro Ile Ile Ile His Leu Lys Asn Lys Lys Phe Val Phe Asn Glu Arg
            325                 330                 335 att aaa tcg gca tta aac gac ttt gac ttt tcc caa gtg gct gga atc     1056
Ile Lys Ser Ala Leu Asn Asp Phe Asp Phe Ser Gln Val Ala Gly Ile
        340                 345                 350 att aac aag aaa ata aaa aac aat ttc aaa gtt gaa cat aac tgg tat     1104
Ile Asn Lys Lys Ile Lys Asn Asn Phe Lys Val Glu His Asn Trp Tyr
    355                 360                 365 tac gat ttc cat ttc ttt gtt cat act tta tta aaa aca tat cca gaa     1152
Tyr Asp Phe His Phe Phe Val His Thr Leu Leu Lys Thr Tyr Pro Glu
370                 375                 380 atc gaa aaa gat atc gaa ttt agt aca gca tta gaa gaa ttc atc atg     1200
Ile Glu Lys Asp Ile Glu Phe Ser Thr Ala Leu Glu Glu Phe Ile Met
385                 390                 395                 400 tgt acc aaa aca gac tgt gat aaa tat aga tta aag gtt tcc att ctt     1248
Cys Thr Lys Thr Asp Cys Asp Lys Tyr Arg Leu Lys Val Ser Ile Leu
            405                 410                 415 cac cca att agt ttc ttg gaa aaa ttt att atg aga gac att ttc tca     1296
His Pro Ile Ser Phe Leu Glu Lys Phe Ile Met Arg Asp Ile Phe Ser
        420                 425                 430 gac tgg ata aat ggc gga aac taa                                     1320
Asp Trp Ile Asn Gly Gly Asn
            435

<210> SEQ ID NO 24
<211> LENGTH: 439
<212> TYPE: PRT
<213> ORGANISM: Monkeypox virus

<400> SEQUENCE: 24

Met Gly Val Ala Asn Asp Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Lys Glu Thr Leu Leu Lys
    50                  55                  60

Ile Glu Glu Asn Asp Tyr Ile Asn Ser Ser Phe Phe Gln Gln Lys Asp
65                  70                  75                  80

Lys Arg Phe Tyr Pro Ile Asn Asp Asp Phe Tyr His Ile Ser Thr Gly
```

```
                85                  90                  95
Gly Tyr Gly Ile Val Phe Lys Ile Asp Asn Tyr Val Val Lys Phe Val
            100                 105                 110

Phe Glu Ala Thr Lys Leu Tyr Ser Pro Met Glu Thr Thr Ala Glu Phe
            115                 120                 125

Thr Val Pro Lys Phe Leu Tyr Asn Asn Leu Lys Gly Asp Glu Lys Lys
130                 135                 140

Leu Ile Val Cys Ala Trp Ala Met Gly Leu Asn Tyr Lys Leu Thr Phe
145                 150                 155                 160

Leu His Thr Leu Tyr Lys Arg Val Leu His Met Leu Leu Leu Leu Ile
                165                 170                 175

Gln Thr Met Asp Gly Gln Glu Leu Ser Leu Arg Tyr Ser Ser Lys Val
            180                 185                 190

Phe Leu Lys Ala Phe Asn Glu Arg Lys Asp Ser Ile Lys Phe Val Lys
            195                 200                 205

Leu Leu Ser His Phe Tyr Pro Ala Val Ile Asn Ser Asn Ile Asn Val
210                 215                 220

Ile Asn Tyr Phe Asn Arg Met Phe His Phe Glu His Glu Lys Arg
225                 230                 235                 240

Thr Asn Tyr Glu Tyr Glu Arg Gly Asn Ile Ile Ile Phe Pro Leu Ala
                245                 250                 255

Leu Tyr Ser Ala Asp Lys Val Asp Thr Glu Leu Ala Ile Lys Leu Gly
            260                 265                 270

Phe Lys Ser Leu Val Gln Tyr Ile Lys Phe Ile Phe Leu Gln Met Ser
            275                 280                 285

Leu Leu Tyr Ile Lys Ile Tyr Glu Leu Pro Cys Cys Asp Asn Phe Leu
290                 295                 300

His Ala Asp Leu Lys Pro Asp Asn Ile Leu Leu Phe Asp Ser Asn Glu
305                 310                 315                 320

Pro Ile Ile Ile His Leu Lys Asn Lys Lys Phe Val Phe Asn Glu Arg
                325                 330                 335

Ile Lys Ser Ala Leu Asn Asp Phe Asp Phe Ser Gln Val Ala Gly Ile
            340                 345                 350

Ile Asn Lys Lys Ile Lys Asn Asn Phe Lys Val Glu His Asn Trp Tyr
            355                 360                 365

Tyr Asp Phe His Phe Phe Val His Thr Leu Leu Lys Thr Tyr Pro Glu
370                 375                 380

Ile Glu Lys Asp Ile Glu Phe Ser Thr Ala Leu Glu Glu Phe Ile Met
385                 390                 395                 400

Cys Thr Lys Thr Asp Cys Asp Lys Tyr Arg Leu Lys Val Ser Ile Leu
                405                 410                 415

His Pro Ile Ser Phe Leu Glu Lys Phe Ile Met Arg Asp Ile Phe Ser
            420                 425                 430

Asp Trp Ile Asn Gly Gly Asn
            435

<210> SEQ ID NO 25
<211> LENGTH: 1320
<212> TYPE: DNA
<213> ORGANISM: Camelpox virus
<220> FEATURE:
<221> NAME/KEY: CDS
<222> LOCATION: (1)..(1320)

<400> SEQUENCE: 25 atg ggt gtt gcc aat gat tca tcc cct gaa tat caa tgg atg tct cca        48
```

```
Met Gly Val Ala Asn Asp Ser Ser Pro Glu Tyr Gln Trp Met Ser Pro
1               5                   10                  15 cat aga tta tct gat act gtt ata tta gga gac tgt tta tat ttt aac    96
His Arg Leu Ser Asp Thr Val Ile Leu Gly Asp Cys Leu Tyr Phe Asn
            20                  25                  30 aac ata atg tca caa tta gat tta cac caa aat tgg gct ccg tca gtt    144
Asn Ile Met Ser Gln Leu Asp Leu His Gln Asn Trp Ala Pro Ser Val
                35                  40                  45 aga ttg tta aat tat ttt aag aat ttt aat agg gaa aca cta cta aag    192
Arg Leu Leu Asn Tyr Phe Lys Asn Phe Asn Arg Glu Thr Leu Leu Lys
            50                  55                  60 ata gaa gag aat gat tac att aat tca tca ttt ttc caa caa aaa gat    240
Ile Glu Glu Asn Asp Tyr Ile Asn Ser Ser Phe Phe Gln Gln Lys Asp
65                  70                  75                  80 aaa aga ttt tat cct ata aac gac gat ttt tat cac ata tct aca gga    288
Lys Arg Phe Tyr Pro Ile Asn Asp Asp Phe Tyr His Ile Ser Thr Gly
                85                  90                  95 gga tat ggt ata gtc ttt aag ata gat aac tat gta gta aaa ttt gta    336
Gly Tyr Gly Ile Val Phe Lys Ile Asp Asn Tyr Val Val Lys Phe Val
            100                 105                 110 ttc gag gcc aca aaa tta tat agt ccc atg gaa act acg gca gag ttc    384
Phe Glu Ala Thr Lys Leu Tyr Ser Pro Met Glu Thr Thr Ala Glu Phe
            115                 120                 125 acg gta cca aaa ttt cta tac aac aat cta aag gga gac gaa aaa aaa    432
Thr Val Pro Lys Phe Leu Tyr Asn Asn Leu Lys Gly Asp Glu Lys Lys
130                 135                 140 tta atc gtg tgt gca tgg gcc atg gga tta aac tat aaa tta aca ttt    480
Leu Ile Val Cys Ala Trp Ala Met Gly Leu Asn Tyr Lys Leu Thr Phe
145                 150                 155                 160 tta cat aca ttg tat aaa cgg gtt ctt aat atg tta cta ttg ata        528
Leu His Thr Leu Tyr Lys Arg Val Leu Asn Met Leu Leu Leu Ile
                165                 170                 175 caa act atg gac ggt cag gaa ctc tca ttg aga tat tcg tct aaa gtt    576
Gln Thr Met Asp Gly Gln Glu Leu Ser Leu Arg Tyr Ser Ser Lys Val
            180                 185                 190 ttt cta aag gcg ttt aac gag aga aag gac agt atc aaa ttc gtg aaa    624
Phe Leu Lys Ala Phe Asn Glu Arg Lys Asp Ser Ile Lys Phe Val Lys
            195                 200                 205 tta cta tcc cac ttt tat ccg gca gtt att aac agt aat att aat gtt    672
Leu Leu Ser His Phe Tyr Pro Ala Val Ile Asn Ser Asn Ile Asn Val
210                 215                 220 ata aac tat ttt aac cgc atg ttt cac ttt ttc gaa cat gaa aag aga    720
Ile Asn Tyr Phe Asn Arg Met Phe His Phe Phe Glu His Glu Lys Arg
225                 230                 235                 240 act aac tac gaa tac gaa aga gga aat att ata att ttt ccc cta gca    768
Thr Asn Tyr Glu Tyr Glu Arg Gly Asn Ile Ile Ile Phe Pro Leu Ala
                245                 250                 255 ctg tat tcg gcg gat aaa gta gat acc gag tta gct att aaa tta gga    816
Leu Tyr Ser Ala Asp Lys Val Asp Thr Glu Leu Ala Ile Lys Leu Gly
            260                 265                 270 ttt aaa tct ttg gta caa tac ata aag ttt atc ttt tta cag atg gct    864
Phe Lys Ser Leu Val Gln Tyr Ile Lys Phe Ile Phe Leu Gln Met Ala
            275                 280                 285 ctg tta tac att aaa atc tac gaa cta ccc tgt tgc gac aac ttt tta    912
Leu Leu Tyr Ile Lys Ile Tyr Glu Leu Pro Cys Cys Asp Asn Phe Leu
290                 295                 300 cac gca gat ctt aaa ccc gat aat atc tta ctt ttt gat tct aat gaa    960
His Ala Asp Leu Lys Pro Asp Asn Ile Leu Leu Phe Asp Ser Asn Glu
305                 310                 315                 320 cca ata ata att cat cta aat gat aaa acg ttt gtt ttt aat gaa cgt    1008
```

```
Pro Ile Ile Ile His Leu Asn Asp Lys Thr Phe Val Phe Asn Glu Arg
            325                 330                 335 att aaa tcg gca tta aac gac ttt gac ttt tcc caa gtg gct gga atc       1056
Ile Lys Ser Ala Leu Asn Asp Phe Asp Phe Ser Gln Val Ala Gly Ile
            340                 345                 350 att aac aag aaa ata aaa aac aat ttc aaa gtt gaa cat aac tgg tat       1104
Ile Asn Lys Lys Ile Lys Asn Asn Phe Lys Val Glu His Asn Trp Tyr
            355                 360                 365 tac gat ttc cat ttc ttt gtt cat act tta tta aaa aca tat cca gaa       1152
Tyr Asp Phe His Phe Phe Val His Thr Leu Leu Lys Thr Tyr Pro Glu
        370                 375                 380 atc gaa aaa gat atc gaa ttt agt aca gca tta gaa gaa ttc atc atg       1200
Ile Glu Lys Asp Ile Glu Phe Ser Thr Ala Leu Glu Glu Phe Ile Met
385                 390                 395                 400 tgt acc aaa aca gac tgt gat aaa tat aga tta aag gtt tcc att ctt       1248
Cys Thr Lys Thr Asp Cys Asp Lys Tyr Arg Leu Lys Val Ser Ile Leu
                405                 410                 415 cac cca att agt ttc ttg gaa aaa ttt att atg agg gac att ttc tca       1296
His Pro Ile Ser Phe Leu Glu Lys Phe Ile Met Arg Asp Ile Phe Ser
            420                 425                 430 gac tgg ata aat ggc gga aac taa                                       1320
Asp Trp Ile Asn Gly Gly Asn
            435

<210> SEQ ID NO 26
<211> LENGTH: 439
<212> TYPE: PRT
<213> ORGANISM: Camelpox virus

<400> SEQUENCE: 26

Met Gly Val Ala Asn Asp Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Arg Glu Thr Leu Leu Lys
    50                  55                  60

Ile Glu Glu Asn Asp Tyr Ile Asn Ser Ser Phe Phe Gln Gln Lys Asp
65                  70                  75                  80

Lys Arg Phe Tyr Pro Ile Asn Asp Asp Phe Tyr His Ile Ser Thr Gly
                85                  90                  95

Gly Tyr Gly Ile Val Phe Lys Ile Asp Asn Tyr Val Lys Phe Val
            100                 105                 110

Phe Glu Ala Thr Lys Leu Tyr Ser Pro Met Glu Thr Thr Ala Glu Phe
        115                 120                 125

Thr Val Pro Lys Phe Leu Tyr Asn Asn Leu Lys Gly Asp Glu Lys Lys
    130                 135                 140

Leu Ile Val Cys Ala Trp Ala Met Gly Leu Asn Tyr Lys Leu Thr Phe
145                 150                 155                 160

Leu His Thr Leu Tyr Lys Arg Val Leu Asn Met Leu Leu Leu Ile
                165                 170                 175

Gln Thr Met Asp Gly Gln Glu Leu Ser Leu Arg Tyr Ser Ser Lys Val
            180                 185                 190

Phe Leu Lys Ala Phe Asn Glu Arg Lys Asp Ser Ile Lys Phe Val Lys
        195                 200                 205

Leu Leu Ser His Phe Tyr Pro Ala Val Ile Asn Ser Asn Ile Asn Val
    210                 215                 220
```

```
Ile Asn Tyr Phe Asn Arg Met Phe His Phe Glu His Glu Lys Arg
225                 230                 235                 240

Thr Asn Tyr Glu Tyr Glu Arg Gly Asn Ile Ile Ile Phe Pro Leu Ala
            245                 250                 255

Leu Tyr Ser Ala Asp Lys Val Asp Thr Glu Leu Ala Ile Lys Leu Gly
            260                 265                 270

Phe Lys Ser Leu Val Gln Tyr Ile Lys Phe Ile Phe Leu Gln Met Ala
        275                 280                 285

Leu Leu Tyr Ile Lys Ile Tyr Glu Leu Pro Cys Cys Asp Asn Phe Leu
        290                 295                 300

His Ala Asp Leu Lys Pro Asp Asn Ile Leu Leu Phe Asp Ser Asn Glu
305                 310                 315                 320

Pro Ile Ile Ile His Leu Asn Asp Lys Thr Phe Val Phe Asn Glu Arg
                325                 330                 335

Ile Lys Ser Ala Leu Asn Asp Phe Asp Phe Ser Gln Val Ala Gly Ile
            340                 345                 350

Ile Asn Lys Lys Ile Lys Asn Phe Lys Val Glu His Asn Trp Tyr
        355                 360                 365

Tyr Asp Phe His Phe Phe Val His Thr Leu Leu Lys Thr Tyr Pro Glu
        370                 375                 380

Ile Glu Lys Asp Ile Glu Phe Ser Thr Ala Leu Glu Glu Phe Ile Met
385                 390                 395                 400

Cys Thr Lys Thr Asp Cys Asp Lys Tyr Arg Leu Lys Val Ser Ile Leu
                405                 410                 415

His Pro Ile Ser Phe Leu Glu Lys Phe Ile Met Arg Asp Ile Phe Ser
            420                 425                 430

Asp Trp Ile Asn Gly Gly Asn
        435

<210> SEQ ID NO 27
<211> LENGTH: 1320
<212> TYPE: DNA
<213> ORGANISM: Variola major virus (Somalia-1977)
<220> FEATURE:
<221> NAME/KEY: CDS
<222> LOCATION: (1)..(1320)

<400> SEQUENCE: 27 atg ggt gtt gcc aat gat tca tcc cct gaa tat caa tgg atg tct cca      48
Met Gly Val Ala Asn Asp Ser Ser Pro Glu Tyr Gln Trp Met Ser Pro
1               5                   10                  15 cat aga tta tct gat act gtt ata tta gga gac tgt tta tat ttt aac      96
His Arg Leu Ser Asp Thr Val Ile Leu Gly Asp Cys Leu Tyr Phe Asn
            20                  25                  30 aac ata atg tca caa tta gat tta cac caa aat tgg gct ccg tca gtt     144
Asn Ile Met Ser Gln Leu Asp Leu His Gln Asn Trp Ala Pro Ser Val
        35                  40                  45 aga ttg tta aat tat ttt aag aat ttt aat agg gaa aca cta cta aag     192
Arg Leu Leu Asn Tyr Phe Lys Asn Phe Asn Arg Glu Thr Leu Leu Lys
50                  55                  60 ata gaa gag aat gat tac att aat tca tca ttt ttc caa caa aaa gat     240
Ile Glu Glu Asn Asp Tyr Ile Asn Ser Ser Phe Phe Gln Gln Lys Asp
65                  70                  75                  80 aaa cga ttt tat cct ata aac gac gat ttt tat cac ata tct aca gga     288
Lys Arg Phe Tyr Pro Ile Asn Asp Asp Phe Tyr His Ile Ser Thr Gly
                85                  90                  95 gga tat ggt ata gtc ttt aag ata gat aac tat gta gta aaa ttt gta     336
Gly Tyr Gly Ile Val Phe Lys Ile Asp Asn Tyr Val Val Lys Phe Val
```

```
                100                 105                 110
ttc gag gcc aca aaa tta tat agt ccc atg gaa act acg gcg gag ttc      384
Phe Glu Ala Thr Lys Leu Tyr Ser Pro Met Glu Thr Thr Ala Glu Phe
            115                 120                 125 acg gta cca aaa ttt cta tac aac aat cta aag gga gac gaa aaa aaa      432
Thr Val Pro Lys Phe Leu Tyr Asn Asn Leu Lys Gly Asp Glu Lys Lys
        130                 135                 140 tta atc gtg tgt gca ttg gcc atg gga tta aac tat aaa tta aca ttt      480
Leu Ile Val Cys Ala Leu Ala Met Gly Leu Asn Tyr Lys Leu Thr Phe
145                 150                 155                 160 tta cat aca ctg tat aaa cgg gtt ctt aat atg tta cta tta ttg ata      528
Leu His Thr Leu Tyr Lys Arg Val Leu Asn Met Leu Leu Leu Leu Ile
                165                 170                 175 caa act atg gac ggt cag gaa ctc tca ttg aga tat tct tct aaa gtt      576
Gln Thr Met Asp Gly Gln Glu Leu Ser Leu Arg Tyr Ser Ser Lys Val
            180                 185                 190 ttt cta aag gcg ttt aac gag aga aag gac agt atc aaa ttt gtg aaa      624
Phe Leu Lys Ala Phe Asn Glu Arg Lys Asp Ser Ile Lys Phe Val Lys
        195                 200                 205 tta cta tcc cac ttt tat ccg gca gtt att aac agt aat att aat gtt      672
Leu Leu Ser His Phe Tyr Pro Ala Val Ile Asn Ser Asn Ile Asn Val
210                 215                 220 ata aac tat ttt aac cgc atg ttt cac ttt ttc gaa cat gaa aag cga      720
Ile Asn Tyr Phe Asn Arg Met Phe His Phe Phe Glu His Glu Lys Arg
225                 230                 235                 240 act aac tac gaa tac gaa aga gga aat att ata att ttt ccc cta gca      768
Thr Asn Tyr Glu Tyr Glu Arg Gly Asn Ile Ile Ile Phe Pro Leu Ala
                245                 250                 255 ctg tat tcg gca gat aaa gta gat acc gag tta gct att aaa tta gga      816
Leu Tyr Ser Ala Asp Lys Val Asp Thr Glu Leu Ala Ile Lys Leu Gly
            260                 265                 270 ttt aaa tct ttg gta caa tac ata aag ttt atc ttt tta cag atg gct      864
Phe Lys Ser Leu Val Gln Tyr Ile Lys Phe Ile Phe Leu Gln Met Ala
        275                 280                 285 ctg tta tac att aaa atc tac gaa cta ccc tgt tgc gac aac ttt tta      912
Leu Leu Tyr Ile Lys Ile Tyr Glu Leu Pro Cys Cys Asp Asn Phe Leu
290                 295                 300 cac gca gat ctt aaa ccc gat aat atc tta ctt ttt gat tcc aat gaa      960
His Ala Asp Leu Lys Pro Asp Asn Ile Leu Leu Phe Asp Ser Asn Glu
305                 310                 315                 320 cca ata ata att cat cta aag gat aaa aag ttt gtt ttt aat gaa cgt     1008
Pro Ile Ile Ile His Leu Lys Asp Lys Lys Phe Val Phe Asn Glu Arg
                325                 330                 335 att aaa tcg gca tta aac gac ttt gac ttt tcc caa gtg gct gga atc     1056
Ile Lys Ser Ala Leu Asn Asp Phe Asp Phe Ser Gln Val Ala Gly Ile
            340                 345                 350 att aac aag aaa ata aaa aac aat ttc aaa gtt gaa cat aac tgg tat     1104
Ile Asn Lys Lys Ile Lys Asn Asn Phe Lys Val Glu His Asn Trp Tyr
        355                 360                 365 tac gat ttc cat ttc ttt gtt cat act tta tta aaa aca tat cca gaa     1152
Tyr Asp Phe His Phe Phe Val His Thr Leu Leu Lys Thr Tyr Pro Glu
370                 375                 380 atc gaa aaa gat att gaa ttt agt aca gca tta gaa gaa ttc atc atg     1200
Ile Glu Lys Asp Ile Glu Phe Ser Thr Ala Leu Glu Glu Phe Ile Met
385                 390                 395                 400 tgt acc aaa aca gac tgt gat aaa tat aga tta aag gtt tcc att ctt     1248
Cys Thr Lys Thr Asp Cys Asp Lys Tyr Arg Leu Lys Val Ser Ile Leu
                405                 410                 415 cac cca att agt ttc ttg gaa aaa ttt att atg agg gac att ttc tca     1296
His Pro Ile Ser Phe Leu Glu Lys Phe Ile Met Arg Asp Ile Phe Ser
```

-continued

```
               420           425           430
gac tgg ata aat ggc aga aac taa                           1320
Asp Trp Ile Asn Gly Arg Asn
        435
```

<210> SEQ ID NO 28
<211> LENGTH: 439
<212> TYPE: PRT
<213> ORGANISM: Variola major virus (Somalia-1977)

<400> SEQUENCE: 28

Met Gly Val Ala Asn Asp Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Arg Glu Thr Leu Leu Lys
    50                  55                  60

Ile Glu Glu Asn Asp Tyr Ile Asn Ser Ser Phe Phe Gln Gln Lys Asp
65                  70                  75                  80

Lys Arg Phe Tyr Pro Ile Asn Asp Asp Phe Tyr His Ile Ser Thr Gly
                85                  90                  95

Gly Tyr Gly Ile Val Phe Lys Ile Asp Asn Tyr Val Val Lys Phe Val
            100                 105                 110

Phe Glu Ala Thr Lys Leu Tyr Ser Pro Met Glu Thr Thr Ala Glu Phe
        115                 120                 125

Thr Val Pro Lys Phe Leu Tyr Asn Asn Leu Lys Gly Asp Glu Lys Lys
    130                 135                 140

Leu Ile Val Cys Ala Leu Ala Met Gly Leu Asn Tyr Lys Leu Thr Phe
145                 150                 155                 160

Leu His Thr Leu Tyr Lys Arg Val Leu Asn Met Leu Leu Leu Leu Ile
                165                 170                 175

Gln Thr Met Asp Gly Gln Glu Leu Ser Leu Arg Tyr Ser Ser Lys Val
            180                 185                 190

Phe Leu Lys Ala Phe Asn Glu Arg Lys Asp Ser Ile Lys Phe Val Lys
        195                 200                 205

Leu Leu Ser His Phe Tyr Pro Ala Val Ile Asn Ser Asn Ile Asn Val
    210                 215                 220

Ile Asn Tyr Phe Asn Arg Met Phe His Phe Phe Glu His Glu Lys Arg
225                 230                 235                 240

Thr Asn Tyr Glu Tyr Glu Arg Gly Asn Ile Ile Ile Phe Pro Leu Ala
                245                 250                 255

Leu Tyr Ser Ala Asp Lys Val Asp Thr Glu Leu Ala Ile Lys Leu Gly
            260                 265                 270

Phe Lys Ser Leu Val Gln Tyr Ile Lys Phe Ile Phe Leu Gln Met Ala
        275                 280                 285

Leu Leu Tyr Ile Lys Ile Tyr Glu Leu Pro Cys Cys Asp Asn Phe Leu
    290                 295                 300

His Ala Asp Leu Lys Pro Asp Asn Ile Leu Leu Phe Asp Ser Asn Glu
305                 310                 315                 320

Pro Ile Ile Ile His Leu Lys Asp Lys Lys Phe Val Phe Asn Glu Arg
                325                 330                 335

Ile Lys Ser Ala Leu Asn Asp Phe Asp Phe Ser Gln Val Ala Gly Ile
            340                 345                 350

```
Ile Asn Lys Lys Ile Lys Asn Asn Phe Lys Val Glu His Asn Trp Tyr
            355                 360                 365

Tyr Asp Phe His Phe Val His Thr Leu Leu Lys Thr Tyr Pro Glu
        370                 375                 380

Ile Glu Lys Asp Ile Glu Phe Ser Thr Ala Leu Glu Glu Phe Ile Met
385                 390                 395                 400

Cys Thr Lys Thr Asp Cys Asp Lys Tyr Arg Leu Lys Val Ser Ile Leu
                405                 410                 415

His Pro Ile Ser Phe Leu Glu Lys Phe Ile Met Arg Asp Ile Phe Ser
                420                 425                 430

Asp Trp Ile Asn Gly Arg Asn
            435

<210> SEQ ID NO 29
<211> LENGTH: 1320
<212> TYPE: DNA
<213> ORGANISM: Variola minor virus (Garcia-1966)
<220> FEATURE:
<221> NAME/KEY: CDS
<222> LOCATION: (1)..(1320)

<400> SEQUENCE: 29 atg ggt gtt gcc aat aat tca tcc cct gaa tat caa tgg atg tct cca    48
Met Gly Val Ala Asn Asn Ser Ser Pro Glu Tyr Gln Trp Met Ser Pro
1               5                   10                  15 cat aga tta tct gat act gtt ata tta gga gac tgt tta tat ttt aac    96
His Arg Leu Ser Asp Thr Val Ile Leu Gly Asp Cys Leu Tyr Phe Asn
                20                  25                  30 aac ata atg tca caa tta gat tta cac caa aat tgg gct ccg tca gtt   144
Asn Ile Met Ser Gln Leu Asp Leu His Gln Asn Trp Ala Pro Ser Val
            35                  40                  45 aga ttg tta aat tat ttt aag aat ttt aat agg gaa aca cta cta aag   192
Arg Leu Leu Asn Tyr Phe Lys Asn Phe Asn Arg Glu Thr Leu Leu Lys
        50                  55                  60 ata gaa gag aat gat tac att aat tca tca ttt ttc caa caa aaa gat   240
Ile Glu Glu Asn Asp Tyr Ile Asn Ser Ser Phe Phe Gln Gln Lys Asp
65                  70                  75                  80 aaa cga ttt tat cct ata aac gac gat ttt tat cac ata tct aca gga   288
Lys Arg Phe Tyr Pro Ile Asn Asp Asp Phe Tyr His Ile Ser Thr Gly
                85                  90                  95 gga tat ggt ata gtc ttt aag ata gat aac tat gta gta aaa ttt gta   336
Gly Tyr Gly Ile Val Phe Lys Ile Asp Asn Tyr Val Val Lys Phe Val
            100                 105                 110 ttc gag gcc aca aaa tta tat agt ccc atg gaa act acg gcg gag ttc   384
Phe Glu Ala Thr Lys Leu Tyr Ser Pro Met Glu Thr Thr Ala Glu Phe
        115                 120                 125 acg gta cca aaa ttt cta tac aac aat cta aag gga gac gaa aaa aaa   432
Thr Val Pro Lys Phe Leu Tyr Asn Asn Leu Lys Gly Asp Glu Lys Lys
    130                 135                 140 tta atc gtg tgt gca ttg gtc atg gga tta aac tat aaa tta aca ttt   480
Leu Ile Val Cys Ala Leu Val Met Gly Leu Asn Tyr Lys Leu Thr Phe
145                 150                 155                 160 tta cat aca ctg tat aaa cgg gtt ctt aat atg tta cta tta ttg ata   528
Leu His Thr Leu Tyr Lys Arg Val Leu Asn Met Leu Leu Leu Leu Ile
                165                 170                 175 caa act atg gac ggt cag gaa ctc tca ttg aga tat tct tct aaa gtt   576
Gln Thr Met Asp Gly Gln Glu Leu Ser Leu Arg Tyr Ser Ser Lys Val
            180                 185                 190 ttt cta aag gcg ttt aac gag aga aag gac agt atc aaa ttc gtg aaa   624
Phe Leu Lys Ala Phe Asn Glu Arg Lys Asp Ser Ile Lys Phe Val Lys
        195                 200                 205
```

| | | |
|---|---|---|
| tta cta tcc cac ttt tat ccg gca gtt att aac agt aat att aat gtt<br>Leu Leu Ser His Phe Tyr Pro Ala Val Ile Asn Ser Asn Ile Asn Val<br>    210             215                 220 | | 672 |
| ata aac tat ttt aac cgc atg ttt cac ttt ttc gaa cat gaa aag cga<br>Ile Asn Tyr Phe Asn Arg Met Phe His Phe Phe Glu His Glu Lys Arg<br>225                 230                 235                 240 | | 720 |
| act aac tac gaa tac gaa aga gga aat att ata att ttt ccc cta gca<br>Thr Asn Tyr Glu Tyr Glu Arg Gly Asn Ile Ile Ile Phe Pro Leu Ala<br>                245                 250                 255 | | 768 |
| ctg tat tcg gca gat aaa gta gat acc gag tta gct att aaa tta gga<br>Leu Tyr Ser Ala Asp Lys Val Asp Thr Glu Leu Ala Ile Lys Leu Gly<br>    260                 265                 270 | | 816 |
| ttt aaa tct ttg gta caa tac ata aag ttt atc ttt tta cag atg gct<br>Phe Lys Ser Leu Val Gln Tyr Ile Lys Phe Ile Phe Leu Gln Met Ala<br>        275                 280                 285 | | 864 |
| ctg tta tac att aaa atc tac gaa cta ccc tct tgc gac aac ttt tta<br>Leu Leu Tyr Ile Lys Ile Tyr Glu Leu Pro Ser Cys Asp Asn Phe Leu<br>290                 295                 300 | | 912 |
| cac gca gat ctt aaa ccc gat aat atc tta ctt ttt gat tcc aat gaa<br>His Ala Asp Leu Lys Pro Asp Asn Ile Leu Leu Phe Asp Ser Asn Glu<br>305                 310                 315                 320 | | 960 |
| cca ata ata att cat cta aag gat aaa aag ttt gtt ttt aat gaa cgt<br>Pro Ile Ile Ile His Leu Lys Asp Lys Lys Phe Val Phe Asn Glu Arg<br>                325                 330                 335 | | 1008 |
| att aaa tcg gca tta aac gac ttt gac ttt tcc caa gtg gct gga atc<br>Ile Lys Ser Ala Leu Asn Asp Phe Asp Phe Ser Gln Val Ala Gly Ile<br>    340                 345                 350 | | 1056 |
| att aac aag aaa ata aaa aac aat ttc aaa gtt gaa cat aac tgg tat<br>Ile Asn Lys Lys Ile Lys Asn Asn Phe Lys Val Glu His Asn Trp Tyr<br>        355                 360                 365 | | 1104 |
| tac gat ttc cat ttc ttt gtt cat act tta tta aaa aca tat cca gaa<br>Tyr Asp Phe His Phe Phe Val His Thr Leu Leu Lys Thr Tyr Pro Glu<br>370                 375                 380 | | 1152 |
| atc gaa aaa gat att gaa ttt agt aca gca tta gaa gaa ttc atc atg<br>Ile Glu Lys Asp Ile Glu Phe Ser Thr Ala Leu Glu Glu Phe Ile Met<br>385                 390                 395                 400 | | 1200 |
| tgt acc aaa aca gac tgt gat aaa tat aga tta aag gtt tcc att ctt<br>Cys Thr Lys Thr Asp Cys Asp Lys Tyr Arg Leu Lys Val Ser Ile Leu<br>                405                 410                 415 | | 1248 |
| cac cca att agt ttc ttg gaa aaa ttt att atg agg gac att ttc tca<br>His Pro Ile Ser Phe Leu Glu Lys Phe Ile Met Arg Asp Ile Phe Ser<br>    420                 425                 430 | | 1296 |
| gac tgg ata aat ggc aga aac taa<br>Asp Trp Ile Asn Gly Arg Asn<br>        435 | | 1320 |

<210> SEQ ID NO 30
<211> LENGTH: 439
<212> TYPE: PRT
<213> ORGANISM: Variola minor virus (Garcia-1966)

<400> SEQUENCE: 30

Met Gly Val Ala Asn Asn Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Arg Glu Thr Leu Leu Lys
    50                  55                  60

Ile Glu Glu Asn Asp Tyr Ile Asn Ser Ser Phe Phe Gln Gln Lys Asp
65                  70                  75                  80

Lys Arg Phe Tyr Pro Ile Asn Asp Asp Phe Tyr His Ile Ser Thr Gly
                85                  90                  95

Gly Tyr Gly Ile Val Phe Lys Ile Asp Asn Tyr Val Val Lys Phe Val
            100                 105                 110

Phe Glu Ala Thr Lys Leu Tyr Ser Pro Met Glu Thr Thr Ala Glu Phe
            115                 120                 125

Thr Val Pro Lys Phe Leu Tyr Asn Asn Leu Lys Gly Asp Glu Lys Lys
130                 135                 140

Leu Ile Val Cys Ala Leu Val Met Gly Leu Asn Tyr Lys Leu Thr Phe
145                 150                 155                 160

Leu His Thr Leu Tyr Lys Arg Val Leu Asn Met Leu Leu Leu Leu Ile
                165                 170                 175

Gln Thr Met Asp Gly Gln Glu Leu Ser Leu Arg Tyr Ser Ser Lys Val
            180                 185                 190

Phe Leu Lys Ala Phe Asn Glu Arg Lys Asp Ser Ile Lys Phe Val Lys
            195                 200                 205

Leu Leu Ser His Phe Tyr Pro Ala Val Ile Asn Ser Asn Ile Asn Val
210                 215                 220

Ile Asn Tyr Phe Asn Arg Met Phe His Phe Glu His Glu Lys Arg
225                 230                 235                 240

Thr Asn Tyr Glu Tyr Gl

<222> LOCATION: (1)..(1335)

<400> SEQUENCE: 31

| | | | | | | | | | | | | | | | | |
|---|---|---|---|---|---|---|---|---|---|---|---|---|---|---|---|---|
| atg | aga | atc | atg | aat | gag | gat | tcg | cca | gaa | tgt | caa | tgg | gaa | tat | aaa | 48 |
| Met | Arg | Ile | Met | Asn | Glu | Asp | Ser | Pro | Glu | Cys | Gln | Trp | Glu | Tyr | Lys | |
| 1 | | | | 5 | | | | | 10 | | | | | 15 | | |
| gat | gat | ata | gaa | aat | act | aca | aca | att | ttg | gga | gat | gat | ata | tat | ttt | 96 |
| Asp | Asp | Ile | Glu | Asn | Thr | Thr | Thr | Ile | Leu | Gly | Asp | Asp | Ile | Tyr | Phe | |
| | | | 20 | | | | | 25 | | | | | 30 | | | |
| gat | tat | ata | att | tct | caa | ttg | gat | att | aac | caa | agt | tgg | tct | cct | aat | 144 |
| Asp | Tyr | Ile | Ile | Ser | Gln | Leu | Asp | Ile | Asn | Gln | Ser | Trp | Ser | Pro | Asn | |
| | | 35 | | | | | 40 | | | | | 45 | | | | |
| agc | aaa | tta | att | agt | tat | ttt | aaa | aat | ttt | aat | aga | gaa | aca | tta | aac | 192 |
| Ser | Lys | Leu | Ile | Ser | Tyr | Phe | Lys | Asn | Phe | Asn | Arg | Glu | Thr | Leu | Asn | |
| | 50 | | | | | 55 | | | | | 60 | | | | | |
| aaa | ata | att | aat | gaa | gat | tat | gta | aat | ccc | tca | ttt | ttt | caa | caa | aaa | 240 |
| Lys | Ile | Ile | Asn | Glu | Asp | Tyr | Val | Asn | Pro | Ser | Phe | Phe | Gln | Gln | Lys | |
| 65 | | | | | 70 | | | | | 75 | | | | | 80 | |
| gat | aaa | agg | ttt | tat | cca | atg | aat | gat | gat | ttt | tat | cat | ata | tca | aca | 288 |
| Asp | Lys | Arg | Phe | Tyr | Pro | Met | Asn | Asp | Asp | Phe | Tyr | His | Ile | Ser | Thr | |
| | | | | 85 | | | | | 90 | | | | | 95 | | |
| gga | gga | tat | ggt | att | gta | ttt | aaa | ata | gat | aag | tat | gta | gta | aag | ttt | 336 |
| Gly | Gly | Tyr | Gly | Ile | Val | Phe | Lys | Ile | Asp | Lys | Tyr | Val | Val | Lys | Phe | |
| | | | 100 | | | | | 105 | | | | | 110 | | | |
| gtc | tat | gaa | ccc | aat | aaa | caa | tat | agt | ccg | ata | gag | aca | acg | gcg | gaa | 384 |
| Val | Tyr | Glu | Pro | Asn | Lys | Gln | Tyr | Ser | Pro | Ile | Glu | Thr | Thr | Ala | Glu | |
| | | 115 | | | | | 120 | | | | | 125 | | | | |
| tat | aca | ata | cct | aaa | ttt | tta | tat | aat | aat | tta | aag | ggc | gat | gaa | aaa | 432 |
| Tyr | Thr | Ile | Pro | Lys | Phe | Leu | Tyr | Asn | Asn | Leu | Lys | Gly | Asp | Glu | Lys | |
| | 130 | | | | | 135 | | | | | 140 | | | | | |
| aaa | tta | att | gta | tgt | gct | tgg | gct | atg | gga | tta | aat | tat | aga | ttg | aca | 480 |
| Lys | Leu | Ile | Val | Cys | Ala | Trp | Ala | Met | Gly | Leu | Asn | Tyr | Arg | Leu | Thr | |
| 145 | | | | | 150 | | | | | 155 | | | | | 160 | |
| ttt | tta | tat | aat | ctt | tat | aaa | cgc | gta | ttg | tat | att | tta | tta | tta | ttg | 528 |
| Phe | Leu | Tyr | Asn | Leu | Tyr | Lys | Arg | Val | Leu | Tyr | Ile | Leu | Leu | Leu | Leu | |
| | | | | 165 | | | | | 170 | | | | | 175 | | |
| tta | cag | acg | ata | gat | aat | caa | caa | tta | aat | tta | cat | cat | ttt | tca | cat | 576 |
| Leu | Gln | Thr | Ile | Asp | Asn | Gln | Gln | Leu | Asn | Leu | His | His | Phe | Ser | His | |
| | | | 180 | | | | | 185 | | | | | 190 | | | |
| aaa | tat | ttt | tta | aaa | tct | ttt | aat | gaa | aaa | aag | gga | gat | ata | aaa | ttt | 624 |
| Lys | Tyr | Phe | Leu | Lys | Ser | Phe | Asn | Glu | Lys | Lys | Gly | Asp | Ile | Lys | Phe | |
| | | 195 | | | | | 200 | | | | | 205 | | | | |
| gta | aaa | cta | tta | tca | tat | ttt | tat | cct | cta | tta | gtt | caa | agt | aat | ata | 672 |
| Val | Lys | Leu | Leu | Ser | Tyr | Phe | Tyr | Pro | Leu | Leu | Val | Gln | Ser | Asn | Ile | |
| | 210 | | | | | 215 | | | | | 220 | | | | | |
| aac | gtt | ata | aat | tat | ttt | act | cat | atg | ttt | cat | ttt | ttt | gaa | cat | gaa | 720 |
| Asn | Val | Ile | Asn | Tyr | Phe | Thr | His | Met | Phe | His | Phe | Phe | Glu | His | Glu | |
| 225 | | | | | 230 | | | | | 235 | | | | | 240 | |
| aaa | aga | tca | aac | tat | ctt | tat | gat | agg | ggc | aat | ata | ata | gta | ttt | cca | 768 |
| Lys | Arg | Ser | Asn | Tyr | Leu | Tyr | Asp | Arg | Gly | Asn | Ile | Ile | Val | Phe | Pro | |
| | | | | 245 | | | | | 250 | | | | | 255 | | |
| ttg | gca | aga | tgt | tct | gca | gat | aaa | att | act | gag | aaa | atg | gca | ttg | gaa | 816 |
| Leu | Ala | Arg | Cys | Ser | Ala | Asp | Lys | Ile | Thr | Glu | Lys | Met | Ala | Leu | Glu | |
| | | | 260 | | | | | 265 | | | | | 270 | | | |
| ttt | gga | ttt | tca | tca | ttg | gta | aac | tat | ata | aaa | ttt | ctt | ttt | tta | caa | 864 |
| Phe | Gly | Phe | Ser | Ser | Leu | Val | Asn | Tyr | Ile | Lys | Phe | Leu | Phe | Leu | Gln | |
| | | 275 | | | | | 280 | | | | | 285 | | | | |
| att | gca | tta | tta | tat | ata | aaa | ata | tat | gaa | tta | ccg | tgt | tgt | aat | aat | 912 |
| Ile | Ala | Leu | Leu | Tyr | Ile | Lys | Ile | Tyr | Glu | Leu | Pro | Cys | Cys | Asn | Asn | |
| | 290 | | | | | 295 | | | | | 300 | | | | | |

```
ttt tta cat gta gat tta aag cct gat aat att tta ttg ttt gat tct    960
Phe Leu His Val Asp Leu Lys Pro Asp Asn Ile Leu Leu Phe Asp Ser
305                 310                 315                 320 aat aaa cct atc aag ata aaa ttt aaa gaa atg tcc tat ata ttt aat   1008
Asn Lys Pro Ile Lys Ile Lys Phe Lys Glu Met Ser Tyr Ile Phe Asn
                325                 330                 335 gaa ccg ata aaa gca tgt tta aat gat ttt gat ttt tcc cag gtt gct   1056
Glu Pro Ile Lys Ala Cys Leu Asn Asp Phe Asp Phe Ser Gln Val Ala
                340                 345                 350 agc ata gta aat aaa aaa atc aaa aat agt tta aag gtg gaa cat aat   1104
Ser Ile Val Asn Lys Lys Ile Lys Asn Ser Leu Lys Val Glu His Asn
            355                 360                 365 tgg tat tat gac ttt cat ttt ttt ata cat act ctt tta cgc acg tat   1152
Trp Tyr Tyr Asp Phe His Phe Phe Ile His Thr Leu Leu Arg Thr Tyr
    370                 375                 380 ccg gaa ata gaa aaa gat gta gaa ttt aac aat gca tta gaa gaa ttc   1200
Pro Glu Ile Glu Lys Asp Val Glu Phe Asn Asn Ala Leu Glu Glu Phe
385                 390                 395                 400 ata ata tgt tgt tca aaa aat aca tgc gat aaa ttt aga tta aaa gtt   1248
Ile Ile Cys Cys Ser Lys Asn Thr Cys Asp Lys Phe Arg Leu Lys Val
                405                 410                 415 tca ata ttg cac cct atc aca ttt ttg gaa aaa ttt gtt tca aaa aac   1296
Ser Ile Leu His Pro Ile Thr Phe Leu Glu Lys Phe Val Ser Lys Asn
                420                 425                 430 att ttc tca cct tgg ata aat gga gga gaa cca agt taa               1335
Ile Phe Ser Pro Trp Ile Asn Gly Gly Glu Pro Ser
            435                 440

<210> SEQ ID NO 32
<211> LENGTH: 444
<212> TYPE: PRT
<213> ORGANISM: Mule deer poxvirus

<400> SEQUENCE: 32

Met Arg Ile Met Asn Glu Asp Ser Pro Glu Cys Gln Trp Glu Tyr Lys
1               5                   10                  15

Asp Asp Ile Glu Asn Thr Thr Thr Ile Leu Gly Asp Asp Ile Tyr Phe
            20                  25                  30

Asp Tyr Ile Ile Ser Gln Leu Asp Ile Asn Gln Ser Trp Ser Pro Asn
        35                  40                  45

Ser Lys Leu Ile Ser Tyr Phe Lys Asn Phe Asn Arg Glu Thr Leu Asn
    50                  55                  60

Lys Ile Ile Asn Glu Asp Tyr Val Asn Pro Ser Phe Phe Gln Gln Lys
65                  70                  75                  80

Asp Lys Arg Phe Tyr Pro Met Asn Asp Asp Phe Tyr His Ile Ser Thr
                85                  90                  95

Gly Gly Tyr Gly Ile Val Phe Lys Ile Asp Lys Tyr Val Val Lys Phe
            100                 105                 110

Val Tyr Glu Pro Asn Lys Gln Tyr Ser Pro Ile Glu Thr Thr Ala Glu
        115                 120                 125

Tyr Thr Ile Pro Lys Phe Leu Tyr Asn Asn Leu Lys Gly Asp Glu Lys
    130                 135                 140

Lys Leu Ile Val Cys Ala Trp Ala Met Gly Leu Asn Tyr Arg Leu Thr
145                 150                 155                 160

Phe Leu Tyr Asn Leu Tyr Lys Arg Val Leu Tyr Ile Leu Leu Leu Leu
                165                 170                 175

Leu Gln Thr Ile Asp Asn Gln Gln Leu Asn Leu His Phe Ser His
            180                 185                 190
```

```
            Lys Tyr Phe Leu Lys Ser Phe Asn Glu Lys Lys Gly Asp Ile Lys Phe
                            195                 200                 205

Val Lys Leu Leu Ser Tyr Phe Tyr Pro Leu Leu Val Gln Ser Asn Ile
                    210                 215                 220

Asn Val Ile Asn Tyr Phe Thr His Met Phe His Phe Phe Glu His Glu
            225                 230                 235                 240

Lys Arg Ser Asn Tyr Leu Tyr Asp Arg Gly Asn Ile Ile Val Phe Pro
                            245                 250                 255

Leu Ala Arg Cys Ser Ala Asp Lys Ile Thr Glu Lys Met Ala Leu Glu
                        260                 265                 270

Phe Gly Phe Ser Ser Leu Val Asn Tyr Ile Lys Phe Leu Phe Leu Gln
                    275                 280                 285

Ile Ala Leu Leu Tyr Ile Lys Ile Tyr Glu Leu Pro Cys Cys Asn Asn
                290                 295                 300

Phe Leu His Val Asp Leu Lys Pro Asp Asn Ile Leu Leu Phe Asp Ser
            305                 310                 315                 320

Asn Lys Pro Ile Lys Ile Lys Phe Lys Glu Met Ser Tyr Ile Phe Asn
                            325                 330                 335

Glu Pro Ile Lys Ala Cys Leu Asn Asp Phe Asp Phe Ser Gln Val Ala
                        340                 345                 350

Ser Ile Val Asn Lys Lys Ile Lys Asn Ser Leu Lys Val Glu His Asn
                    355                 360                 365

Trp Tyr Tyr Asp Phe His Phe Phe Ile His Thr Leu Leu Arg Thr Tyr
                370                 375                 380

Pro Glu Ile Glu Lys Asp Val Glu Phe Asn Asn Ala Leu Glu Glu Phe
            385                 390                 395                 400

Ile Ile Cys Cys Ser Lys Asn Thr Cys Asp Lys Phe Arg Leu Lys Val
                            405                 410                 415

Ser Ile Leu His Pro Ile Thr Phe Leu Glu Lys Phe Val Ser Lys Asn
                        420                 425                 430

Ile Phe Ser Pro Trp Ile Asn Gly Gly Glu Pro Ser
                    435                 440

<210> SEQ ID NO 33
<211> LENGTH: 1338
<212> TYPE: DNA
<213> ORGANISM: Yaba monkey tumor virus
<220> FEATURE:
<221> NAME/KEY: CDS
<222> LOCATION: (1)..(1338)

<400> SEQUENCE: 33 atg ggg gtt aaa acc gat aat tct ctt gaa tgt caa tgg gaa tta aaa      48
Met Gly Val Lys Thr Asp Asn Ser Leu Glu Cys Gln Trp Glu Leu Lys
1               5                   10                  15 aac gat gag agg ata gaa aca aca ata ttg gga gat gat ata tat ttt      96
Asn Asp Glu Arg Ile Glu Thr Thr Ile Leu Gly Asp Asp Ile Tyr Phe
                20                  25                  30 gac tat gta att tct caa atc gat aca cat cag agt tgg tct ccc agt     144
Asp Tyr Val Ile Ser Gln Ile Asp Thr His Gln Ser Trp Ser Pro Ser
            35                  40                  45 atc agg tta gtg aaa tat ttt aaa aat ttt aac aaa gag tta tta gaa     192
Ile Arg Leu Val Lys Tyr Phe Lys Asn Phe Asn Lys Glu Leu Leu Glu
        50                  55                  60 aca ata gca agt aac gaa tac gtt aac cca tct ttt ttc caa caa aaa     240
Thr Ile Ala Ser Asn Glu Tyr Val Asn Pro Ser Phe Phe Gln Gln Lys
65                  70                  75                  80 gat aag agg ttt tac cca gtt aac gat gat ttt tat cat ata tcc acg     288
```

```
Asp Lys Arg Phe Tyr Pro Val Asn Asp Asp Phe Tyr His Ile Ser Thr
                85                  90                  95 ggg ggg tat gga ata gtt ttt aaa ata gat aag tac gtt gta aaa ttt      336
Gly Gly Tyr Gly Ile Val Phe Lys Ile Asp Lys Tyr Val Val Lys Phe
            100                 105                 110 gtt tat gaa cca aat aaa agc tat agt ccg ata gac acc aca gcg gaa      384
Val Tyr Glu Pro Asn Lys Ser Tyr Ser Pro Ile Asp Thr Thr Ala Glu
        115                 120                 125 tac acg ata cct aag ttt ctg tat att aat ctt aag gga gac gaa aaa      432
Tyr Thr Ile Pro Lys Phe Leu Tyr Ile Asn Leu Lys Gly Asp Glu Lys
    130                 135                 140 aaa tta ata gtt tgc gca tgg gcg atg gga ttg aat tat aga tta acg      480
Lys Leu Ile Val Cys Ala Trp Ala Met Gly Leu Asn Tyr Arg Leu Thr
145                 150                 155                 160 ttt ctt cat gat cta tac aaa aga gtt ttg tat atg tta ata tta tta      528
Phe Leu His Asp Leu Tyr Lys Arg Val Leu Tyr Met Leu Ile Leu Leu
                165                 170                 175 ata cag ata atg gac ggg gaa aag ctt aat ctt aat aat ttt tca cat      576
Ile Gln Ile Met Asp Gly Glu Lys Leu Asn Leu Asn Asn Phe Ser His
            180                 185                 190 aaa cag ttt tta aaa tct ttt aac gat aaa aag gat gac ata aaa ttt      624
Lys Gln Phe Leu Lys Ser Phe Asn Asp Lys Lys Asp Asp Ile Lys Phe
        195                 200                 205 gtt agg tta ata tct tat ttt tat cct att gtt att caa agt aac ata      672
Val Arg Leu Ile Ser Tyr Phe Tyr Pro Ile Val Ile Gln Ser Asn Ile
    210                 215                 220 aac gtt ata aat tac ttt tcg tac atg ttt cat ttt ttt gaa cat gag      720
Asn Val Ile Asn Tyr Phe Ser Tyr Met Phe His Phe Phe Glu His Glu
225                 230                 235                 240 aaa aga tcg gat tat tta tac gaa agg ggt aac ata ata ata ttt cca      768
Lys Arg Ser Asp Tyr Leu Tyr Glu Arg Gly Asn Ile Ile Ile Phe Pro
                245                 250                 255 cta gca aga tgt tct gca gac aaa gta aca gaa aaa atg gcg aaa aaa      816
Leu Ala Arg Cys Ser Ala Asp Lys Val Thr Glu Lys Met Ala Lys Lys
            260                 265                 270 ttg ggt ttt agc tct ctt gtt agt tat atc aag ttt tta ttt ttg cag      864
Leu Gly Phe Ser Ser Leu Val Ser Tyr Ile Lys Phe Leu Phe Leu Gln
        275                 280                 285 atg tcg ctg tta tat ata aaa ata tac gaa tta cca tgt tgt gac aat      912
Met Ser Leu Leu Tyr Ile Lys Ile Tyr Glu Leu Pro Cys Cys Asp Asn
    290                 295                 300 ttt ttg cat gta gat ctt aaa cct gac aac ata tta ttg ttt gat tct      960
Phe Leu His Val Asp Leu Lys Pro Asp Asn Ile Leu Leu Phe Asp Ser
305                 310                 315                 320 gat gaa aag ttg caa ata aaa ttt aat aat aac ttg tac gtt ttt aac     1008
Asp Glu Lys Leu Gln Ile Lys Phe Asn Asn Asn Leu Tyr Val Phe Asn
                325                 330                 335 gaa aaa gtt aaa tcg tgt tta aac gac ttt gat ttt tct cag gtt gcg     1056
Glu Lys Val Lys Ser Cys Leu Asn Asp Phe Asp Phe Ser Gln Val Ala
            340                 345                 350 aac ata acg aac aaa aaa att aaa aac agt tta aaa gtg gaa cat aac     1104
Asn Ile Thr Asn Lys Lys Ile Lys Asn Ser Leu Lys Val Glu His Asn
        355                 360                 365 tgg tac tac gat ttt cat ttt ttt aca cat aca ctg tta aaa aca tat     1152
Trp Tyr Tyr Asp Phe His Phe Phe Thr His Thr Leu Leu Lys Thr Tyr
    370                 375                 380 cca gaa att aaa aac gac gca gaa ttt aac aac tct tta gaa gag cta     1200
Pro Glu Ile Lys Asn Asp Ala Glu Phe Asn Asn Ser Leu Glu Glu Leu
385                 390                 395                 400 ata atg tgt tgt aac aaa agt ata tgc gac aag ttt agg tta aaa gta     1248
```

```
Ile Met Cys Cys Asn Lys Ser Ile Cys Asp Lys Phe Arg Leu Lys Val
                    405                 410                 415 tcc att tta cat cct ata agt ttt tta gaa aaa ttt gta acg aga gac    1296
Ser Ile Leu His Pro Ile Ser Phe Leu Glu Lys Phe Val Thr Arg Asp
                    420                 425                 430 att ttc tca gag tgg ata aat gga aga gat aca gag agt taa            1338
Ile Phe Ser Glu Trp Ile Asn Gly Arg Asp Thr Glu Ser
                    435                 440             445
```

<210> SEQ ID NO 34
<211> LENGTH: 445
<212> TYPE: PRT
<213> ORGANISM: Yaba monkey tumor virus

<400> SEQUENCE: 34

```
Met Gly Val Lys Thr Asp Asn Ser Leu Glu Cys Gln Trp Glu Leu Lys
1               5                   10                  15

Asn Asp Glu Arg Ile Glu Thr Thr Ile Leu Gly Asp Asp Ile Tyr Phe
                20                  25                  30

Asp Tyr Val Ile Ser Gln Ile Asp Thr His Gln Ser Trp Ser Pro Ser
            35                  40                  45

Ile Arg Leu Val Lys Tyr Phe Lys Asn Phe Asn Lys Glu Leu Leu Glu
50                  55                  60

Thr Ile Ala Ser Asn Glu Tyr Val Asn Pro Ser Phe Phe Gln Gln Lys
65                  70                  75                  80

Asp Lys Arg Phe Tyr Pro Val Asn Asp Asp Phe Tyr His Ile Ser Thr
                85                  90                  95

Gly Gly Tyr Gly Ile Val Phe Lys Ile Asp Lys Tyr Val Val Lys Phe
                100                 105                 110

Val Tyr Glu Pro Asn Lys Ser Tyr Ser Pro Ile Asp Thr Thr Ala Glu
            115                 120                 125

Tyr Thr Ile Pro Lys Phe Leu Tyr Ile Asn Leu Lys Gly Asp Glu Lys
130                 135                 140

Lys Leu Ile Val Cys Ala Trp Ala Met Gly Leu Asn Tyr Arg Leu Thr
145                 150                 155                 160

Phe Leu His Asp Leu Tyr Lys Arg Val Leu Tyr Met Leu Ile Leu Leu
                165                 170                 175

Ile Gln Ile Met Asp Gly Glu Lys Leu Asn Leu Asn Asn Phe Ser His
            180                 185                 190

Lys Gln Phe Leu Lys Ser Phe Asn Asp Lys Lys Asp Ile Lys Phe
            195                 200                 205

Val Arg Leu Ile Ser Tyr Phe Tyr Pro Ile Val Ile Gln Ser Asn Ile
210                 215                 220

Asn Val Ile Asn Tyr Phe Ser Tyr Met Phe His Phe Glu His Glu
225                 230                 235                 240

Lys Arg Ser Asp Tyr Leu Tyr Glu Arg Gly Asn Ile Ile Phe Pro
                245                 250                 255

Leu Ala Arg Cys Ser Ala Asp Lys Val Thr Glu Lys Met Ala Lys Lys
                260                 265                 270

Leu Gly Phe Ser Ser Leu Val Ser Tyr Ile Lys Phe Leu Phe Leu Gln
            275                 280                 285

Met Ser Leu Leu Tyr Ile Lys Ile Tyr Glu Leu Pro Cys Cys Asp Asn
            290                 295                 300

Phe Leu His Val Asp Leu Lys Pro Asp Asn Ile Leu Leu Phe Asp Ser
305                 310                 315                 320

Asp Glu Lys Leu Gln Ile Lys Phe Asn Asn Asn Leu Tyr Val Phe Asn
```

```
            325                 330                 335
Glu Lys Val Lys Ser Cys Leu Asn Asp Phe Asp Phe Ser Gln Val Ala
        340                 345                 350

Asn Ile Thr Asn Lys Lys Ile Lys Asn Ser Leu Lys Val Glu His Asn
    355                 360                 365

Trp Tyr Tyr Asp Phe His Phe Phe Thr His Thr Leu Leu Lys Thr Tyr
370                 375                 380

Pro Glu Ile Lys Asn Asp Ala Glu Phe Asn Asn Ser Leu Glu Glu Leu
385                 390                 395                 400

Ile Met Cys Cys Asn Lys Ser Ile Cys Asp Lys Phe Arg Leu Lys Val
                405                 410                 415

Ser Ile Leu His Pro Ile Ser Phe Leu Glu Lys Phe Val Thr Arg Asp
            420                 425                 430

Ile Phe Ser Glu Trp Ile Asn Gly Arg Asp Thr Glu Ser
        435                 440                 445

<210> SEQ ID NO 35
<211> LENGTH: 1338
<212> TYPE: DNA
<213> ORGANISM: Yaba-like disease virus
<220> FEATURE:
<221> NAME/KEY: CDS
<222> LOCATION: (1)..(1338)

<400> SEQUENCE: 35 atg ggg gta aaa act gat aat tcc ttg gaa tgt caa tgg gat tta caa      48
Met Gly Val Lys Thr Asp Asn Ser Leu Glu Cys Gln Trp Asp Leu Gln
1               5                   10                  15 gac gac aaa aaa cta gaa aca acc ata tta ggc gat gat att tat ttt      96
Asp Asp Lys Lys Leu Glu Thr Thr Ile Leu Gly Asp Asp Ile Tyr Phe
            20                  25                  30 gac tat gta ttt tca caa att gat gta aat caa aat tgg tct cca agt     144
Asp Tyr Val Phe Ser Gln Ile Asp Val Asn Gln Asn Trp Ser Pro Ser
        35                  40                  45 att aga tta att aag tat ttt aaa aac ttt aac aaa gaa tta tta gat     192
Ile Arg Leu Ile Lys Tyr Phe Lys Asn Phe Asn Lys Glu Leu Leu Asp
    50                  55                  60 aca ata gca agt aaa gag tat gta aat cca tct ttt ttt caa caa aaa     240
Thr Ile Ala Ser Lys Glu Tyr Val Asn Pro Ser Phe Phe Gln Gln Lys
65                  70                  75                  80 gac aaa cga ttt tat cca ata aat gat gat ttt tat cat tta tct acc     288
Asp Lys Arg Phe Tyr Pro Ile Asn Asp Asp Phe Tyr His Leu Ser Thr
                85                  90                  95 gga ggt tat gga ata gtt ttt aaa ata gac aaa tat gta gta aaa ttt     336
Gly Gly Tyr Gly Ile Val Phe Lys Ile Asp Lys Tyr Val Val Lys Phe
            100                 105                 110 gtt tat gaa cca aat aaa aac tat agt ccg ata gat act act gca gag     384
Val Tyr Glu Pro Asn Lys Asn Tyr Ser Pro Ile Asp Thr Thr Ala Glu
        115                 120                 125 tat acc ata cct aag ttt tta tat ctt aac ctt aaa ggt gat gaa aaa     432
Tyr Thr Ile Pro Lys Phe Leu Tyr Leu Asn Leu Lys Gly Asp Glu Lys
    130                 135                 140 aag tta att gta tgt gcg tgg gca atg gga cta aat tat aaa tta aca     480
Lys Leu Ile Val Cys Ala Trp Ala Met Gly Leu Asn Tyr Lys Leu Thr
145                 150                 155                 160 ttt ctt tat gat ctt tac aaa cga gtt tta tac atg cta ata tta ttg     528
Phe Leu Tyr Asp Leu Tyr Lys Arg Val Leu Tyr Met Leu Ile Leu Leu
                165                 170                 175 ttg caa ata atg gat ggc gaa aaa ctc gat ctt cat aat ttt tca cat     576
Leu Gln Ile Met Asp Gly Glu Lys Leu Asp Leu His Asn Phe Ser His
```

```
                   180                 185                 190
aaa cat ttt tta aaa tct ttt aac gat aaa aaa gat gat ata aaa ttt        624
Lys His Phe Leu Lys Ser Phe Asn Asp Lys Lys Asp Asp Ile Lys Phe
        195                 200                 205 gta aaa tta ata tct tac ttt tat cct atc gtt att caa agt aac ata        672
Val Lys Leu Ile Ser Tyr Phe Tyr Pro Ile Val Ile Gln Ser Asn Ile
    210                 215                 220 aat gtt ata aat tac ttt tct tat atg ttt cat ttt ttt gaa cat gaa        720
Asn Val Ile Asn Tyr Phe Ser Tyr Met Phe His Phe Phe Glu His Glu
225                 230                 235                 240 aaa aga tca gat tat tta tac gaa aga ggt aac ata ata att ttt ccc        768
Lys Arg Ser Asp Tyr Leu Tyr Glu Arg Gly Asn Ile Ile Ile Phe Pro
                245                 250                 255 tta gct aga tgt tct gct gat aaa gta acg gaa aaa atg gca aaa aaa        816
Leu Ala Arg Cys Ser Ala Asp Lys Val Thr Glu Lys Met Ala Lys Lys
            260                 265                 270 tta ggt ttt tgc tct ctt gtt gat tat att aag ttt tta ttt tta cag       864
Leu Gly Phe Cys Ser Leu Val Asp Tyr Ile Lys Phe Leu Phe Leu Gln
        275                 280                 285 atg gcg ttg cta tat ata aag ata tat gag tta cca tgt tgt gac aat       912
Met Ala Leu Leu Tyr Ile Lys Ile Tyr Glu Leu Pro Cys Cys Asp Asn
    290                 295                 300 ttt tta cac gta gat ctt aaa ccg gat aac ata cta tta ttt gat tca       960
Phe Leu His Val Asp Leu Lys Pro Asp Asn Ile Leu Leu Phe Asp Ser
305                 310                 315                 320 gat gaa gaa ata tgt ata agt ttt aat aac aat gta tat gtg ttt aaa      1008
Asp Glu Glu Ile Cys Ile Ser Phe Asn Asn Asn Val Tyr Val Phe Lys
                325                 330                 335 gaa aaa att aaa tca tgt tta aac gat ttt gat ttt tca cag gta gct     1056
Glu Lys Ile Lys Ser Cys Leu Asn Asp Phe Asp Phe Ser Gln Val Ala
            340                 345                 350 aat ata aca aac aaa aaa ata aaa aac agc tta aaa gta gaa cat aat     1104
Asn Ile Thr Asn Lys Lys Ile Lys Asn Ser Leu Lys Val Glu His Asn
        355                 360                 365 tgg tac tat gat ttt cat ttt ttt aca cac acc ttg tta aaa acg tat     1152
Trp Tyr Tyr Asp Phe His Phe Phe Thr His Thr Leu Leu Lys Thr Tyr
    370                 375                 380 cct gag att aag aac gat gta ata ttt aat agc gca tta gaa gaa cta     1200
Pro Glu Ile Lys Asn Asp Val Ile Phe Asn Ser Ala Leu Glu Glu Leu
385                 390                 395                 400 ata atg tgt tgt aat aaa agt aca tgt gac aag ttt cga tta aaa gta     1248
Ile Met Cys Cys Asn Lys Ser Thr Cys Asp Lys Phe Arg Leu Lys Val
                405                 410                 415 tcc att cta cat cct ata agt ttt tta gaa aaa ttt gta aca agg gac     1296
Ser Ile Leu His Pro Ile Ser Phe Leu Glu Lys Phe Val Thr Arg Asp
            420                 425                 430 att ttc tca acg tgg ata aat gac gga aat aca acg ggt taa             1338
Ile Phe Ser Thr Trp Ile Asn Asp Gly Asn Thr Thr Gly
        435                 440                 445

<210> SEQ ID NO 36
<211> LENGTH: 445
<212> TYPE: PRT
<213> ORGANISM: Yaba-like disease virus

<400> SEQUENCE: 36

Met Gly Val Lys Thr Asp Asn Ser Leu Glu Cys Gln Trp Asp Leu Gln
1               5                   10                  15

Asp Asp Lys Lys Leu Glu Thr Thr Ile Leu Gly Asp Asp Ile Tyr Phe
            20                  25                  30
```

```
Asp Tyr Val Phe Ser Gln Ile Asp Val Asn Gln Asn Trp Ser Pro Ser
         35                  40                  45

Ile Arg Leu Ile Lys Tyr Phe Lys Asn Phe Asn Lys Glu Leu Leu Asp
 50                  55                  60

Thr Ile Ala Ser Lys Glu Tyr Val Asn Pro Ser Phe Phe Gln Gln Lys
 65                  70                  75                  80

Asp Lys Arg Phe Tyr Pro Ile Asn Asp Phe Tyr His Leu Ser Thr
                 85                  90                  95

Gly Gly Tyr Gly Ile Val Phe Lys Ile Asp Lys Tyr Val Val Lys Phe
                 100                 105                 110

Val Tyr Glu Pro Asn Lys Asn Tyr Ser Pro Ile Asp Thr Thr Ala Glu
         115                 120                 125

Tyr Thr Ile Pro Lys Phe Leu Tyr Leu Asn Leu Lys Gly Asp Glu Lys
         130                 135                 140

Lys Leu Ile Val Cys Ala Trp Ala Met Gly Leu Asn Tyr Lys Leu Thr
145                 150                 155                 160

Phe Leu Tyr Asp Leu Tyr Lys Arg Val Leu Tyr Met Leu Ile Leu Leu
                 165                 170                 175

Leu Gln Ile Met Asp Gly Glu Lys Leu Asp Leu His Asn Phe Ser His
                 180                 185                 190

Lys His Phe Leu Lys Ser Phe Asn Asp Lys Lys Asp Ile Lys Phe
         195                 200                 205

Val Lys Leu Ile Ser Tyr Phe Tyr Pro Ile Val Ile Gln Ser Asn Ile
 210                 215                 220

Asn Val Ile Asn Tyr Phe Ser Tyr Met Phe His Phe Phe Glu His Glu
225                 230                 235                 240

Lys Arg Ser Asp Tyr Leu Tyr Glu Arg Gly Asn Ile Ile Ile Phe Pro
                 245                 250                 255

Leu Ala Arg Cys Ser Ala Asp Lys Val Thr Glu Lys Met Ala Lys Lys
                 260                 265                 270

Leu Gly Phe Cys Ser Leu Val Asp Tyr Ile Lys Phe Leu Phe Leu Gln
                 275                 280                 285

Met Ala Leu Leu Tyr Ile Lys Ile Tyr Glu Leu Pro Cys Cys Asp Asn
 290                 295                 300

Phe Leu His Val Asp Leu Lys Pro Asp Asn Ile Leu Leu Phe Asp Ser
305                 310                 315                 320

Asp Glu Glu Ile Cys Ile Ser Phe Asn Asn Asn Val Tyr Val Phe Lys
                 325                 330                 335

Glu Lys Ile Lys Ser Cys Leu Asn Asp Phe Asp Phe Ser Gln Val Ala
                 340                 345                 350

Asn Ile Thr Asn Lys Lys Ile Lys Asn Ser Leu Lys Val Glu His Asn
                 355                 360                 365

Trp Tyr Tyr Asp Phe His Phe Phe Thr His Thr Leu Leu Lys Thr Tyr
 370                 375                 380

Pro Glu Ile Lys Asn Asp Val Ile Phe Asn Ser Ala Leu Glu Glu Leu
385                 390                 395                 400

Ile Met Cys Cys Asn Lys Ser Thr Cys Asp Lys Phe Arg Leu Lys Val
                 405                 410                 415

Ser Ile Leu His Pro Ile Ser Phe Leu Glu Lys Phe Val Thr Arg Asp
                 420                 425                 430

Ile Phe Ser Thr Trp Ile Asn Asp Gly Asn Thr Thr Gly
                 435                 440                 445

<210> SEQ ID NO 37
```

<211> LENGTH: 1323
<212> TYPE: DNA
<213> ORGANISM: Swinepox virus
<220> FEATURE:
<221> NAME/KEY: CDS
<222> LO

```
tta tat ata aaa ata tac gaa ctt cct tgt tgt gat aat ttt tta cac    912
Leu Tyr Ile Lys Ile Tyr Glu Leu Pro Cys Cys Asp Asn Phe Leu His
    290                 295                 300 gtt gat tta aaa ccc gat aat att tta ata ttt aat tct gat tgt cct    960
Val Asp Leu Lys Pro Asp Asn Ile Leu Ile Phe Asn Ser Asp Cys Pro
305                 310                 315                 320 ata act att aaa ttt aag aaa tat aca tac gta ttt aat gaa ccg att   1008
Ile Thr Ile Lys Phe Lys Lys Tyr Thr Tyr Val Phe Asn Glu Pro Ile
            325                 330                 335 aaa gcg tgt ctt aac gat ttc gat ttt tca cag gtg gct aat ata tta   1056
Lys Ala Cys Leu Asn Asp Phe Asp Phe Ser Gln Val Ala Asn Ile Leu
340                 345                 350 aat aag aaa att aaa aat agt tta aaa ata gaa cac aat tgg tat tat   1104
Asn Lys Lys Ile Lys Asn Ser Leu Lys Ile Glu His Asn Trp Tyr Tyr
        355                 360                 365 gat ttt cat ttt ttt ata cat aca ctt cta cga act tat cca gaa ata   1152
Asp Phe His Phe Phe Ile His Thr Leu Leu Arg Thr Tyr Pro Glu Ile
    370                 375                 380 gaa tct gat aaa gaa ttc agc gat tct tta gag gat ttt ata atg tgt   1200
Glu Ser Asp Lys Glu Phe Ser Asp Ser Leu Glu Asp Phe Ile Met Cys
385                 390                 395                 400 tgt aca aaa aat aca tgt gag aaa ttt aga tta aaa gta tcc ata ctg   1248
Cys Thr Lys Asn Thr Cys Glu Lys Phe Arg Leu Lys Val Ser Ile Leu
            405                 410                 415 cat cct ata tca ttt tta gaa aat ttg att aca aaa aac att ttc tca   1296
His Pro Ile Ser Phe Leu Glu Asn Leu Ile Thr Lys Asn Ile Phe Ser
    420                 425                 430 aat tgg ata aat gga gaa tcc tgt tag                                1323
Asn Trp Ile Asn Gly Glu Ser Cys
        435                 440

<210> SEQ ID NO 38
<211> LENGTH: 440
<212> TYPE: PRT
<213> ORGANISM: Swinepox virus

<400> SEQUENCE: 38

Met Lys Glu Ile Asn Ser Leu Glu Cys Gln Trp Glu Ser Ile Asp Asp
1               5                   10                  15

Asn Asn Asp Thr Thr Ile Leu Gly Asp Asp Ile Tyr Phe Asp Tyr Ile
            20                  25                  30

Ile Ser Gln Leu Asp Ile His Gln Asn Trp Ser Pro Asp Ile Arg Leu
        35                  40                  45

Ile Arg Tyr Phe Arg Lys Phe Asn Lys Glu Ser Phe Asp Lys Ile Ser
    50                  55                  60

Asp Thr Glu Tyr Ile Asn Pro Ser Phe Phe Gln Gln Arg Asp Lys Arg
65                  70                  75                  80

Phe Tyr Pro Leu Asn Asp Asp Phe Tyr His Ile Ser Thr Gly Gly Tyr
                85                  90                  95

Gly Ile Val Phe Lys Met Asp Lys Tyr Val Val Lys Phe Val Tyr Glu
            100                 105                 110

Pro Asn Lys Gln Tyr Ser Pro Ile Asp Thr Thr Ala Glu Tyr Thr Ile
        115                 120                 125

Pro Lys Phe Leu Tyr Asn Asn Leu Lys Gly Asp Glu Lys Lys Leu Ile
    130                 135                 140

Val Cys Ala Trp Ala Met Gly Leu Asn Tyr Lys Leu Thr Phe Leu His
145                 150                 155                 160

Arg Leu Tyr Lys Arg Val Leu Tyr Met Leu Leu Leu Ile Ile Gln Thr
```

```
                     165                 170                 175
Ile Asp Asn Gln Arg Leu Asn Ile His His Phe Ser His Lys Tyr Phe
            180                 185                 190

Leu Lys Ser Phe Asn Glu Lys Lys Ser Asp Ile Lys Phe Val Lys Leu
        195                 200                 205

Leu Ser Tyr Phe Tyr Pro Ile Val Gln Ser Asn Ile Asn Val Ile
    210                 215                 220

Asn Tyr Phe Thr His Met Phe His Phe Phe Glu His Glu Lys Arg Ala
225                 230                 235                 240

Asn Tyr Leu Tyr Asp Arg Gly Asn Ile Ile Ile Phe Pro Leu Ala Arg
            245                 250                 255

Phe Ser Ser Asp Lys Val Thr Glu Gln Met Ala Ile Glu Leu Gly Phe
        260                 265                 270

Lys Ser Ile Val Gln Tyr Val Lys Phe Ile Phe Leu Gln Ile Ser Leu
    275                 280                 285

Leu Tyr Ile Lys Ile Tyr Glu Leu Pro Cys Cys Asp Asn Phe Leu His
    290                 295                 300

Val Asp Leu Lys Pro Asp Asn Ile Leu Ile Phe Asn Ser Asp Cys Pro
305                 310                 315                 320

Ile Thr Ile Lys Phe Lys Lys Tyr Thr Tyr Val Phe Asn Glu Pro Ile
            325                 330                 335

Lys Ala Cys Leu Asn Asp Phe Asp Ser Gln Val Ala Asn Ile Leu
        340                 345                 350

Asn Lys Lys Ile Lys Asn Ser Leu Lys Ile Glu His Asn Trp Tyr Tyr
    355                 360                 365

Asp Phe His Phe Phe Ile His Thr Leu Leu Arg Thr Tyr Pro Glu Ile
    370                 375                 380

Glu Ser Asp Lys Glu Phe Ser Asp Ser Leu Glu Asp Phe Ile Met Cys
385                 390                 395                 400

Cys Thr Lys Asn Thr Cys Glu Lys Phe Arg Leu Lys Val Ser Ile Leu
            405                 410                 415

His Pro Ile Ser Phe Leu Glu Asn Leu Ile Thr Lys Asn Ile Phe Ser
        420                 425                 430

Asn Trp Ile Asn Gly Glu Ser Cys
        435                 440

<210> SEQ ID NO 39
<211> LENGTH: 1344
<212> TYPE: DNA
<213> ORGANISM: Lumpy skin disease virus
<220> FEATURE:
<221> NAME/KEY: CDS
<222> LOCATION: (1)..(1344)

<400> SEQUENCE: 39 atg gta atc atg gaa ata gat gat aac tca tta gaa tgc caa tgg gat        48
Met Val Ile Met Glu Ile Asp Asp Asn Ser Leu Glu Cys Gln Trp Asp
1               5                   10                  15 aac gat gaa gat ata aaa tct aca aca gta tta ggc gat gat att tat        96
Asn Asp Glu Asp Ile Lys Ser Thr Thr Val Leu Gly Asp Asp Ile Tyr
            20                  25                  30 ttt gat tat gta ata tct caa tta gat att tac caa agt tgg tca cct       144
Phe Asp Tyr Val Ile Ser Gln Leu Asp Ile Tyr Gln Ser Trp Ser Pro
        35                  40                  45 aat gtt agg tta ata aga tac ttt aaa aag ttt aca aaa gaa aca tta       192
Asn Val Arg Leu Ile Arg Tyr Phe Lys Lys Phe Thr Lys Glu Thr Leu
    50                  55                  60
```

```
aat aaa att gct gaa aac gaa tat atc aat cca tcg ttt ttt cag caa      240
Asn Lys Ile Ala Glu Asn Glu Tyr Ile Asn Pro Ser Phe Phe Gln Gln
 65                  70                  75                  80 aaa gat aag aga ttt tat cca att aat gat gac ttt tat cat att tca      288
Lys Asp Lys Arg Phe Tyr Pro Ile Asn Asp Asp Phe Tyr His Ile Ser
                     85                  90                  95 act gga gga tat ggt ata gtt ttt aaa att gat aag tat gtt gta aaa      336
Thr Gly Gly Tyr Gly Ile Val Phe Lys Ile Asp Lys Tyr Val Val Lys
                100                 105                 110 ttt gtt tat gaa cct aat aaa cag tat agt cct att gaa aca act gca      384
Phe Val Tyr Glu Pro Asn Lys Gln Tyr Ser Pro Ile Glu Thr Thr Ala
            115                 120                 125 gaa tat aca ata cca aag ttc ttg ttt aat aac tta aag gga gat gaa      432
Glu Tyr Thr Ile Pro Lys Phe Leu Phe Asn Asn Leu Lys Gly Asp Glu
130                 135                 140 aaa aaa cta ata gtg tgt gcg tgg gca atg ggt gta aac ttt aaa ctt      480
Lys Lys Leu Ile Val Cys Ala Trp Ala Met Gly Val Asn Phe Lys Leu
145                 150                 155                 160 aca ttt tta tat aac tta tat aag cgg gta cta tat atg ata tta tta      528
Thr Phe Leu Tyr Asn Leu Tyr Lys Arg Val Leu Tyr Met Ile Leu Leu
                165                 170                 175 ctt att caa aca atg gat gat caa aaa tta agt ata agt aat ttt tca      576
Leu Ile Gln Thr Met Asp Asp Gln Lys Leu Ser Ile Ser Asn Phe Ser
            180                 185                 190 cat aaa tat ttt tta aaa tcg ttt aat gag aaa aaa gga gat gta aaa      624
His Lys Tyr Phe Leu Lys Ser Phe Asn Glu Lys Lys Gly Asp Val Lys
        195                 200                 205 ttt gta aaa cta tta tca tat ttt tac cct ata gtt ata caa agt aat      672
Phe Val Lys Leu Leu Ser Tyr Phe Tyr Pro Ile Val Ile Gln Ser Asn
210                 215                 220 gta aat gta ata aac tat ttt aca cac atg ttt cat ttt ttt gaa cac      720
Val Asn Val Ile Asn Tyr Phe Thr His Met Phe His Phe Phe Glu His
225                 230                 235                 240 gaa aaa cgg tct aat tat tta tac gat aga gga aat att att ata ttt      768
Glu Lys Arg Ser Asn Tyr Leu Tyr Asp Arg Gly Asn Ile Ile Ile Phe
                245                 250                 255 cct ttg gca aaa ttc tct tct gat aaa gtt agt gaa aaa atg gct att      816
Pro Leu Ala Lys Phe Ser Ser Asp Lys Val Ser Glu Lys Met Ala Ile
            260                 265                 270 gaa tta ggt ttt aag tca tta gtt gag tat ata aaa ttt att ttt tta      864
Glu Leu Gly Phe Lys Ser Leu Val Glu Tyr Ile Lys Phe Ile Phe Leu
        275                 280                 285 cag atg gct ctt tta tat gtt aaa ata tat gaa tta cca tgc tgt aac      912
Gln Met Ala Leu Leu Tyr Val Lys Ile Tyr Glu Leu Pro Cys Cys Asn
290                 295                 300 aac ttt tta cat gtt gat tta aaa cct gat aat att tta att ttt gat      960
Asn Phe Leu His Val Asp Leu Lys Pro Asp Asn Ile Leu Ile Phe Asp
305                 310                 315                 320 tcg gac gaa tca ata aaa ata tca tta aat gaa aat act tat att ttt     1008
Ser Asp Glu Ser Ile Lys Ile Ser Leu Asn Glu Asn Thr Tyr Ile Phe
                325                 330                 335 aat gaa cct ata aaa gct tgt tta aat gat ttt gac ttt tca cag gtt     1056
Asn Glu Pro Ile Lys Ala Cys Leu Asn Asp Phe Asp Phe Ser Gln Val
            340                 345                 350 gcg aac ata ata aat aaa aaa ata aaa aat aat ata aaa gtt gaa cat     1104
Ala Asn Ile Ile Asn Lys Lys Ile Lys Asn Asn Ile Lys Val Glu His
        355                 360                 365 aat tgg tac tac gat ttt cat ttt ttc att cat aca ctt tta aaa aca     1152
Asn Trp Tyr Tyr Asp Phe His Phe Phe Ile His Thr Leu Leu Lys Thr
370                 375                 380
```

-continued

```
tat cca gaa ata gaa aca gat aaa gaa ttt tat aat aca tta gaa gaa    1200
Tyr Pro Glu Ile Glu Thr Asp Lys Glu Phe Tyr Asn Thr Leu Glu Glu
385                 390                 395                 400 ttt att ata tgt tgt aat aaa aat acg tgt gat aaa ttt agg tta aaa    1248
Phe Ile Ile Cys Cys Asn Lys Asn Thr Cys Asp Lys Phe Arg Leu Lys
            405                 410                 415 ata tca ata tta cat cct att tct ttt tta gaa aaa att att tca aag    1296
Ile Ser Ile Leu His Pro Ile Ser Phe Leu Glu Lys Ile Ile Ser Lys
        420                 425                 430 aaa aac att ttc tca acg tgg ata aat gga aaa cca ctt tca agt tga    1344
Lys Asn Ile Phe Ser Thr Trp Ile Asn Gly Lys Pro Leu Ser Ser
    435                 440                 445
```

<210> SEQ ID NO 40
<211> LENGTH: 447
<212> TYPE: PRT
<213> ORGANISM: Lumpy skin disease virus

<400> SEQUENCE: 40

```
Met Val Ile Met Glu Ile Asp Asp Asn Ser Leu Glu Cys Gln Trp Asp
1               5                   10                  15

Asn Asp Glu Asp Ile Lys Ser Thr Thr Val Leu Gly Asp Asp Ile Tyr
            20                  25                  30

Phe Asp Tyr Val Ile Ser Gln Leu Asp Ile Tyr Gln Ser Trp Ser Pro
        35                  40                  45

Asn Val Arg Leu Ile Arg Tyr Phe Lys Lys Phe Thr Lys Glu Thr Leu
    50                  55                  60

Asn Lys Ile Ala Glu Asn Glu Tyr Ile Asn Pro Ser Phe Phe Gln Gln
65                  70                  75                  80

Lys Asp Lys Arg Phe Tyr Pro Ile Asn Asp Asp Phe Tyr His Ile Ser
            85                  90                  95

Thr Gly Gly Tyr Gly Ile Val Phe Lys Ile Asp Lys Tyr Val Val Lys
        100                 105                 110

Phe Val Tyr Glu Pro Asn Lys Gln Tyr Ser Pro Ile Glu Thr Thr Ala
    115                 120                 125

Glu Tyr Thr Ile Pro Lys Phe Leu Phe Asn Asn Leu Lys Gly Asp Glu
130                 135                 140

Lys Lys Leu Ile Val Cys Ala Trp Ala Met Gly Val Asn Phe Lys Leu
145                 150                 155                 160

Thr Phe Leu Tyr Asn Leu Tyr Lys Arg Val Leu Tyr Met Ile Leu Leu
                165                 170                 175

Leu Ile Gln Thr Met Asp Asp Gln Lys Leu Ser Ile Ser Asn Phe Ser
            180                 185                 190

His Lys Tyr Phe Leu Lys Ser Phe Asn Glu Lys Lys Gly Asp Val Lys
        195                 200                 205

Phe Val Lys Leu Leu Ser Tyr Phe Tyr Pro Ile Val Ile Gln Ser Asn
    210                 215                 220

Val Asn Val Ile Asn Tyr Phe Thr His Met Phe His Phe Glu His
225                 230                 235                 240

Glu Lys Arg Ser Asn Tyr Leu Tyr Asp Arg Gly Asn Ile Ile Phe
                245                 250                 255

Pro Leu Ala Lys Phe Ser Ser Asp Lys Val Ser Glu Lys Met Ala Ile
            260                 265                 270

Glu Leu Gly Phe Lys Ser Leu Val Glu Tyr Ile Lys Phe Ile Phe Leu
        275                 280                 285

Gln Met Ala Leu Leu Tyr Val Lys Ile Tyr Glu Leu Pro Cys Cys Asn
    290                 295                 300
```

```
Asn Phe Leu His Val Asp Leu Lys Pro Asp Asn Ile Leu Ile Phe Asp
305                 310                 315                 320

Ser Asp Glu Ser Ile Lys Ile Ser Leu Asn Glu Asn Thr Tyr Ile Phe
            325                 330                 335

Asn Glu Pro Ile Lys Ala Cys Leu Asn Asp Phe Asp Phe Ser Gln Val
            340                 345                 350

Ala Asn Ile Ile Asn Lys Lys Ile Lys Asn Asn Ile Lys Val Glu His
            355                 360                 365

Asn Trp Tyr Tyr Asp Phe His Phe Phe Ile His Thr Leu Leu Lys Thr
370                 375                 380

Tyr Pro Glu Ile Glu Thr Asp Lys Glu Phe Tyr Asn Thr Leu Glu Glu
385                 390                 395                 400

Phe Ile Ile Cys Cys Asn Lys Asn Thr Cys Asp Lys Phe Arg Leu Lys
                405                 410                 415

Ile Ser Ile Leu His Pro Ile Ser Phe Leu Glu Lys Ile Ile Ser Lys
            420                 425                 430

Lys Asn Ile Phe Ser Thr Trp Ile Asn Gly Lys Pro Leu Ser Ser
            435                 440                 445

<210> SEQ ID NO 41
<211> LENGTH: 1335
<212> TYPE: DNA
<213> ORGANISM: Sheeppox virus
<220> FEATURE:
<221> NAME/KEY: CDS
<222> LOCATION: (1)..(1335)

<400> SEQUENCE: 41 atg gaa ata gat tat aac tca tta gaa tgc caa tgg gat aac aat gaa      48
Met Glu Ile Asp Tyr Asn Ser Leu Glu Cys Gln Trp Asp Asn Asn Glu
1               5                   10                  15 gat ata aaa tct aca aca gta tta ggt gat gat att tat ttt gat tat      96
Asp Ile Lys Ser Thr Thr Val Leu Gly Asp Asp Ile Tyr Phe Asp Tyr
            20                  25                  30 gta ata tct caa tta gat att tac caa agt tgg tca cct aat gtt agg     144
Val Ile Ser Gln Leu Asp Ile Tyr Gln Ser Trp Ser Pro Asn Val Arg
        35                  40                  45 tta ata aga tac ttt aaa aag ttt aca aag gaa aca tta aat aaa atc     192
Leu Ile Arg Tyr Phe Lys Lys Phe Thr Lys Glu Thr Leu Asn Lys Ile
    50                  55                  60 gct gaa aac gaa tat atc aat cca tcg ttt ttt caa caa aaa gat aag     240
Ala Glu Asn Glu Tyr Ile Asn Pro Ser Phe Phe Gln Gln Lys Asp Lys
65                  70                  75                  80 aga ttc tat cca att aat gat gac ttt tat cat att tca act gga gga     288
Arg Phe Tyr Pro Ile Asn Asp Asp Phe Tyr His Ile Ser Thr Gly Gly
                85                  90                  95 tat ggt ata gtt ttt aaa att gat aag tat gtt gta aaa ttt gtt tac     336
Tyr Gly Ile Val Phe Lys Ile Asp Lys Tyr Val Val Lys Phe Val Tyr
            100                 105                 110 gaa cct aat aaa aat tat agt cct att gaa aca act gca gaa tat aca     384
Glu Pro Asn Lys Asn Tyr Ser Pro Ile Glu Thr Thr Ala Glu Tyr Thr
        115                 120                 125 ata cca aag ttc ttg ttt aat aac tta aag gga gat gaa aaa aaa cta     432
Ile Pro Lys Phe Leu Phe Asn Asn Leu Lys Gly Asp Glu Lys Lys Leu
    130                 135                 140 ata gtg tgt gcg tgg gca atg ggt gta aac ttt aaa ctt aca ttt tta     480
Ile Val Cys Ala Trp Ala Met Gly Val Asn Phe Lys Leu Thr Phe Leu
145                 150                 155                 160 tat aac tta tat aag cgg gta cta tat atg ata tta tta ctt att caa     528
Tyr Asn Leu Tyr Lys Arg Val Leu Tyr Met Ile Leu Leu Leu Ile Gln
```

```
                       165                 170                 175
aca atg gat gat caa aaa tta agt ata agt aat ttt tca cat aaa tat        576
Thr Met Asp Asp Gln Lys Leu Ser Ile Ser Asn Phe Ser His Lys Tyr
            180                 185                 190 ttt tta aaa tcg ttt aat gag aag aaa gga gat gta aaa ttt gta aaa        624
Phe Leu Lys Ser Phe Asn Glu Lys Lys Gly Asp Val Lys Phe Val Lys
            195                 200                 205 cta tta tca tat ttt tac cct ata gtt ata caa agt aat gta aat gta        672
Leu Leu Ser Tyr Phe Tyr Pro Ile Val Ile Gln Ser Asn Val Asn Val
            210                 215                 220 ata aac tat ttt acg cac atg ttt cat ttt ttt gaa cat gaa aaa cgg        720
Ile Asn Tyr Phe Thr His Met Phe His Phe Phe Glu His Glu Lys Arg
225                 230                 235                 240 tct aat tat tta tac gat aga gga aat att att ata ttt cct tta gca        768
Ser Asn Tyr Leu Tyr Asp Arg Gly Asn Ile Ile Ile Phe Pro Leu Ala
            245                 250                 255 aaa ttc tct tct gat aaa gtt aat gaa aaa atg gct att gag tta ggt        816
Lys Phe Ser Ser Asp Lys Val Asn Glu Lys Met Ala Ile Glu Leu Gly
            260                 265                 270 ttt aag tca tta gtt gag tat ata aaa ttt att ttt tta caa atg gct        864
Phe Lys Ser Leu Val Glu Tyr Ile Lys Phe Ile Phe Leu Gln Met Ala
            275                 280                 285 ctt tta tat gtt aaa ata tat gaa tta cca tgc tgt aac aac ttt tta        912
Leu Leu Tyr Val Lys Ile Tyr Glu Leu Pro Cys Cys Asn Asn Phe Leu
            290                 295                 300 cat gtt gat tta aaa cct gat aat att tta att ttt gat tcg gac gaa        960
His Val Asp Leu Lys Pro Asp Asn Ile Leu Ile Phe Asp Ser Asp Glu
305                 310                 315                 320 tca ata aaa ata tca tta aat gaa aat att tat att ttt aat gaa cct       1008
Ser Ile Lys Ile Ser Leu Asn Glu Asn Ile Tyr Ile Phe Asn Glu Pro
            325                 330                 335 ata aaa gct tgt tta aat gat ttt gac ttt tca cag gtt gca aac ata       1056
Ile Lys Ala Cys Leu Asn Asp Phe Asp Phe Ser Gln Val Ala Asn Ile
            340                 345                 350 ata aat aaa aaa ata aaa aat aat ata aaa gtt gaa cat aat tgg tac       1104
Ile Asn Lys Lys Ile Lys Asn Asn Ile Lys Val Glu His Asn Trp Tyr
            355                 360                 365 tac gat ttt cat ttt ttc att cat aca ctt tta aaa aca tat cca gaa       1152
Tyr Asp Phe His Phe Phe Ile His Thr Leu Leu Lys Thr Tyr Pro Glu
370                 375                 380 ata gaa aca gat aaa gaa ttt tat aat aca tta gaa gaa ttt att ata       1200
Ile Glu Thr Asp Lys Glu Phe Tyr Asn Thr Leu Glu Glu Phe Ile Ile
385                 390                 395                 400 tgt tgt aat aaa aat acg tgt gat aaa ttt agg tta aaa ata tca ata       1248
Cys Cys Asn Lys Asn Thr Cys Asp Lys Phe Arg Leu Lys Ile Ser Ile
            405                 410                 415 tta cat cct att tct ttt tta gaa aaa att att tca aag aaa aac att       1296
Leu His Pro Ile Ser Phe Leu Glu Lys Ile Ile Ser Lys Lys Asn Ile
            420                 425                 430 ttc tca aca tgg ata aat gga aaa cca ctt tca agt tga                   1335
Phe Ser Thr Trp Ile Asn Gly Lys Pro Leu Ser Ser
            435                 440

<210> SEQ ID NO 42
<211> LENGTH: 444
<212> TYPE: PRT
<213> ORGANISM: Sheeppox virus

<400> SEQUENCE: 42

Met Glu Ile Asp Tyr Asn Ser Leu Glu Cys Gln Trp Asp Asn Asn Glu
1               5                   10                  15
```

```
Asp Ile Lys Ser Thr Thr Val Leu Gly Asp Asp Ile Tyr Phe Asp Tyr
             20                  25                  30

Val Ile Ser Gln Leu Asp Ile Tyr Gln Ser Trp Ser Pro Asn Val Arg
         35                  40                  45

Leu Ile Arg Tyr Phe Lys Lys Phe Thr Lys Glu Thr Leu Asn Lys Ile
     50                  55                  60

Ala Glu Asn Glu Tyr Ile Asn Pro Ser Phe Phe Gln Gln Lys Asp Lys
 65                  70                  75                  80

Arg Phe Tyr Pro Ile Asn Asp Asp Phe Tyr His Ile Ser Thr Gly Gly
                 85                  90                  95

Tyr Gly Ile Val Phe Lys Ile Asp Lys Tyr Val Val Lys Phe Val Tyr
            100                 105                 110

Glu Pro Asn Lys Asn Tyr Ser Pro Ile Glu Thr Thr Ala Glu Tyr Thr
        115                 120                 125

Ile Pro Lys Phe Leu Phe Asn Asn Leu Lys Gly Asp Glu Lys Lys Leu
130                 135                 140

Ile Val Cys Ala Trp Ala Met Gly Val Asn Phe Lys Leu Thr Phe Leu
145                 150                 155                 160

Tyr Asn Leu Tyr Lys Arg Val Leu Tyr Met Ile Leu Leu Leu Ile Gln
                165                 170                 175

Thr Met Asp Asp Gln Lys Leu Ser Ile Ser Asn Phe Ser His Lys Tyr
            180                 185                 190

Phe Leu Lys Ser Phe Asn Glu Lys Lys Gly Asp Val Lys Phe Val Lys
        195                 200                 205

Leu Leu Ser Tyr Phe Tyr Pro Ile Val Ile Gln Ser Asn Val Asn Val
    210                 215                 220

Ile Asn Tyr Phe Thr His Met Phe His Phe Phe Glu His Glu Lys Arg
225                 230                 235                 240

Ser Asn Tyr Leu Tyr Asp Arg Gly Asn Ile Ile Ile Phe Pro Leu Ala
                245                 250                 255

Lys Phe Ser Ser Asp Lys Val Asn Glu Lys Met Ala Ile Glu Leu Gly
            260                 265                 270

Phe Lys Ser Leu Val Glu Tyr Ile Lys Phe Ile Phe Leu Gln Met Ala
        275                 280                 285

Leu Leu Tyr Val Lys Ile Tyr Glu Leu Pro Cys Cys Asn Asn Phe Leu
    290                 295                 300

His Val Asp Leu Lys Pro Asp Asn Ile Leu Ile Phe Asp Ser Asp Glu
305                 310                 315                 320

Ser Ile Lys Ile Ser Leu Asn Glu Asn Ile Tyr Ile Phe Asn Glu Pro
                325                 330                 335

Ile Lys Ala Cys Leu Asn Asp Phe Asp Phe Ser Gln Val Ala Asn Ile
            340                 345                 350

Ile Asn Lys Lys Ile Lys Asn Asn Ile Lys Val Glu His Asn Trp Tyr
        355                 360                 365

Tyr Asp Phe His Phe Phe Ile His Thr Leu Leu Lys Thr Tyr Pro Glu
    370                 375                 380

Ile Glu Thr Asp Lys Glu Phe Tyr Asn Thr Leu Glu Glu Phe Ile Ile
385                 390                 395                 400

Cys Cys Asn Lys Asn Thr Cys Asp Lys Phe Arg Leu Lys Leu Ile Ser Ile
                405                 410                 415

Leu His Pro Ile Ser Phe Leu Glu Lys Ile Ile Ser Lys Lys Asn Ile
            420                 425                 430

Phe Ser Thr Trp Ile Asn Gly Lys Pro Leu Ser Ser
```

-continued

```
                435                 440

<210> SEQ ID NO 43
<211> LENGTH: 1338
<212> TYPE: DNA
<213> ORGANISM: Rabbit fibroma virus
<220> FEATURE:
<221> NAME/KEY: CDS
<222> LOCATION: (1)..(1338)

<400> SEQUENCE: 43 atg gga att atg gaa gac att aac tcg tta gag ggt caa tgg gaa ccc     48
Met Gly Ile Met Glu Asp Ile Asn Ser Leu Glu Gly Gln Trp Glu Pro
1               5                   10                  15 gtc gac aat gaa gat gat acg acc gta cta gga gac gat att tat ttt     96
Val Asp Asn Glu Asp Asp Thr Thr Val Leu Gly Asp Asp Ile Tyr Phe
            20                  25                  30 gat tac gtg ata tca cag cta gac aca cac aag agt tgg tcc cct agc    144
Asp Tyr Val Ile Ser Gln Leu Asp Thr His Lys Ser Trp Ser Pro Ser
        35                  40                  45 gtt aaa ctt gtt cgt tat ttt aaa aac ttt aac aaa aca gcg ctc gat    192
Val Lys Leu Val Arg Tyr Phe Lys Asn Phe Asn Lys Thr Ala Leu Asp
    50                  55                  60 aaa ata gcg aac gaa gaa tac att aat ccg tcg ttc ttt caa caa aag    240
Lys Ile Ala Asn Glu Glu Tyr Ile Asn Pro Ser Phe Phe Gln Gln Lys
65                  70                  75                  80 gat gat cgg ttt tac cca gcg aat gac gac ttt tat cat atc tcc acg    288
Asp Asp Arg Phe Tyr Pro Ala Asn Asp Asp Phe Tyr His Ile Ser Thr
                85                  90                  95 ggt ggc tac ggt atc gtg ttt aag ata gac aag tac gtc gta aag ttt    336
Gly Gly Tyr Gly Ile Val Phe Lys Ile Asp Lys Tyr Val Val Lys Phe
            100                 105                 110 gtg tac gaa cct aat aaa aac tat acg cct ata gac acg aca gca gaa    384
Val Tyr Glu Pro Asn Lys Asn Tyr Thr Pro Ile Asp Thr Thr Ala Glu
        115                 120                 125 tat acc att ccc aag ttc tta tat aat aac tta aag ggg gat gaa aaa    432
Tyr Thr Ile Pro Lys Phe Leu Tyr Asn Asn Leu Lys Gly Asp Glu Lys
    130                 135                 140 aaa tta atc gta tgt gcc tgg gcc atg ggg gta aat tat aac ctg tca    480
Lys Leu Ile Val Cys Ala Trp Ala Met Gly Val Asn Tyr Asn Leu Ser
145                 150                 155                 160 ttt ttg tac aac ttg tat aaa cgc gta tta tat atg ctg cta tta att    528
Phe Leu Tyr Asn Leu Tyr Lys Arg Val Leu Tyr Met Leu Leu Leu Ile
                165                 170                 175 gta cag ata ctc gac gag caa cca ttg aac ctt acc cat ttt tca cac    576
Val Gln Ile Leu Asp Glu Gln Pro Leu Asn Leu Thr His Phe Ser His
            180                 185                 190 aag tat ttt tta aag tcg ttt aac gag aag aaa gga gac gtt aaa ttc    624
Lys Tyr Phe Leu Lys Ser Phe Asn Glu Lys Lys Gly Asp Val Lys Phe
        195                 200                 205 gtt aag tta ttg tcg tac ttt tac cct att gtc gta caa agt aac ata    672
Val Lys Leu Leu Ser Tyr Phe Tyr Pro Ile Val Val Gln Ser Asn Ile
    210                 215                 220 aat gta att aat tac ttt acg cac atg ttt tat ttc ttc gaa cat gag    720
Asn Val Ile Asn Tyr Phe Thr His Met Phe Tyr Phe Phe Glu His Glu
225                 230                 235                 240 aaa cgt tcc aat tat gca tat gat aaa ggc aac atc atc gtg ttt ccg    768
Lys Arg Ser Asn Tyr Ala Tyr Asp Lys Gly Asn Ile Ile Val Phe Pro
                245                 250                 255 ttg gcc aaa tgt tcc gcg gat aaa att acg ggg aaa gtc ata aca cga    816
Leu Ala Lys Cys Ser Ala Asp Lys Ile Thr Gly Lys Val Ile Thr Arg
            260                 265                 270
```

```
ttc gga ttt aaa tcg ttg acg gat tac gta aag ttt tta ttt tta caa       864
Phe Gly Phe Lys Ser Leu Thr Asp Tyr Val Lys Phe Leu Phe Leu Gln
        275                 280                 285 atc gct tta ttg tac gta aaa ata tac gag tta ccg tgt tgt aat aac       912
Ile Ala Leu Leu Tyr Val Lys Ile Tyr Glu Leu Pro Cys Cys Asn Asn
        290                 295                 300 ttc gta cac gta gac ctc aaa ccc gat aac att ctc gta ttc gat tct       960
Phe Val His Val Asp Leu Lys Pro Asp Asn Ile Leu Val Phe Asp Ser
305                 310                 315                 320 cct acg ccc ctc agt att acg ttt aaa cac aac acg tac gtg ttt aac      1008
Pro Thr Pro Leu Ser Ile Thr Phe Lys His Asn Thr Tyr Val Phe Asn
                325                 330                 335 gag ccc att aag gcg tgt tta aac gat ttt gat ttt tct cag gta gcg      1056
Glu Pro Ile Lys Ala Cys Leu Asn Asp Phe Asp Phe Ser Gln Val Ala
                340                 345                 350 agt ata acg aat aag aag ata aag aac agt ttg aaa gta gaa cac aac      1104
Ser Ile Thr Asn Lys Lys Ile Lys Asn Ser Leu Lys Val Glu His Asn
                355                 360                 365 tgg tat tac gat ttt cac ttc ttt aca cat acg ttg ttt cgt acg tat      1152
Trp Tyr Tyr Asp Phe His Phe Phe Thr His Thr Leu Phe Arg Thr Tyr
        370                 375                 380 ccg gaa ata gaa acg gat aag gaa ttc aca aag gca ttg agc gaa ttc      1200
Pro Glu Ile Glu Thr Asp Lys Glu Phe Thr Lys Ala Leu Ser Glu Phe
385                 390                 395                 400 att atg tgt tgt acg aag acg aca tgt gat aag ttt aga tta aaa acg      1248
Ile Met Cys Cys Thr Lys Thr Thr Cys Asp Lys Phe Arg Leu Lys Thr
                405                 410                 415 tcc atc cta cat cct att tcg ttt tta gaa aag ttt ata aca aaa aac      1296
Ser Ile Leu His Pro Ile Ser Phe Leu Glu Lys Phe Ile Thr Lys Asn
                420                 425                 430 att ttc tca aat tgg ata aat gga acc cgt tgc aca act taa              1338
Ile Phe Ser Asn Trp Ile Asn Gly Thr Arg Cys Thr Thr
        435                 440                 445

<210> SEQ ID NO 44
<211> LENGTH: 445
<212> TYPE: PRT
<213> ORGANISM: Rabbit fibroma virus

<400> SEQUENCE: 44

Met Gly Ile Met Glu Asp Ile Asn Ser Leu Glu Gly Gln Trp Glu

```
Lys Leu Ile Val Cys Ala Trp Ala Met Gly Val Asn Tyr Asn Leu Ser
145                 150                 155                 160

Phe Leu Tyr Asn Leu Tyr Lys Arg Val Leu Tyr Met Leu Leu Leu Ile
            165                 170                 175

Val Gln Ile Leu Asp Glu Gln Pro Leu Asn Leu Thr His Phe Ser His
        180                 185                 190

Lys Tyr Phe Leu Lys Ser Phe Asn Glu Lys Lys Gly Asp Val Lys Phe
    195                 200                 205

Val Lys Leu Leu Ser Tyr Phe Tyr Pro Ile Val Val Gln Ser Asn Ile
210                 215                 220

Asn Val Ile Asn Tyr Phe Thr His Met Phe Tyr Phe Glu His Glu
225                 230                 235                 240

Lys Arg Ser Asn Tyr Ala Tyr Asp Lys Gly Asn Ile Ile Val Phe Pro
            245                 250                 255

Leu Ala Lys Cys Ser Ala Asp Lys Ile Thr Gly Lys Val Ile Thr Arg
        260                 265                 270

Phe Gly Phe Lys Ser Leu Thr Asp Tyr Val Lys Phe Leu Phe Leu Gln
    275                 280                 285

Ile Ala Leu Leu Tyr Val Lys Ile Tyr Glu Leu Pro Cys Cys Asn Asn
290                 295                 300

Phe Val His Val Asp Leu Lys Pro Asp Asn Ile Leu Val Phe Asp Ser
305                 310                 315                 320

Pro Thr Pro Leu Ser Ile Thr Phe Lys His Asn Thr Tyr Val Phe Asn
            325                 330                 335

Glu Pro Ile Lys Ala Cys Leu Asn Asp Phe Asp Phe Ser Gln Val Ala
        340                 345                 350

Ser Ile Thr Asn Lys Lys Ile Lys Asn Ser Leu Lys Val Glu His Asn
    355                 360                 365

Trp Tyr Tyr Asp Phe His Phe Phe Thr His Thr Leu Phe Arg Thr Tyr
370                 375                 380

Pro Glu Ile Glu Thr Asp Lys Glu Phe Thr Lys Ala Leu Ser Glu Phe
385                 390                 395                 400

Ile Met Cys Cys Thr Lys Thr Thr Cys Asp Lys Phe Arg Leu Lys
            405                 410                 415

Ser Ile Leu His Pro Ile Ser Phe Leu Glu Lys Phe Ile Thr Lys Asn
        420                 425                 430

Ile Phe Ser Asn Trp Ile Asn Gly Thr Arg Cys Thr Thr
    435                 440                 445

<210> SEQ ID NO 45
<211> LENGTH: 1338
<212> TYPE: DNA
<213> ORGANISM: Myxoma virus
<220> FEATURE:
<221> NAME/KEY: CDS
<222> LOCATION: (1)..

| | | | | | | | | | | | | | | | | |
|---|---|---|---|---|---|---|---|---|---|---|---|---|---|---|---|---|
| agt | gtt | aaa | gtt | cgt | tat | ttt | aaa | aac | ttt | aac | aaa | tcg | gcg | ttc | gat | 192 |
| Ser | Val | Lys | Val | Arg | Tyr | Phe | Lys | Asn | Phe | Asn | Lys | Ser | Ala | Phe | Asp | |
| 50 | | | | 55 | | | | | 60 | | | | | | | |
| aaa | ata | gcg | aac | gag | gaa | tac | att | aac | ccg | tcg | ttc | ttt | caa | cag | aag | 240 |
| Lys | Ile | Ala | Asn | Glu | Glu | Tyr | Ile | Asn | Pro | Ser | Phe | Phe | Gln | Gln | Lys | |
| 65 | | | | | 70 | | | | | 75 | | | | | 80 | |
| gat | gat | agg | ttt | tac | ccg | acg | aac | gac | gac | ttt | tat | cat | atc | tcc | acg | 288 |
| Asp | Asp | Arg | Phe | Tyr | Pro | Thr | Asn | Asp | Asp | Phe | Tyr | His | Ile | Ser | Thr | |
| | | | | 85 | | | | | 90 | | | | | 95 | | |
| gga | gga | tac | ggt | atc | gtg | ttt | aaa | ata | gac | aaa | tac | gtc | gta | aag | ttt | 336 |
| Gly | Gly | Tyr | Gly | Ile | Val | Phe | Lys | Ile | Asp | Lys | Tyr | Val | Val | Lys | Phe | |
| | | | 100 | | | | | 105 | | | | | 110 | | | |
| gta | tac | gaa | ccc | aat | aaa | aac | tat | acg | cct | ata | gat | gcg | acg | gct | gaa | 384 |
| Val | Tyr | Glu | Pro | Asn | Lys | Asn | Tyr | Thr | Pro | Ile | Asp | Ala | Thr | Ala | Glu | |
| | | 115 | | | | | 120 | | | | | 125 | | | | |
| tac | act | att | ccc | aag | ttc | tta | tac | aat | aac | ttg | aag | gga | gat | gag | aag | 432 |
| Tyr | Thr | Ile | Pro | Lys | Phe | Leu | Tyr | Asn | Asn | Leu | Lys | Gly | Asp | Glu | Lys | |
| | 130 | | | | | 135 | | | | | 140 | | | | | |
| aaa | tta | atc | gta | tgc | gct | tgg | gct | atg | ggg | gta | aat | tat | aac | ctg | tcc | 480 |
| Lys | Leu | Ile | Val | Cys | Ala | Trp | Ala | Met | Gly | Val | Asn | Tyr | Asn | Leu | Ser | |
| 145 | | | | 150 | | | | | 155 | | | | | 160 | | |
| ttt | ttg | tac | aat | tta | tac | aaa | cgg | gta | tta | tac | atg | ctg | ttg | tta | att | 528 |
| Phe | Leu | Tyr | Asn | Leu | Tyr | Lys | Arg | Val | Leu | Tyr | Met | Leu | Leu | Leu | Ile | |
| | | | 165 | | | | | 170 | | | | | 175 | | | |
| gta | caa | ata | ctc | gac | gaa | caa | ccg | tta | aac | ctc | aca | cat | ttt | tca | cac | 576 |
| Val | Gln | Ile | Leu | Asp | Glu | Gln | Pro | Leu | Asn | Leu | Thr | His | Phe | Ser | His | |
| | | 180 | | | | | 185 | | | | | 190 | | | | |
| aag | tac | ttt | tta | aag | tcg | ttt | aac | gaa | aag | aaa | ggc | gac | gtt | aaa | ttc | 624 |
| Lys | Tyr | Phe | Leu | Lys | Ser | Phe | Asn | Glu | Lys | Lys | Gly | Asp | Val | Lys | Phe | |
| | 195 | | | | | 200 | | | | | 205 | | | | | |
| gtt | aag | tta | tta | tcg | tac | ttt | tat | ccc | atc | gtt | gta | caa | agt | aac | ata | 672 |
| Val | Lys | Leu | Leu | Ser | Tyr | Phe | Tyr | Pro | Ile | Val | Val | Gln | Ser | Asn | Ile | |
| 210 | | | | | 215 | | | | | 220 | | | | | | |
| aac | gta | atc | aac | tac | ttt | acg | cac | atg | ttt | tat | ttt | ttc | gaa | cac | gag | 720 |
| Asn | Val | Ile | Asn | Tyr | Phe | Thr | His | Met | Phe | Tyr | Phe | Phe | Glu | His | Glu | |
| 225 | | | | 230 | | | | | 235 | | | | | 240 | | |
| aaa | cgt | tcc | aat | tat | tct | tac | gat | aag | ggt | aac | atc | atc | gtg | ttt | cca | 768 |
| Lys | Arg | Ser | Asn | Tyr | Ser | Tyr | Asp | Lys | Gly | Asn | Ile | Ile | Val | Phe | Pro | |
| | | | 245 | | | | | 250 | | | | | 255 | | | |
| ctg | gcc | aaa | tgt | tcg | gcg | gat | aag | att | acg | gga | aaa | gtc | gct | gaa | cgg | 816 |
| Leu | Ala | Lys | Cys | Ser | Ala | Asp | Lys | Ile | Thr | Gly | Lys | Val | Ala | Glu | Arg | |
| | | 260 | | | | | 265 | | | | | 270 | | | | |
| ttc | ggg | ttt | aag | tca | ttg | acg | gag | tac | gta | aag | ttt | tta | ttt | tta | caa | 864 |
| Phe | Gly | Phe | Lys | Ser | Leu | Thr | Glu | Tyr | Val | Lys | Phe | Leu | Phe | Leu | Gln | |
| | 275 | | | | | 280 | | | | | 285 | | | | | |
| atc | gcg | tta | ttg | tac | gta | aaa | ata | tat | gaa | tta | ccg | tgt | tgt | aat | aac | 912 |
| Ile | Ala | Leu | Leu | Tyr | Val | Lys | Ile | Tyr | Glu | Leu | Pro | Cys | Cys | Asn | Asn | |
| 290 | | | | | 295 | | | | | 300 | | | | | | |
| ttc | gta | cac | gta | gac | ctg | aaa | ccc | gat | aac | ctt | ctc | ata | ttc | gat | tcc | 960 |
| Phe | Val | His | Val | Asp | Leu | Lys | Pro | Asp | Asn | Leu | Leu | Ile | Phe | Asp | Ser | |
| 305 | | | | 310 | | | | | 315 | | | | | 320 | | |
| ccc | aca | ccc | ctc | cgt | att | acg | ttt | aaa | cat | aac | acg | tac | gta | ttt | aac | 1008 |
| Pro | Thr | Pro | Leu | Arg | Ile | Thr | Phe | Lys | His | Asn | Thr | Tyr | Val | Phe | Asn | |
| | | | 325 | | | | | 330 | | | | | 335 | | | |
| gag | ccc | atc | aag | gtg | tgt | tta | aac | gat | ttt | gat | ttc | tct | cag | gta | gcg | 1056 |
| Glu | Pro | Ile | Lys | Val | Cys | Leu | Asn | Asp | Phe | Asp | Phe | Ser | Gln | Val | Ala | |
| | | | 340 | | | | | 345 | | | | | 350 | | | |
| agt | ata | atg | aat | aag | aag | ata | aag | aat | agt | ttg | aag | gta | gaa | cac | aac | 1104 |
| Ser | Ile | Met | Asn | Lys | Lys | Ile | Lys | Asn | Ser | Leu | Lys | Val | Glu | His | Asn | |
| | | 355 | | | | | 360 | | | | | 365 | | | | |

```
tgg tat tac gat ttc cac ttc ttt aca cac acg tta ttc cgc acg tat       1152
Trp Tyr Tyr Asp Phe His Phe Phe Thr His Thr Leu Phe Arg Thr Tyr
    370                 375                 380 ccg gaa ata gaa aca gac aaa gaa ttt aca aag gcg tta agt gaa ttc       1200
Pro Glu Ile Glu Thr Asp Lys Glu Phe Thr Lys Ala Leu Ser Glu Phe
385                 390                 395                 400 att atg tgt tgt acg aag acg acg tgc gat aag ttt aga tta aaa aca       1248
Ile Met Cys Cys Thr Lys Thr Thr Cys Asp Lys Phe Arg Leu Lys Thr
                405                 410                 415 tcc atc cta cat cct att tcg ttt tta gaa aag ttt ata aca aaa aac       1296
Ser Ile Leu His Pro Ile Ser Phe Leu Glu Lys Phe Ile Thr Lys Asn
            420                 425                 430 att ttc tca aac tgg ata aat gga acc cac ggc gca gct taa              1338
Ile Phe Ser Asn Trp Ile Asn Gly Thr His Gly Ala Ala
        435                 440                 445

<210> SEQ ID NO 46
<211> LENGTH: 445
<212> TYPE: PRT
<213> ORGANISM: Myxoma virus

<400> SEQUENCE: 46

Met Gly Ile Met Glu Asp Val Glu Asn Ser Leu Glu Gly Gln Trp Glu
1               5                   10                  15

Arg Gly Glu Thr Glu Asp Asp Thr Thr Val Leu Gly Asp Asp Ile Tyr
            20                  25                  30

Phe Asp Tyr Val Ile Ser Gln Leu Asp Thr His Lys Ser Trp Ser Pro
        35                  40                  45

Ser Val Lys Val Arg Tyr Phe Lys Asn Phe Asn Lys Ser Ala Phe Asp
    50                  55                  60

Lys Ile Ala Asn Glu Glu Tyr Ile Asn Pro Ser Phe Phe Gln Gln Lys
65                  70                  75                  80

Asp Asp Arg Phe Tyr Pro Thr Asn Asp Asp Phe Tyr His Ile Ser Thr
                85                  90                  95

Gly Gly Tyr Gly Ile Val Phe Lys Ile Asp Lys Tyr Val Val Lys Phe
            100                 105                 110

Val Tyr Glu Pro Asn Lys Asn Tyr Thr Pro Ile Asp Ala Thr Ala Glu
        115                 120                 125

Tyr Thr Ile Pro Lys Phe Leu Tyr Asn Asn Leu Lys Gly Asp Glu Lys
    130                 135                 140

Lys Leu Ile Val Cys Ala Trp Ala Met Gly Val Asn Tyr Asn Leu Ser
145                 150                 155                 160

Phe Leu Tyr Asn Leu Tyr Lys Arg Val Leu Tyr Met Leu Leu Leu Ile
                165                 170                 175

Val Gln Ile Leu Asp Glu Gln Pro Leu Asn Leu Thr His Phe Ser His
            180                 185                 190

Lys Tyr Phe Leu Lys Ser Phe Asn Glu Lys Lys Gly Asp Val Lys Phe
        195                 200                 205

Val Lys Leu Leu Ser Tyr Phe Tyr Pro Ile Val Val Gln Ser Asn Ile
    210                 215                 220

Asn Val Ile Asn Tyr Phe Thr His Met Phe Tyr Phe Phe Glu His Glu
225                 230                 235                 240

Lys Arg Ser Asn Tyr Ser Tyr Asp Lys Gly Asn Ile Ile Val Phe Pro
                245                 250                 255

Leu Ala Lys Cys Ser Ala Asp Lys Ile Thr Gly Lys Val Ala Glu Arg
            260                 265                 270

Phe Gly Phe Lys Ser Leu Thr Glu Tyr Val Lys Phe Leu Phe Leu Gln
```

```
                        275                 280                 285
Ile Ala Leu Leu Tyr Val Lys Ile Tyr Glu Leu Pro Cys Cys Asn Asn
            290                 295                 300
Phe Val His Val Asp Leu Lys Pro Asp Asn Leu Leu Ile Phe Asp Ser
305                 310                 315                 320
Pro Thr Pro Leu Arg Ile Thr Phe Lys His Asn Thr Tyr Val Phe Asn
                325                 330                 335
Glu Pro Ile Lys Val Cys Leu Asn Asp Phe Asp Phe Ser Gln Val Ala
            340                 345                 350
Ser Ile Met Asn Lys Lys Ile Lys Asn Ser Leu Lys Val Glu His Asn
        355                 360                 365
Trp Tyr Tyr Asp Phe His Phe Thr His Thr Leu Phe Arg Thr Tyr
    370                 375                 380
Pro Glu Ile Glu Thr Asp Lys Glu Phe Thr Lys Ala Leu Ser Glu Phe
385                 390                 395                 400
Ile Met Cys Cys Thr Lys Thr Thr Cys Asp Lys Phe Arg Leu Lys Thr
                405                 410                 415
Ser Ile Leu His Pro Ile Ser Phe Leu Glu Lys Phe Ile Thr Lys Asn
            420                 425                 430
Ile Phe Ser Asn Trp Ile Asn Gly Thr His Gly Ala Ala
        435                 440                 445

<210> SEQ ID NO 47
<211> LENGTH: 1332
<212> TYPE: DNA
<213> ORGANISM: Molluscum contagiosum virus
<220> FEATURE:
<221> NAME/KEY: CDS
<222> LOCATION: (1)..(1332)

<400> SEQUENCE: 47 atg gca ttc tcg gac agt gcc tcc gcg gac gcg ccc tgg agc gca gtc        48
Met Ala Phe Ser Asp Ser Ala Ser Ala Asp Ala Pro Trp Ser Ala Val
1               5                   10                  15 cca gca ccg cgc cgc gac gag acc acg gtc ctg ggc gac gaa atc tac        96
Pro Ala Pro Arg Arg Asp Glu Thr Thr Val Leu Gly Asp Glu Ile Tyr
            20                  25                  30 ttt aac tac gtg tac ggg cag ctc gag ctc agc gac agt tgg atc cct       144
Phe Asn Tyr Val Tyr Gly Gln Leu Glu Leu Ser Asp Ser Trp Ile Pro
        35                  40                  45 cac gtg cgc atg ctg cgc tac ttc cgc aac ttc tcg cgc gcc gcg ctg       192
His Val Arg Met Leu Arg Tyr Phe Arg Asn Phe Ser Arg Ala Ala Leu
    50                  55                  60 ctg cgc atc gcc agc acg gag tac gtg aac ccg tcc tat ttc cag cag       240
Leu Arg Ile Ala Ser Thr Glu Tyr Val Asn Pro Ser Tyr Phe Gln Gln
65                  70                  75                  80 aag gac aag cgc ttt gcg ccc gtc aac aac gac ttc tac cac ctg tcc       288
Lys Asp Lys Arg Phe Ala Pro Val Asn Asn Asp Phe Tyr His Leu Ser
                85                  90                  95 acc ggc tac ggc att gtc ttc cgc gtg gaa gag tac gtg gtc aag            336
Thr Gly Tyr Gly Ile Val Phe Arg Val Glu Glu Tyr Val Val Lys
            100                 105                 110 ttc gtc ttc gag cct ggc agc cag ttc cac ccc atg gat ctc acg tcc       384
Phe Val Phe Glu Pro Gly Ser Gln Phe His Pro Met Asp Leu Thr Ser
        115                 120                 125 gaa tac acc gtg ccg cgc ttc ctc tac aac aac ctg cgg ggc gac gag       432
Glu Tyr Thr Val Pro Arg Phe Leu Tyr Asn Asn Leu Arg Gly Asp Glu
    130                 135                 140 cgc ctg ctg gtg gtg cgc gcg ctg gcc atg ggg ctc aac tac aag att       480
Arg Leu Leu Val Val Arg Ala Leu Ala Met Gly Leu Asn Tyr Lys Ile
```

```
Arg Leu Leu Val Val Arg Ala Leu Ala Met Gly Leu Asn Tyr Lys Ile
145                 150                 155                 160 ggc ttc ctg tac acg ctc tac aag cgc gtg ctg cac atg gtc ctg cta       528
Gly Phe Leu Tyr Thr Leu Tyr Lys Arg Val Leu His Met Val Leu Leu
                165                 170                 175 ctg gca cgc atc ctg gac ggg cag ccg ctg tcg cta gcg tac tcg cgc       576
Leu Ala Arg Ile Leu Asp Gly Gln Pro Leu Ser Leu Ala Tyr Ser Arg
            180                 185                 190 cgc cag gtg gcc aag ctc ttc gcg gag cgc aag gac agc gcc aag ttc       624
Arg Gln Val Ala Lys Leu Phe Ala Glu Arg Lys Asp Ser Ala Lys Phe
        195                 200                 205 gtg cgc ttg ctg tcc tac ttc tac ccc gcc gtg att aag agc aac ctc       672
Val Arg Leu Leu Ser Tyr Phe Tyr Pro Ala Val Ile Lys Ser Asn Leu
    210                 215                 220 aac gtc atc aac cac ttc ggg cac atg ata cat ttc ttc gag cac gag       720
Asn Val Ile Asn His Phe Gly His Met Ile His Phe Phe Glu His Glu
225                 230                 235                 240 aaa cgc gcc aac tac acc tat gac cgc ggc aac atc atc gtt ttt ccg       768
Lys Arg Ala Asn Tyr Thr Tyr Asp Arg Gly Asn Ile Ile Val Phe Pro
                245                 250                 255 ctg gca cgc tgc tcg gcg gag aag gtc acc gcg gcg aac tgt gcc gag       816
Leu Ala Arg Cys Ser Ala Glu Lys Val Thr Ala Ala Asn Cys Ala Glu
            260                 265                 270 ttc ggc ttc gcg tca gtg gtg cac tac gtc aag ttc ctc ttc cta cag       864
Phe Gly Phe Ala Ser Val Val His Tyr Val Lys Phe Leu Phe Leu Gln
        275                 280                 285 atg gcg ctg cta tac atc aag att tac gaa ctg tcc tgc cac aac ttt       912
Met Ala Leu Leu Tyr Ile Lys Ile Tyr Glu Leu Ser Cys His Asn Phe
    290                 295                 300 atc cac gtg gac ctc aag ccc gac aac atc ttg ctc ttc gac tcg gaa       960
Ile His Val Asp Leu Lys Pro Asp Asn Ile Leu Leu Phe Asp Ser Glu
305                 310                 315                 320 cgc gag atg cgc atc cac gtg ggc gag cgt agc tac gtc ttc cgc gag      1008
Arg Glu Met Arg Ile His Val Gly Glu Arg Ser Tyr Val Phe Arg Glu
                325                 330                 335 ccc gta cgc agc gcg ctc aac gat ttt gac ttc tcg cag gtt tcc gaa      1056
Pro Val Arg Ser Ala Leu Asn Asp Phe Asp Phe Ser Gln Val Ser Glu
            340                 345                 350 atc ccc aac aag aaa atc acg gcc agc ctg cgc gtc gag cag aac tgg      1104
Ile Pro Asn Lys Lys Ile Thr Ala Ser Leu Arg Val Glu Gln Asn Trp
        355                 360                 365 ttc tat gac ttc cac ttt ttc gtg cac aca cta ctc aag gtc tac ccc      1152
Phe Tyr Asp Phe His Phe Phe Val His Thr Leu Leu Lys Val Tyr Pro
    370                 375                 380 gag ctc gag cgc gac gca gcc tgg agc aag gcg ctg ggc gag ttc ctg      1200
Glu Leu Glu Arg Asp Ala Ala Trp Ser Lys Ala Leu Gly Glu Phe Leu
385                 390                 395                 400 gtc tgc tgc aac cgc aac acc tgc gag aag ttc cgc ctg cgc gta cgc      1248
Val Cys Cys Asn Arg Asn Thr Cys Glu Lys Phe Arg Leu Arg Val Arg
                405                 410                 415 cgc ctg cac ccc att agc ttc ctc gtg cgc ttc gtg gcg cgg gac ctt      1296
Arg Leu His Pro Ile Ser Phe Leu Val Arg Phe Val Ala Arg Asp Leu
            420                 425                 430 ttc tcc gac tgg ata aat ggc gag cgc cgc cct tag                      1332
Phe Ser Asp Trp Ile Asn Gly Glu Arg Arg Pro
        435                 440
```

<210> SEQ ID NO 48
<211> LENGTH: 443
<212> TYPE: PRT
<213> ORGANISM: Molluscum contagiosum virus

<400> SEQUENCE: 48

```
Met Ala Phe Ser Asp Ser Ala Ser Ala Asp Ala Pro Trp Ser Ala Val
1               5                   10                  15

Pro Ala Pro Arg Arg Asp Glu Thr Thr Val Leu Gly Asp Glu Ile Tyr
            20                  25                  30

Phe Asn Tyr Val Tyr Gly Gln Leu Glu Leu Ser Asp Ser Trp Ile Pro
            35                  40                  45

His Val Arg Met Leu Arg Tyr Phe Arg Asn Phe Ser Arg Ala Ala Leu
        50                  55                  60

Leu Arg Ile Ala Ser Thr Glu Tyr Val Asn Pro Ser Tyr Phe Gln Gln
65                  70                  75                  80

Lys Asp Lys Arg Phe Ala Pro Val Asn Asn Asp Phe Tyr His Leu Ser
                85                  90                  95

Thr Gly Gly Tyr Gly Ile Val Phe Arg Val Glu Glu Tyr Val Val Lys
            100                 105                 110

Phe Val Phe Glu Pro Gly Ser Gln Phe His Pro Met Asp Leu Thr Ser
        115                 120                 125

Glu Tyr Thr Val Pro Arg Phe Leu Tyr Asn Asn Leu Arg Gly Asp Glu
130                 135                 140

Arg Leu Leu Val Val Arg Ala Leu Ala Met Gly Leu Asn Tyr Lys Ile
145                 150                 155                 160

Gly Phe Leu Tyr Thr Leu Tyr Lys Arg Val Leu His Met Val Leu Leu
                165                 170                 175

Leu Ala Arg Ile Leu Asp Gly Gln Pro Leu Ser Leu Ala Tyr Ser Arg
            180                 185                 190

Arg Gln Val Ala Lys Leu Phe Ala Glu Arg Lys Asp Ser Ala Lys Phe
        195                 200                 205

Val Arg Leu Leu Ser Tyr Phe Tyr Pro Ala Val Ile Lys Ser Asn Leu
210                 215                 220

Asn Val Ile Asn His Phe Gly His Met Ile His Phe Phe Glu His Glu
225                 230                 235                 240

Lys Arg Ala Asn Tyr Thr Tyr Asp Arg Gly Asn Ile Ile Val Phe Pro
                245                 250                 255

Leu Ala Arg Cys Ser Ala Glu Lys Val Thr Ala Ala Asn Cys Ala Glu
            260                 265                 270

Phe Gly Phe Ala Ser Val Val His Tyr Val Lys Phe Leu Phe Leu Gln
        275                 280                 285

Met Ala Leu Leu Tyr Ile Lys Ile Tyr Glu Leu Ser Cys His Asn Phe
290                 295                 300

Ile His Val Asp Leu Lys Pro Asp Asn Ile Leu Leu Phe Asp Ser Glu
305                 310                 315                 320

Arg Glu Met Arg Ile His Val Gly Glu Arg Ser Tyr Val Phe Arg Glu
                325                 330                 335

Pro Val Arg Ser Ala Leu Asn Asp Phe Asp Phe Ser Gln Val Ser Glu
            340                 345                 350

Ile Pro Asn Lys Lys Ile Thr Ala Ser Leu Arg Val Glu Gln Asn Trp
        355                 360                 365

Phe Tyr Asp Phe His Phe Phe Val His Thr Leu Leu Lys Val Tyr Pro
370                 375                 380

Glu Leu Glu Arg Asp Ala Ala Trp Ser Lys Ala Leu Gly Glu Phe Leu
385                 390                 395                 400

Val Cys Cys Asn Arg Asn Thr Cys Glu Lys Phe Arg Leu Arg Val Arg
                405                 410                 415
```

```
Arg Leu His Pro Ile Ser Phe Leu Val Arg Phe Val Ala Arg Asp Leu
            420                 425                 430

Phe Ser Asp Trp Ile Asn Gly Glu Arg Arg Pro
            435                 440

<210> SEQ ID NO 49
<211> LENGTH: 1497
<212> TYPE: DNA
<213> ORGANISM: Orf virus
<220> FEATURE:
<221> NAME/KEY: CDS
<222> LOCATION: (1)..(1497)

<400> SEQUENCE: 49 atg atc ctc gcg cgc gcc ggc ggg cga cct cgc acg ccc gcg gcg gcc      48
Met Ile Leu Ala Arg Ala Gly Gly Arg Pro Arg Thr Pro Ala Ala Ala
1               5                   10                  15 gcg gcc gcc gcc gag gac gga gag cac agt gat cgc cgg aag cgc aag      96
Ala Ala Ala Ala Glu Asp Gly Glu His Ser Asp Arg Arg Lys Arg Lys
                20                  25                  30 cgc aag acg ccc aac tgc gaa gac gcc gac aac tcc gac gac gag cta     144
Arg Lys Thr Pro Asn Cys Glu Asp Ala Asp Asn Ser Asp Asp Glu Leu
            35                  40                  45 gcg cag acg ccg tgt gac cgc gag tgg ccg gac tgt cgc gcg agc tcg     192
Ala Gln Thr Pro Cys Asp Arg Glu Trp Pro Asp Cys Arg Ala Ser Ser
        50                  55                  60 atc acg agc tcc gac tcg gtc tct ctc ggc gac gag atc tac ctg cga     240
Ile Thr Ser Ser Asp Ser Val Ser Leu Gly Asp Glu Ile Tyr Leu Arg
65                  70                  75                  80 tac gtg gcc tcg cag gtg gac ttc gcg cag acc tgg gcc ccg ccg gtg     288
Tyr Val Ala Ser Gln Val Asp Phe Ala Gln Thr Trp Ala Pro Pro Val
                85                  90                  95 cgg ctg ctg cgc ttc ttc ggg aac ttc tcg aag gaa acg ctc aac cgc     336
Arg Leu Leu Arg Phe Phe Gly Asn Phe Ser Lys Glu Thr Leu Asn Arg
            100                 105                 110 atg tcg cgg cgc ggg tac gtg aac cgc tcc tac ttc cag atg gcg cac     384
Met Ser Arg Arg Gly Tyr Val Asn Arg Ser Tyr Phe Gln Met Ala His
        115                 120                 125 gcg cgc ttc tcg ccc acc aac gac gac atg tac cac atg gcc acg ggc     432
Ala Arg Phe Ser Pro Thr Asn Asp Asp Met Tyr His Met Ala Thr Gly
    130                 135                 140 ggg tac ggc atc gtg ttc cgc ttc gac cgc tac gtg gtc aag tac gtc     480
Gly Tyr Gly Ile Val Phe Arg Phe Asp Arg Tyr Val Val Lys Tyr Val
145                 150                 155                 160 ttc gag cac cgc aac ggc atg tcc gag atg gac gcc tct acg gag tac     528
Phe Glu His Arg Asn Gly Met Ser Glu Met Asp Ala Ser Thr Glu Tyr
                165                 170                 175 aca gtg ccg cgg ttc ctg cgc aat aac ctc aag ggc gac gag cgc gag     576
Thr Val Pro Arg Phe Leu Arg Asn Asn Leu Lys Gly Asp Glu Arg Glu
            180                 185                 190 ttc gtg gtc tgc gcg ctg gcc atg ggg ctg aac tac cgg ctg ggc ttc     624
Phe Val Val Cys Ala Leu Ala Met Gly Leu Asn Tyr Arg Leu Gly Phe
        195                 200                 205 ctg cac tcg ctg tac cgg cgc gtg ctg cac acg ctg ctg ctc atg         672
Leu His Ser Leu Tyr Arg Arg Val Leu His Thr Leu Leu Leu Met
    210                 215                 220 cgc gtg gag gaa ggc cag cgg ccc tcg gtg gag atg tcc aag aag ccg     720
Arg Val Glu Glu Gly Gln Arg Pro Ser Val Glu Met Ser Lys Lys Pro
225                 230                 235                 240 ctg ctg cgc tgg ttc gag gcg cgc aag gac agc gag tcc ttc gtg cgc     768
Leu Leu Arg Trp Phe Glu Ala Arg Lys Asp Ser Glu Ser Phe Val Arg
```

```
                      245                 250                 255
ctg atc tcg tac ttc tac ccc tcg gcc gtg cag agc aac gtg aac ctg    816
Leu Ile Ser Tyr Phe Tyr Pro Ser Ala Val Gln Ser Asn Val Asn Leu
            260                 265                 270 atc aac aac ttc cac cac ctg gtg cac ttc ttc gag cac gag aag cgc    864
Ile Asn Asn Phe His His Leu Val His Phe Phe Glu His Glu Lys Arg
                275                 280                 285 gcg cgg tac gtg ttc gac cgc ggg gcc gtg atc gtg ttc cct ctg gcg    912
Ala Arg Tyr Val Phe Asp Arg Gly Ala Val Ile Val Phe Pro Leu Ala
            290                 295                 300 cgc ggg tcc gcg gac tcg atc tcg ccg gag gcg gcg gcg gcg ctg ggc    960
Arg Gly Ser Ala Asp Ser Ile Ser Pro Glu Ala Ala Ala Ala Leu Gly
305                 310                 315                 320 ttc gcg ccg cac tcg gag ttc ctc aag ttc gtg ttc ctg cag atc gcg   1008
Phe Ala Pro His Ser Glu Phe Leu Lys Phe Val Phe Leu Gln Ile Ala
                325                 330                 335 ctg ctg tac ctg aag atc tac gag ctc ccg gtc tgc acg aac ttc ctg   1056
Leu Leu Tyr Leu Lys Ile Tyr Glu Leu Pro Val Cys Thr Asn Phe Leu
            340                 345                 350 cac gtg gac ctg aag ccc gac aac gtg ctc atc ttc gac agc gcg cgc   1104
His Val Asp Leu Lys Pro Asp Asn Val Leu Ile Phe Asp Ser Ala Arg
                355                 360                 365 gcg ctc agc gtg acc gcg gcc ggc gcg act ttc cgc ttc gag gag ccc   1152
Ala Leu Ser Val Thr Ala Ala Gly Ala Thr Phe Arg Phe Glu Glu Pro
370                 375                 380 gtg cgc gcg gcg ctg aac gac ttc gac ttc gcg cgc gtg gcc acc atc   1200
Val Arg Ala Ala Leu Asn Asp Phe Asp Phe Ala Arg Val Ala Thr Ile
385                 390                 395                 400 gag aac cgc aag atc tcg ggc agc gtc cgc gtg ccg cag aac tgg tac   1248
Glu Asn Arg Lys Ile Ser Gly Ser Val Arg Val Pro Gln Asn Trp Tyr
                405                 410                 415 tac gac ttc cac ttc ttc gcg cac acg ctg ctg cgc gcg tac ccg cac   1296
Tyr Asp Phe His Phe Phe Ala His Thr Leu Leu Arg Ala Tyr Pro His
            420                 425                 430 atc gcc gcg gag gac ccg ggc ttc cac gcg ctg ctc tcg gag ctc acg   1344
Ile Ala Ala Glu Asp Pro Gly Phe His Ala Leu Leu Ser Glu Leu Thr
                435                 440                 445 gtc tcg tgc tcg cgc ggg acc tgc gac cgc ttc cgg ctg cgc gtg tcc   1392
Val Ser Cys Ser Arg Gly Thr Cys Asp Arg Phe Arg Leu Arg Val Ser
450                 455                 460 tcg ccg cac ccc atc gag cac ctc gcg cgg ctg gtg cgc cgc gac gtg   1440
Ser Pro His Pro Ile Glu His Leu Ala Arg Leu Val Arg Arg Asp Val
465                 470                 475                 480 ttc tcc cgc tgg ata aat gcc gct gca gac gcc ccc gac gcc gcc gca   1488
Phe Ser Arg Trp Ile Asn Ala Ala Ala Asp Ala Pro Asp Ala Ala Ala
                485                 490                 495 ctc tcc tga                                                        1497
Leu Ser

<210> SEQ ID NO 50
<211> LENGTH: 498
<212> TYPE: PRT
<213> ORGANISM: Orf virus

<400> SEQUENCE: 50

Met Ile Leu Ala Arg Ala Gly Gly Arg Pro Ar

```
              35                  40                  45
Ala Gln Thr Pro Cys Asp Arg Glu Trp Pro Asp Cys Arg Ala Ser Ser
 50                  55                  60

Ile Thr Ser Ser Asp Ser Val Ser Leu Gly Asp Glu Ile Tyr Leu Arg
 65                  70                  75                  80

Tyr Val Ala Ser Gln Val Asp Phe Ala Gln Thr Trp Ala Pro Pro Val
                     85                  90                  95

Arg Leu Leu Arg Phe Phe Gly Asn Phe Ser Lys Glu Thr Leu Asn Arg
                100                 105                 110

Met Ser Arg Arg Gly Tyr Val Asn Arg Ser Tyr Phe Gln Met Ala His
                115                 120                 125

Ala Arg Phe Ser Pro Thr Asn Asp Asp Met Tyr His Met Ala Thr Gly
            130                 135                 140

Gly Tyr Gly Ile Val Phe Arg Phe Asp Arg Tyr Val Val Lys Tyr Val
145                 150                 155                 160

Phe Glu His Arg Asn Gly Met Ser Glu Met Asp Ala Ser Thr Glu Tyr
                165                 170                 175

Thr Val Pro Arg Phe Leu Arg Asn Asn Leu Lys Gly Asp Glu Arg Glu
                180                 185                 190

Phe Val Val Cys Ala Leu Ala Met Gly Leu Asn Tyr Arg Leu Gly Phe
                195                 200                 205

Leu His Ser Leu Tyr Arg Arg Val Leu His Thr Leu Leu Leu Leu Met
            210                 215                 220

Arg Val Glu Glu Gly Gln Arg Pro Ser Val Glu Met Ser Lys Lys Pro
225                 230                 235                 240

Leu Leu Arg Trp Phe Glu Ala Arg Lys Asp Ser Glu Ser Phe Val Arg
                245                 250                 255

Leu Ile Ser Tyr Phe Tyr Pro Ser Ala Val Gln Ser Asn Val Asn Leu
                260                 265                 270

Ile Asn Asn Phe His His Leu Val His Phe Glu His Glu Lys Arg
            275                 280                 285

Ala Arg Tyr Val Phe Asp Arg Gly Ala Val Ile Val Phe Pro Leu Ala
            290                 295                 300

Arg Gly Ser Ala Asp Ser Ile Ser Pro Glu Ala Ala Ala Leu Gly
305                 310                 315                 320

Phe Ala Pro His Ser Glu Phe Leu Lys Phe Val Phe Leu Gln Ile Ala
                325                 330                 335

Leu Leu Tyr Leu Lys Ile Tyr Glu Leu Pro Val Cys Thr Asn Phe Leu
                340                 345                 350

His Val Asp Leu Lys Pro Asp Asn Val Leu Ile Phe Asp Ser Ala Arg
            355                 360                 365

Ala Leu Ser Val Thr Ala Ala Gly Ala Thr Phe Arg Phe Glu Glu Pro
            370                 375                 380

Val Arg Ala Ala Leu Asn Asp Phe Asp Phe Ala Arg Val Ala Thr Ile
385                 390                 395                 400

Glu Asn Arg Lys Ile Ser Gly Ser Val Arg Val Pro Gln Asn Trp Tyr
                405                 410                 415

Tyr Asp Phe His Phe Ala His Thr Leu Leu Arg Ala Tyr Pro His
                420                 425                 430

Ile Ala Ala Glu Asp Pro Gly Phe His Ala Leu Leu Ser Glu Leu Thr
            435                 440                 445

Val Ser Cys Ser Arg Gly Thr Cys Asp Arg Phe Arg Leu Arg Val Ser
450                 455                 460
```

```
Ser Pro His Pro Ile Glu His Leu Ala Arg Leu Val Arg Arg Asp Val
465                 470                 475                 480

Phe Ser Arg Trp Ile Asn Ala Ala Ala Asp Ala Pro Asp Ala Ala Ala
            485                 490                 495

Leu Ser

<210> SEQ ID NO 51
<211> LENGTH: 1440
<212> TYPE: DNA
<213> ORGANISM: Bovine papular stomatitis virus
<220> FEATURE:
<221> NAME/KEY: CDS
<222> LOCATION: (1)..(1440)

<400> SEQUENCE: 51 atg tcg ccc cct ggc gcc gag gac aag aag ccg cgt cgg gcg cga cgc      48
Met Ser Pro Pro Gly Ala Glu Asp Lys Lys Pro Arg Arg Ala Arg Arg
1               5                   10                  15 aag acc ccc gac tgc gcg gac gac gag gcc gcg gcg ctg gac gca cag      96
Lys Thr Pro Asp Cys Ala Asp Asp Glu Ala Ala Ala Leu Asp Ala Gln
            20                  25                  30 gtg ccc tgc gac cgc gag tgg gcg gac tgc cgc tcg tcc gcg ctg acg     144
Val Pro Cys Asp Arg Glu Trp Ala Asp Cys Arg Ser Ser Ala Leu Thr
        35                  40                  45 ggc ccg gac tcc gtg tcg ctc ggc gac gag atc tac ctg cgc tac gtg     192
Gly Pro Asp Ser Val Ser Leu Gly Asp Glu Ile Tyr Leu Arg Tyr Val
    50                  55                  60 gcc tcg cag gtg gac ttc gcg cag acc tgg gcg ccg ccg gtg cgg ctg     240
Ala Ser Gln Val Asp Phe Ala Gln Thr Trp Ala Pro Pro Val Arg Leu
65                  70                  75                  80 ctg cgc ttc ttc ggc aac ttc tcc aag gac acg ctc gac cgc atg tcc     288
Leu Arg Phe Phe Gly Asn Phe Ser Lys Asp Thr Leu Asp Arg Met Ser
                85                  90                  95 aag cgc ggg tac gtc aac cgc tcc tac tac cag atg gcg cac gcg cgc     336
Lys Arg Gly Tyr Val Asn Arg Ser Tyr Tyr Gln Met Ala His Ala Arg
            100                 105                 110 ttc tcg ccc acg aac gac gac atg tac cac atg gcc acc ggg ggc tac     384
Phe Ser Pro Thr Asn Asp Asp Met Tyr His Met Ala Thr Gly Gly Tyr
        115                 120                 125 ggc atc gtc tgc cgc ttc gac cgg tac gtg gtc aag ttc gtc ttc gag     432
Gly Ile Val Cys Arg Phe Asp Arg Tyr Val Val Lys Phe Val Phe Glu
    130                 135                 140 cac cgc aac ggc atg tcc gag atc gac gcc tcc aca gag tac acg gtg     480
His Arg Asn Gly Met Ser Glu Ile Asp Ala Ser Thr Glu Tyr Thr Val
145                 150                 155                 160 ccg cgc ttc ctg cgc tcc aac ctc aag ggc gac gag cgc gag ttc gtg     528
Pro Arg Phe Leu Arg Ser Asn Leu Lys Gly Asp Glu Arg Glu Phe Val
                165                 170                 175 gtc tgc gcg ctg gcc atg ggg ctg aac tac cgc ctc ggg ttc ctg cac     576
Val Cys Ala Leu Ala Met Gly Leu Asn Tyr Arg Leu Gly Phe Leu His
            180                 185                 190 tcg ctg tac cgg cgc gtg ctg cac acg ctg ctg ctg atg cgc gcg         624
Ser Leu Tyr Arg Arg Val Leu His Thr Leu Leu Leu Met Arg Ala
        195                 200                 205 gag gag ggc cag cgc ccc tcc gtg gag atg gcc aag aag ccg ctg ctg     672
Glu Glu Gly Gln Arg Pro Ser Val Glu Met Ala Lys Lys Pro Leu Leu
    210                 215                 220 cgc tgg ttc gag tcg cgc aag gac tcg gag tcc ttc gtg cgg ctc gtc     720
Arg Trp Phe Glu Ser Arg Lys Asp Ser Glu Ser Phe Val Arg Leu Val
225                 230                 235                 240 tcg tac ttc tac ccc tcg gcc gtg cag agc aac gtc aac ctc gtc aac     768
```

```
Ser Tyr Phe Tyr Pro Ser Ala Val Gln Ser Asn Val Asn Leu Val Asn
                245                 250                 255 aac ttc ccg cac ctg gtg cac ttt ttc gag cac gag aag cgc gcg cgg       816
Asn Phe Pro His Leu Val His Phe Phe Glu His Glu Lys Arg Ala Arg
                260                 265                 270 tac gtc ttc gac cgc ggg gcc gtg atc gtg ttc ccg ctg gcg cgc ggc       864
Tyr Val Phe Asp Arg Gly Ala Val Ile Val Phe Pro Leu Ala Arg Gly
                275                 280                 285 tcc gcg gac tcc gtc tcc gcg gag gcc gcg ctc ggc ctg ggc ttc tcc       912
Ser Ala Asp Ser Val Ser Ala Glu Ala Ala Leu Gly Leu Gly Phe Ser
            290                 295                 300 tcg cac gcg gag ttc ctc aag ttc gtg ttc ctg cag atc gcg ctg ctg       960
Ser His Ala Glu Phe Leu Lys Phe Val Phe Leu Gln Ile Ala Leu Leu
305                 310                 315                 320 tac ctc aag atc tac gag atg ccg ggg tgc gcg aac ttc ctg cac gtg      1008
Tyr Leu Lys Ile Tyr Glu Met Pro Gly Cys Ala Asn Phe Leu His Val
                325                 330                 335 gac ctc aag ccc gac aac gtg ctc atc ttc gac agc tcg cgc gca ctc      1056
Asp Leu Lys Pro Asp Asn Val Leu Ile Phe Asp Ser Ser Arg Ala Leu
                340                 345                 350 agc gtg gag gcg gcc ggc gcc acc ttc cgc ttc gag gag ccc gtg cgc      1104
Ser Val Glu Ala Ala Gly Ala Thr Phe Arg Phe Glu Glu Pro Val Arg
                355                 360                 365 gcc gcg ctg aac gac ttc gac ttc gcg cgc gtg gct aac atc gag aac      1152
Ala Ala Leu Asn Asp Phe Asp Phe Ala Arg Val Ala Asn Ile Glu Asn
                370                 375                 380 cgc aag atc gcg ggc agc atc cgc gtg ccg cag aac tgg tac tac gac      1200
Arg Lys Ile Ala Gly Ser Ile Arg Val Pro Gln Asn Trp Tyr Tyr Asp
385                 390                 395                 400 ttc cac ttc ttc gca cac acg ctg ctg cgc gcg tac ccg aac ata gcc      1248
Phe His Phe Phe Ala His Thr Leu Leu Arg Ala Tyr Pro Asn Ile Ala
                405                 410                 415 gcc gag gac ccc gcg ttc cac tcg gtg ctc tcg gag ctg acc atc tcg      1296
Ala Glu Asp Pro Ala Phe His Ser Val Leu Ser Glu Leu Thr Ile Ser
                420                 425                 430 tgc tcg cgc tcc acg tgc gac cgc ttc cgc ctg cgc gtg tcg tcg acg      1344
Cys Ser Arg Ser Thr Cys Asp Arg Phe Arg Leu Arg Val Ser Ser Thr
            435                 440                 445 cac ccg ata gag cac ctg gcg cgg atc gtg cgc cgc gac cta ttc tcc      1392
His Pro Ile Glu His Leu Ala Arg Ile Val Arg Arg Asp Leu Phe Ser
450                 455                 460 cgc tgg ata aat gcc gcc acc gac gct ccc gac ccc gcc gca gcc tga      1440
Arg Trp Ile Asn Ala Ala Thr Asp Ala Pro Asp Pro Ala Ala Ala
465                 470                 475

<210> SEQ ID NO 52
<211> LENGTH: 479
<212> TYPE: PRT
<213> ORGANISM: Bovine papular stomatitis virus

<400> SEQUENCE: 52

Met Ser Pro Pro Gly Ala Glu Asp Lys Lys Pro Arg Ala Arg Arg
1               5                   10                  15

Lys Thr Pro Asp Cys Ala Asp Asp Glu

```
                65                  70                  75                  80
Leu Arg Phe Phe Gly Asn Phe Ser Lys Asp Thr Leu Asp Arg Met Ser
                        85                  90                  95
Lys Arg Gly Tyr Val Asn Arg Ser Tyr Gln Met Ala His Ala Arg
                    100                 105                 110
Phe Ser Pro Thr Asn Asp Asp Met Tyr His Met Ala Thr Gly Gly Tyr
                    115                 120                 125
Gly Ile Val Cys Arg Phe Asp Arg Tyr Val Val Lys Phe Val Phe Glu
            130                 135                 140
His Arg Asn Gly Met Ser Glu Ile Asp Ala Ser Thr Glu Tyr Thr Val
145                 150                 155                 160
Pro Arg Phe Leu Arg Ser Asn Leu Lys Gly Asp Glu Arg Glu Phe Val
                    165                 170                 175
Val Cys Ala Leu Ala Met Gly Leu Asn Tyr Arg Leu Gly Phe Leu His
                180                 185                 190
Ser Leu Tyr Arg Arg Val Leu His Thr Leu Leu Leu Met Arg Ala
            195                 200                 205
Glu Glu Gly Gln Arg Pro Ser Val Glu Met Ala Lys Lys Pro Leu Leu
    210                 215                 220
Arg Trp Phe Glu Ser Arg Lys Asp Ser Glu Ser Phe Val Arg Leu Val
225                 230                 235                 240
Ser Tyr Phe Tyr Pro Ser Ala Val Gln Ser Asn Val Asn Leu Val Asn
                    245                 250                 255
Asn Phe Pro His Leu Val His Phe Phe Glu His Glu Lys Arg Ala Arg
                260                 265                 270
Tyr Val Phe Asp Arg Gly Ala Val Ile Val Phe Pro Leu Ala Arg Gly
                275                 280                 285
Ser Ala Asp Ser Val Ser Ala Glu Ala Ala Leu Gly Leu Gly Phe Ser
    290                 295                 300
Ser His Ala Glu Phe Leu Lys Pro Val Phe Leu Gln Ile Ala Leu Leu
305                 310                 315                 320
Tyr Leu Lys Ile Tyr Glu Met Pro Gly Cys Ala Asn Phe Leu His Val
                325                 330                 335
Asp Leu Lys Pro Asp Asn Val Leu Ile Phe Asp Ser Ser Arg Ala Leu
                340                 345                 350
Ser Val Glu Ala Ala Gly Ala Thr Phe Arg Phe Glu Pro Val Arg
    355                 360                 365
Ala Ala Leu Asn Asp Phe Asp Phe Ala Arg Val Ala Asn Ile Glu Asn
    370                 375                 380
Arg Lys Ile Ala Gly Ser Ile Arg Val Pro Gln Asn Trp Tyr Tyr Asp
385                 390                 395                 400
Phe His Phe Phe Ala His Thr Leu Leu Arg Ala Tyr Pro Asn Ile Ala
                405                 410                 415
Ala Glu Asp Pro Ala Phe His Ser Val Leu Ser Glu Leu Thr Ile Ser
                420                 425                 430
Cys Ser Arg Ser Thr Cys Asp Arg Phe Arg Leu Arg Val Ser Ser Thr
                435                 440                 445
His Pro Ile Glu His Leu Ala Arg Ile Val Arg Arg Asp Leu Phe Ser
                450                 455                 460
Arg Trp Ile Asn Ala Ala Thr Asp Ala Pro Pro Ala Ala Ala
465                 470                 475

<210> SEQ ID NO 53
<211> LENGTH: 1335
```

```
<212> TYPE: DNA
<213> ORGANISM: Fowlpox virus
<220> FEATURE:
<221> NAME/KEY: CDS
<222> LOCATION: (1)..(1335)

<400> SEQUENCE: 53 atg gaa ttt ccg gac ata cat gct tat aat tct acc aag tat tta gaa        48
Met Glu Phe Pro Asp Ile His Ala Tyr Asn Ser Thr Lys Tyr Leu Glu
1               5                   10                  15 gat gga gac act acg ata tta gga gat act att cag ttt cag ttt ata        96
Asp Gly Asp Thr Thr Ile Leu Gly Asp Thr Ile Gln Phe Gln Phe Ile
                20                  25                  30 tac gaa aat ata gac aat aag gag cat atc tcc tta cca aaa ata aag       144
Tyr Glu Asn Ile Asp Asn Lys Glu His Ile Ser Leu Pro Lys Ile Lys
            35                  40                  45 att ttc aag tat ttt aga gat aag ata tct ttt gaa aca cta gat aga       192
Ile Phe Lys Tyr Phe Arg Asp Lys Ile Ser Phe Glu Thr Leu Asp Arg
        50                  55                  60 att att aaa aat gat tac ata aat cct tcc tat ttt cag tta aaa gat       240
Ile Ile Lys Asn Asp Tyr Ile Asn Pro Ser Tyr Phe Gln Leu Lys Asp
65                  70                  75                  80 aaa aag ttt tgt gcg cac aat agg gat ttt tac cat cta tct acc ggg       288
Lys Lys Phe Cys Ala His Asn Arg Asp Phe Tyr His Leu Ser Thr Gly
                85                  90                  95 gga tat ggt att att ttt agg atg gaa aaa tat gta gtt aaa ttt gtt       336
Gly Tyr Gly Ile Ile Phe Arg Met Glu Lys Tyr Val Val Lys Phe Val
                100                 105                 110 ttc gaa gac ggg agt aaa aaa tat aaa cct atg gaa gta aca tct gaa       384
Phe Glu Asp Gly Ser Lys Lys Tyr Lys Pro Met Glu Val Thr Ser Glu
            115                 120                 125 ttt aca att cct aga ttt tta tat aat aat ctt aaa ggt gat gaa agg       432
Phe Thr Ile Pro Arg Phe Leu Tyr Asn Asn Leu Lys Gly Asp Glu Arg
        130                 135                 140 aag ttt ata gtt tgt gca atc gcg atg ggg att aat ttt aag ata gat       480
Lys Phe Ile Val Cys Ala Ile Ala Met Gly Ile Asn Phe Lys Ile Asp
145                 150                 155                 160 ttc tta cgt aca atc tat tat aac acg atg agt tta atg tct gcg tta       528
Phe Leu Arg Thr Ile Tyr Tyr Asn Thr Met Ser Leu Met Ser Ala Leu
                165                 170                 175 ttt aac atc atg gaa gga gaa cct cta gaa aac aaa tat tct cat aga       576
Phe Asn Ile Met Glu Gly Glu Pro Leu Glu Asn Lys Tyr Ser His Arg
                180                 185                 190 aaa gta tta cgt tat ttc gct aag tac aaa caa tct aat gat ttt gta       624
Lys Val Leu Arg Tyr Phe Ala Lys Tyr Lys Gln Ser Asn Asp Phe Val
            195                 200                 205 aaa ttg ata tca cag ttt tat ccg tat gtt gtt aac tct aat atc aat       672
Lys Leu Ile Ser Gln Phe Tyr Pro Tyr Val Val Asn Ser Asn Ile Asn
        210                 215                 220 gta att aat aac ttt aat tat cta att aat ttt ttt gaa cgt agt agg       720
Val Ile Asn Asn Phe Asn Tyr Leu Ile Asn Phe Phe Glu Arg Ser Arg
225                 230                 235                 240 aga tca aac ggt tat ttt aac aga ggt aac ata ata ttc cct tta            768
Arg Ser Asn Gly Tyr Phe Asn Arg Gly Asn Ile Ile Ile Phe Pro Leu
                245                 250                 255 gca aaa tgt tcc gca gaa aaa ata act ccg gat aac tat gca caa tat       816
Ala Lys Cys Ser Ala Glu Lys Ile Thr Pro Asp Asn Tyr Ala Gln Tyr
                260                 265                 270 gga ttt tct agt ata gta gaa tat act aaa ttt atg ttt tta caa ata       864
Gly Phe Ser Ser Ile Val Glu Tyr Thr Lys Phe Met Phe Leu Gln Ile
            275                 280                 285
```

```
gct tta ttg tac ata aaa att tat gaa ttg cca tgc agt aac ttt gtt      912
Ala Leu Leu Tyr Ile Lys Ile Tyr Glu Leu Pro Cys Ser Asn Phe Val
290                 295                 300 cat tta gac ttg aaa ccg gat aac ata tta att ttt gat tcc aaa gaa      960
His Leu Asp Leu Lys Pro Asp Asn Ile Leu Ile Phe Asp Ser Lys Glu
305                 310                 315                 320 cct ata aat ata tac gta ggt gat atg cat tat gtg ttt aaa gaa cct     1008
Pro Ile Asn Ile Tyr Val Gly Asp Met His Tyr Val Phe Lys Glu Pro
                325                 330                 335 ata aga tgt aca tta aac gac ttt gac ttt tca cag ata tcg gaa att     1056
Ile Arg Cys Thr Leu Asn Asp Phe Asp Phe Ser Gln Ile Ser Glu Ile
                340                 345                 350 att cct aat aag aaa gct gta acc gct att aac aaa gaa cag aat tgg     1104
Ile Pro Asn Lys Lys Ala Val Thr Ala Ile Asn Lys Glu Gln Asn Trp
                355                 360                 365 tat tac gac ttc cac ttt ttc tcg cat gta cta ttt aaa gta tat cca     1152
Tyr Tyr Asp Phe His Phe Phe Ser His Val Leu Phe Lys Val Tyr Pro
370                 375                 380 gaa ata tct aaa gac gaa gat ttt act tct ttg ctt aac gaa ttt act     1200
Glu Ile Ser Lys Asp Glu Asp Phe Thr Ser Leu Leu Asn Glu Phe Thr
385                 390                 395                 400 atc tgt gat aaa tat atc tgt gaa aac ttt aga cta caa gta aat aaa     1248
Ile Cys Asp Lys Tyr Ile Cys Glu Asn Phe Arg Leu Gln Val Asn Lys
                405                 410                 415 tta cct tct ata tcg ttt tta ata aat ata gtt tct aga gat att ttt     1296
Leu Pro Ser Ile Ser Phe Leu Ile Asn Ile Val Ser Arg Asp Ile Phe
                420                 425                 430 tca aag tgg ata gat gga aaa tca aca agt cat cag taa                 1335
Ser Lys Trp Ile Asp Gly Lys Ser Thr Ser His Gln
                435                 440

<210> SEQ ID NO 54
<211> LENGTH: 444
<212> TYPE: PRT
<213> ORGANISM: Fowlpox virus

<400> SEQUENCE: 54

Met Glu Phe Pro Asp Ile His Ala Tyr Asn Ser Thr Lys Tyr Leu Glu
1               5                   10                  15

Asp Gly Asp Thr Thr Ile Leu Gly Asp Thr Ile Gln Phe Gln Phe Ile
            20                  25                  30

Tyr Glu Asn Ile Asp Asn Lys Glu His Ile Ser Leu Pro Lys Ile Lys
        35                  40                  45

Ile Phe Lys Tyr Phe Arg Asp Lys Ile Ser Phe Glu Thr Leu Asp Arg
    50                  55                  60

Ile Ile Lys Asn Asp Tyr Ile Asn Pro Ser Tyr Phe Gln Leu Lys Asp
65                  70                  75                  80

Lys Lys Phe Cys Ala His Asn Arg Asp Phe Tyr His Leu Ser Thr Gly
                85                  90                  95

Gly Tyr Gly Ile Ile Phe Arg Met Glu Lys Tyr Val Val Lys Phe Val
            100                 105                 110

Phe Glu Asp Gly Ser Lys Lys Tyr Lys Pro Met Glu Val Thr Ser Glu
        115                 120                 125

Phe Thr Ile Pro Arg Phe Leu Tyr Asn Asn Leu Lys Gly Asp Glu Arg
    130                 135                 140

Lys Phe Ile Val Cys Ala Ile Ala Met Gly Ile Asn Phe Lys Ile Asp
145                 150                 155                 160

Phe Leu Arg Thr Ile Tyr Tyr Asn Thr Met Ser Leu Met Ser Ala Leu
                165                 170                 175
```

```
Phe Asn Ile Met Glu Gly Glu Pro Leu Glu Asn Lys Tyr Ser His Arg
                180                 185                 190

Lys Val Leu Arg Tyr Phe Ala Lys Tyr Lys Gln Ser Asn Asp Phe Val
            195                 200                 205

Lys Leu Ile Ser Gln Phe Tyr Pro Tyr Val Val Asn Ser Asn Ile Asn
        210                 215                 220

Val Ile Asn Asn Phe Asn Tyr Leu Ile Asn Phe Phe Glu Arg Ser Arg
225                 230                 235                 240

Arg Ser Asn Gly Tyr Phe Asn Arg Gly Asn Ile Ile Ile Phe Pro Leu
                245                 250                 255

Ala Lys Cys Ser Ala Glu Lys Ile Thr Pro Asp Asn Tyr Ala Gln Tyr
            260                 265                 270

Gly Phe Ser Ser Ile Val Glu Tyr Thr Lys Phe Met Phe Leu Gln Ile
        275                 280                 285

Ala Leu Leu Tyr Ile Lys Ile Tyr Glu Leu Pro Cys Ser Asn Phe Val
        290                 295                 300

His Leu Asp Leu Lys Pro Asp Asn Ile Leu Ile Phe Asp Ser Lys Glu
305                 310                 315                 320

Pro Ile Asn Ile Tyr Val Gly Asp Met His Tyr Val Phe Lys Glu Pro
                325                 330                 335

Ile Arg Cys Thr Leu Asn Asp Phe Asp Phe Ser Gln Ile Ser Glu Ile
            340                 345                 350

Ile Pro Asn Lys Lys Ala Val Thr Ala Ile Asn Lys Glu Gln Asn Trp
        355                 360                 365

Tyr Tyr Asp Phe His Phe Phe Ser His Val Leu Phe Lys Val Tyr Pro
        370                 375                 380

Glu Ile Ser Lys Asp Glu Asp Phe Thr Ser Leu Leu Asn Glu Phe Thr
385                 390                 395                 400

Ile Cys Asp Lys Tyr Ile Cys Glu Asn Phe Arg Leu Gln Val Asn Lys
                405                 410                 415

Leu Pro Ser Ile Ser Phe Leu Ile Asn Ile Val Ser Arg Asp Ile Phe
            420                 425                 430

Ser Lys Trp Ile Asp Gly Lys Ser Thr Ser His Gln
        435                 440

<210> SEQ ID NO 55
<211> LENGTH: 1335
<212> TYPE: DNA
<213> ORGANISM: Canarypox virus
<220> FEATURE:
<221> NAME/KEY: CDS
<222> LOCATION: (1)..(1335)

<400> SEQUENCE: 55 atg gag ttt aca gat tta tac tat tca gat tcc aat aac tat gct aaa      48
Met Glu Phe Thr Asp Leu Tyr Tyr Ser Asp Ser Asn Asn Tyr Ala Lys
1               5                   10                  15 gat gat aaa act ata ata tta gga gat act att cag ttt caa ttt ata      96
Asp Asp Lys Thr Ile Ile Leu Gly Asp Thr Ile Gln Phe Gln Phe Ile
            20                  25                  30 tat gaa cat ata ggt aat tac caa caa tta cct aaa ata aaa ata tct     144
Tyr Glu His Ile Gly Asn Tyr Gln Gln Leu Pro Lys Ile Lys Ile Ser
        35                  40                  45 aaa tat ttt aaa gag aaa atc tct tta gat aca tta aaa aga att gca     192
Lys Tyr Phe Lys Glu Lys Ile Ser Leu Asp Thr Leu Lys Arg Ile Ala
    50                  55                  60 aaa aac gat tct att gat cct tct tat tat cag tta aaa gat aaa cat     240
```

-continued

```
Lys Asn Asp Ser Ile Asp Pro Ser Tyr Tyr Gln Leu Lys Asp Lys His
 65                  70                  75                  80 ttt att ccg ttg aat aat gtt ttt tat cat ctg tct aca gga gga tac      288
Phe Ile Pro Leu Asn Asn Val Phe Tyr His Leu Ser Thr Gly Gly Tyr
                     85                  90                  95 ggt ata gtt ttt aag ata ggg aaa tac gta gtt aag ttt gta ttt gaa      336
Gly Ile Val Phe Lys Ile Gly Lys Tyr Val Val Lys Phe Val Phe Glu
                100                 105                 110 gat act agt aaa aaa tat gac ccg atg gaa gtc act tcg gag ttt acc      384
Asp Thr Ser Lys Lys Tyr Asp Pro Met Glu Val Thr Ser Glu Phe Thr
            115                 120                 125 gtt cct aga ttt tta tac aat aat ctt aag ggt gat gag cgt aag ctt      432
Val Pro Arg Phe Leu Tyr Asn Asn Leu Lys Gly Asp Glu Arg Lys Leu
130                 135                 140 ata gtt tgt gct ata gcc atg ggt ctt aac ttc aaa ata aac ttc tta      480
Ile Val Cys Ala Ile Ala Met Gly Leu Asn Phe Lys Ile Asn Phe Leu
145                 150                 155                 160 cgt act att tat tat aat act att aat ttg cta tct gct tta ttc agt      528
Arg Thr Ile Tyr Tyr Asn Thr Ile Asn Leu Leu Ser Ala Leu Phe Ser
                165                 170                 175 atc tta gaa aga gaa cct ata aaa gaa aaa tat tct cat aaa aaa gta      576
Ile Leu Glu Arg Glu Pro Ile Lys Glu Lys Tyr Ser His Lys Lys Val
            180                 185                 190 ctg agt tat ttt tct aag tac aaa aat act aaa gat ttt gtt aaa ata      624
Leu Ser Tyr Phe Ser Lys Tyr Lys Asn Thr Lys Asp Phe Val Lys Ile
        195                 200                 205 ata tct cag ttt tat cct ttt gta gtt agt aat aat ata aat ata ata      672
Ile Ser Gln Phe Tyr Pro Phe Val Val Ser Asn Asn Ile Asn Ile Ile
210                 215                 220 aat aat ttt aac tat ctg att aat ttt ttc gaa agt aca aag aga gct      720
Asn Asn Phe Asn Tyr Leu Ile Asn Phe Phe Glu Ser Thr Lys Arg Ala
225                 230                 235                 240 aac gga tac ttt gaa aga ggt aat att ata atc ttc cct tta gca aaa      768
Asn Gly Tyr Phe Glu Arg Gly Asn Ile Ile Ile Phe Pro Leu Ala Lys
                245                 250                 255 ttt tct gct gaa aag ata acg cct tct aac tgt act aag tat gga ttt      816
Phe Ser Ala Glu Lys Ile Thr Pro Ser Asn Cys Thr Lys Tyr Gly Phe
            260                 265                 270 gtt gat ata gta gaa tac act aaa ttc atg ttt tta caa ata gct ctt      864
Val Asp Ile Val Glu Tyr Thr Lys Phe Met Phe Leu Gln Ile Ala Leu
        275                 280                 285 ctg tac att aaa ata tat gaa tta ccg tgt aat aat ttt gta cac ttg      912
Leu Tyr Ile Lys Ile Tyr Glu Leu Pro Cys Asn Asn Phe Val His Leu
    290                 295                 300 gat cta aaa ccg gat aac att tta ata ttt gat tct aag gat act att      960
Asp Leu Lys Pro Asp Asn Ile Leu Ile Phe Asp Ser Lys Asp Thr Ile
305                 310                 315                 320 aat ata tat gta gga aat act cat tac gtt ttt aac gag cct ata aga     1008
Asn Ile Tyr Val Gly Asn Thr His Tyr Val Phe Asn Glu Pro Ile Arg
                325                 330                 335 tgc acg ttg aac gat ttt gat ttc tca caa ata tcg gaa ata ctt cct     1056
Cys Thr Leu Asn Asp Phe Asp Phe Ser Gln Ile Ser Glu Ile Leu Pro
            340                 345                 350 aac aga aaa act gtt act gcg ata cat aga gaa caa aac tgg tat tac     1104
Asn Arg Lys Thr Val Thr Ala Ile His Arg Glu Gln Asn Trp Tyr Tyr
        355                 360                 365 gat ttt cat ttt ttt tca cac gta tta ttt aag gta tat cct gag ata     1152
Asp Phe His Phe Phe Ser His Val Leu Phe Lys Val Tyr Pro Glu Ile
370                 375                 380 aac aag gac tca gaa ttt aca tct gtg tta cat gaa ttc ata gtt tgt     1200
```

```
Asn Lys Asp Ser Glu Phe Thr Ser Val Leu His Glu Phe Ile Val Cys
385                 390                 395                 400 aat aaa tcc ata tgt gaa aac ttc aga tta cag gtg aac aga tta ccc    1248
Asn Lys Ser Ile Cys Glu Asn Phe Arg Leu Gln Val Asn Arg Leu Pro
                405                 410                 415 tct ata tct ttt ctt act aac atc gtt tct agg agt att ttt tct aag    1296
Ser Ile Ser Phe Leu Thr Asn Ile Val Ser Arg Ser Ile Phe Ser Lys
                420                 425                 430 tgg ata tct aaa gat gga aaa caa tca agt tct gag taa                1335
Trp Ile Ser Lys Asp Gly Lys Gln Ser Ser Ser Glu
                435                 440

<210> SEQ ID NO 56
<211> LENGTH: 444
<212> TYPE: PRT
<213> ORGANISM: Canarypox virus

<400> SEQUENCE: 56

Met Glu Phe Thr Asp Leu Tyr Tyr Ser Asp Ser Asn Asn Tyr Ala Lys
1               5                   10                  15

Asp Asp Lys Thr Ile Ile Leu Gly Asp Thr Ile Gln Phe Gln Phe Ile
                20                  25                  30

Tyr Glu His Ile Gly Asn Tyr Gln Gln Leu Pro Lys Ile Lys Ile Ser
            35                  40                  45

Lys Tyr Phe Lys Glu Lys Ile Ser Leu Asp Thr Leu Lys Arg Ile Ala
50                  55                  60

Lys Asn Asp Ser Ile Asp Pro Ser Tyr Tyr Gln Leu Lys Asp Lys His
65                  70                  75                  80

Phe Ile Pro Leu Asn Asn Val Phe Tyr His Leu Ser Thr Gly Gly Tyr
                85                  90                  95

Gly Ile Val Phe Lys Ile Gly Lys Tyr Val Val Lys Phe Val Phe Glu
            100                 105                 110

Asp Thr Ser Lys Lys Tyr Asp Pro Met Glu Val Thr Ser Glu Phe Thr
        115                 120                 125

Val Pro Arg Phe Leu Tyr Asn Asn Leu Lys Gly Asp Glu Arg Lys Leu
130                 135                 140

Ile Val Cys Ala Ile Ala Met Gly Leu Asn Phe Lys Ile Asn Phe Leu
145                 150                 155                 160

Arg Thr Ile Tyr Tyr Asn Thr Ile Asn Leu Leu Ser Ala Leu Phe Ser
                165                 170                 175

Ile Leu Glu Arg Glu Pro Ile Lys Glu Lys Tyr Ser His Lys Lys Val
            180                 185                 190

Leu Ser Tyr Phe Ser Lys Tyr Lys Asn Thr Lys Asp Phe Val Lys Ile
        195                 200                 205

Ile Ser Gln Phe Tyr Pro Phe Val Val Ser Asn Asn Ile Asn Ile Ile
210                 215                 220

Asn Asn Phe Asn Tyr Leu Ile Asn Phe Glu Ser Thr Lys Arg Ala
225                 230                 235                 240

Asn Gly Tyr Phe Glu Arg Gly Asn Ile Ile Phe Pro Leu Ala Lys
                245                 250                 255

Phe Ser Ala Glu Lys Ile Thr Pro Ser Asn Cys Thr Lys Tyr Gly Phe
            260                 265                 270

Val Asp Ile Val Glu Tyr Thr Lys Phe Met Phe Leu Gln Ile Ala Leu
        275                 280                 285

Leu Tyr Ile Lys Ile Tyr Glu Leu Pro Cys Asn Asn Val His Leu
    290                 295                 300
```

-continued

| Asp | Leu | Lys | Pro | Asp | Asn | Ile | Leu | Ile | Phe | Asp | Ser | Lys | Asp | Thr | Ile |
| 305 | | | | 310 | | | | | 315 | | | | | 320 | |

| Asn | Ile | Tyr | Val | Gly | Asn | Thr | His | Tyr | Val | Phe | Asn | Glu | Pro | Ile | Arg |
| | | | 325 | | | | | 330 | | | | | 335 | | |

| Cys | Thr | Leu | Asn | Asp | Phe | Asp | Phe | Ser | Gln | Ile | Ser | Glu | Ile | Leu | Pro |
| | | | 340 | | | | | 345 | | | | | 350 | | |

| Asn | Arg | Lys | Thr | Val | Thr | Ala | Ile | His | Arg | Glu | Gln | Asn | Trp | Tyr | Tyr |
| | | 355 | | | | | 360 | | | | | 365 | | | |

| Asp | Phe | His | Phe | Phe | Ser | His | Val | Leu | Phe | Lys | Val | Tyr | Pro | Glu | Ile |
| | 370 | | | | | 375 | | | | | 380 | | | | |

| Asn | Lys | Asp | Ser | Glu | Phe | Thr | Ser | Val | Leu | His | Glu | Phe | Ile | Val | Cys |
| 385 | | | | | 390 | | | | | 395 | | | | | 400 |

| Asn | Lys | Ser | Ile | Cys | Glu | Asn | Phe | Arg | Leu | Gln | Val | Asn | Arg | Leu | Pro |
| | | | | 405 | | | | | 410 | | | | | 415 | |

| Ser | Ile | Ser | Phe | Leu | Thr | Asn | Ile | Val | Ser | Arg | Ser | Ile | Phe | Ser | Lys |
| | | | 420 | | | | | 425 | | | | | 430 | | |

| Trp | Ile | Ser | Lys | Asp | Gly | Lys | Gln | Ser | Ser | Ser | Glu |
| | | 435 | | | | | 440 | | | | |

```
<210> SEQ ID NO 57
<211> LENGTH: 903
<212> TYPE: DNA
<213> ORGANISM: Vaccinia virus (Western Reserve)
<220> FEATURE:
<221> NAME/KEY: CDS
<222> LOCATION: (1)..(903)

<400> SEQUENCE: 57
```

| atg | aac | ttt | caa | gga | ctt | gtg | tta | act | gac | aat | tgc | aaa | aat | caa | tgg | 48 |
| Met | Asn | Phe | Gln | Gly | Leu | Val | Leu | Thr | Asp | Asn | Cys | Lys | Asn | Gln | Trp | |
| 1 | | | | 5 | | | | | 10 | | | | | 15 | | |

| gtc | gtt | gga | cca | tta | ata | gga | aaa | ggt | gga | ttc | ggt | agt | att | tat | act | 96 |
| Val | Val | Gly | Pro | Leu | Ile | Gly | Lys | Gly | Gly | Phe | Gly | Ser | Ile | Tyr | Thr | |
| | | | 20 | | | | | 25 | | | | | 30 | | | |

| act | aat | gac | aat | aat | tat | gta | gta | aaa | ata | gag | ccc | aaa | gct | aac | gga | 144 |
| Thr | Asn | Asp | Asn | Asn | Tyr | Val | Val | Lys | Ile | Glu | Pro | Lys | Ala | Asn | Gly | |
| | | 35 | | | | | 40 | | | | | 45 | | | | |

| tca | tta | ttt | acc | gaa | cag | gca | ttt | tat | act | aga | gta | ctt | aaa | cca | tcc | 192 |
| Ser | Leu | Phe | Thr | Glu | Gln | Ala | Phe | Tyr | Thr | Arg | Val | Leu | Lys | Pro | Ser | |
| | 50 | | | | | 55 | | | | | 60 | | | | | |

| gtt | atc | gaa | gaa | tgg | aaa | aaa | tct | cac | aat | ata | aag | cac | gta | ggt | ctt | 240 |
| Val | Ile | Glu | Glu | Trp | Lys | Lys | Ser | His | Asn | Ile | Lys | His | Val | Gly | Leu | |
| 65 | | | | | 70 | | | | | 75 | | | | | 80 | |

| atc | acg | tgc | aag | gca | ttt | ggt | cta | tac | aaa | tcc | att | aat | gtg | gaa | tat | 288 |
| Ile | Thr | Cys | Lys | Ala | Phe | Gly | Leu | Tyr | Lys | Ser | Ile | Asn | Val | Glu | Tyr | |
| | | | | 85 | | | | | 90 | | | | | 95 | | |

| cga | ttc | ttg | gta | att | aat | aga | tta | ggt | gca | gat | cta | gat | gcg | gtg | atc | 336 |
| Arg | Phe | Leu | Val | Ile | Asn | Arg | Leu | Gly | Ala | Asp | Leu | Asp | Ala | Val | Ile | |
| | | | | 100 | | | | | 105 | | | | | 110 | | |

| aga | gcc | aat | aat | aat | aga | tta | cca | aaa | agg | tcg | gtg | atg | ttg | atc | gga | 384 |
| Arg | Ala | Asn | Asn | Asn | Arg | Leu | Pro | Lys | Arg | Ser | Val | Met | Leu | Ile | Gly | |
| | | | 115 | | | | | 120 | | | | | 125 | | | |

| atc | gaa | atc | tta | aat | acc | ata | caa | ttt | atg | cac | gag | caa | gga | tat | tct | 432 |
| Ile | Glu | Ile | Leu | Asn | Thr | Ile | Gln | Phe | Met | His | Glu | Gln | Gly | Tyr | Ser | |
| | 130 | | | | | 135 | | | | | 140 | | | | | |

| cac | gga | gat | att | aaa | gcg | agt | aat | ata | gtc | ttg | gat | caa | ata | gat | aag | 480 |
| His | Gly | Asp | Ile | Lys | Ala | Ser | Asn | Ile | Val | Leu | Asp | Gln | Ile | Asp | Lys | |
| 145 | | | | | 150 | | | | | 155 | | | | | 160 | |

| aat | aaa | tta | tat | cta | gtg | gat | tac | gga | ttg | gtt | tct | aaa | ttc | atg | tct | 528 |
| Asn | Lys | Leu | Tyr | Leu | Val | Asp | Tyr | Gly | Leu | Val | Ser | Lys | Phe | Met | Ser | |

```
                                   165                 170                 175
aat  gga  gaa  cat  gtt  cca  ttt  ata  aga  aat  cca  aat  aaa  atg  gat  aac       576
Asn  Gly  Glu  His  Val  Pro  Phe  Ile  Arg  Asn  Pro  Asn  Lys  Met  Asp  Asn
               180                      185                      190 ggt  act  cta  gaa  ttt  aca  cct  ata  gat  tcg  cat  aaa  gga  tac  gtt  gta       624
Gly  Thr  Leu  Glu  Phe  Thr  Pro  Ile  Asp  Ser  His  Lys  Gly  Tyr  Val  Val
               195                      200                      205 tct  aga  cgt  gga  gat  cta  gaa  aca  ctt  gga  tat  tgt  atg  att  aga  tgg       672
Ser  Arg  Arg  Gly  Asp  Leu  Glu  Thr  Leu  Gly  Tyr  Cys  Met  Ile  Arg  Trp
               210                      215                      220 ttg  gga  ggt  atc  ttg  cca  tgg  act  aag  ata  tct  gaa  aca  aag  aat  tgt       720
Leu  Gly  Gly  Ile  Leu  Pro  Trp  Thr  Lys  Ile  Ser  Glu  Thr  Lys  Asn  Cys
225                      230                      235                      240 gca  tta  gta  agt  gcc  aca  aaa  cag  aaa  tat  gtt  aac  aat  act  gcg  act       768
Ala  Leu  Val  Ser  Ala  Thr  Lys  Gln  Lys  Tyr  Val  Asn  Asn  Thr  Ala  Thr
               245                      250                      255 ttg  tta  atg  acc  agt  ttg  caa  tat  gca  cct  aga  gaa  ttg  ctg  caa  tat       816
Leu  Leu  Met  Thr  Ser  Leu  Gln  Tyr  Ala  Pro  Arg  Glu  Leu  Leu  Gln  Tyr
               260                      265                      270 att  acc  atg  gta  aac  tct  ttg  aca  tat  ttt  gag  gaa  ccc  aat  tat  gac       864
Ile  Thr  Met  Val  Asn  Ser  Leu  Thr  Tyr  Phe  Glu  Glu  Pro  Asn  Tyr  Asp
               275                      280                      285 gag  ttt  cgg  cac  ata  tta  atg  cag  ggt  gta  tat  tat  taa                      903
Glu  Phe  Arg  His  Ile  Leu  Met  Gln  Gly  Val  Tyr  Tyr
               290                      295                      300

<210> SEQ ID NO 58
<211> LENGTH: 300
<212> TYPE: PRT
<213> ORGANISM: Vaccinia virus (Western Reserve)

<400> SEQUENCE: 58

Met  Asn  Phe  Gln  Gly  Leu  Val  Leu  Thr  Asp  Asn  Cys  Lys  Asn  Gln  Trp
1                  5                      10                      15

Val  Val  Gly  Pro  Leu  Ile  Gly  Lys  Gly  Gly  Phe  Gly  Ser  Ile  Tyr  Thr
               20                      25                      30

Thr  Asn  Asp  Asn  Asn  Tyr  Val  Val  Lys  Ile  Glu  Pro  Lys  Ala  Asn  Gly
               35                      40                      45

Ser  Leu  Phe  Thr  Glu  Gln  Ala  Phe  Tyr  Thr  Arg  Val  Leu  Lys  Pro  Ser
50                      55                      60

Val  Ile  Glu  Glu  Trp  Lys  Lys  Ser  His  Asn  Ile  Lys  His  Val  Gly  Leu
65                      70                      75                      80

Ile  Thr  Cys  Lys  Ala  Phe  Gly  Leu  Tyr  Lys  Ser  Ile  Asn  Val  Glu  Tyr
                    85                      90                      95

Arg  Phe  Leu  Val  Ile  Asn  Arg  Leu  Gly  Ala  Asp  Leu  Asp  Ala  Val  Ile
               100                     105                     110

Arg  Ala  Asn  Asn  Asn  Arg  Leu  Pro  Lys  Arg  Ser  Val  Met  Leu  Ile  Gly
               115                     120                     125

Ile  Glu  Ile  Leu  Asn  Thr  Ile  Gln  Phe  Met  His  Glu  Gln  Gly  Tyr  Ser
               130                     135                     140

His  Gly  Asp  Ile  Lys  Ala  Ser  Asn  Ile  Val  Leu  Asp  Gln  Ile  Asp  Lys
145                     150                     155                     160

Asn  Lys  Leu  Tyr  Leu  Val  Asp  Tyr  Gly  Leu  Val  Ser  Lys  Phe  Met  Ser
                    165                     170                     175

Asn  Gly  Glu  His  Val  Pro  Phe  Ile  Arg  Asn  Pro  Asn  Lys  Met  Asp  Asn
               180                     185                     190

Gly  Thr  Leu  Glu  Phe  Thr  Pro  Ile  Asp  Ser  His  Lys  Gly  Tyr  Val  Val
               195                     200                     205
```

| | | | | | | | | | | | | |
|---|---|---|---|---|---|---|---|---|---|---|---|---|
|Ser|Arg|Arg|Gly|Asp|Leu|Glu|Thr|Leu|Gly|Tyr|Cys|Met|Ile|Arg|Trp|
| |210| | | |215| | | |220| | | | | | |

Leu Gly Gly Ile Leu Pro Trp Thr Lys Ile Ser Glu Thr Lys Asn Cys
225 230 235 240

Ala Leu Val Ser Ala Thr Lys Gln Lys Tyr Val Asn Asn Thr Ala Thr
245 250 255

Leu Leu Met Thr Ser Leu Gln Tyr Ala Pro Arg Glu Leu Leu Gln Tyr
260 265 270

Ile Thr Met Val Asn Ser Leu Thr Tyr Phe Glu Glu Pro Asn Tyr Asp
275 280 285

Glu Phe Arg His Ile Leu Met Gln Gly Val Tyr Tyr
290 295 300

<210> SEQ ID NO 59
<211> LENGTH: 903
<212> TYPE: DNA
<213> ORGANISM: Vaccinia virus (Ankara)
<220> FEATURE:
<221> NAME/KEY: CDS
<222> LOCATION: (1)..(903)

<400> SEQUENCE: 59

```
atg aac ttt caa gga ctt gtg tta act gac aat tgc aaa aat caa tgg       48
Met Asn Phe Gln Gly Leu Val Leu Thr Asp Asn Cys Lys Asn Gln Trp
1               5                   10                  15 gtc gtt gga cca tta ata gga aaa ggt gga ttt ggt agt att tat act       96
Val Val Gly Pro Leu Ile Gly Lys Gly Gly Phe Gly Ser Ile Tyr Thr
                20                  25                  30 act aat gac aat aat tat gta gta aaa ata gag ccc aaa gct aac gga      144
Thr Asn Asp Asn Asn Tyr Val Val Lys Ile Glu Pro Lys Ala Asn Gly
            35                  40                  45 tca tta ttt acc gaa cag gca ttt tat act aga gta ctt aaa cca tcc      192
Ser Leu Phe Thr Glu Gln Ala Phe Tyr Thr Arg Val Leu Lys Pro Ser
        50                  55                  60 gtt atc gaa gaa tgg aaa aaa tct cac aat ata aag cac gta ggt ctt      240
Val Ile Glu Glu Trp Lys Lys Ser His Asn Ile Lys His Val Gly Leu
65                  70                  75                  80 atc acg tgc aag gca ttt ggt cta tac aaa tcc att aat gtg gaa tat      288
Ile Thr Cys Lys Ala Phe Gly Leu Tyr Lys Ser Ile Asn Val Glu Tyr
                85                  90                  95 cga ttc ttg gta att aat aga tta ggt gca gat cta gat gcg gtg atc      336
Arg Phe Leu Val Ile Asn Arg Leu Gly Ala Asp Leu Asp Ala Val Ile
                100                 105                 110 aga gcc aat aat aat aga tta cca aaa agg tcg gtg atg ttg atc gga      384
Arg Ala Asn Asn Asn Arg Leu Pro Lys Arg Ser Val Met Leu Ile Gly
            115                 120                 125 atc gaa atc tta aat acc ata caa ttt atg cac gag caa gga tat tct      432
Ile Glu Ile Leu Asn Thr Ile Gln Phe Met His Glu Gln Gly Tyr Ser
        130                 135                 140 cac gga gat att aaa gcg agt aat ata gtc ttg gat caa ata gat aag      480
His Gly Asp Ile Lys Ala Ser Asn Ile Val Leu Asp Gln Ile Asp Lys
145                 150                 155                 160 aat aaa tta tat cta gtg gat tac gga ttg gtt tct aaa ttc atg tct      528
Asn Lys Leu Tyr Leu Val Asp Tyr Gly Leu Val Ser Lys Phe Met Ser
                165                 170                 175 aat ggc gaa cat gtt cca ttt ata aga aat cca aat aaa atg gat aac      576
Asn Gly Glu His Val Pro Phe Ile Arg Asn Pro Asn Lys Met Asp Asn
                180                 185                 190 ggt act cta gaa ttt aca cct ata gat tcg cat aaa gga tac gtt gta      624
Gly Thr Leu Glu Phe Thr Pro Ile Asp Ser His Lys Gly Tyr Val Val
```

```
                195                 200                 205
tct aga cgt gga gat cta gaa aca ctt gga tat tgt atg att aga tgg    672
Ser Arg Arg Gly Asp Leu Glu Thr Leu Gly Tyr Cys Met Ile Arg Trp
    210                 215                 220 ttg gga ggt atc ttg cca tgg act aag ata tct gaa aca aag aat tgt    720
Leu Gly Gly Ile Leu Pro Trp Thr Lys Ile Ser Glu Thr Lys Asn Cys
225                 230                 235                 240 gca tta gta agt gcc aca aaa cag aaa tat gtt aac aat act gcg act    768
Ala Leu Val Ser Ala Thr Lys Gln Lys Tyr Val Asn Asn Thr Ala Thr
            245                 250                 255 ttg tta atg acc agt ttg caa tat gca cct aga gaa ttg ctg caa tat    816
Leu Leu Met Thr Ser Leu Gln Tyr Ala Pro Arg Glu Leu Leu Gln Tyr
            260                 265                 270 att acc atg gta aac tct ttg aca tat ttt gag gaa ccc aat tac gac    864
Ile Thr Met Val Asn Ser Leu Thr Tyr Phe Glu Glu Pro Asn Tyr Asp
            275                 280                 285 aag ttt cgg cac ata tta atg cag ggt gta tat tat taa                903
Lys Phe Arg His Ile Leu Met Gln Gly Val Tyr Tyr
            290                 295                 300

<210> SEQ ID NO 60
<211> LENGTH: 300
<212> TYPE: PRT
<213> ORGANISM: Vaccinia virus (Ankara)

<400> SEQUENCE: 60

Met Asn Phe Gln Gly Leu Val Leu Thr Asp Asn Cys Lys Asn Gln Trp
1               5                   10                  15

Val Val Gly Pro Leu Ile Gly Lys Gly Gly Phe Gly Ser Ile Tyr Thr
            20                  25                  30

Thr Asn Asp Asn Tyr Val Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His Asn Ile Lys His Val Gly Leu
65                  70                  75                  80

Ile Thr Cys Lys Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Lys Arg Ser Val Met Leu Ile Gly
        115                 120                 125

Ile Glu Ile Leu Asn Thr Ile Gln Phe Met His Glu Gln Gly Tyr Ser
    130                 135                 140

His Gly Asp Ile Lys Ala Ser Asn Ile Val Leu Asp Gln Ile Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
    210                 215                 220

Leu Gly Gly Ile Leu Pro Trp Thr Lys Ile Ser Glu Thr Lys Asn Cys
225                 230                 235                 240

Ala Leu Val Ser Ala Thr Lys Gln Lys Tyr Val Asn Asn Thr Ala Thr
```

```
                         245                 250                 255
Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
        275                 280                 285

Lys Phe Arg His Ile Leu Met Gln Gly Val Tyr Tyr
    290                 295                 300

<210> SEQ ID NO 61
<211> LENGTH: 903
<212> TYPE: DNA
<213> ORGANISM: Vaccinia virus (Acambis 3000 Modified Virus Ankara)
<220> FEATURE:
<221> NAME/KEY: CDS
<222> LOCATION: (1)..(903)

<400> SEQUENCE: 61 atg aac ttt caa gga ctt gtg tta act gac aat tgc aaa aat caa tgg     48
Met Asn Phe Gln Gly Leu Val Leu Thr Asp Asn Cys Lys Asn

```
                  225                 230                 235                 240
gca tta gta agt gcc aca aaa cag aaa tat gtt aac aat act gcg act         768
Ala Leu Val Ser Ala Thr Lys Gln Lys Tyr Val Asn Asn Thr Ala Thr
                          245                 250                 255 ttg tta atg acc agt ttg caa tat gca cct aga gaa ttg ctg caa tat         816
Leu Leu Met Thr Ser Leu Gln Tyr Ala Pro Arg Glu Leu Leu Gln Tyr
                  260                 265                 270 att acc atg gta aac tct ttg aca tat ttt gag gaa ccc aat tac gac         864
Ile Thr Met Val Asn Ser Leu Thr Tyr Phe Glu Glu Pro Asn Tyr Asp
              275                 280                 285 aag ttt cgg cac ata tta atg cag ggt gta tat tat taa                     903
Lys Phe Arg His Ile Leu Met Gln Gly Val Tyr Tyr
      290                 295                 300

<210> SEQ ID NO 62
<211> LENGTH: 300
<212> TYPE: PRT
<213> ORGANISM: Vaccinia virus (Acambis 3000 Modified Virus Ankara)

<400> SEQUENCE: 62

Met Asn Phe Gln Gly Leu Val Leu Thr Asp Asn Cys Lys Asn Gln Trp
1               5                   10                  15

Val Val Gly Pro Leu Ile Gly Lys Gly Gly Phe Gly Ser Ile Tyr Thr
            20                  25                  30

Thr Asn Asp Asn Asn Tyr Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His Asn Ile Lys His Val Gly Leu
65                  70                  75                  80

Ile Thr Cys Lys Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Lys Arg Ser Val Met Leu Ile Gly
        115                 120                 125

Ile Glu Ile Leu Asn Thr Ile Gln Phe Met His Glu Gln Gly Tyr Ser
    130                 135                 140

His Gly Asp Ile Lys Ala Ser Asn Ile Val Leu Asp Gln Ile Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
    210                 215                 220

Leu Gly Gly Ile Leu Pro Trp Thr Lys Ile Ser Glu Thr Lys Asn Cys
225                 230                 235                 240

Ala Leu Val Ser Ala Thr Lys Gln Lys Tyr Val Asn Asn Thr Ala Thr
                245                 250                 255

Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
        275                 280                 285
```

```
            Lys Phe Arg His Ile Leu Met Gln Gly Val Tyr Tyr
                290                 295                 300

<210> SEQ ID NO 63
<211> LENGTH: 903
<212> TYPE: DNA
<213> ORGANISM: Vaccinia virus (Tian Tan)
<220> FEATURE:
<221> NAME/KEY: CDS
<222> LOCATION: (1)..(903)

<400> SEQUENCE: 63 atg aac ttt caa gga ctt gtg tta act gac aat tgc aaa aat caa tgg       48
Met Asn Phe Gln Gly Leu Val Leu Thr Asp Asn Cys Lys Asn Gln Trp
1               5                   10                  15 gtt gtt gga cca tta ata gga aaa ggt gga ttt ggt agt att tat act       96
Val Val Gly Pro Leu Ile Gly Lys Gly Gly Phe Gly Ser Ile Tyr Thr
                20                  25                  30 act aat gac aat aat tat gta gta aaa ata gag ccc aaa gct aac gga      144
Thr Asn Asp Asn Asn Tyr Val Val Lys Ile Glu Pro Lys Ala Asn Gly
            35                  40                  45 tca tta ttt acc gaa cag gca ttt tat act aga gta ctt aaa cca tcc      192
Ser Leu Phe Thr Glu Gln Ala Phe Tyr Thr Arg Val Leu Lys Pro Ser
        50                  55                  60 gtt atc gaa gaa tgg aaa aaa tct cac aat ata aag cac gta ggt ctt      240
Val Ile Glu Glu Trp Lys Lys Ser His Asn Ile Lys His Val Gly Leu
65                  70                  75                  80 atc acg tgc aag gca ttt ggt cta tac aaa tcc att aat gtg gaa tat      288
Ile Thr Cys Lys Ala Phe Gly Leu Tyr Lys Ser Ile Asn Val Glu Tyr
                85                  90                  95 aga ttc ttg gta att aat aga tta ggt gca gat cta gat gcg gtg atc      336
Arg Phe Leu Val Ile Asn Arg Leu Gly Ala Asp Leu Asp Ala Val Ile
                100                 105                 110 aga gcc aat aat aat aga tta cca aaa agg tcg gtg atg ttg atc gga      384
Arg Ala Asn Asn Asn Arg Leu Pro Lys Arg Ser Val Met Leu Ile Gly
            115                 120                 125 atc gaa atc tta aat acc ata caa ttt atg cac gag caa gga tat tct      432
Ile Glu Ile Leu Asn Thr Ile Gln Phe Met His Glu Gln Gly Tyr Ser
        130                 135                 140 cac gga gat att aaa gcg agt aat ata gtc ttg gat caa ata gat aag      480
His Gly Asp Ile Lys Ala Ser Asn Ile Val Leu Asp Gln Ile Asp Lys
145                 150                 155                 160 aat aaa tta tat cta gtg gat tac gga ttg gtt tct aaa ttc atg tct      528
Asn Lys Leu Tyr Leu Val Asp Tyr Gly Leu Val Ser Lys Phe Met Ser
                165                 170                 175 aat ggc gaa cat gtt cca ttt ata aga aat cca aat aaa atg gat aac      576
Asn Gly Glu His Val Pro Phe Ile Arg Asn Pro Asn Lys Met Asp Asn
                180                 185                 190 ggt act cta gaa ttt aca cct ata gat tcg cat aaa gga tac gtt gta      624
Gly Thr Leu Glu Phe Thr Pro Ile Asp Ser His Lys Gly Tyr Val Val
            195                 200                 205 tct aga cgt gga gat cta gaa aca ctt gga tat tgt atg att aga tgg      672
Ser Arg Arg Gly Asp Leu Glu Thr Leu Gly Tyr Cys Met Ile Arg Trp
        210                 215                 220 ttg gga ggt atc ttg cca tgg act aag ata tct gaa aca aag aat tgt      720
Leu Gly Gly Ile Leu Pro Trp Thr Lys Ile Ser Glu Thr Lys Asn Cys
225                 230                 235                 240 gca tta gta agt gcc aca aaa cag aaa tat gtt aac aat act gcg act      768
Ala Leu Val Ser Ala Thr Lys Gln Lys Tyr Val Asn Asn Thr Ala Thr
                245                 250                 255 ttg tta atg acc agt ttg caa tat gca cct aga gaa ttg ctg caa tat      816
Leu Leu Met Thr Ser Leu Gln Tyr Ala Pro Arg Glu Leu Leu Gln Tyr
```

```
                    260                 265                 270
att acc atg gta aac tct ttg aca tat ttt gag gaa ccc aat tac gac    864
Ile Thr Met Val Asn Ser Leu Thr Tyr Phe Glu Glu Pro Asn Tyr Asp
            275                 280                 285 gag ttt cgg cac ata tta atg cag ggt gta tat tat taa                903
Glu Phe Arg His Ile Leu Met Gln Gly Val Tyr Tyr
            290                 295                 300

<210> SEQ ID NO 64
<211> LENGTH: 300
<212> TYPE: PRT
<213> ORGANISM: Vaccinia virus (Tian Tan)

<400> SEQUENCE: 64

Met Asn Phe Gln Gly Leu Val Leu Thr Asp Asn Cys Lys Asn Gln Trp
1               5                   10                  15

Val Val Gly Pro Leu Ile Gly Lys Gly Gly Phe Gly Ser Ile Tyr Thr
            20                  25                  30

Thr Asn Asp Asn Asn Tyr Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His Asn Ile Lys His Val Gly Leu
65                  70                  75                  80

Ile Thr Cys Lys Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Lys Arg Ser Val Met Leu Ile Gly
        115                 120                 125

Ile Glu Ile Leu Asn Thr Ile Gln Phe Met His Glu Gln Gly Tyr Ser
130                 135                 140

His Gly Asp Ile Lys Ala Ser Asn Ile Val Leu Asp Gln Ile Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
    210                 215                 220

Leu Gly Gly Ile Leu Pro Trp Thr Lys Ile Ser Glu Thr Lys Asn Cys
225                 230                 235                 240

Ala Leu Val Ser Ala Thr Lys Gln Lys Tyr Val Asn Asn Thr Ala Thr
                245                 250                 255

Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
        275                 280                 285

Glu Phe Arg His Ile Leu Met Gln Gly Val Tyr Tyr
    290                 295                 300

<210> SEQ ID NO 65
<211> LENGTH: 903
<212> TYPE: DNA
<213> ORGANISM: Vaccinia virus (LC16mO)
```

```
<220> FEATURE:
<221> NAME/KEY: CDS
<222> LOCATION: (1)..(903)

<400> SEQUENCE: 65 atg aac ttt caa gga ctt gtg tta act gac aat tgc aaa aat caa tgg      48
Met Asn Phe Gln Gly Leu Val Leu Thr Asp Asn Cys Lys Asn Gln Trp
1               5                   10                  15 gtc gtt gga cca tta ata gga aaa ggt gga ttc ggt agt att tat act      96
Val Val Gly Pro Leu Ile Gly Lys Gly Gly Phe Gly Ser Ile Tyr Thr
            20                  25                  30 act aat gac aat aat tat gta gta aaa ata gag ccc aaa gct aac gga     144
Thr Asn Asp Asn Asn Tyr Val Val Lys Ile Glu Pro Lys Ala Asn Gly
        35                  40                  45 tca tta ttt acc gaa cag gca ttt tat act aga gta ctt aaa cca tcc     192
Ser Leu Phe Thr Glu Gln Ala Phe Tyr Thr Arg Val Leu Lys Pro Ser
    50                  55                  60 gtt atc gaa gaa tgg aaa aaa tct cac aat ata aag cac gta ggt ctt     240
Val Ile Glu Glu Trp Lys Lys Ser His Asn Ile Lys His Val Gly Leu
65                  70                  75                  80 atc acg tgc aag gca ttt ggt cta tac aaa tcc att aat gtg gaa tat     288
Ile Thr Cys Lys Ala Phe Gly Leu Tyr Lys Ser Ile Asn Val Glu Tyr
                85                  90                  95 cga ttc ttg gta att aat aga tta ggt gca gat cta gat gcg gtg atc     336
Arg Phe Leu Val Ile Asn Arg Leu Gly Ala Asp Leu Asp Ala Val Ile
            100                 105                 110 aga gcc aat aat aat aga tta cca aaa agg tcg gtg atg ttg atc gga     384
Arg Ala Asn Asn Asn Arg Leu Pro Lys Arg Ser Val Met Leu Ile Gly
        115                 120                 125 atc gaa atc tta aat acc ata caa ttt atg cac gag caa gga tat tct     432
Ile Glu Ile Leu Asn Thr Ile Gln Phe Met His Glu Gln Gly Tyr Ser
    130                 135                 140 cac gga gat att aaa gcg agt aat ata gtc ttg gat caa ata gat aag     480
His Gly Asp Ile Lys Ala Ser Asn Ile Val Leu Asp Gln Ile Asp Lys
145                 150                 155                 160 aat aaa tta tat cta gtg gat tac gga ttg gtt tct aaa ttc atg tct     528
Asn Lys Leu Tyr Leu Val Asp Tyr Gly Leu Val Ser Lys Phe Met Ser
                165                 170                 175 aat ggc gaa cat gtt cca ttt ata aga aat cca aat aaa atg gat aac     576
Asn Gly Glu His Val Pro Phe Ile Arg Asn Pro Asn Lys Met Asp Asn
            180                 185                 190 ggt act cta gaa ttt aca cct ata gat tcg cat aaa gga tac gtt gta     624
Gly Thr Leu Glu Phe Thr Pro Ile Asp Ser His Lys Gly Tyr Val Val
        195                 200                 205 tct aga cgt gga gat cta gaa aca ctt gga tat tgt atg att aga tgg     672
Ser Arg Arg Gly Asp Leu Glu Thr Leu Gly Tyr Cys Met Ile Arg Trp
    210                 215                 220 ttg gga ggt atc ttg cca tgg act aag ata tct gaa aca aag aat tgt     720
Leu Gly Gly Ile Leu Pro Trp Thr Lys Ile Ser Glu Thr Lys Asn Cys
225                 230                 235                 240 gca tta gta agt gcc aca aaa cag aaa tat gtt aac aat act gcg act     768
Ala Leu Val Ser Ala Thr Lys Gln Lys Tyr Val Asn Asn Thr Ala Thr
                245                 250                 255 ttg tta atg acc agt ttg caa tat gaa cct aga gaa ttg ctg caa tat     816
Leu Leu Met Thr Ser Leu Gln Tyr Glu Pro Arg Glu Leu Leu Gln Tyr
            260                 265                 270 att acc atg gta aac tct ttg aca tat ttt gag gaa ccc aat tac gac     864
Ile Thr Met Val Asn Ser Leu Thr Tyr Phe Glu Glu Pro Asn Tyr Asp
        275                 280                 285 aag ttt cgg cac ata tta atg cag ggt gta tat tat taa                 903
Lys Phe Arg His Ile Leu Met Gln Gly Val Tyr Tyr
```

<210> SEQ ID NO 66
<211> LENGTH: 300
<212> TYPE: PRT
<213> ORGANISM: Vaccinia virus (LC16mO)

<400> SEQUENCE: 66

Met Asn Phe Gln Gly Leu Val Leu Thr Asp Asn Cys Lys Asn Gln Trp
1               5                   10                  15

Val Val Gly Pro Leu Ile Gly Lys Gly Gly Phe Gly Ser Ile Tyr Thr
            20                  25                  30

Thr Asn Asp Asn Asn Tyr Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His Asn Ile Lys His Val Gly Leu
65                  70                  75                  80

Ile Thr Cys Lys Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Lys Arg Ser Val Met Leu Ile Gly
        115                 120                 125

Ile Glu Ile Leu Asn Thr Ile Gln Phe Met His Glu Gln Gly Tyr Ser
130                 135                 140

His Gly Asp Ile Lys Ala Ser Asn Ile Val Leu Asp Gln Ile Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
    210                 215                 220

Leu Gly Gly Ile Leu Pro Trp Thr Lys Ile Ser Glu Thr Lys Asn Cys
225                 230                 235                 240

Ala Leu Val Ser Ala Thr Lys Gln Lys Tyr Val Asn Asn Thr Ala Thr
                245                 250                 255

Leu Leu Met Thr Ser Leu Gln Tyr Glu Pro Arg Glu Leu Leu Gln Tyr
            260                 265                 270

Ile Thr Met Val Asn Ser Leu Thr Tyr Phe Glu Glu Pro Asn Tyr Asp
        275                 280                 285

Lys Phe Arg His Ile Leu Met Gln Gly Val Tyr Tyr
    290                 295                 300

<210> SEQ ID NO 67
<211> LENGTH: 903
<212> TYPE: DNA
<213> ORGANISM: Vaccinia virus (LC16m8)
<220> FEATURE:
<221> NAME/KEY: CDS
<222> LOCATION: (1)..(903)

<400> SEQUENCE: 67 atg aac ttt caa gga ctt gtg tta act gac aat tgc aaa aat caa tgg    48
Met Asn Phe Gln Gly Leu Val Leu Thr Asp Asn Cys Lys Asn Gln Trp

```
                                                                        1               5               10              15 gtc gtt gga cca tta ata gga aaa ggt gga ttc ggt agt att tat act             96
Val Val Gly Pro Leu Ile Gly Lys Gly Gly Phe Gly Ser Ile Tyr Thr
                20              25              30 act aat gac aat aat tat gta gta aaa ata gag ccc aaa gct aac gga            144
Thr Asn Asp Asn Asn Tyr Val Val Lys Ile Glu Pro Lys Ala Asn Gly
    35              40              45 tca tta ttt acc gaa cag gca ttt tat act aga gta ctt aaa cca tcc            192
Ser Leu Phe Thr Glu Gln Ala Phe Tyr Thr Arg Val Leu Lys Pro Ser
50              55              60 gtt atc gaa gaa tgg aaa aaa tct cac aat ata aag cac gta ggt ctt            240
Val Ile Glu Glu Trp Lys Lys Ser His Asn Ile Lys His Val Gly Leu
65              70              75              80 atc acg tgc aag gca ttt ggt cta tac aaa tcc att aat gtg gaa tat            288
Ile Thr Cys Lys Ala Phe Gly Leu Tyr Lys Ser Ile Asn Val Glu Tyr
                85              90              95 cga ttc ttg gta att aat aga tta ggt gca gat cta gat gcg gtg atc            336
Arg Phe Leu Val Ile Asn Arg Leu Gly Ala Asp Leu Asp Ala Val Ile
            100             105             110 aga gcc aat aat aat aga tta cca aaa agg tcg gtg atg ttg atc gga            384
Arg Ala Asn Asn Asn Arg Leu Pro Lys Arg Ser Val Met Leu Ile Gly
        115             120             125 atc gaa atc tta aat acc ata caa ttt atg cac gag caa gga tat tct            432
Ile Glu Ile Leu Asn Thr Ile Gln Phe Met His Glu Gln Gly Tyr Ser
130             135             140 cac gga gat att aaa gcg agt aat ata gtc ttg gat caa ata gat aag            480
His Gly Asp Ile Lys Ala Ser Asn Ile Val Leu Asp Gln Ile Asp Lys
145             150             155             160 aat aaa tta tat cta gtg gat tac gga ttg gtt tct aaa ttc atg tct            528
Asn Lys Leu Tyr Leu Val Asp Tyr Gly Leu Val Ser Lys Phe Met Ser
                165             170             175 aat ggc gaa cat gtt cca ttt ata aga aat cca aat aaa atg gat aac            576
Asn Gly Glu His Val Pro Phe Ile Arg Asn Pro Asn Lys Met Asp Asn
    180             185             190 ggt act cta gaa ttt aca cct ata gat tcg cat aaa gga tac gtt gta            624
Gly Thr Leu Glu Phe Thr Pro Ile Asp Ser His Lys Gly Tyr Val Val
195             200             205 tct aga cgt gga gat cta gaa aca ctt gga tat tgt atg att aga tgg            672
Ser Arg Arg Gly Asp Leu Glu Thr Leu Gly Tyr Cys Met Ile Arg Trp
210             215             220 ttg gga ggt atc ttg cca tgg act aag ata tct gaa aca aag aat tgt            720
Leu Gly Gly Ile Leu Pro Trp Thr Lys Ile Ser Glu Thr Lys Asn Cys
225             230             235             240 gca tta gta agt gcc aca aaa cag aaa tat gtt aac aat act gcg act            768
Ala Leu Val Ser Ala Thr Lys Gln Lys Tyr Val Asn Asn Thr Ala Thr
                245             250             255 ttg tta atg acc agt ttg caa tat gaa cct aga gaa ttg ctg caa tat            816
Leu Leu Met Thr Ser Leu Gln Tyr Glu Pro Arg Glu Leu Leu Gln Tyr
    260             265             270 att acc atg gta aac tct ttg aca tat ttt gag gaa ccc aat tac gac            864
Ile Thr Met Val Asn Ser Leu Thr Tyr Phe Glu Glu Pro Asn Tyr Asp
275             280             285 aag ttt cgg cac ata tta atg cag ggt gta tat tat taa                        903
Lys Phe Arg His Ile Leu Met Gln Gly Val Tyr Tyr
290             295             300

<210> SEQ ID NO 68
<211> LENGTH: 300
<212> TYPE: PRT
<213> ORGANISM: Vaccinia virus (LC16m8)
```

<400> SEQUENCE: 68

```
Met Asn Phe Gln Gly Leu Val Leu Thr Asp Asn Cys Lys Asn Gln Trp
1               5                   10                  15

Val Val Gly Pro Leu Ile Gly Lys Gly Gly Phe Gly Ser Ile Tyr Thr
            20                  25                  30

Thr Asn Asp Asn Asn Tyr Val Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His Asn Ile Lys His Val Gly Leu
65                  70                  75                  80

Ile Thr Cys Lys Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Lys Arg Ser Val Met Leu Ile Gly
        115                 120                 125

Ile Glu Ile Leu Asn Thr Ile Gln Phe Met His Glu Gln Gly Tyr Ser
130                 135                 140

His Gly Asp Ile Lys Ala Ser Asn Ile Val Leu Asp Gln Ile Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
    210                 215                 220

Leu Gly Gly Ile Leu Pro Trp Thr Lys Ile Ser Glu Thr Lys Asn Cys
225                 230                 235                 240

Ala Leu Val Ser Ala Thr Lys Gln Lys Tyr Val Asn Asn Thr Ala Thr
                245                 250                 255

Leu Leu Met Thr Ser Leu Gln Tyr Glu Pro Arg Glu Leu Leu Gln Tyr
            260                 265                 270

Ile Thr Met Val Asn Ser Leu Thr Tyr Phe Glu Glu Pro Asn Tyr Asp
        275                 280                 285

Lys Phe Arg His Ile Leu Met Gln Gly Val Tyr Tyr
    290                 295                 300
```

<210> SEQ ID NO 69
<211> LENGTH: 903
<212> TYPE: DNA
<213> ORGANISM: Variola major virus (Bangladesh-1975)
<220> FEATURE:
<221> NAME/KEY: CDS
<222> LOCATION: (1)..(903)

<400> SEQUENCE: 69

```
atg aac ttt caa gga ctt gtc tta act gac aat tgc aaa aat caa tgg      48
Met Asn Phe Gln Gly Leu Val Leu Thr Asp Asn Cys Lys Asn Gln Trp
1               5                   10                  15 gtc gtt gga cca tta ata gga aaa ggt gga ttc ggt agt att tat act      96
Val Val Gly Pro Leu Ile Gly Lys Gly Gly Phe Gly Ser Ile Tyr Thr
            20                  25                  30 act aat gac aat aat tat gta gta aaa ata gag ccc aaa gct aac gga     144
Thr Asn Asp Asn Asn Tyr Val Val Lys Ile Glu Pro Lys Ala Asn Gly
```

```
                        35                   40                   45
tca tta ttt act gaa cag gca ttt tat act aga gta ctt aaa cca tcc     192
Ser Leu Phe Thr Glu Gln Ala Phe Tyr Thr Arg Val Leu Lys Pro Ser
 50                   55                   60 gtt atc gaa gaa tgg aaa aaa tct cac cat ata agc cac gta gga gtt     240
Val Ile Glu Glu Trp Lys Lys Ser His His Ile Ser His Val Gly Val
 65                   70                   75                   80 atc aca tgc aag gca ttt ggt cta tac aaa tcc att aat acg gaa tat     288
Ile Thr Cys Lys Ala Phe Gly Leu Tyr Lys Ser Ile Asn Thr Glu Tyr
                  85                   90                   95 aga ttc ttg gta att aat aga ttg ggt gta gat cta gat gcg gtg atc     336
Arg Phe Leu Val Ile Asn Arg Leu Gly Val Asp Leu Asp Ala Val Ile
            100                  105                  110 agg gct aac aat aat aga cta ccg aaa aga tcg gtg atg tta gta gga     384
Arg Ala Asn Asn Asn Arg Leu Pro Lys Arg Ser Val Met Leu Val Gly
        115                  120                  125 ata gaa atc ttg aat acc ata caa ttt atg cac gag caa gga tat tct     432
Ile Glu Ile Leu Asn Thr Ile Gln Phe Met His Glu Gln Gly Tyr Ser
130                  135                  140 cat gga gat att aaa gcg agc aat ata gtt ttg gat caa atg gat aag     480
His Gly Asp Ile Lys Ala Ser Asn Ile Val Leu Asp Gln Met Asp Lys
145                  150                  155                  160 aat aaa tta tat cta gtg gat tac gga ttg gtt tct aaa ttc atg tat     528
Asn Lys Leu Tyr Leu Val Asp Tyr Gly Leu Val Ser Lys Phe Met Tyr
                 165                  170                  175 aac ggc gaa cat gtt cca ttt ata aga aat cca aat aaa atg gat aat     576
Asn Gly Glu His Val Pro Phe Ile Arg Asn Pro Asn Lys Met Asp Asn
            180                  185                  190 ggt act cta gaa ttt aca cct ata gat tca cat aaa gga tac gtt gta     624
Gly Thr Leu Glu Phe Thr Pro Ile Asp Ser His Lys Gly Tyr Val Val
       195                  200                  205 tcg aga cgt gga gat cta gaa aca ctt gga tat tgt atg att aga tgg     672
Ser Arg Arg Gly Asp Leu Glu Thr Leu Gly Tyr Cys Met Ile Arg Trp
210                  215                  220 ttg gga ggt atc ttg cca tgg act aag ata gct gaa aca aag aat tgc     720
Leu Gly Gly Ile Leu Pro Trp Thr Lys Ile Ala Glu Thr Lys Asn Cys
225                  230                  235                  240 gca tta gta agt gct aca aaa cag aaa tat gtg aac aat act acg act     768
Ala Leu Val Ser Ala Thr Lys Gln Lys Tyr Val Asn Asn Thr Thr Thr
                 245                  250                  255 ttg tta atg acc agt ttg caa tat gcg cct aga gaa ttg ctg caa tat     816
Leu Leu Met Thr Ser Leu Gln Tyr Ala Pro Arg Glu Leu Leu Gln Tyr
            260                  265                  270 att acc atg gta aac tct ttg aca tat ttt gag gaa ccc aat tac gat     864
Ile Thr Met Val Asn Ser Leu Thr Tyr Phe Glu Glu Pro Asn Tyr Asp
       275                  280                  285 aag ttt cgg cac ata tta atg cag ggt gca tat tat taa                 903
Lys Phe Arg His Ile Leu Met Gln Gly Ala Tyr Tyr
290                  295                  300

<210> SEQ ID NO 70
<211> LENGTH: 300
<212> TYPE: PRT
<213> ORGANISM: Variola major virus (Bangladesh-1975)

<400> SEQUENCE: 70

Met Asn Phe Gln Gly Leu Val Leu Thr Asp Asn Cys Lys Asn Gln Trp
 1               5                  10                  15

Val Val Gly Pro Leu Ile Gly Lys Gly Gly Phe Gly Ser Ile Tyr Thr
            20                  25                  30
```

```
Thr Asn Asp Asn Asn Tyr Val Val Lys Ile Glu Pro Lys Ala Asn Gly
         35                  40                  45

Ser Leu Phe Thr Glu Gln Ala Phe Tyr Thr Arg Val Leu Lys Pro Ser
     50                  55                  60

Val Ile Glu Glu Trp Lys Lys Ser His His Ile Ser His Val Gly Val
 65                  70                  75                  80

Ile Thr Cys Lys Ala Phe Gly Leu Tyr Lys Ser Ile Asn Thr Glu Tyr
                 85                  90                  95

Arg Phe Leu Val Ile Asn Arg Leu Gly Val Asp Leu Asp Ala Val Ile
                100                 105                 110

Arg Ala Asn Asn Asn Arg Leu Pro Lys Arg Ser Val Met Leu Val Gly
                115                 120                 125

Ile Glu Ile Leu Asn Thr Ile Gln Phe Met His Glu Gln Gly Tyr Ser
130                 135                 140

His Gly Asp Ile Lys Ala Ser Asn Ile Val Leu Asp Gln Met Asp Lys
145                 150                 155                 160

Asn Lys Leu Tyr Leu Val Asp Tyr Gly Leu Val Ser Lys Phe Met Tyr
                165                 170                 175

Asn Gly Glu His Val Pro Phe Ile Arg Asn Pro Asn Lys Met Asp Asn
                180                 185                 190

Gly Thr Leu Glu Phe Thr Pro Ile Asp Ser His Lys Gly Tyr Val Val
                195                 200                 205

Ser Arg Arg Gly Asp Leu Glu Thr Leu Gly Tyr Cys Met Ile Arg Trp
210                 215                 220

Leu Gly Gly Ile Leu Pro Trp Thr Lys Ile Ala Glu Thr Lys Asn Cys
225                 230                 235                 240

Ala Leu Val Ser Ala Thr Lys Gln Lys Tyr Val Asn Asn Thr Thr Thr
                245                 250                 255

Leu Leu Met Thr Ser Leu Gln Tyr Ala Pro Arg Glu Leu Leu Gln Tyr
                260                 265                 270

Ile Thr Met Val Asn Ser Leu Thr Tyr Phe Glu Glu Pro Asn Tyr Asp
                275                 280                 285

Lys Phe Arg His Ile Leu Met Gln Gly Ala Tyr Tyr
290                 295                 300

<210> SEQ ID NO 71
<211> LENGTH: 903
<212> TYPE: DNA
<213> ORGANISM: Variola minor virus (Garcia-1966)
<220> FEATURE:
<221> NAME/KEY: CDS
<222> LOCATION: (1)..(903)

<400> SEQUENCE: 71 atg aac ttt caa gga ctt gtc tta act gac aat tgc aaa aat caa tgg      48
Met Asn Phe Gln Gly Leu Val Leu Thr Asp Asn Cys Lys Asn Gln Trp
1               5                  10                  15 gtc gtt gga cca tta ata gga aaa ggt gga ttc ggt agt att tat act      96
Val Val Gly Pro Leu Ile Gly Lys Gly Gly Phe Gly Ser Ile Tyr Thr
                20                  25                  30 act aat gac aat aat tat gta gta aaa ata gag ccc aaa gct aac gga     144
Thr Asn Asp Asn Asn Tyr Val Val Lys Ile Glu Pro Lys Ala Asn Gly
         35                  40                  45 tca tta ttt act gaa cag gca ttt tat act aga gta ctt aaa cca tcc     192
Ser Leu Phe Thr Glu Gln Ala Phe Tyr Thr Arg Val Leu Lys Pro Ser
     50                  55                  60 gtt atc gaa gaa tgg aaa aaa tct cac cat ata agc cac gta gga gtt     240
Val Ile Glu Glu Trp Lys Lys Ser His His Ile Ser His Val Gly Val
 65                  70                  75                  80
```

```
                 65                  70                  75                  80
atc aca tgc aag gca ttt ggt cta tac aaa tcc att aat acg gaa tat         288
Ile Thr Cys Lys Ala Phe Gly Leu Tyr Lys Ser Ile Asn Thr Glu Tyr
                         85                  90                  95 aga ttc ttg gta att aat aga ttg ggt gca gat cta gat gcg gtg atc         336
Arg Phe Leu Val Ile Asn Arg Leu Gly Ala Asp Leu Asp Ala Val Ile
                    100                 105                 110 agg gct aac aat aat aga cta ccg aaa aga tcg gtg atg tta gta gga         384
Arg Ala Asn Asn Asn Arg Leu Pro Lys Arg Ser Val Met Leu Val Gly
                115                 120                 125 ata gaa att ttg aat acc ata caa ttt atg cac gag caa gga tat tct         432
Ile Glu Ile Leu Asn Thr Ile Gln Phe Met His Glu Gln Gly Tyr Ser
            130                 135                 140 cat gga gat att aaa gcg agc aat ata gtt ttg gat caa atg gat aag         480
His Gly Asp Ile Lys Ala Ser Asn Ile Val Leu Asp Gln Met Asp Lys
145                 150                 155                 160 aat aaa tta tat cta gtg gat tac gga ttg gtt tct aaa ttc atg tca         528
Asn Lys Leu Tyr Leu Val Asp Tyr Gly Leu Val Ser Lys Phe Met Ser
                    165                 170                 175 aac ggc gaa cat gtt cca ttt ata aga aat cca aat aaa atg gat aat         576
Asn Gly Glu His Val Pro Phe Ile Arg Asn Pro Asn Lys Met Asp Asn
                180                 185                 190 ggt act cta gaa ttt aca cct ata gat tca cat aaa gga tac gtt gta         624
Gly Thr Leu Glu Phe Thr Pro Ile Asp Ser His Lys Gly Tyr Val Val
            195                 200                 205 tcg aga cgt gga gat cta gaa aca ctt gga tat tgt atg att aga tgg         672
Ser Arg Arg Gly Asp Leu Glu Thr Leu Gly Tyr Cys Met Ile Arg Trp
        210                 215                 220 ttg gga ggt atc ttg cca tgg act aag ata gct gaa aca aag aat tgc         720
Leu Gly Gly Ile Leu Pro Trp Thr Lys Ile Ala Glu Thr Lys Asn Cys
225                 230                 235                 240 gca tta gta agt gct aca aaa cag aaa tat gtg aac aat act gcg act         768
Ala Leu Val Ser Ala Thr Lys Gln Lys Tyr Val Asn Asn Thr Ala Thr
                    245                 250                 255 ttg tta atg acc agt ttg caa tat gcg cct aga gaa ttg ctg caa tat         816
Leu Leu Met Thr Ser Leu Gln Tyr Ala Pro Arg Glu Leu Leu Gln Tyr
                260                 265                 270 att acc atg gta aac tct ttg aca tat ttt gag gaa ccc aat tac gat         864
Ile Thr Met Val Asn Ser Leu Thr Tyr Phe Glu Glu Pro Asn Tyr Asp
            275                 280                 285 aag ttt cgg cac ata tta atg cag ggt gca tat tat taa                     903
Lys Phe Arg His Ile Leu Met Gln Gly Ala Tyr Tyr
        290                 295                 300

<210> SEQ ID NO 72
<211> LENGTH: 300
<212> TYPE: PRT
<213> ORGANISM: Variola minor virus (Garcia-1966)

<400> SEQUENCE: 72

Met Asn Phe Gln Gly Leu Val Leu Thr Asp Asn Cys Lys Asn Gln Trp
1               5                   10                  15

Val Val Gly Pro Leu Ile Gly Lys Gly Phe Gly Ser Ile Tyr Thr
            20                  25                  30

Thr Asn Asp Asn Asn Tyr Val Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His His Ile Ser His Val Gly Val
65                  70                  75                  80
```

```
Ile Thr Cys Lys Ala Phe Gly Leu Tyr Lys Ser Ile Asn Thr Glu Tyr
             85                  90                  95

Arg Phe Leu Val Ile Asn Arg Leu Gly Ala Asp Leu Asp Ala Val Ile
            100                 105                 110

Arg Ala Asn Asn Asn Arg Leu Pro Lys Arg Ser Val Met Leu Val Gly
            115                 120                 125

Ile Glu Ile Leu Asn Thr Ile Gln Phe Met His Glu Gln Gly Tyr Ser
            130                 135                 140

His Gly Asp Ile Lys Ala Ser Asn Ile Val Leu Asp Gln Met Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
            195                 200                 205

Ser Arg Arg Gly Asp Leu Glu Thr Leu Gly Tyr Cys Met Ile Arg Trp
            210                 215                 220

Leu Gly Gly Ile Leu Pro Trp Thr Lys Ile Ala Glu Thr Lys Asn Cys
225                 230                 235                 240

Ala Leu Val Ser Ala Thr Lys Gln Lys Tyr Val Asn Asn Thr Ala Thr
                245                 250                 255

Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
            275                 280                 285

Lys Phe Arg His Ile Leu Met Gln Gly Ala Tyr Tyr
            290                 295                 300

<210> SEQ ID NO 73
<211> LENGTH: 903
<212> TYPE: DNA
<213> ORGANISM: Cowpox virus (GRI-90)
<220> FEATURE:
<221> NAME/KEY: CDS
<222> LOCATION: (1)..(903)

<400> SEQUENCE: 73 atg aac ttt caa gga ctt gtg tta act gac aat tgc aaa aat caa tgg      48
Met Asn Phe Gln Gly Leu Val Leu Thr Asp Asn Cys Lys Asn Gln Trp
1               5                   10                  15 gtc gtt gga cca tta ata gga aaa ggt gga ttc ggt agt att tat act      96
Val Val Gly Pro Leu Ile Gly Lys Gly Gly Phe Gly Ser Ile Tyr Thr
            20                  25                  30 act aat gac aat aat tat gta gta aaa ata gag ccc aaa gct aac gga     144
Thr Asn Asp Asn Asn Tyr Val Val Lys Ile Glu Pro Lys Ala Asn Gly
        35                  40                  45 tca tta ttt acc gaa cag gca ttt tat act aga gta ctt aaa cca tcc     192
Ser Leu Phe Thr Glu Gln Ala Phe Tyr Thr Arg Val Leu Lys Pro Ser
    50                  55                  60 gtt atc gaa gaa tgg aaa aaa tct cac aat ata aag cac gta ggt ctt     240
Val Ile Glu Glu Trp Lys Lys Ser His Asn Ile Lys His Val Gly Leu
65                  70                  75                  80 atc acg tgc aag gca ttt ggt cta tac aaa tcc att aat gtg gaa tat     288
Ile Thr Cys Lys Ala Phe Gly Leu Tyr Lys Ser Ile Asn Val Glu Tyr
                85                  90                  95 cga ttc ttg gta att aat aga tta ggt gca gat cta gat gcg gtg atc     336
Arg Phe Leu Val Ile Asn Arg Leu Gly Ala Asp Leu Asp Ala Val Ile
            100                 105                 110
```

```
aga gcc aat aat aat aga cta cca aaa agg tcg gtg atg ttg atc gga      384
Arg Ala Asn Asn Asn Arg Leu Pro Lys Arg Ser Val Met Leu Ile Gly
        115                 120                 125 atc gaa atc tta aat acc ata caa ttt atg cac gag caa gga tat tct      432
Ile Glu Ile Leu Asn Thr Ile Gln Phe Met His Glu Gln Gly Tyr Ser
130                 135                 140 cac gga gat att aaa gcg agt aat ata gtc ttg gat caa ata gat aag      480
His Gly Asp Ile Lys Ala Ser Asn Ile Val Leu Asp Gln Ile Asp Lys
145                 150                 155                 160 aat aaa tta tat cta gtg gat tac gga ttg gtt tct aaa ttc atg tct      528
Asn Lys Leu Tyr Leu Val Asp Tyr Gly Leu Val Ser Lys Phe Met Ser
                165                 170                 175 aac ggc gaa cat gtt cca ttt ata aga aat cca aat aaa atg gat aac      576
Asn Gly Glu His Val Pro Phe Ile Arg Asn Pro Asn Lys Met Asp Asn
            180                 185                 190 ggt act cta gaa ttt aca cct ata gat tcg cat aaa gga tac gtt gta      624
Gly Thr Leu Glu Phe Thr Pro Ile Asp Ser His Lys Gly Tyr Val Val
        195                 200                 205 tct aga cgt gga gat cta gaa aca ctt gga tat tgt atg att aga tgg      672
Ser Arg Arg Gly Asp Leu Glu Thr Leu Gly Tyr Cys Met Ile Arg Trp
210                 215                 220 ttg gga ggt atc ttg cca tgg act aag ata tct gaa aca aag aat tgt      720
Leu Gly Gly Ile Leu Pro Trp Thr Lys Ile Ser Glu Thr Lys Asn Cys
225                 230                 235                 240 gca tta gta agt gcc aca aaa cag aaa tat gtt aac aat act gcg act      768
Ala Leu Val Ser Ala Thr Lys Gln Lys Tyr Val Asn Asn Thr Ala Thr
                245                 250                 255 ttg tta atg acc agt ctg caa tat gca cct aga gaa ttg ctg caa tat      816
Leu Leu Met Thr Ser Leu Gln Tyr Ala Pro Arg Glu Leu Leu Gln Tyr
            260                 265                 270 att acc atg gta aac tct ttg aca tat ttt gag gaa ccc aat tac gac      864
Ile Thr Met Val Asn Ser Leu Thr Tyr Phe Glu Glu Pro Asn Tyr Asp
        275                 280                 285 gag ttt cgg cac ata tta atg cag ggt gta tat tag                      903
Glu Phe Arg His Ile Leu Met Gln Gly Val Tyr Tyr
290                 295                 300

<210> SEQ ID NO 74
<211> LENGTH: 300
<212> TYPE: PRT
<213> ORGANISM: Cowpox virus (GRI-90)

<400> SEQUENCE: 74

Met Asn Phe Gln Gly Leu Val Leu Thr Asp Asn Cys Lys Asn Gln Trp
1               5                   10                  15

Val Val Gly Pro Leu Ile Gly Lys Gly Phe Gly Ser Ile Tyr Thr
            20                  25                  30

Thr Asn Asp Asn Asn Tyr Val Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His Asn Ile Lys His Val Gly Leu
65                  70                  75                  80

Ile Thr Cys Lys Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Lys Arg Ser Val Met Leu Ile Gly
```

```
                    115                 120                 125
Ile Glu Ile Leu Asn Thr Ile Gln Phe Met His Glu Gln Gly Tyr Ser
        130                 135                 140

His Gly Asp Ile Lys Ala Ser Asn Ile Val Leu Asp Gln Ile Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
    210                 215                 220

Leu Gly Gly Ile Leu Pro Trp Thr Lys Ile Ser Glu Thr Lys Asn Cys
225                 230                 235                 240

Ala Leu Val Ser Ala Thr Lys Gln Lys Tyr Val Asn Asn Thr Ala Thr
                245                 250                 255

Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
        275                 280                 285

Glu Phe Arg His Ile Leu Met Gln Gly Val Tyr Tyr
    290                 295                 300

<210> SEQ ID NO 75
<211> LENGTH: 900
<212> TYPE: DNA
<213> ORGANISM: Cowpox virus (Brighton Red)
<220> FEATURE

```
                130                 135                 140
cac gga gac att aaa gcg agc aat ata gtc ttg gat caa atg gat aag        480
His Gly Asp Ile Lys Ala Ser Asn Ile Val Leu Asp Gln Met Asp Lys
145                 150                 155                 160 aat aaa tta tat cta gtg gat tac gga ttg gtt tct aaa ttc atg tct        528
Asn Lys Leu Tyr Leu Val Asp Tyr Gly Leu Val Ser Lys Phe Met Ser
                165                 170                 175 aac ggc gaa cat gtt cca ttt ata aga aat cca aat aga atg gat aac        576
Asn Gly Glu His Val Pro Phe Ile Arg Asn Pro Asn Arg Met Asp Asn
            180                 185                 190 ggt act cta gaa ttt aca cct ata gat tcg cat aaa gga tac gtt gta        624
Gly Thr Leu Glu Phe Thr Pro Ile Asp Ser His Lys Gly Tyr Val Val
        195                 200                 205 tcg aga cgt gga gat cta gaa aca ctt gga tat tgt atg att aga tgg        672
Ser Arg Arg Gly Asp Leu Glu Thr Leu Gly Tyr Cys Met Ile Arg Trp
    210                 215                 220 ttg gga ggt atc ttg cca tgg act aag ata tct gaa aca aag aat tgt        720
Leu Gly Gly Ile Leu Pro Trp Thr Lys Ile Ser Glu Thr Lys Asn Cys
225                 230                 235                 240 gca ttg gta agt gcc aca aaa cag aaa tat gtg aac aat act gcg act        768
Ala Leu Val Ser Ala Thr Lys Gln Lys Tyr Val Asn Asn Thr Ala Thr
                245                 250                 255 ttg tta atg acc agt ttg caa tat gca cct aga gaa ttg ctg caa tat        816
Leu Leu Met Thr Ser Leu Gln Tyr Ala Pro Arg Glu Leu Leu Gln Tyr
            260                 265                 270 att acc atg gta aac tct ttg aca tat ttt gag gaa ccc aat tac gac        864
Ile Thr Met Val Asn Ser Leu Thr Tyr Phe Glu Glu Pro Asn Tyr Asp
        275                 280                 285 gag ttt cgg cgc gta tta atg aat gga gtt atg taa                        900
Glu Phe Arg Arg Val Leu Met Asn Gly Val Met
    290                 295

<210> SEQ ID NO 76
<211> LENGTH: 299
<212> TYPE: PRT
<213> ORGANISM: Cowpox virus (Brighton Red)

<400> SEQUENCE: 76

Met Asn Phe Gln Gly Leu Val Leu Thr Asp Asn Cys Lys Asn Gln Trp
1               5                   10                  15

Val Val Gly Pro Leu Ile Gly Lys Gly Phe Gly Ser Ile Tyr Thr
            20                  25                  30

Thr Asn Asp Asn Asn Tyr Val Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Thr Arg His Ile Lys His Val Gly Val
65                  70                  75                  80

Ile Thr Cys Lys Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Lys Arg Ser Val Met Leu Val Gly
        115                 120                 125

Ile Glu Ile Leu Asn Thr Ile Gln Phe Met His Glu Gln Gly Tyr Ser
    130                 135                 140

His Gly Asp Ile Lys Ala Ser Asn Ile Val Leu Asp Gln Met Asp Lys
145                 150                 155                 160
```

```
Asn Lys Leu Tyr Leu Val Asp Tyr Gly Leu Val Ser Lys Phe Met Ser
            165                 170                 175

Asn Gly Glu His Val Pro Phe Ile Arg Asn Pro Asn Arg Met Asp Asn
            180                 185                 190

Gly Thr Leu Glu Phe Thr Pro Ile Asp Ser His Lys Gly Tyr Val Val
            195                 200                 205

Ser Arg Arg Gly Asp Leu Glu Thr Leu Gly Tyr Cys Met Ile Arg Trp
        210                 215                 220

Leu Gly Gly Ile Leu Pro Trp Thr Lys Ile Ser Glu Thr Lys Asn Cys
225                 230                 235                 240

Ala Leu Val Ser Ala Thr Lys Gln Lys Tyr Val Asn Asn Thr Ala Thr
                245                 250                 255

Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
            275                 280                 285

Glu Phe Arg Arg Val Leu Met Asn Gly Val Met
        290                 295

<210> SEQ ID NO 77
<211> LENGTH: 903
<212> TYPE: DNA
<213> ORGANISM: Rabbitpox virus
<220> FEATURE:
<221> NAME/KEY: CDS
<222> LOCATION: (1)..(903)

<400> SEQUENCE: 77 atg aac ttt caa gga ctt gtg tta act gac aat tgc aaa aat caa tgg      48
Met Asn Phe Gln Gly Leu Val Leu Thr Asp Asn Cys Lys Asn Gln Trp
1               5                   10                  15 gtc gtt gga cca tta ata gga aaa ggt gga ttc ggt agt att tat act      96
Val Val Gly Pro Leu Ile Gly Lys Gly Gly Phe Gly Ser Ile Tyr Thr
            20                  25                  30 act aat gac aat aat tat gta gta aaa ata gag ccc aaa gct aac gga     144
Thr Asn Asp Asn Asn Tyr Val Val Lys Ile Glu Pro Lys Ala Asn Gly
        35                  40                  45 tca tta ttt acc gaa cag gca ttt tat act aga gta ctt aaa cca tcc     192
Ser Leu Phe Thr Glu Gln Ala Phe Tyr Thr Arg Val Leu Lys Pro Ser
    50                  55                  60 gtt atc gaa gaa tgg aaa aaa tct cac aat ata aag cac gta ggt ctt     240
Val Ile Glu Glu Trp Lys Lys Ser His Asn Ile Lys His Val Gly Leu
65                  70                  75                  80 atc acg tgc aag gca ttt ggt cta tac aaa tcc att aat gtg gaa tat     288
Ile Thr Cys Lys Ala Phe Gly Leu Tyr Lys Ser Ile Asn Val Glu Tyr
                85                  90                  95 aga ttc ttg gta att aat aga tta ggt gca gat cta gat gcg gtg atc     336
Arg Phe Leu Val Ile Asn Arg Leu Gly Ala Asp Leu Asp Ala Val Ile
            100                 105                 110 aga gcc aat aat aat aga tta cca aaa agg tcg gtg atg ttg atc gga     384
Arg Ala Asn Asn Asn Arg Leu Pro Lys Arg Ser Val Met Leu Ile Gly
        115                 120                 125 atc gaa atc tta aat acc ata caa ttt atg cac gag caa gga tat tct     432
Ile Glu Ile Leu Asn Thr Ile Gln Phe Met His Glu Gln Gly Tyr Ser
    130                 135                 140 cac gga gat att aaa gcg agt aat ata gtc ttg gat caa ata gat aag     480
His Gly Asp Ile Lys Ala Ser Asn Ile Val Leu Asp Gln Ile Asp Lys
145                 150                 155                 160 aat aaa tta tat cta gtg gat tac gga ttg gtt tct aaa ttc atg tct     528
Asn Lys Leu Tyr Leu Val Asp Tyr Gly Leu Val Ser Lys Phe Met Ser
```

```
                165                 170                 175
aat ggc gaa cat gtt cca ttt ata aga aat cca aat aaa atg gat aac      576
Asn Gly Glu His Val Pro Phe Ile Arg Asn Pro Asn Lys Met Asp Asn
            180                 185                 190 ggt act cta gaa ttt aca cct ata gat tcg cat aaa gga tac gtt gta      624
Gly Thr Leu Glu Phe Thr Pro Ile Asp Ser His Lys Gly Tyr Val Val
        195                 200                 205 tct aga cgt gga gat cta gaa aca ctt gga tat tgt atg att aga tgg      672
Ser Arg Arg Gly Asp Leu Glu Thr Leu Gly Tyr Cys Met Ile Arg Trp
    210                 215                 220 ttg gga ggt atc ttg cca tgg act aag ata tct gaa aca aag aat tgt      720
Leu Gly Gly Ile Leu Pro Trp Thr Lys Ile Ser Glu Thr Lys Asn Cys
225                 230                 235                 240 gca tta gta agt gcc aca aaa cag aaa tat gtt aac aat act gcg act      768
Ala Leu Val Ser Ala Thr Lys Gln Lys Tyr Val Asn Asn Thr Ala Thr
                245                 250                 255 ttg tta atg acc agt ttg caa tat gca cct aga gaa ttg ctg caa tat      816
Leu Leu Met Thr Ser Leu Gln Tyr Ala Pro Arg Glu Leu Leu Gln Tyr
            260                 265                 270 att acc atg gta aac tct ttg aca tat ttt gag gaa ccc aat tac gac      864
Ile Thr Met Val Asn Ser Leu Thr Tyr Phe Glu Glu Pro Asn Tyr Asp
        275                 280                 285 gag ttt cgg cac ata tta atg cag ggt gta tat tat taa                  903
Glu Phe Arg His Ile Leu Met Gln Gly Val Tyr Tyr
    290                 295                 300

<210> SEQ ID NO 78
<211> LENGTH: 300
<212> TYPE: PRT
<213> ORGANISM: Rabbitpox virus

<400> SEQUENCE: 78

Met Asn Phe Gln Gly Leu Val Leu Thr Asp Asn Cys Lys Asn Gln Trp
1               5                   10                  15

Val Val Gly Pro Leu Ile Gly Lys Gly Gly Phe Gly Ser Ile Tyr Thr
            20                  25                  30

Thr Asn Asp Asn Tyr Val Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His Asn Ile Lys His Val Gly Leu
65                  70                  75                  80

Ile Thr Cys Lys Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Lys Arg Ser Val Met Leu Ile Gly
        115                 120                 125

Ile Glu Ile Leu Asn Thr Ile Gln Phe Met His Glu Gln Gly Tyr Ser
    130                 135                 140

His Gly Asp Ile Lys Ala Ser Asn Ile Val Leu Asp Gln Ile Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205
```

-continued

```
Ser Arg Arg Gly Asp Leu Glu Thr Leu Gly Tyr Cys Met Ile Arg Trp
    210                 215                 220
Leu Gly Gly Ile Leu Pro Trp Thr Lys Ile Ser Glu Thr Lys Asn Cys
225                 230                 235                 240
Ala Leu Val Ser Ala Thr Lys Gln Lys Tyr Val Asn Asn Thr Ala Thr
            245                 250                 255
Leu Leu Met Thr Ser Leu Gln Tyr Ala Pro Arg Glu Leu Leu Gln Tyr
                260                 265                 270
Ile Thr Met Val Asn Ser Leu Thr Tyr Phe Glu Glu Pro Asn Tyr Asp
            275                 280                 285
Glu Phe Arg His Ile Leu Met Gln Gly Val Tyr Tyr
    290                 295                 300

<210> SEQ ID NO 79
<211> LENGTH: 903
<212> TYPE: DNA
<213> ORGANISM: Camelpox virus (M-96)
<220> FEATURE:
<221> NAME/KEY: CDS
<222> LOCATION: (1)..(903)

<400> SEQUENCE: 79
```

| | | | | | | | | | | | | | | | | |
|---|---|---|---|---|---|---|---|---|---|---|---|---|---|---|---|---|
| atg | aac | ttt | caa | gga | ctt | gtc | tta | act | gac | aat | tgc | aaa | aat | caa | tgg | 48 |
| Met | Asn | Phe | Gln | Gly | Leu | Val | Leu | Thr | Asp | Asn | Cys | Lys | Asn | Gln | Trp | |
| 1 | | | | 5 | | | | | 10 | | | | | 15 | | |
| gtc | gtt | gga | cca | tta | ata | gga | aaa | ggt | gga | ttc | ggt | agt | att | tat | act | 96 |
| Val | Val | Gly | Pro | Leu | Ile | Gly | Lys | Gly | Gly | Phe | Gly | Ser | Ile | Tyr | Thr | |
| | | | 20 | | | | | 25 | | | | | 30 | | | |
| act | aat | gac | aat | aat | tat | gta | gta | aaa | ata | gag | ccc | aaa | gct | aac | gga | 144 |
| Thr | Asn | Asp | Asn | Asn | Tyr | Val | Val | Lys | Ile | Glu | Pro | Lys | Ala | Asn | Gly | |
| | 35 | | | | | 40 | | | | | 45 | | | | | |
| tca | tta | ttt | act | gaa | cag | gca | ttt | tat | act | aga | gta | ctt | aaa | cca | tcc | 192 |
| Ser | Leu | Phe | Thr | Glu | Gln | Ala | Phe | Tyr | Thr | Arg | Val | Leu | Lys | Pro | Ser | |
| 50 | | | | | 55 | | | | | 60 | | | | | | |
| gtt | atc | gaa | gaa | tgg | aaa | aaa | tat | cac | cat | ata | agc | cac | gta | gga | gtt | 240 |
| Val | Ile | Glu | Glu | Trp | Lys | Lys | Tyr | His | His | Ile | Ser | His | Val | Gly | Val | |
| 65 | | | | | 70 | | | | | 75 | | | | | 80 | |
| atc | aca | tgc | aag | gca | ttt | ggt | cta | tac | aaa | tcc | att | aat | gct | gaa | tat | 288 |
| Ile | Thr | Cys | Lys | Ala | Phe | Gly | Leu | Tyr | Lys | Ser | Ile | Asn | Ala | Glu | Tyr | |
| | | | | 85 | | | | | 90 | | | | | 95 | | |
| aga | ttc | ttg | gta | att | aat | aga | ttg | ggt | gta | gat | cta | gat | gcg | gtg | atc | 336 |
| Arg | Phe | Leu | Val | Ile | Asn | Arg | Leu | Gly | Val | Asp | Leu | Asp | Ala | Val | Ile | |
| | | | | 100 | | | | | 105 | | | | | 110 | | |
| agg | gct | aac | aat | aat | aga | cta | ccg | aaa | aga | tcg | gtg | atg | tta | gta | gga | 384 |
| Arg | Ala | Asn | Asn | Asn | Arg | Leu | Pro | Lys | Arg | Ser | Val | Met | Leu | Val | Gly | |
| | | | 115 | | | | | 120 | | | | | 125 | | | |
| ata | gaa | atc | ttg | aat | acc | ata | caa | ttt | atg | cac | gag | caa | gga | tat | tct | 432 |
| Ile | Glu | Ile | Leu | Asn | Thr | Ile | Gln | Phe | Met | His | Glu | Gln | Gly | Tyr | Ser | |
| | 130 | | | | | 135 | | | | | 140 | | | | | |
| cac | gga | gat | att | aaa | gcg | agc | aat | ata | gtt | ttg | gat | caa | atg | gat | aag | 480 |
| His | Gly | Asp | Ile | Lys | Ala | Ser | Asn | Ile | Val | Leu | Asp | Gln | Met | Asp | Lys | |
| 145 | | | | | 150 | | | | | 155 | | | | | 160 | |
| aat | aaa | tta | tat | cta | gtg | gat | tac | gga | ttg | gtt | tct | aaa | ttc | atg | tct | 528 |
| Asn | Lys | Leu | Tyr | Leu | Val | Asp | Tyr | Gly | Leu | Val | Ser | Lys | Phe | Met | Ser | |
| | | | | 165 | | | | | 170 | | | | | 175 | | |
| aac | ggc | gaa | cat | gtt | cca | ttt | ata | aga | aat | cca | aat | aaa | atg | gat | aat | 576 |
| Asn | Gly | Glu | His | Val | Pro | Phe | Ile | Arg | Asn | Pro | Asn | Lys | Met | Asp | Asn | |
| | | | | 180 | | | | | 185 | | | | | 190 | | |
| ggt | act | cta | gaa | ttt | aca | cct | ata | gat | tcg | cat | aaa | gga | tac | gtt | gta | 624 |
| Gly | Thr | Leu | Glu | Phe | Thr | Pro | Ile | Asp | Ser | His | Lys | Gly | Tyr | Val | Val | |

```
            195                 200                 205
tcg aga cgt gga gat cta gaa aca ctt gga tat tgt atg att aga tgg      672
Ser Arg Arg Gly Asp Leu Glu Thr Leu Gly Tyr Cys Met Ile Arg Trp
    210                 215                 220 ttg gga ggt atc ttg cca tgg act aag ata gct gaa aca aag aat tgc      720
Leu Gly Gly Ile Leu Pro Trp Thr Lys Ile Ala Glu Thr Lys Asn Cys
225                 230                 235                 240 gca tta gta agt gct aca aaa cag aaa tat gtg aac aat act gcg act      768
Ala Leu Val Ser Ala Thr Lys Gln Lys Tyr Val Asn Asn Thr Ala Thr
                245                 250                 255 ttg tta atg acc agt ttg caa tat gcg cct aga gaa ttg ctg caa tat      816
Leu Leu Met Thr Ser Leu Gln Tyr Ala Pro Arg Glu Leu Leu Gln Tyr
            260                 265                 270 att acc atg gta aac tct ttg aca tat ttt gag gaa ccc aat tac gat      864
Ile Thr Met Val Asn Ser Leu Thr Tyr Phe Glu Glu Pro Asn Tyr Asp
        275                 280                 285 gag ttt cgg cgc ata tta atg cag ggt gta tat tat taa                  903
Glu Phe Arg Arg Ile Leu Met Gln Gly Val Tyr Tyr
    290                 295                 300

<210> SEQ ID NO 80
<211> LENGTH: 300
<212> TYPE: PRT
<213> ORGANISM: Camelpox virus (M-96)

<400> SEQUENCE: 80

Met Asn Phe Gln Gly Leu Val Leu Thr Asp Asn Cys Lys Asn Gln Trp
1               5                   10                  15

Val Val Gly Pro Leu Ile Gly Lys Gly Gly Phe Gly Ser Ile Tyr Thr
            20                  25                  30

Thr Asn Asp Asn Asn Tyr Val Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Tyr His His Ile Ser His Val Gly Val
65                  70                  75                  80

Ile Thr Cys Lys Ala Phe Gly Leu Tyr Lys Ser Ile Asn Ala Glu Tyr
                85                  90                  95

Arg Phe Leu Val Ile Asn Arg Leu Gly Val Asp Leu Asp Ala Val Ile
            100                 105                 110

Arg Ala Asn Asn Asn Arg Leu Pro Lys Arg Ser Val Met Leu Val Gly
        115                 120                 125

Ile Glu Ile Leu Asn Thr Ile Gln Phe Met His Glu Gln Gly Tyr Ser
    130                 135                 140

His Gly Asp Ile Lys Ala Ser Asn Ile Val Leu Asp Gln Met Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
    210                 215                 220

Leu Gly Gly Ile Leu Pro Trp Thr Lys Ile Ala Glu Thr Lys Asn Cys
225                 230                 235                 240

Ala Leu Val Ser Ala Thr Lys Gln Lys Tyr Val Asn Asn Thr Ala Thr
```

Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
        275                 280                 285

Glu Phe Arg Arg Ile Leu Met Gln Gly Val Tyr Tyr
290                 295                 300

<210> SEQ ID NO 81
<211> LENGTH: 903
<212> TYPE: DNA
<213> ORGANISM: Camelpox virus (CMS)
<220> FEATURE:
<221> NAME/KEY: CDS
<222> LOCATION: (1)..(903)

<400> SEQUENCE: 81

| atg aac ttt caa gga ctt gtc tta act gac aat tgc aaa aat caa tgg | 48 |
|---|---|
| Met Asn Phe Gln Gly Leu Val Leu Thr Asp Asn Cys Lys Asn Gln Trp | |
| 1               5                   10                  15 | |
| gtc gtt gga cca tta ata gga aaa ggt gga ttc ggt agt att tat act | 96 |
| Val Val Gly Pro Leu Ile Gly Lys Gly Gly Phe Gly Ser Ile Tyr Thr | |
|              20                  25                  30 | |
| act aat gac aat aat tat gta gta aaa ata gag ccc aaa gct aac gga | 144 |
| Thr Asn Asp Asn Asn Tyr Val Val Lys Ile Glu Pro Lys Ala Asn Gly | |
|          35                  40                  45 | |
| tca tta ttt act gaa cag gca ttt tat act aga gta ctt aaa cca tcc | 192 |
| Ser Leu Phe Thr Glu Gln Ala Phe Tyr Thr Arg Val Leu Lys Pro Ser | |
|      50                  55                  60 | |
| gtt atc gaa gaa tgg aaa aaa tat cac cat ata agc cac gta gga gtt | 240 |
| Val Ile Glu Glu Trp Lys Lys Tyr His His Ile Ser His Val Gly Val | |
| 65                  70                  75                  80 | |
| atc aca tgc aag gca ttt ggt cta tac aaa tcc att aat gct gaa tat | 288 |
| Ile Thr Cys Lys Ala Phe Gly Leu Tyr Lys Ser Ile Asn Ala Glu Tyr | |
|                  85                  90                  95 | |
| aga ttc ttg gta att aat aga ttg ggt gta gat cta gat gcg gtg atc | 336 |
| Arg Phe Leu Val Ile Asn Arg Leu Gly Val Asp Leu Asp Ala Val Ile | |
|              100                 105                 110 | |
| agg gct aac aat aat aga cta ccg aaa aga tcg gtg atg tta gta gga | 384 |
| Arg Ala Asn Asn Asn Arg Leu Pro Lys Arg Ser Val Met Leu Val Gly | |
|          115                 120                 125 | |
| ata gaa atc ttg aat acc ata caa ttt atg cac gag caa gga tat tct | 432 |
| Ile Glu Ile Leu Asn Thr Ile Gln Phe Met His Glu Gln Gly Tyr Ser | |
|      130                 135                 140 | |
| cac gga gat att aaa gcg agc aat ata gtt ttg gat caa atg gat aag | 480 |
| His Gly Asp Ile Lys Ala Ser Asn Ile Val Leu Asp Gln Met Asp Lys | |
| 145                 150                 155                 160 | |
| aat aaa tta tat cta gtg gat tac gga ttg gtt tct aaa ttc atg tct | 528 |
| Asn Lys Leu Tyr Leu Val Asp Tyr Gly Leu Val Ser Lys Phe Met Ser | |
|                  165                 170                 175 | |
| aac ggc gaa cat gtt cca ttt ata aga aat cca aat aaa atg gat aat | 576 |
| Asn Gly Glu His Val Pro Phe Ile Arg Asn Pro Asn Lys Met Asp Asn | |
|              180                 185                 190 | |
| ggt act cta gaa ttt aca cct ata gat tcg cat aaa gga tac gtt gta | 624 |
| Gly Thr Leu Glu Phe Thr Pro Ile Asp Ser His Lys Gly Tyr Val Val | |
|          195                 200                 205 | |
| tcg aga cgt gga gat cta gaa aca ctt gga tat tgt atg att aga tgg | 672 |
| Ser Arg Arg Gly Asp Leu Glu Thr Leu Gly Tyr Cys Met Ile Arg Trp | |
|      210                 215                 220 | |
| ttg gga ggt atc ttg cca tgg act aag ata gct gaa aca aag aat tgc | 720 |
| Leu Gly Gly Ile Leu Pro Trp Thr Lys Ile Ala Glu Thr Lys Asn Cys | |

```
                225                 230                 235                 240
gca tta gta agt gct aca aaa cag aaa tat gtg aac aat act gcg act      768
Ala Leu Val Ser Ala Thr Lys Gln Lys Tyr Val Asn Asn Thr Ala Thr
                    245                 250                 255 ttg tta atg acc agt ttg caa tat gcg cct aga gaa ttg ctg caa tat      816
Leu Leu Met Thr Ser Leu Gln Tyr Ala Pro Arg Glu Leu Leu Gln Tyr
                    260                 265                 270 att acc atg gta aac tct ttg aca tat ttt gag gaa ccc aat tac gat      864
Ile Thr Met Val Asn Ser Leu Thr Tyr Phe Glu Glu Pro Asn Tyr Asp
                    275                 280                 285 gag ttt cgg cgc ata tta atg cag ggt gta tat tat taa                  903
Glu Phe Arg Arg Ile Leu Met Gln Gly Val Tyr Tyr
                    290                 295                 300

<210> SEQ ID NO 82
<211> LENGTH: 300
<212> TYPE: PRT
<213> ORGANISM: Camelpox virus (CMS)

<400> SEQUENCE: 82

Met Asn Phe Gln Gly Leu Val Leu Thr Asp Asn Cys Lys Asn Gln Trp
1               5                   10                  15

Val Val Gly Pro Leu Ile Gly Lys Gly Gly Phe Gly Ser Ile Tyr Thr
            20                  25                  30

Thr Asn Asp Asn Asn Tyr Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Tyr His His Ile Ser His Val Gly Val
65                  70                  75                  80

Ile Thr Cys Lys Ala Phe Gly Leu Tyr Lys Ser Ile Asn Ala Glu Tyr
                85                  90                  95

Arg Phe Leu Val Ile Asn Arg Leu Gly Val Asp Leu Asp Ala Val Ile
            100                 105                 110

Arg Ala Asn Asn Asn Arg Leu Pro Lys Arg Ser Val Met Leu Val Gly
        115                 120                 125

Ile Glu Ile Leu Asn Thr Ile Gln Phe Met His Glu Gln Gly Tyr Ser
    130                 135                 140

His Gly Asp Ile Lys Ala Ser Asn Ile Val Leu Asp Gln Met Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
    210                 215                 220

Leu Gly Gly Ile Leu Pro Trp Thr Lys Ile Ala Glu Thr Lys Asn Cys
225                 230                 235                 240

Ala Leu Val Ser Ala Thr Lys Gln Lys Tyr Val Asn Asn Thr Ala Thr
                245                 250                 255

Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
        275                 280                 285
```

-continued

```
Glu Phe Arg Arg Ile Leu Met Gln Gly Val Tyr Tyr
        290             295             300

<210> SEQ ID NO 83
<211> LENGTH: 900
<212> TYPE: DNA
<213> ORGANISM: Ectromelia virus (Moscow)
<220> FEATURE

```
                     260                 265                 270
att act atg gta aac tct ttg aca tat ttt gag gaa ccc aat tac gac         864
Ile Thr Met Val Asn Ser Leu Thr Tyr Phe Glu Glu Pro Asn Tyr Asp
        275                 280                 285 gag ttt cgg cgc gta tta atg aat gga gtt atg taa                         900
Glu Phe Arg Arg Val Leu Met Asn Gly Val Met
290                 295

<210> SEQ ID NO 84
<211> LENGTH: 299
<212> TYPE: PRT
<213> ORGANISM: Ectromelia virus (Moscow)

<400> SEQUENCE: 84

Met Asn Phe Gln Gly Leu Val Leu Thr Asp Asn Cys Lys Asn Gln Trp
1               5                   10                  15

Val Val Gly Pro Leu Ile Gly Lys Gly Gly Phe Gly Ser Ile Tyr Thr
            20                  25                  30

Thr Asn Asp Asn Asn Tyr Val Lys Ile Glu Pro Lys Ala Asn Gly
        35                  40                  45

Ser Leu Phe Thr Glu Gln Ala Phe Tyr Thr Arg Val Leu Lys Pro Ser
50                  55                  60

Val Ile Glu Glu Trp Lys Lys Ser His Asn Ile Lys His Val Gly Leu
65                  70                  75                  80

Ile Thr Cys Thr Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Lys Arg Ser Val Met Leu Ile Gly
        115                 120                 125

Ile Glu Ile Leu Asn Thr Ile Gln Phe Met His Glu Gln Gly Tyr Ser
130                 135                 140

His Gly Asp Ile Lys Ala Ser Asn Ile Val Leu Asp Gln Met Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
210                 215                 220

Leu Gly Gly Ile Leu Pro Trp Thr Lys Met Ser Glu Thr Lys Asn Cys
225                 230                 235                 240

Ala Leu Val Ser Ala Thr Lys Gln Lys Tyr Val Asn Asn Thr Ala Thr
                245                 250                 255

Leu Leu Met Thr Ser Leu Gln Tyr Ala Pro Lys Glu Leu Leu Gln Tyr
            260                 265                 270

Ile Thr Met Val Asn Ser Leu Thr Tyr Phe Glu Glu Pro Asn Tyr Asp
        275                 280                 285

Glu Phe Arg Arg Val Leu Met Asn Gly Val Met
290                 295

<210> SEQ ID NO 85
<211> LENGTH: 912
<212> TYPE: DNA
<213> ORGANISM: Monkeypox virus (MPXV-WRAIR7-61)
```

<220> FEATURE:
<221> NAME/KEY: CDS
<222> LOCATION: (1)..(912)

<400> SEQUENCE: 85

```
atg aag ttt caa gga ctt gtg tta att gac aat tgc aaa aat caa tgg      48
Met Lys Phe Gln Gly Leu Val Leu Ile Asp Asn Cys Lys Asn Gln Trp
1               5                   10                  15 gtc gtt gga cca tta ata gga aaa ggt gga ttc ggt agt att tat act      96
Val Val Gly Pro Leu Ile Gly Lys Gly Gly Phe Gly Ser Ile Tyr Thr
            20                  25                  30 act aat gac aat aat tat gta gta aaa ata gag ccc aaa gct aac gga     144
Thr Asn Asp Asn Asn Tyr Val Val Lys Ile Glu Pro Lys Ala Asn Gly
        35                  40                  45 tca tta ttt acc gaa cag gca ttt tat act aga gta ctt aaa cca tcc     192
Ser Leu Phe Thr Glu Gln Ala Phe Tyr Thr Arg Val Leu Lys Pro Ser
    50                  55                  60 gtt atc gaa gaa tgg aaa aaa tct cac aat ata aag cac gta ggt ctt     240
Val Ile Glu Glu Trp Lys Lys Ser His Asn Ile Lys His Val Gly Leu
65                  70                  75                  80 atc acg tgc aag gca ttt ggt tta tac aaa tcc att aat gtg gaa tat     288
Ile Thr Cys Lys Ala Phe Gly Leu Tyr Lys Ser Ile Asn Val Glu Tyr
                85                  90                  95 cga ttc ttg gta ata aat aga tta ggt gca gat cta gat gcg gtg atc     336
Arg Phe Leu Val Ile Asn Arg Leu Gly Ala Asp Leu Asp Ala Val Ile
            100                 105                 110 aga gcc aat aat aat aga cta cca gaa agg tcg gtg atg ttg atc gga     384
Arg Ala Asn Asn Asn Arg Leu Pro Glu Arg Ser Val Met Leu Ile Gly
        115                 120                 125 atc gaa atc tta aat acc ata caa ttt atg cac gag caa gga tat tct     432
Ile Glu Ile Leu Asn Thr Ile Gln Phe Met His Glu Gln Gly Tyr Ser
    130                 135                 140 cac gga gat att aaa gcg agt aat ata gtc ttg gat caa ata gat aag     480
His Gly Asp Ile Lys Ala Ser Asn Ile Val Leu Asp Gln Ile Asp Lys
145                 150                 155                 160 aat aaa tta tat cta gtg gat tac gga ttg gtt tct aaa ttc atg tct     528
Asn Lys Leu Tyr Leu Val Asp Tyr Gly Leu Val Ser Lys Phe Met Ser
                165                 170                 175 aac ggc gaa cat gtt cca ttt ata aga aat cca aat aaa atg gat aac     576
Asn Gly Glu His Val Pro Phe Ile Arg Asn Pro Asn Lys Met Asp Asn
            180                 185                 190 ggt act cta gaa ttt aca cct ata gat tcg cat aaa gga tac gtt gta     624
Gly Thr Leu Glu Phe Thr Pro Ile Asp Ser His Lys Gly Tyr Val Val
        195                 200                 205 tct aga cgt ggt gat cta gaa aca ctt gga tat tgt atg att aga tgg     672
Ser Arg Arg Gly Asp Leu Glu Thr Leu Gly Tyr Cys Met Ile Arg Trp
    210                 215                 220 ttg gga ggt atc ttg cca tgg act aag ata tct gaa aca aag aat tct     720
Leu Gly Gly Ile Leu Pro Trp Thr Lys Ile Ser Glu Thr Lys Asn Ser
225                 230                 235                 240 gca tta gta agt gcc gca aaa cag aaa tat gtt aac aat act gcg act     768
Ala Leu Val Ser Ala Ala Lys Gln Lys Tyr Val Asn Asn Thr Ala Thr
                245                 250                 255 ttg tta atg acc agt ttg caa tat gca cct aga gaa ttg ctg caa tat     816
Leu Leu Met Thr Ser Leu Gln Tyr Ala Pro Arg Glu Leu Leu Gln Tyr
            260                 265                 270 att acc atg gta aac tct ttg aca tat ttt gag gaa ccc aat tac gac     864
Ile Thr Met Val Asn Ser Leu Thr Tyr Phe Glu Glu Pro Asn Tyr Asp
        275                 280                 285 gag ttt cgt cga gta tta atg aat gga gtt atg aaa aat ttt tgt tga     912
Glu Phe Arg Arg Val Leu Met Asn Gly Val Met Lys Asn Phe Cys
    290                 295                 300
```

<210> SEQ ID NO 86
<211> LENGTH: 303
<212> TYPE: PRT
<213> ORGANISM: Monkeypox virus (MPXV-WRAIR7-61)

<400> SEQUENCE: 86

Met Lys Phe Gln Gly Leu Val Leu Ile Asp Asn Cys Lys Asn Gln Trp
1               5                   10                  15

Val Val Gly Pro Leu Ile Gly Lys Gly Gly Phe Gly Ser Ile Tyr Thr
            20                  25                  30

Thr Asn Asp Asn Asn Tyr Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His Asn Ile Lys His Val Gly Leu
65                  70                  75                  80

Ile Thr Cys Lys Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Glu Arg Ser Val Met Leu Ile Gly
        115                 120                 125

Ile Glu Ile Leu Asn Thr Ile Gln Phe Met His Glu Gln Gly Tyr Ser
130                 135                 140

His Gly Asp Ile Lys Ala Ser Asn Ile Val Leu Asp Gln Ile Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
    210                 215                 220

Leu Gly Gly Ile Leu Pro Trp Thr Lys Ile Ser Glu Thr Lys Asn Ser
225                 230                 235                 240

Ala Leu Val Ser Ala Ala Lys Gln Lys Tyr Val Asn Asn Thr Ala Thr
                245                 250                 255

Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
        275                 280                 285

Glu Phe Arg Arg Val Leu Met Asn Gly Val Met Lys Asn Phe Cys
    290                 295                 300

<210> SEQ ID NO 87
<211> LENGTH: 900
<212> TYPE: DNA
<213> ORGANISM: Monkeypox virus (Zaire-96-I-16)
<220> FEATURE:
<221> NAME/KEY: CDS
<222> LOCATION: (1)..(900)

<400> SEQUENCE: 87 atg aag ttt caa gga ctt gtg tta att gac aat tgc aaa aat caa tgg    48
Met Lys Phe Gln Gly Leu Val Leu Ile Asp Asn Cys Lys Asn Gln Trp

```
                    1               5                  10                 15
gtc gtt gga cca tta ata gga aaa ggt gga ttc ggt agt att tat act          96
Val Val Gly Pro Leu Ile Gly Lys Gly Gly Phe Gly Ser Ile Tyr Thr
                    20                 25                 30 act aat gac aat aat tat gta gta aaa ata gag ccc aaa gct aac gga         144
Thr Asn Asp Asn Asn Tyr Val Val Lys Ile Glu Pro Lys Ala Asn Gly
             35                 40                 45 tca tta ttt acc gaa cag gca ttt tat act aga gta ctt aaa cca tcc         192
Ser Leu Phe Thr Glu Gln Ala Phe Tyr Thr Arg Val Leu Lys Pro Ser
    50                 55                 60 gtt atc gaa gaa tgg aaa aaa tct cac aat ata aag cac gta ggt ctt         240
Val Ile Glu Glu Trp Lys Lys Ser His Asn Ile Lys His Val Gly Leu
65                 70                 75                 80 atc acg tgc aag gca ttt ggt tta tac aaa tcc att aat gtg gaa tat         288
Ile Thr Cys Lys Ala Phe Gly Leu Tyr Lys Ser Ile Asn Val Glu Tyr
                85                 90                 95 cga ttc ttg gta att aat aga tta ggt gca gat cta gat gcg gtg atc         336
Arg Phe Leu Val Ile Asn Arg Leu Gly Ala Asp Leu Asp Ala Val Ile
            100                105                110 aga gcc aat aat aat aga cta cca gaa agg tcg gtg atg ttg atc gga         384
Arg Ala Asn Asn Asn Arg Leu Pro Glu Arg Ser Val Met Leu Ile Gly
        115                120                125 atc gaa atc tta aat acc ata caa ttt atg cac gag caa gga tat tct         432
Ile Glu Ile Leu Asn Thr Ile Gln Phe Met His Glu Gln Gly Tyr Ser
130                135                140 cac gga gat att aaa gcg agt aat ata gtc ttg gat caa ata gat aag         480
His Gly Asp Ile Lys Ala Ser Asn Ile Val Leu Asp Gln Ile Asp Lys
145                150                155                160 aat aaa tta tat cta gtg gat tac gga ttg gtt tct aaa ttc atg tct         528
Asn Lys Leu Tyr Leu Val Asp Tyr Gly Leu Val Ser Lys Phe Met Ser
                165                170                175 aac ggc gaa cat gtt cca ttt ata aga aat cca aat aaa atg gat aac         576
Asn Gly Glu His Val Pro Phe Ile Arg Asn Pro Asn Lys Met Asp Asn
            180                185                190 ggt act cta gaa ttt aca cct ata gat tcg cat aaa gga tac gtt gta         624
Gly Thr Leu Glu Phe Thr Pro Ile Asp Ser His Lys Gly Tyr Val Val
        195                200                205 tct aga cgt ggt gat cta gaa aca ctt gga tat tgt atg att aga tgg         672
Ser Arg Arg Gly Asp Leu Glu Thr Leu Gly Tyr Cys Met Ile Arg Trp
210                215                220 ttg gga ggt atc ttg cca tgg act aag ata tct gaa aca aag aat tct         720
Leu Gly Gly Ile Leu Pro Trp Thr Lys Ile Ser Glu Thr Lys Asn Ser
225                230                235                240 gca tta gta agt gct gca aaa cag aaa tat gtt aac aat act gcg act         768
Ala Leu Val Ser Ala Ala Lys Gln Lys Tyr Val Asn Asn Thr Ala Thr
                245                250                255 ttg tta atg acc agt ttg caa tat gca cct aga gaa ttg ctg caa tat         816
Leu Leu Met Thr Ser Leu Gln Tyr Ala Pro Arg Glu Leu Leu Gln Tyr
            260                265                270 att acc atg gta aac tct ttg aca tat ttt gag gaa ccc aat tac gac         864
Ile Thr Met Val Asn Ser Leu Thr Tyr Phe Glu Glu Pro Asn Tyr Asp
        275                280                285 gag ttt cgt cga gta tta atg aat gga gtt atg taa                         900
Glu Phe Arg Arg Val Leu Met Asn Gly Val Met
290                295

<210> SEQ ID NO 88
<211> LENGTH: 299
<212> TYPE: PRT
<213> ORGANISM: Monkeypox virus (Zaire-96-I-16)
```

<400> SEQUENCE: 88

Met Lys Phe Gln Gly Leu Val Leu Ile Asp Asn Cys Lys Asn Gln Trp
1               5                   10                  15

Val Val Gly Pro Leu Ile Gly Lys Gly Gly Phe Gly Ser Ile Tyr Thr
            20                  25                  30

Thr Asn Asp Asn Asn Tyr Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His Asn Ile Lys His Val Gly Leu
65                  70                  75                  80

Ile Thr Cys Lys Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Glu Arg Ser Val Met Leu Ile Gly
        115                 120                 125

Ile Glu Ile Leu Asn Thr Ile Gln Phe Met His Glu Gln Gly Tyr Ser
130                 135                 140

His Gly Asp Ile Lys Ala Ser Asn Ile Val Leu Asp Gln Ile Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
210                 215                 220

Leu Gly Gly Ile Leu Pro Trp Thr Lys Ile Ser Glu Thr Lys Asn Ser
225                 230                 235                 240

Ala Leu Val Ser Ala Ala Lys Gln Lys Tyr Val Asn Asn Thr Ala Thr
                245                 250                 255

Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
        275                 280                 285

Glu Phe Arg Arg Val Leu Met Asn Gly Val Met
    290                 295

<210> SEQ ID NO 89
<211> LENGTH: 918
<212> TYPE: DNA
<213> ORGANISM: Lumpy skin disease virus
<220> FEATURE:
<221> NAME/KEY: CDS
<222> LOCATION: (1)..(918)

<400> SEQUENCE: 89 atg cca aaa cgt aac ata aac gtt ttt gag gaa ggt gat gtg tta gta    48
Met Pro Lys Arg Asn Ile Asn Val Phe Glu Glu Gly Asp Val Leu Val
1               5                   10                  15 gat tct gta aag aaa gaa tgg cga tta ggg aaa ata att ggt caa ggt    96
Asp Ser Val Lys Lys Glu Trp Arg Leu Gly Lys Ile Ile Gly Gln Gly
            20                  25                  30 ggg ttc ggt ttc ata ttt tta gca tat tca caa aat aat gaa gaa tat   144
Gly Phe Gly Phe Ile Phe Leu Ala Tyr Ser Gln Asn Asn Glu Glu Tyr

```
             35                  40                  45
gtg gta aaa att gaa cct aag agc aat gga cca tta ttt gta gaa caa         192
Val Val Lys Ile Glu Pro Lys Ser Asn Gly Pro Leu Phe Val Glu Gln
 50                  55                  60 gtg ttt tat caa cgg ata gga aaa cga gac atg ata acg tta tgg tca         240
Val Phe Tyr Gln Arg Ile Gly Lys Arg Asp Met Ile Thr Leu Trp Ser
 65                  70                  75                  80 aaa aat aat cac ata gat cat tta gga att cca gta ttt tat ggt ttt         288
Lys Asn Asn His Ile Asp His Leu Gly Ile Pro Val Phe Tyr Gly Phe
                 85                  90                  95 gga ttt cat aaa aaa aat gga ata gat tat agg ttt ata att att aat         336
Gly Phe His Lys Lys Asn Gly Ile Asp Tyr Arg Phe Ile Ile Ile Asn
                100                 105                 110 aga tta ggt tgt gat tta aat aaa ata ata cag tgt aat aac aat aaa         384
Arg Leu Gly Cys Asp Leu Asn Lys Ile Ile Gln Cys Asn Asn Asn Lys
            115                 120                 125 ctt cct gaa aga tct gtg ttt tta ata gcg tct aaa ata ata atg ata         432
Leu Pro Glu Arg Ser Val Phe Leu Ile Ala Ser Lys Ile Ile Met Ile
        130                 135                 140 tta aaa tac cta cat gaa aat ggc tat acg cat agt gat att aaa gca         480
Leu Lys Tyr Leu His Glu Asn Gly Tyr Thr His Ser Asp Ile Lys Ala
145                 150                 155                 160 tct aat ata gca att gat atc aat aat aaa aat aaa att tat tta ttg         528
Ser Asn Ile Ala Ile Asp Ile Asn Asn Lys Asn Lys Ile Tyr Leu Leu
                165                 170                 175 gat tat gga tta tct tat aga ttc atg ata aac ggc aac cat gtg gag         576
Asp Tyr Gly Leu Ser Tyr Arg Phe Met Ile Asn Gly Asn His Val Glu
                180                 185                 190 tat aag cga gat ccc aaa aag atg cat aat gga aca ata gaa tac aca         624
Tyr Lys Arg Asp Pro Lys Lys Met His Asn Gly Thr Ile Glu Tyr Thr
                195                 200                 205 agt ata gat atg cat aaa ggt gta tcc ccg tct agg cga gga gat ttg         672
Ser Ile Asp Met His Lys Gly Val Ser Pro Ser Arg Arg Gly Asp Leu
        210                 215                 220 gaa att tta gga tat tgt ata ata aaa tgg tta ggt ggt aaa ttg cca         720
Glu Ile Leu Gly Tyr Cys Ile Ile Lys Trp Leu Gly Gly Lys Leu Pro
225                 230                 235                 240 tgg gaa aat gat tta aaa aat tgt aaa tat gta atg gag tca aag att         768
Trp Glu Asn Asp Leu Lys Asn Cys Lys Tyr Val Met Glu Ser Lys Ile
                245                 250                 255 aaa tac atg aac gat att gga aat tta atg act gac tcg cta gga tct         816
Lys Tyr Met Asn Asp Ile Gly Asn Leu Met Thr Asp Ser Leu Gly Ser
            260                 265                 270 aat tat cct gaa aaa att tta aag tat ttt aat tat ata aaa aca tta         864
Asn Tyr Pro Glu Lys Ile Leu Lys Tyr Phe Asn Tyr Ile Lys Thr Leu
        275                 280                 285 caa tac gat tct att cca gat tat gaa aaa ata atg tca ttt ttt ctt         912
Gln Tyr Asp Ser Ile Pro Asp Tyr Glu Lys Ile Met Ser Phe Phe Leu
    290                 295                 300 ctt taa                                                                  918
Leu
305

<210> SEQ ID NO 90
<211> LENGTH: 305
<212> TYPE: PRT
<213> ORGANISM: Lumpy skin disease virus

<400> SEQUENCE: 90

Met Pro Lys Arg Asn Ile Asn Val Phe Glu Glu Gly Asp Val Leu Val
 1               5                  10                  15
```

```
Asp Ser Val Lys Lys Glu Trp Arg Leu Gly Lys Ile Ile Gly Gln Gly
         20                  25                  30

Gly Phe Gly Phe Ile Phe Leu Ala Tyr Ser Gln Asn Asn Glu Glu Tyr
         35                  40                  45

Val Val Lys Ile Glu Pro Lys Ser Asn Gly Pro Leu Phe Val Glu Gln
 50                  55                  60

Val Phe Tyr Gln Arg Ile Gly Lys Arg Asp Met Ile Thr Leu Trp Ser
 65                  70                  75                  80

Lys Asn Asn His Ile Asp His Leu Gly Ile Pro Val Phe Tyr Gly Phe
                 85                  90                  95

Gly Phe His Lys Lys Asn Gly Ile Asp Tyr Arg Phe Ile Ile Ile Asn
                100                 105                 110

Arg Leu Gly Cys Asp Leu Asn Lys Ile Ile Gln Cys Asn Asn Asn Lys
            115                 120                 125

Leu Pro Glu Arg Ser Val Phe Leu Ile Ala Ser Lys Ile Ile Met Ile
130                 135                 140

Leu Lys Tyr Leu His Glu Asn Gly Tyr Thr His Ser Asp Ile Lys Ala
145                 150                 155                 160

Ser Asn Ile Ala Ile Asp Ile Asn Asn Lys Asn Lys Ile Tyr Leu Leu
                165                 170                 175

Asp Tyr Gly Leu Ser Tyr Arg Phe Met Ile Asn Gly Asn His Val Glu
            180                 185                 190

Tyr Lys Arg Asp Pro Lys Lys Met His Asn Gly Thr Ile Glu Tyr Thr
        195                 200                 205

Ser Ile Asp Met His Lys Gly Val Ser Pro Ser Arg Arg Gly Asp Leu
210                 215                 220

Glu Ile Leu Gly Tyr Cys Ile Ile Lys Trp Leu Gly Gly Lys Leu Pro
225                 230                 235                 240

Trp Glu Asn Asp Leu Lys Asn Cys Lys Tyr Val Met Glu Ser Lys Ile
                245                 250                 255

Lys Tyr Met Asn Asp Ile Gly Asn Leu Met Thr Asp Ser Leu Gly Ser
            260                 265                 270

Asn Tyr Pro Glu Lys Ile Leu Lys Tyr Phe Asn Tyr Ile Lys Thr Leu
        275                 280                 285

Gln Tyr Asp Ser Ile Pro Asp Tyr Glu Lys Ile Met Ser Phe Phe Leu
290                 295                 300

Leu
305

<210> SEQ ID NO 91
<211> LENGTH: 918
<212> TYPE: DNA
<213> ORGANISM: Sheeppox virus (TU-V02127)
<220> FEATURE:
<221> NAME/KEY: CDS
<222> LOCATION: (1)..(918)

<400> SEQUENCE: 91 atg cca aaa cct aac ata aac gtt ttt gag gaa ggt gat gtg tta gta      48
Met Pro Lys Pro Asn Ile Asn Val Phe Glu Glu Gly Asp Val Leu Val
1               5                   10                  15 gat tct tta aag aaa gaa tgg aaa tta ggg aaa ata att ggt caa ggt      96
Asp Ser Leu Lys Lys Glu Trp Lys Leu Gly Lys Ile Ile Gly Gln Gly
            20                  25                  30 ggg ttc ggt ttc ata ttt tta gca tat tca caa aat aat gaa gaa tat     144
Gly Phe Gly Phe Ile Phe Leu Ala Tyr Ser Gln Asn Asn Glu Glu Tyr
        35                  40                  45
```

```
gtg gta aaa att gaa cct aag agc aac gga cca tta ttt gta gaa caa       192
Val Val Lys Ile Glu Pro Lys Ser Asn Gly Pro Leu Phe Val Glu Gln
 50                  55                  60 gtg ttt tat caa cgg ata ggg aaa cga gac atg ata acg tta tgg tca       240
Val Phe Tyr Gln Arg Ile Gly Lys Arg Asp Met Ile Thr Leu Trp Ser
 65                  70                  75                  80 aaa aaa aat cac ata gat cat tta gga att cca gta ttt tat ggt ttt       288
Lys Lys Asn His Ile Asp His Leu Gly Ile Pro Val Phe Tyr Gly Phe
                 85                  90                  95 gga ttt cat aaa aaa aat gga ata gat tat agg ttt ata att att agt       336
Gly Phe His Lys Lys Asn Gly Ile Asp Tyr Arg Phe Ile Ile Ile Ser
            100                 105                 110 aga tta ggt tgt gat tta aat aaa ata ata cag tgt aat aac aat aaa       384
Arg Leu Gly Cys Asp Leu Asn Lys Ile Ile Gln Cys Asn Asn Asn Lys
115                 120                 125 ctt cct gaa aga tct gtg ttt tta ata gcg tct aaa ata ata atg ata       432
Leu Pro Glu Arg Ser Val Phe Leu Ile Ala Ser Lys Ile Ile Met Ile
130                 135                 140 tta aaa tac cta cat gaa aat ggc tat act cat agt gat att aaa gca       480
Leu Lys Tyr Leu His Glu Asn Gly Tyr Thr His Ser Asp Ile Lys Ala
145                 150                 155                 160 tct aat ata gca att gat atc aat aat aaa aat aaa att tat tta ttg       528
Ser Asn Ile Ala Ile Asp Ile Asn Asn Lys Asn Lys Ile Tyr Leu Leu
                165                 170                 175 gat tat gga tta tct tat aga ttt atg ata aac ggc aac cat gtg gag       576
Asp Tyr Gly Leu Ser Tyr Arg Phe Met Ile Asn Gly Asn His Val Glu
            180                 185                 190 tat aag aga gat cca aaa aag atg cat aat gga aca ata gaa tac aca       624
Tyr Lys Arg Asp Pro Lys Lys Met His Asn Gly Thr Ile Glu Tyr Thr
        195                 200                 205 agt ata gat atg cat aac ggt gta tcc ccg tct agg cga gga gat tta       672
Ser Ile Asp Met His Asn Gly Val Ser Pro Ser Arg Arg Gly Asp Leu
    210                 215                 220 gaa att tta gga tat tgt ata ata aaa tgg tta ggc ggt aaa ttg cca       720
Glu Ile Leu Gly Tyr Cys Ile Ile Lys Trp Leu Gly Gly Lys Leu Pro
225                 230                 235                 240 tgg gaa aat gat tta aaa aat tgt aaa tat gta atg gag tca aag att       768
Trp Glu Asn Asp Leu Lys Asn Cys Lys Tyr Val Met Glu Ser Lys Ile
                245                 250                 255 aaa tac atg aac gat att gga aat tta atg act gac tcg cta gga tct       816
Lys Tyr Met Asn Asp Ile Gly Asn Leu Met Thr Asp Ser Leu Gly Ser
            260                 265                 270 aat tat cct gaa aaa att tta aag tat ttt aat tat ata aaa aca tta       864
Asn Tyr Pro Glu Lys Ile Leu Lys Tyr Phe Asn Tyr Ile Lys Thr Leu
        275                 280                 285 caa tac gat tct att cca gat tat gaa aaa ata atg tca tct ttt ctt       912
Gln Tyr Asp Ser Ile Pro Asp Tyr Glu Lys Ile Met Ser Ser Phe Leu
    290                 295                 300 ctt taa                                                               918
Leu
305
```

<210> SEQ ID NO 92
<211> LENGTH: 305
<212> TYPE: PRT
<213> ORGANISM: Sheeppox virus (TU-V02127)

<400> SEQUENCE: 92

```
Met Pro Lys Pro Asn Ile Asn Val Phe Glu Glu Gly Asp Val Leu Val
 1               5                  10                  15
```

-continued

```
Asp Ser Leu Lys Lys Glu Trp Lys Leu Gly Lys Ile Ile Gly Gln Gly
         20                  25                  30
Gly Phe Gly Phe Ile Phe Leu Ala Tyr Ser Gln Asn Asn Glu Glu Tyr
             35                  40                  45
Val Val Lys Ile Glu Pro Lys Ser Asn Gly Pro Leu Phe Val Glu Gln
 50                  55                  60
Val Phe Tyr Gln Arg Ile Gly Lys Arg Asp Met Ile Thr Leu Trp Ser
 65                  70                  75                  80
Lys Lys Asn His Ile Asp His Leu Gly Ile Pro Val Phe Tyr Gly Phe
                 85                  90                  95
Gly Phe His Lys Lys Asn Gly Ile Asp Tyr Arg Phe Ile Ile Ile Ser
            100                 105                 110
Arg Leu Gly Cys Asp Leu Asn Lys Ile Ile Gln Cys Asn Asn Asn Lys
        115                 120                 125
Leu Pro Glu Arg Ser Val Phe Leu Ile Ala Ser Lys Ile Ile Met Ile
    130                 135                 140
Leu Lys Tyr Leu His Glu Asn Gly Tyr Thr His Ser Asp Ile Lys Ala
145                 150                 155                 160
Ser Asn Ile Ala Ile Asp Ile Asn Asn Lys Lys Ile Tyr Leu Leu
                165                 170                 175
Asp Tyr Gly Leu Ser Tyr Arg Phe Met Ile Asn Gly Asn His Val Glu
            180                 185                 190
Tyr Lys Arg Asp Pro Lys Lys Met His Asn Gly Thr Ile Glu Tyr Thr
        195                 200                 205
Ser Ile Asp Met His Asn Gly Val Ser Pro Ser Arg Arg Gly Asp Leu
    210                 215                 220
Glu Ile Leu Gly Tyr Cys Ile Ile Lys Trp Leu Gly Gly Lys Leu Pro
225                 230                 235                 240
Trp Glu Asn Asp Leu Lys Asn Cys Lys Tyr Val Met Glu Ser Lys Ile
                245                 250                 255
Lys Tyr Met Asn Asp Ile Gly Asn Leu Met Thr Asp Ser Leu Gly Ser
            260                 265                 270
Asn Tyr Pro Glu Lys Ile Leu Lys Tyr Phe Asn Tyr Ile Lys Thr Leu
        275                 280                 285
Gln Tyr Asp Ser Ile Pro Asp Tyr Glu Lys Ile Met Ser Ser Phe Leu
    290                 295                 300
Leu
305

<210> SEQ ID NO 93
<211> LENGTH: 948
<212> TYPE: DNA
<213> ORGANISM: Mule deer poxvirus (W-848-83)
<220> FEATURE:
<221> N

```
cac atc gat aca gaa gaa aga tat gta ata aag ata gaa ccc aaa agt      192
His Ile Asp Thr Glu Glu Arg Tyr Val Ile Lys Ile Glu Pro Lys Ser
    50                  55                  60 aat gga cca tta ttc gtg gaa caa ata ttt tat caa aga ata tgc aaa      240
Asn Gly Pro Leu Phe Val Glu Gln Ile Phe Tyr Gln Arg Ile Cys Lys
65                  70                  75                  80 aag gag cta ata gaa aag tgg tta aag gaa aat aat atc caa tat ata      288
Lys Glu Leu Ile Glu Lys Trp Leu Lys Glu Asn Asn Ile Gln Tyr Ile
                85                  90                  95 ggt att cct aca ttt tat gga ttt gga ttt tgt aaa aaa aat aaa ata      336
Gly Ile Pro Thr Phe Tyr Gly Phe Gly Phe Cys Lys Lys Asn Lys Ile
            100                 105                 110 gaa tat aga ttt ata att ata gat aga tta ggt tgt gat ttg aat aaa      384
Glu Tyr Arg Phe Ile Ile Ile Asp Arg Leu Gly Cys Asp Leu Asn Lys
        115                 120                 125 atc att agt gtt aat aac aat aaa ctt cct gtt agg tct gta ttc cta      432
Ile Ile Ser Val Asn Asn Asn Lys Leu Pro Val Arg Ser Val Phe Leu
    130                 135                 140 ata gct ata aat ata ata aat aca tta aaa tat tta cat aat aac gga      480
Ile Ala Ile Asn Ile Ile Asn Thr Leu Lys Tyr Leu His Asn Asn Gly
145                 150                 155                 160 tat aca cac agt gat ata aaa tca tct aat ata gct att ggg tta cat      528
Tyr Thr His Ser Asp Ile Lys Ser Ser Asn Ile Ala Ile Gly Leu His
                165                 170                 175 gat aaa aac aaa att tac ttg tta gat tac gga tta tca tat aga tat      576
Asp Lys Asn Lys Ile Tyr Leu Leu Asp Tyr Gly Leu Ser Tyr Arg Tyr
            180                 185                 190 atg att aat ggt aaa cat gtt gaa tat aaa aga gac cct aaa aag atg      624
Met Ile Asn Gly Lys His Val Glu Tyr Lys Arg Asp Pro Lys Lys Met
        195                 200                 205 cat aat gga acc ata gaa ttt act agc atc gat atg cat cgt gga gca      672
His Asn Gly Thr Ile Glu Phe Thr Ser Ile Asp Met His Arg Gly Ala
    210                 215                 220 tgc cct tct agg cga gga gat tta gaa ata ttg ggt tat tgt atg att      720
Cys Pro Ser Arg Arg Gly Asp Leu Glu Ile Leu Gly Tyr Cys Met Ile
225                 230                 235                 240 act tgg tta ggt ggt aaa tta cca tgg gag gat aat tta aaa aat tgt      768
Thr Trp Leu Gly Gly Lys Leu Pro Trp Glu Asp Asn Leu Lys Asn Cys
                245                 250                 255 aat tat gta atg aat tca aaa gta gac cat tta aaa gac gta aga tta      816
Asn Tyr Val Met Asn Ser Lys Val Asp His Leu Lys Asp Val Arg Leu
            260                 265                 270 ttt att gaa aaa tgt ttg ggc gat aat tat cct aaa aaa tta tta gat      864
Phe Ile Glu Lys Cys Leu Gly Asp Asn Tyr Pro Lys Lys Leu Leu Asp
        275                 280                 285 tat ttt atc tat ata aac tct ctc gaa tat gac tcc acc cct gat tat      912
Tyr Phe Ile Tyr Ile Asn Ser Leu Glu Tyr Asp Ser Thr Pro Asp Tyr
    290                 295                 300 aaa aaa ctt ata tca ttt tta tct gta aaa aca taa                      948
Lys Lys Leu Ile Ser Phe Leu Ser Val Lys Thr
305                 310                 315
```

<210> SEQ ID NO 94
<211> LENGTH: 315
<212> TYPE: PRT
<213> ORGANISM: Mule deer poxvirus (W-848-83)

<400> SEQUENCE: 94

```
Met Pro Lys Lys Ile Asn Asn Glu Met Phe Asp Glu Gly Glu Thr Leu
1               5                   10                  15

Thr Asp Asn Thr Gly Arg Arg Trp Lys Leu Gly Asn Ile Ile Gly Lys
```

```
                20                  25                  30
Gly Gly Phe Gly Phe Ile Tyr Leu Ser Phe Leu Tyr Ile Asp Asp Thr
                35                  40                  45

His Ile Asp Thr Glu Glu Arg Tyr Val Ile Lys Ile Glu Pro Lys Ser
 50                  55                  60

Asn Gly Pro Leu Phe Val Glu Gln Ile Phe Tyr Gln Arg Ile Cys Lys
 65                  70                  75                  80

Lys Glu Leu Ile Glu Lys Trp Leu Lys Glu Asn Asn Ile Gln Tyr Ile
                85                  90                  95

Gly Ile Pro Thr Phe Tyr Gly Phe Gly Phe Cys Lys Lys Asn Lys Ile
                100                 105                 110

Glu Tyr Arg Phe Ile Ile Ile Asp Arg Leu Gly Cys Asp Leu Asn Lys
                115                 120                 125

Ile Ile Ser Val Asn Asn Lys Leu Pro Val Arg Ser Val Phe Leu
130                 135                 140

Ile Ala Ile Asn Ile Ile Asn Thr Leu Lys Tyr Leu His Asn Asn Gly
145                 150                 155                 160

Tyr Thr His Ser Asp Ile Lys Ser Ser Asn Ile Ala Ile Gly Leu His
                165                 170                 175

Asp Lys Asn Lys Ile Tyr Leu Leu Asp Tyr Gly Leu Ser Tyr Arg Tyr
                180                 185                 190

Met Ile Asn Gly Lys His Val Glu Tyr Lys Arg Asp Pro Lys Lys Met
                195                 200                 205

His Asn Gly Thr Ile Glu Phe Thr Ser Ile Asp Met His Arg Gly Ala
                210                 215                 220

Cys Pro Ser Arg Arg Gly Asp Leu Glu Ile Leu Gly Tyr Cys Met Ile
225                 230                 235                 240

Thr Trp Leu Gly Gly Lys Leu Pro Trp Glu Asp Asn Leu Lys Asn Cys
                245                 250                 255

Asn Tyr Val Met Asn Ser Lys Val Asp His Leu Lys Asp Val Arg Leu
                260                 265                 270

Phe Ile Glu Lys Cys Leu Gly Asp Asn Tyr Pro Lys Lys Leu Leu Asp
                275                 280                 285

Tyr Phe Ile Tyr Ile Asn Ser Leu Glu Tyr Asp Ser Thr Pro Asp Tyr
                290                 295                 300

Lys Lys Leu Ile Ser Phe Leu Ser Val Lys Thr
305                 310                 315

<210> SEQ ID NO 95
<211> LENGTH: 930
<212> TYPE: DNA
<213> ORGANISM: Yaba monkey tumor virus
<220> FEATURE:
<221

|    |    |    |    |    |    |    |    |    |    |    |    |    |    |     |
|----|----|----|----|----|----|----|----|----|----|----|----|----|----|-----|
| Thr | His | Val | Ile | Lys | Val | Glu | Pro | Lys | Ser | Asn | Gly | Pro | Leu | Phe | Val |
|     | 50 |     |     |     | 55 |     |     |     | 60 |     |     |     |    |     |

```
gaa cag gta ttt tat caa aga act ggg aaa aaa gaa ata ata gat aac      240
Glu Gln Val Phe Tyr Gln Arg Thr Gly Lys Lys Glu Ile Ile Asp Asn
 65              70                  75                  80 tgg atg tta gaa aac aat gtt tct cac tta gga ata cct aaa tgt tat      288
Trp Met Leu Glu Asn Asn Val Ser His Leu Gly Ile Pro Lys Cys Tyr
                 85                  90                  95 ggt ttt ggg ttt cac aaa aac ggc aat aac gag tat agg ttt ata att      336
Gly Phe Gly Phe His Lys Asn Gly Asn Asn Glu Tyr Arg Phe Ile Ile
             100                 105                 110 ata gat cgt tta ggt tgc gac ctt caa aga ata att caa gcc aac gat      384
Ile Asp Arg Leu Gly Cys Asp Leu Gln Arg Ile Ile Gln Ala Asn Asp
         115                 120                 125 aac aag ctt cct aaa aaa aca gtt tta aag ata gga gcg gtt gtt ttg      432
Asn Lys Leu Pro Lys Lys Thr Val Leu Lys Ile Gly Ala Val Val Leu
     130                 135                 140 gtt att tta aaa ttt att cac gat aac gga tat aca cac agt gat ata      480
Val Ile Leu Lys Phe Ile His Asp Asn Gly Tyr Thr His Ser Asp Ile
145                 150                 155                 160 aaa gct tct aac ata gct ctt aac aaa gac gat aaa aat aag ata tac      528
Lys Ala Ser Asn Ile Ala Leu Asn Lys Asp Asp Lys Asn Lys Ile Tyr
                 165                 170                 175 tta ata gat tat ggg tta gcg ttt agg ttt atg gta aac ggt aaa cat      576
Leu Ile Asp Tyr Gly Leu Ala Phe Arg Phe Met Val Asn Gly Lys His
             180                 185                 190 gta gat ttt aaa aaa gat cca aag agg atg cat aac gga aca gta gag      624
Val Asp Phe Lys Lys Asp Pro Lys Arg Met His Asn Gly Thr Val Glu
         195                 200                 205 ttt aca agt atc gac gct cac tgc gga gca tat cct tcg aga agg ggc      672
Phe Thr Ser Ile Asp Ala His Cys Gly Ala Tyr Pro Ser Arg Arg Gly
     210                 215                 220 gat ctt gaa att tta gga tac tgc atg ata aaa tgg atg agc ggt aaa      720
Asp Leu Glu Ile Leu Gly Tyr Cys Met Ile Lys Trp Met Ser Gly Lys
225                 230                 235                 240 ctg cct tgg gaa gac aat tta aaa aat aaa gaa tat gtt aaa agt tca      768
Leu Pro Trp Glu Asp Asn Leu Lys Asn Lys Glu Tyr Val Lys Ser Ser
                 245                 250                 255 aaa ata aaa tac atg aat aac tta aaa ctc tta atg aat gaa tgt ttt      816
Lys Ile Lys Tyr Met Asn Asn Leu Lys Leu Leu Met Asn Glu Cys Phe
             260                 265                 270 aaa gac ggc agc gat ttt aca gaa tta gaa aaa tac atg aat att gtt      864
Lys Asp Gly Ser Asp Phe Thr Glu Leu Glu Lys Tyr Met Asn Ile Val
         275                 280                 285 aaa tct ctt aat tac gat agc ttg cca aat tac gtt gag ctg ata agt      912
Lys Ser Leu Asn Tyr Asp Ser Leu Pro Asn Tyr Val Glu Leu Ile Ser
     290                 295                 300 gtt tta gat ggt ttt taa                                              930
Val Leu Asp Gly Phe
305
```

<210> SEQ ID NO 96
<211> LENGTH: 309
<212> TYPE: PRT
<213> ORGANISM: Yaba monkey tumor virus

<400> SEQUENCE: 96

```
Met Ser Lys Asn Gln Glu Leu Lys Glu Gly Glu Ile Leu Ile Asp Ser
 1               5                  10                  15

Thr Lys Thr Lys Trp Lys Leu Gly Gln Ile Val Gly Lys Gly Gly Phe
                 20                  25                  30
```

```
Gly Tyr Ile Tyr Phe Ala Val Lys Asp Cys Asp Lys Tyr Ser Asp Phe
                35                  40                  45

Thr His Val Ile Lys Val Glu Pro Lys Ser Asn Gly Pro Leu Phe Val
 50                  55                  60

Glu Gln Val Phe Tyr Gln Arg Thr Gly Lys Lys Glu Ile Ile Asp Asn
 65                  70                  75                  80

Trp Met Leu Glu Asn Asn Val Ser His Leu Gly Ile Pro Lys Cys Tyr
                 85                  90                  95

Gly Phe Gly Phe His Lys Asn Gly Asn Asn Glu Tyr Arg Phe Ile Ile
                100                 105                 110

Ile Asp Arg Leu Gly Cys Asp Leu Gln Arg Ile Ile Gln Ala Asn Asp
            115                 120                 125

Asn Lys Leu Pro Lys Lys Thr Val Leu Lys Ile Gly Ala Val Val Leu
130                 135                 140

Val Ile Leu Lys Phe Ile His Asp Asn Gly Tyr Thr His Ser Asp Ile
145                 150                 155                 160

Lys Ala Ser Asn Ile Ala Leu Asn Lys Asp Asp Lys Asn Lys Ile Tyr
                165                 170                 175

Leu Ile Asp Tyr Gly Leu Ala Phe Arg Phe Met Val Asn Gly Lys His
            180                 185                 190

Val Asp Phe Lys Lys Asp Pro Lys Arg Met His Asn Gly Thr Val Glu
        195                 200                 205

Phe Thr Ser Ile Asp Ala His Cys Gly Ala Tyr Pro Ser Arg Arg Gly
    210                 215                 220

Asp Leu Glu Ile Leu Gly Tyr Cys Met Ile Lys Trp Met Ser Gly Lys
225                 230                 235                 240

Leu Pro Trp Glu Asp Asn Leu Lys Asn Lys Glu Tyr Val Lys Ser Ser
                245                 250                 255

Lys Ile Lys Tyr Met Asn Asn Leu Lys Leu Leu Met Asn Glu Cys Phe
            260                 265                 270

Lys Asp Gly Ser Asp Phe Thr Glu Leu Glu Lys Tyr Met Asn Ile Val
        275                 280                 285

Lys Ser Leu Asn Tyr Asp Ser Leu Pro Asn Tyr Val Glu Leu Ile Ser
290                 295                 300

Val Leu Asp Gly Phe
305

<210> SEQ ID NO 97
<211> LENGTH: 930
<212> TYPE: DNA
<213> ORGANISM: Yaba-like disease virus
<220> FEATURE:
<221> NAME/KEY: CDS
<222> LOCATION: (1)..(930)

<400> SEQUENCE: 97 atg tca aaa aac caa gaa tta aaa gaa ggt gag gtt tta act gac acc      48
Met Ser Lys Asn Gln Glu Leu Lys Glu Gly Glu Val Leu Thr Asp Thr
 1               5                  10                  15 act aaa aca aaa tgg aag ata gga aaa att gtg gga aag gga gga ttt      96
Thr Lys Thr Lys Trp Lys Ile Gly Lys Ile Val Gly Lys Gly Gly Phe
            20                  25                  30 ggc ttt ata tat ttt gca gtt aaa gat agt gaa aaa aat aaa gat ttt     144
Gly Phe Ile Tyr Phe Ala Val Lys Asp Ser Glu Lys Asn Lys Asp Phe
        35                  40                  45 aca cat gtg gtt aag gtt gaa cca aaa agc aac gga cca ttg ttt gta    192
Thr His Val Val Lys Val Glu Pro Lys Ser Asn Gly Pro Leu Phe Val
```

```
                50                   55                   60
gaa caa ata ttt tat caa aga att ggg aaa aaa gaa ata att aat aat        240
Glu Gln Ile Phe Tyr Gln Arg Ile Gly Lys Lys Glu Ile Ile Asn Asn
 65                  70                  75                  80 tgg atg tta aca aac aac gtt tct tat tta gga ata cca aag tgt tat        288
Trp Met Leu Thr Asn Asn Val Ser Tyr Leu Gly Ile Pro Lys Cys Tyr
                     85                  90                  95 ggt ttt ggt ttt cat aaa agc gat aaa aat gat tat agg ttt ata att        336
Gly Phe Gly Phe His Lys Ser Asp Lys Asn Asp Tyr Arg Phe Ile Ile
                100                 105                 110 atc gat cgt ttg ggt tgt gat ctt caa aga ata att caa gct aat gat        384
Ile Asp Arg Leu Gly Cys Asp Leu Gln Arg Ile Ile Gln Ala Asn Asp
            115                 120                 125 aac aaa ctt cct aaa aaa act gtt tta aaa ata gga gct ata att ttg        432
Asn Lys Leu Pro Lys Lys Thr Val Leu Lys Ile Gly Ala Ile Ile Leu
        130                 135                 140 gtt att tta aaa ttt att cac gac aac ggg tac gta cat agc gat ata        480
Val Ile Leu Lys Phe Ile His Asp Asn Gly Tyr Val His Ser Asp Ile
145                 150                 155                 160 aag gct tct aat ata gct ctt gac aaa aac gat aaa aac aaa ctt tat        528
Lys Ala Ser Asn Ile Ala Leu Asp Lys Asn Asp Lys Asn Lys Leu Tyr
                165                 170                 175 tta ata gat tac gga tta gca ttt agg ttt atg gta aac gat ata cac        576
Leu Ile Asp Tyr Gly Leu Ala Phe Arg Phe Met Val Asn Asp Ile His
                180                 185                 190 gtt gaa ttt aaa aaa gat cca aaa aga atg cat aac gga aca ata gaa        624
Val Glu Phe Lys Lys Asp Pro Lys Arg Met His Asn Gly Thr Ile Glu
            195                 200                 205 ttt aca agc ata gat gcg cat tgc gga gca tat cct tct aga aga gga        672
Phe Thr Ser Ile Asp Ala His Cys Gly Ala Tyr Pro Ser Arg Arg Gly
        210                 215                 220 gac ctt gaa att tta gga tat tgt atg ata aag tgg atg agt ggt aaa        720
Asp Leu Glu Ile Leu Gly Tyr Cys Met Ile Lys Trp Met Ser Gly Lys
225                 230                 235                 240 tta cca tgg gag gac gat tta aaa aat aaa gaa tat gtt aaa atg tca        768
Leu Pro Trp Glu Asp Asp Leu Lys Asn Lys Glu Tyr Val Lys Met Ser
                245                 250                 255 aag ata aaa tac atg aat gat gta aac ctt tta atg aaa gaa tgt ttt        816
Lys Ile Lys Tyr Met Asn Asp Val Asn Leu Leu Met Lys Glu Cys Phe
                260                 265                 270 aat gat agt aaa gaa ttt tta gaa tta gaa aaa tac atg aac gca gtt        864
Asn Asp Ser Lys Glu Phe Leu Glu Leu Glu Lys Tyr Met Asn Ala Val
            275                 280                 285 aag ttg ctt aac tat gat agt tta cca aat tat acc gaa cta ata agt        912
Lys Leu Leu Asn Tyr Asp Ser Leu Pro Asn Tyr Thr Glu Leu Ile Ser
        290                 295                 300 att tta aac cat ttt taa                                                930
Ile Leu Asn His Phe
305

<210> SEQ ID NO 98
<211> LENGTH: 309
<212> TYPE: PRT
<213> ORGANISM: Yaba-like disease virus

<400> SEQUENCE: 98

Met Ser Lys Asn Gln Glu Leu Lys Glu Gly Glu Val Leu Thr Asp Thr
 1               5                  10                  15

Thr Lys Thr Lys Trp Lys Ile Gly Lys Ile Val Gly Lys Gly Gly Phe
                20                  25                  30
```

```
Gly Phe Ile Tyr Phe Ala Val Lys Asp Ser Glu Lys Asn Lys Asp Phe
         35                  40                  45

Thr His Val Val Lys Val Glu Pro Lys Ser Asn Gly Pro Leu Phe Val
 50                  55                  60

Glu Gln Ile Phe Tyr Gln Arg Ile Gly Lys Lys Glu Ile Ile Asn Asn
 65                  70                  75                  80

Trp Met Leu Thr Asn Asn Val Ser Tyr Leu Gly Ile Pro Lys Cys Tyr
                 85                  90                  95

Gly Phe Gly Phe His Lys Ser Asp Lys Asn Asp Tyr Arg Phe Ile Ile
             100                 105                 110

Ile Asp Arg Leu Gly Cys Asp Leu Gln Arg Ile Ile Gln Ala Asn Asp
         115                 120                 125

Asn Lys Leu Pro Lys Lys Thr Val Leu Lys Ile Gly Ala Ile Ile Leu
130                 135                 140

Val Ile Leu Lys Phe Ile His Asp Asn Gly Tyr Val His Ser Asp Ile
145                 150                 155                 160

Lys Ala Ser Asn Ile Ala Leu Asp Lys Asn Asp Lys Asn Lys Leu Tyr
                 165                 170                 175

Leu Ile Asp Tyr Gly Leu Ala Phe Arg Phe Met Val Asn Asp Ile His
             180                 185                 190

Val Glu Phe Lys Lys Asp Pro Lys Arg Met His Asn Gly Thr Ile Glu
         195                 200                 205

Phe Thr Ser Ile Asp Ala His Cys Gly Ala Tyr Pro Ser Arg Arg Gly
210                 215                 220

Asp Leu Glu Ile Leu Gly Tyr Cys Met Ile Lys Trp Met Ser Gly Lys
225                 230                 235                 240

Leu Pro Trp Glu Asp Asp Leu Lys Asn Lys Glu Tyr Val Lys Met Ser
                 245                 250                 255

Lys Ile Lys Tyr Met Asn Asp Val Asn Leu Leu Met Lys Glu Cys Phe
             260                 265                 270

Asn Asp Ser Lys Glu Phe Leu Glu Leu Glu Lys Tyr Met Asn Ala Val
         275                 280                 285

Lys Leu Leu Asn Tyr Asp Ser Leu Pro Asn Tyr Thr Glu Leu Ile Ser
290                 295                 300

Ile Leu Asn His Phe
305

<210> SEQ ID NO 99
<211> LENGTH: 930
<212> TYPE: DNA
<213> ORGANISM: Swinepox virus (17077-99)
<220> FEATURE:
<221> NAME/KEY: CDS
<222> LOCATION: (1)..(930)

<400> SEQUENCE: 99 atg tct gga cgt

| | | | | | | | | | | | | | | | | |
|---|---|---|---|---|---|---|---|---|---|---|---|---|---|---|---|---|
| ttt | gtt | gaa | cag | gta | ttt | tat | caa | cgg | ata | gga | aaa | tgg | gat | atg | att | 240 |
| Phe | Val | Glu | Gln | Val | Phe | Tyr | Gln | Arg | Ile | Gly | Lys | Trp | Asp | Met | Ile | |
| 65 | | | | 70 | | | | | 75 | | | | | 80 | | |
| gat | tca | tgg | aaa | aag | tct | aat | ggt | att | aat | cat | tta | gga | ata | cct | aac | 288 |
| Asp | Ser | Trp | Lys | Lys | Ser | Asn | Gly | Ile | Asn | His | Leu | Gly | Ile | Pro | Asn | |
| | | | 85 | | | | | 90 | | | | | 95 | | | |
| ttc | tat | gga | ttt | gga | ttt | tat | aca | aag | aat | aag | aaa | gag | tat | aga | ttt | 336 |
| Phe | Tyr | Gly | Phe | Gly | Phe | Tyr | Thr | Lys | Asn | Lys | Lys | Glu | Tyr | Arg | Phe | |
| | | | 100 | | | | | 105 | | | | | 110 | | | |
| att | ata | gta | gat | aga | tta | ggt | tgc | gat | ctt | aat | aag | att | att | caa | aat | 384 |
| Ile | Ile | Val | Asp | Arg | Leu | Gly | Cys | Asp | Leu | Asn | Lys | Ile | Ile | Gln | Asn | |
| | | | 115 | | | | | 120 | | | | | 125 | | | |
| aat | aat | aat | aag | tta | ccg | caa | tcg | acc | gtg | ttt | aag | ata | gct | gat | aga | 432 |
| Asn | Asn | Asn | Lys | Leu | Pro | Gln | Ser | Thr | Val | Phe | Lys | Ile | Ala | Asp | Arg | |
| 130 | | | | | 135 | | | | | 140 | | | | | | |
| att | ata | aca | gtg | ttg | cga | tac | ata | cat | gat | cat | gga | tat | aca | cac | gga | 480 |
| Ile | Ile | Thr | Val | Leu | Arg | Tyr | Ile | His | Asp | His | Gly | Tyr | Thr | His | Gly | |
| 145 | | | | | 150 | | | | | 155 | | | | | 160 | |
| gat | ata | aaa | gca | tct | aat | atc | gct | ata | gac | tat | tat | gat | aaa | aat | aaa | 528 |
| Asp | Ile | Lys | Ala | Ser | Asn | Ile | Ala | Ile | Asp | Tyr | Tyr | Asp | Lys | Asn | Lys | |
| | | | | 165 | | | | | 170 | | | | | 175 | | |
| ata | tat | ttg | atc | gac | tat | ggt | cta | tca | cat | aga | tat | aag | gta | aat | gat | 576 |
| Ile | Tyr | Leu | Ile | Asp | Tyr | Gly | Leu | Ser | His | Arg | Tyr | Lys | Val | Asn | Asp | |
| | | | 180 | | | | | 185 | | | | | 190 | | | |
| gtt | cat | att | caa | tat | aag | cgc | gat | ccg | aag | aaa | atg | cat | aac | ggt | act | 624 |
| Val | His | Ile | Gln | Tyr | Lys | Arg | Asp | Pro | Lys | Lys | Met | His | Asn | Gly | Thr | |
| | | | 195 | | | | | 200 | | | | | 205 | | | |
| ata | gag | ttt | act | agt | ata | gat | atg | cat | aat | ggt | gca | tcg | ata | act | aga | 672 |
| Ile | Glu | Phe | Thr | Ser | Ile | Asp | Met | His | Asn | Gly | Ala | Ser | Ile | Thr | Arg | |
| | | 210 | | | | | 215 | | | | | 220 | | | | |
| cgt | gga | gat | ctt | gag | ata | tta | ggg | tat | tgc | atg | gtt | aaa | tgg | ttg | ggt | 720 |
| Arg | Gly | Asp | Leu | Glu | Ile | Leu | Gly | Tyr | Cys | Met | Val | Lys | Trp | Leu | Gly | |
| 225 | | | | | 230 | | | | | 235 | | | | | 240 | |
| ggt | att | ctt | cct | tgg | gag | aat | gat | cta | aag | aat | cgt | aaa | tat | gtg | atg | 768 |
| Gly | Ile | Leu | Pro | Trp | Glu | Asn | Asp | Leu | Lys | Asn | Arg | Lys | Tyr | Val | Met | |
| | | | | 245 | | | | | 250 | | | | | 255 | | |
| gag | cag | aaa | ata | cgt | tgt | ata | ggc | gat | ata | cat | aat | ttc | tta | acc | gaa | 816 |
| Glu | Gln | Lys | Ile | Arg | Cys | Ile | Gly | Asp | Ile | His | Asn | Phe | Leu | Thr | Glu | |
| | | | 260 | | | | | 265 | | | | | 270 | | | |
| tca | tta | ggt | aga | tat | cct | gtt | gag | tta | tat | aac | tat | ttc | ata | tat | att | 864 |
| Ser | Leu | Gly | Arg | Tyr | Pro | Val | Glu | Leu | Tyr | Asn | Tyr | Phe | Ile | Tyr | Ile | |
| | | | | 275 | | | | | 280 | | | | | 285 | | |
| tcg | tcc | cta | aaa | tat | gac | gaa | tgt | ccc | gat | tat | aat | tta | ata | aca | cgt | 912 |
| Ser | Ser | Leu | Lys | Tyr | Asp | Glu | Cys | Pro | Asp | Tyr | Asn | Leu | Ile | Thr | Arg | |
| | | | | 290 | | | | | 295 | | | | | 300 | | |
| atg | att | aat | aaa | aca | taa | | | | | | | | | | | 930 |
| Met | Ile | Asn | Lys | Thr | | | | | | | | | | | | |
| 305 | | | | | | | | | | | | | | | | |

<210> SEQ ID NO 100
<211> LENGTH: 309
<212> TYPE: PRT
<213> ORGANISM: Swinepox virus (17077-99)

<400> SEQUENCE: 100

Met Ser Gly Arg Gly Asn Met Phe Asn Glu Gly Glu Ile Leu Ile Asp
1               5                   10                  15

Thr Lys Arg Arg Ser Trp Lys Leu Gly Thr Leu Ile Gly Lys Gly Gly
            20                  25                  30

Phe Gly Cys Ile Tyr Thr Ala Ser Ile His Gly Lys Glu Asp Val Ser

```
                 35                   40                  45
Glu Thr Gln Tyr Ala Ile Lys Ile Glu Pro Lys Ser Asn Gly Pro Leu
 50                   55                  60

Phe Val Glu Gln Val Phe Tyr Gln Arg Ile Gly Lys Trp Asp Met Ile
 65                  70                  75                  80

Asp Ser Trp Lys Lys Ser Asn Gly Ile Asn His Leu Gly Ile Pro Asn
                 85                  90                  95

Phe Tyr Gly Phe Gly Phe Tyr Thr Lys Asn Lys Lys Glu Tyr Arg Phe
                100                 105                 110

Ile Ile Val Asp Arg Leu Gly Cys Asp Leu Asn Lys Ile Ile Gln Asn
                115                 120                 125

Asn Asn Asn Lys Leu Pro Gln Ser Thr Val Phe Lys Ile Ala Asp Arg
130                 135                 140

Ile Ile Thr Val Leu Arg Tyr Ile His Asp His Gly Tyr Thr His Gly
145                 150                 155                 160

Asp Ile Lys Ala Ser Asn Ile Ala Ile Asp Tyr Tyr Asp Lys Asn Lys
                165                 170                 175

Ile Tyr Leu Ile Asp Tyr Gly Leu Ser His Arg Tyr Lys Val Asn Asp
                180                 185                 190

Val His Ile Gln Tyr Lys Arg Asp Pro Lys Lys Met His Asn Gly Thr
                195                 200                 205

Ile Glu Phe Thr Ser Ile Asp Met His Asn Gly Ala Ser Ile Thr Arg
210                 215                 220

Arg Gly Asp Leu Glu Ile Leu Gly Tyr Cys Met Val Lys Trp Leu Gly
225                 230                 235                 240

Gly Ile Leu Pro Trp Glu Asn Asp Leu Lys Asn Arg Lys Tyr Val Met
                245                 250                 255

Glu Gln Lys Ile Arg Cys Ile Gly Asp Ile His Asn Phe Leu Thr Glu
                260                 265                 270

Ser Leu Gly Arg Tyr Pro Val Glu Leu Tyr Asn Tyr Phe Ile Tyr Ile
                275                 280                 285

Ser Ser Leu Lys Tyr Asp Glu Cys Pro Asp Tyr Asn Leu Ile Thr Arg
290                 295                 300

Met Ile Asn Lys Thr
305

<210> SEQ ID NO 101
<211> LENGTH: 921
<212> TYPE: DNA
<213> ORGANISM: Myxoma virus (L

```
cag gtg ttt tat caa cgg gtg ggt aaa acc gac atg gtc acg gac tgg      240
Gln Val Phe Tyr Gln Arg Val Gly Lys Thr Asp Met Val Thr Asp Trp
 65              70                  75                  80 tgt aag aaa aat aac tta ccg tat ttg gga att cct tcc ttt cac gga      288
Cys Lys Lys Asn Asn Leu Pro Tyr Leu Gly Ile Pro Ser Phe His Gly
                 85                  90                  95 ttt gga ttt tat aca aag aac aaa aaa gac tac agg ttt att att ata      336
Phe Gly Phe Tyr Thr Lys Asn Lys Lys Asp Tyr Arg Phe Ile Ile Ile
            100                 105                 110 gat cgt ctg gga tgc gat ttg tat aat ata cta caa tac aac aat tac      384
Asp Arg Leu Gly Cys Asp Leu Tyr Asn Ile Leu Gln Tyr Asn Asn Tyr
        115                 120                 125 aca ctt cct ttg aaa acc gta tgt ctc ata gcc atc aag atc atc gtc      432
Thr Leu Pro Leu Lys Thr Val Cys Leu Ile Ala Ile Lys Ile Ile Val
    130                 135                 140 gta tta aag tat tta cac gaa cac gga tac gca cac agt gac ata aag      480
Val Leu Lys Tyr Leu His Glu His Gly Tyr Ala His Ser Asp Ile Lys
145                 150                 155                 160 gcg tcc aat ata gca atc ggt gca cgt gat aaa aac aaa atc tac ctg      528
Ala Ser Asn Ile Ala Ile Gly Ala Arg Asp Lys Asn Lys Ile Tyr Leu
                165                 170                 175 ttg gat tac gga ctg tcg tac aga ttt atg gtg gac gga cga cac gtg      576
Leu Asp Tyr Gly Leu Ser Tyr Arg Phe Met Val Asp Gly Arg His Val
            180                 185                 190 tta tac aaa cga gat cct aag aaa atg cac aac ggc aca ata gag ttt      624
Leu Tyr Lys Arg Asp Pro Lys Lys Met His Asn Gly Thr Ile Glu Phe
        195                 200                 205 acc agt acg gac atg cac aac ggg gca tgt ccg tca cgt agg ggt gac      672
Thr Ser Thr Asp Met His Asn Gly Ala Cys Pro Ser Arg Arg Gly Asp
    210                 215                 220 ttg gag aca cta gga tat tgt ctc att aag tgg ttg ggc ggt act ctt      720
Leu Glu Thr Leu Gly Tyr Cys Leu Ile Lys Trp Leu Gly Gly Thr Leu
225                 230                 235                 240 ccc tgg gaa gat aat ctg aaa aat tgc aaa tac gta atg gaa tcg aaa      768
Pro Trp Glu Asp Asn Leu Lys Asn Cys Lys Tyr Val Met Glu Ser Lys
                245                 250                 255 ata aag ttt tta aac gat ata aaa caa ggg ata gaa aca tcc tta tcc      816
Ile Lys Phe Leu Asn Asp Ile Lys Gln Gly Ile Glu Thr Ser Leu Ser
            260                 265                 270 gcg tgc gtg gaa ccc cta cgg aga tac ttt ctg tac gta aaa tca ctc      864
Ala Cys Val Glu Pro Leu Arg Arg Tyr Phe Leu Tyr Val Lys Ser Leu
        275                 280                 285 gcg tat gaa caa cgt ccc gat tac gat tta ctt ata caa ttg tta aca      912
Ala Tyr Glu Gln Arg Pro Asp Tyr Asp Leu Leu Ile Gln Leu Leu Thr
    290                 295                 300 aaa gca taa                                                          921
Lys Ala
305

<210> SEQ ID NO 102
<211> LENGTH: 306
<212> TYPE: PRT
<213> ORGANISM: Myxoma virus (Lausanne)

<400> SEQUENCE: 102

Met Ser Lys Arg Asn Glu Ile Glu Pro Gly Asp Val Leu Ile Asp Ala
1               5                   10                  15

Ser Lys Arg Glu Trp Val Leu Gly Asp Ile Leu Gly Lys Gly Gly Phe
            20                  25                  30

Gly Tyr Ile Tyr Thr Ala Arg Leu Cys Ser Glu Glu Phe Asp Lys
        35                  40                  45
```

```
Tyr Val Ile Lys Ile Glu Pro Lys Ser Asn Gly Pro Leu Phe Val Glu
         50                  55                  60

Gln Val Phe Tyr Gln Arg Val Gly Lys Thr Asp Met Val Thr Asp Trp
 65                  70                  75                  80

Cys Lys Lys Asn Asn Leu Pro Tyr Leu Gly Ile Pro Ser Phe His Gly
                 85                  90                  95

Phe Gly Phe Tyr Thr Lys Asn Lys Lys Asp Tyr Arg Phe Ile Ile Ile
            100                 105                 110

Asp Arg Leu Gly Cys Asp Leu Tyr Asn Ile Leu Gln Tyr Asn Asn Tyr
        115                 120                 125

Thr Leu Pro Leu Lys Thr Val Cys Leu Ile Ala Ile Lys Ile Ile Val
    130                 135                 140

Val Leu Lys Tyr Leu His Glu His Gly Tyr Ala His Ser Asp Ile Lys
145                 150                 155                 160

Ala Ser Asn Ile Ala Ile Gly Ala Arg Asp Lys Asn Lys Ile Tyr Leu
                165                 170                 175

Leu Asp Tyr Gly Leu Ser Tyr Arg Phe Met Val Asp Gly Arg His Val
            180                 185                 190

Leu Tyr Lys Arg Asp Pro Lys Lys Met His Asn Gly Thr Ile Glu Phe
        195                 200                 205

Thr Ser Thr Asp Met His Asn Gly Ala Cys Pro Ser Arg Arg Gly Asp
    210                 215                 220

Leu Glu Thr Leu Gly Tyr Cys Leu Ile Lys Trp Leu Gly Gly Thr Leu
225                 230                 235                 240

Pro Trp Glu Asp Asn Leu Lys Asn Cys Lys Tyr Val Met Glu Ser Lys
                245                 250                 255

Ile Lys Phe Leu Asn Asp Ile Lys Gln Gly Ile Glu Thr Ser Leu Ser
            260                 265                 270

Ala Cys Val Glu Pro Leu Arg Arg Tyr Phe Leu Tyr Val Lys Ser Leu
        275                 280                 285

Ala Tyr Glu Gln Arg Pro Asp Tyr Asp Leu Leu Ile Gln Leu Leu Thr
    290                 295                 300

Lys Ala
305

<210> SEQ ID NO 103
<211> LENGTH: 921
<212> TYPE: DNA
<213> ORGANISM: Rabbit fibroma virus (Kasza)
<220> FEATURE:
<221> NAME/KEY: CDS
<222> LOCATION: (1)..(921)

<400> SEQUENCE: 103 atg tta aag cga aac ggg ata gag cca ggg gac gcg tta acc gat tcg      48
Met Leu Lys Arg Asn Gly Ile Glu Pro Gly Asp Ala Leu Thr Asp Ser
 1               5                  10                  15 tcg aaa cgg gaa tgg ata ctc gga gac gtt ttg gga aag gga ggg ttc      96
Ser Lys Arg Glu Trp Ile Leu Gly Asp Val Leu Gly Lys Gly Gly Phe
             20                  25                  30 gga tac att tac acg gcc cgt ttg tgt tcg gaa gag gaa cgt gac aaa     144
Gly Tyr Ile Tyr Thr Ala Arg Leu Cys Ser Glu Glu Glu Arg Asp Lys
         35                  40                  45 tac gtt ata aaa ata gaa ccg aaa agc aat ggc ccc ttg ttc gta gaa     192
Tyr Val Ile Lys Ile Glu Pro Lys Ser Asn Gly Pro Leu Phe Val Glu
     50                  55                  60 cag gtg ttt tat caa cgt gtg ggt aaa gtc gac atg atc gcg gat tgg     240
```

```
Gln Val Phe Tyr Gln Arg Val Gly Lys Val Asp Met Ile Ala Asp Trp
 65                  70                  75                  80 tgt aag aaa cac aac ttg acg tat ttg ggg atc cct tct ttt cac gga    288
Cys Lys Lys His Asn Leu Thr Tyr Leu Gly Ile Pro Ser Phe His Gly
                 85                  90                  95 ttt gga ttt tgt aca aaa aac aag aaa gac tat cga ttt att att atc    336
Phe Gly Phe Cys Thr Lys Asn Lys Lys Asp Tyr Arg Phe Ile Ile Ile
            100                 105                 110 gat cgt cta gga tgt gat ctg tat aat ata ttg cag cac aac aat tac    384
Asp Arg Leu Gly Cys Asp Leu Tyr Asn Ile Leu Gln His Asn Asn Tyr
        115                 120                 125 act ctt cct ttg aga acc gtg tgt ctc ata gcc gtt agg att att att    432
Thr Leu Pro Leu Arg Thr Val Cys Leu Ile Ala Val Arg Ile Ile Ile
    130                 135                 140 ata tta aag tac tta cat gaa cat gga tac act cat agt gac ata aaa    480
Ile Leu Lys Tyr Leu His Glu His Gly Tyr Thr His Ser Asp Ile Lys
145                 150                 155                 160 gcg tcc aat ata gct atc gac gta cgt gat aaa aac aaa att tac ctg    528
Ala Ser Asn Ile Ala Ile Asp Val Arg Asp Lys Asn Lys Ile Tyr Leu
                165                 170                 175 ttg gat tac ggt ttg tcg tat aga ttt atg gtg gat ggt cgg cac gtt    576
Leu Asp Tyr Gly Leu Ser Tyr Arg Phe Met Val Asp Gly Arg His Val
            180                 185                 190 ttg tac aaa cga gat cct aag aaa atg cac aat ggg aca ata gag ttt    624
Leu Tyr Lys Arg Asp Pro Lys Lys Met His Asn Gly Thr Ile Glu Phe
        195                 200                 205 acc agt acg gat atg cat aac gga gca tgc ccg tcg cgt aga ggc gat    672
Thr Ser Thr Asp Met His Asn Gly Ala Cys Pro Ser Arg Arg Gly Asp
    210                 215                 220 ttg gaa ata ctg ggg tat tgt ctt att aag tgg tta gga ggg act ctc    720
Leu Glu Ile Leu Gly Tyr Cys Leu Ile Lys Trp Leu Gly Gly Thr Leu
225                 230                 235                 240 ccg tgg gaa gat aat cta aaa aat tgt aaa tac gta atg gaa tcg aaa    768
Pro Trp Glu Asp Asn Leu Lys Asn Cys Lys Tyr Val Met Glu Ser Lys
                245                 250                 255 ata aag ttt tta aac gat ata aaa caa gga ata gaa gcg tct tta tcc    816
Ile Lys Phe Leu Asn Asp Ile Lys Gln Gly Ile Glu Ala Ser Leu Ser
            260                 265                 270 gca tgc gta gaa ccc ttg cgg cga tac ttt cta tac gta aag tcg ctc    864
Ala Cys Val Glu Pro Leu Arg Arg Tyr Phe Leu Tyr Val Lys Ser Leu
        275                 280                 285 tct tac gaa cag tgt cca gat tac gat tta ctc ata cag ttg tta aaa    912
Ser Tyr Glu Gln Cys Pro Asp Tyr Asp Leu Leu Ile Gln Leu Leu Lys
    290                 295                 300 aaa aca taa                                                        921
Lys Thr
305

<210> SEQ ID NO 104
<211> LENGTH: 306
<212> TYPE: PRT
<213> ORGANISM: Rabbit fibroma virus (Kasza)

<400> SEQUENCE: 104

Met Leu Lys Arg Asn Gly Ile Glu Pro Gly Asp Ala Leu Thr Asp Ser
1               5                   10                  15

Ser Lys Arg Glu Trp Ile Leu Gly Asp Val Leu Gly Lys Gly Gly Phe
                20                  25                  30

Gly Tyr Ile Tyr Thr Ala Arg Leu Cys Ser Glu Glu Arg Asp Lys
            35                  40                  45
```

```
Tyr Val Ile Lys Ile Glu Pro Lys Ser Asn Gly Pro Leu Phe Val Glu
    50                  55                  60

Gln Val Phe Tyr Gln Arg Val Gly Lys Val Asp Met Ile Ala Asp Trp
65                  70                  75                  80

Cys Lys Lys His Asn Leu Thr Tyr Leu Gly Ile Pro Ser Phe His Gly
                85                  90                  95

Phe Gly Phe Cys Thr Lys Asn Lys Lys Asp Tyr Arg Phe Ile Ile Ile
            100                 105                 110

Asp Arg Leu Gly Cys Asp Leu Tyr Asn Ile Leu Gln His Asn Asn Tyr
        115                 120                 125

Thr Leu Pro Leu Arg Thr Val Cys Leu Ile Ala Val Arg Ile Ile Ile
    130                 135                 140

Ile Leu Lys Tyr Leu His Glu His Gly Tyr Thr His Ser Asp Ile Lys
145                 150                 155                 160

Ala Ser Asn Ile Ala Ile Asp Val Arg Asp Lys Asn Lys Ile Tyr Leu
                165                 170                 175

Leu Asp Tyr Gly Leu Ser Tyr Arg Phe Met Val Asp Gly Arg His Val
            180                 185                 190

Leu Tyr Lys Arg Asp Pro Lys Lys Met His Asn Gly Thr Ile Glu Phe
        195                 200                 205

Thr Ser Thr Asp Met His Asn Gly Ala Cys Pro Ser Arg Arg Gly Asp
    210                 215                 220

Leu Glu Ile Leu Gly Tyr Cys Leu Ile Lys Trp Leu Gly Gly Thr Leu
225                 230                 235                 240

Pro Trp Glu Asp Asn Leu Lys Asn Cys Lys Tyr Val Met Glu Ser Lys
                245                 250                 255

Ile Lys Phe Leu Asn Asp Ile Lys Gln Gly Ile Glu Ala Ser Leu Ser
            260                 265                 270

Ala Cys Val Glu Pro Leu Arg Arg Tyr Phe Leu Tyr Val Lys Ser Leu
        275                 280                 285

Ser Tyr Glu Gln Cys Pro Asp Tyr Asp Leu Leu Ile Gln Leu Leu Lys
    290                 295                 300

Lys Thr
305

<210> SEQ ID NO 105
<211> LENGTH: 912
<212> TYPE: DNA
<213> ORGANISM: Fowlpox virus (HP-438[Munich])
<220> FEATURE:
<221> NAME/KEY: CDS
<222> LOCATION: (1)..

| | | | | | | | | | | | | | | | | |
|---|---|---|---|---|---|---|---|---|---|---|---|---|---|---|---|---|
| | | 65 | | | 70 | | | | 75 | | | | 80 | | | |
| gat | aca | tgg | atg | aag | gaa | caa | aaa | ata | gat | tat | ata | ggt | ata | cct | tct | 288 |
| Asp | Thr | Trp | Met | Lys | Glu | Gln | Lys | Ile | Asp | Tyr | Ile | Gly | Ile | Pro | Ser | |
| | | | | 85 | | | | | 90 | | | | | 95 | | |
| ttc | cat | gga | ttt | ggt | att | act | atc | tac | aag | aac | gta | gaa | tat | aga | ttt | 336 |
| Phe | His | Gly | Phe | Gly | Ile | Thr | Ile | Tyr | Lys | Asn | Val | Glu | Tyr | Arg | Phe | |
| | | | 100 | | | | | 105 | | | | | 110 | | | |
| gcg | ata | ata | caa | aga | ctg | ggt | aga | gat | ctg | gaa | aat | ata | ctc | tca | gaa | 384 |
| Ala | Ile | Ile | Gln | Arg | Leu | Gly | Arg | Asp | Leu | Glu | Asn | Ile | Leu | Ser | Glu | |
| | | | 115 | | | | | 120 | | | | | 125 | | | |
| aaa | gaa | aaa | ttt | aat | att | act | gtt | att | aaa | aaa | tta | gct | att | aag | ata | 432 |
| Lys | Glu | Lys | Phe | Asn | Ile | Thr | Val | Ile | Lys | Lys | Leu | Ala | Ile | Lys | Ile | |
| | | | 130 | | | | | 135 | | | | | 140 | | | |
| ctg | gat | ata | tta | aaa | ttt | ata | cat | agt | aaa | gag | ttt | tct | cac | ggt | gat | 480 |
| Leu | Asp | Ile | Leu | Lys | Phe | Ile | His | Ser | Lys | Glu | Phe | Ser | His | Gly | Asp | |
| 145 | | | | | 150 | | | | | 155 | | | | | 160 | |
| att | aaa | gct | gga | aac | ata | cta | ttc | ggt | aag | gat | gat | gac | aaa | gta | tac | 528 |
| Ile | Lys | Ala | Gly | Asn | Ile | Leu | Phe | Gly | Lys | Asp | Asp | Asp | Lys | Val | Tyr | |
| | | | | 165 | | | | | 170 | | | | | 175 | | |
| tta | gta | gac | tac | gga | tta | gcg | acg | aaa | tat | tca | tcg | aat | ggt | aaa | cac | 576 |
| Leu | Val | Asp | Tyr | Gly | Leu | Ala | Thr | Lys | Tyr | Ser | Ser | Asn | Gly | Lys | His | |
| | | | 180 | | | | | 185 | | | | | 190 | | | |
| aaa | gaa | tat | act | att | aat | ccc | aaa | aac | aga | cat | aac | ggt | act | atg | gct | 624 |
| Lys | Glu | Tyr | Thr | Ile | Asn | Pro | Lys | Asn | Arg | His | Asn | Gly | Thr | Met | Ala | |
| | | | 195 | | | | | 200 | | | | | 205 | | | |
| ttc | aca | agt | ata | gac | gct | cat | aaa | gga | gtt | acg | gta | tct | agg | aga | ggc | 672 |
| Phe | Thr | Ser | Ile | Asp | Ala | His | Lys | Gly | Val | Thr | Val | Ser | Arg | Arg | Gly | |
| | | 210 | | | | | 215 | | | | | 220 | | | | |
| gat | tta | gaa | tct | ctt | gga | ttt | tgt | atg | cta | aaa | tgg | tac | tct | ggg | aaa | 720 |
| Asp | Leu | Glu | Ser | Leu | Gly | Phe | Cys | Met | Leu | Lys | Trp | Tyr | Ser | Gly | Lys | |
| 225 | | | | | 230 | | | | | 235 | | | | | 240 | |
| tta | ccg | tgg | gag | aaa | tac | gaa | aaa | gaa | cct | gaa | aat | gtt | caa | ggc | atg | 768 |
| Leu | Pro | Trp | Glu | Lys | Tyr | Glu | Lys | Glu | Pro | Glu | Asn | Val | Gln | Gly | Met | |
| | | | | 245 | | | | | 250 | | | | | 255 | | |
| aaa | gaa | gca | ttt | gtc | aat | aat | ata | tct | aaa | aaa | act | ata | ccc | ttc | aaa | 816 |
| Lys | Glu | Ala | Phe | Val | Asn | Asn | Ile | Ser | Lys | Lys | Thr | Ile | Pro | Phe | Lys | |
| | | | 260 | | | | | 265 | | | | | 270 | | | |
| aac | gcg | ggt | ata | att | tac | aat | tat | ata | aag | gta | gtc | act | aag | tta | gaa | 864 |
| Asn | Ala | Gly | Ile | Ile | Tyr | Asn | Tyr | Ile | Lys | Val | Val | Thr | Lys | Leu | Glu | |
| | | | 275 | | | | | 280 | | | | | 285 | | | |
| tac | gaa | gaa | gcc | cct | aac | tac | gaa | tca | ctg | aaa | caa | atg | ttt | tta | taa | 912 |
| Tyr | Glu | Glu | Ala | Pro | Asn | Tyr | Glu | Ser | Leu | Lys | Gln | Met | Phe | Leu | | |
| | | | 290 | | | | | 295 | | | | | 300 | | | |

<210> SEQ ID NO 106
<211> LENGTH: 303
<212> TYPE: PRT
<213> ORGANISM: Fowlpox virus (HP-438[Munich])

<400> SEQUENCE: 106

Met Pro Gln Asn Lys Val Leu Ser Phe Pro Leu Pro Glu Gly Thr Leu
1               5                   10                  15

Leu Glu Asp Ile Thr Lys Asn Lys Trp Ile Leu Gly Lys Gln Leu Gly
            20                  25                  30

Ser Gly Gly Phe Gly Leu Val Tyr Gln Val Ser Cys Lys Ser Lys Glu
        35                  40                  45

Ile Asp Cys Val Ala Lys Ile Glu Leu Lys Glu Ser Gly Gly Leu Phe
    50                  55                  60

Cys Glu Ile Asn Phe Tyr Asn Arg Val Met Lys Asn Lys Thr Ser Leu
65                  70                  75                  80

```
Asp Thr Trp Met Lys Glu Gln Lys Ile Asp Tyr Ile Gly Ile Pro Ser
                85                  90                  95

Phe His Gly Phe Gly Ile Thr Ile Tyr Lys Asn Val Glu Tyr Arg Phe
            100                 105                 110

Ala Ile Ile Gln Arg Leu Gly Arg Asp Leu Glu Asn Ile Leu Ser Glu
            115                 120                 125

Lys Glu Lys Phe Asn Ile Thr Val Ile Lys Leu Ala Ile Lys Ile
130                 135                 140

Leu Asp Ile Leu Lys Phe Ile His Ser Lys Glu Phe Ser His Gly Asp
145                 150                 155                 160

Ile Lys Ala Gly Asn Ile Leu Phe Gly Lys Asp Asp Lys Val Tyr
                165                 170                 175

Leu Val Asp Tyr Gly Leu Ala Thr Lys Tyr Ser Ser Asn Gly Lys His
                180                 185                 190

Lys Glu Tyr Thr Ile Asn Pro Lys Asn Arg His Asn Gly Thr Met Ala
                195                 200                 205

Phe Thr Ser Ile Asp Ala His Lys Gly Val Thr Val Ser Arg Arg Gly
            210                 215                 220

Asp Leu Glu Ser Leu Gly Phe Cys Met Leu Lys Trp Tyr Ser Gly Lys
225                 230                 235                 240

Leu Pro Trp Glu Lys Tyr Glu Lys Glu Pro Glu Asn Val Gln Gly Met
                245                 250                 255

Lys Glu Ala Phe Val Asn Asn Ile Ser Lys Lys Thr Ile Pro Phe Lys
                260                 265                 270

Asn Ala Gly Ile Ile Tyr Asn Tyr Ile Lys Val Val Thr Lys Leu Glu
            275                 280                 285

Tyr Glu Glu Ala Pro Asn Tyr Glu Ser Leu Lys Gln Met Phe Leu
            290                 295                 300

<210> SEQ ID NO 107
<211> LENGTH: 918
<212> TYPE: DNA
<213> ORGANISM: Canarypox virus (ATCC VR-111)
<220> FEATURE:
<221> NAME/KEY: CDS
<222> LOCATION: (1)..(918)

<400> SEQUENCE: 107 atg gct tta atc aac aag aaa gta tta ccc ttg cct tca gga acc gta      48
Met Ala Leu Ile Asn Lys Lys Val Leu Pro Leu Pro Ser Gly Thr Val
1               5                   10                  15 tta aca gac tta gca aaa cga agg tgg gtg tta gag aaa cag ata gga      96
Leu Thr Asp Leu Ala Lys Arg Arg Trp Val Leu Glu Lys Gln Ile Gly
            20                  25                  30 tgt ggt ggt ttt gga tta gta tat gat gtg tat cct gaa aat gat aac     144
Cys Gly Gly Phe Gly Leu Val Tyr Asp Val Tyr Pro Glu Asn Asp Asn
        35                  40                  45 act aac atg aga tat ata gca aag tta gaa cat aaa gat agt gga ggg     192
Thr Asn Met Arg Tyr Ile Ala Lys Leu Glu His Lys Asp Ser Gly Gly
    50                  55                  60 tta ttt tgt gaa ata aat ttc tat att agg gtt atg aga aac aac tat     240
Leu Phe Cys Glu Ile Asn Phe Tyr Ile Arg Val Met Arg Asn Asn Tyr
65                  70                  75                  80 ttt gtc gat gaa tgg aaa aag aac aac tta ata agt cat ttg gga ata     288
Phe Val Asp Glu Trp Lys Lys Asn Asn Leu Ile Ser His Leu Gly Ile
                85                  90                  95 cca aaa tac cac ggt tct ggt att agt atg tat aac ggg aaa gaa tat     336
Pro Lys Tyr His Gly Ser Gly Ile Ser Met Tyr Asn Gly Lys Glu Tyr
```

```
                    100                 105                 110
agg ttt tta ata atc gag aaa cta gga tct gat ata cat agg tta tta      384
Arg Phe Leu Ile Ile Glu Lys Leu Gly Ser Asp Ile His Arg Leu Leu
        115                 120                 125 gtc gat aga aaa aaa ttt aac att agt gga gta aaa act tta gct act      432
Val Asp Arg Lys Lys Phe Asn Ile Ser Gly Val Lys Thr Leu Ala Thr
130                 135                 140 aat att ttg act ata tta gag ttt ata cac gat aaa ggt tat tct cac      480
Asn Ile Leu Thr Ile Leu Glu Phe Ile His Asp Lys Gly Tyr Ser His
145                 150                 155                 160 ggt gat ata aag tct gaa aat ata ctt tta gga ttg cgt gat aat aga      528
Gly Asp Ile Lys Ser Glu Asn Ile Leu Leu Gly Leu Arg Asp Asn Arg
            165                 170                 175 att tac tta gta gac tat ggg tta tcg gct aaa ttt ctt cag ggt aag      576
Ile Tyr Leu Val Asp Tyr Gly Leu Ser Ala Lys Phe Leu Gln Gly Lys
                180                 185                 190 gaa cat aga cct tat ttt aga gat ccg aag gct agg cat aat ggt acg      624
Glu His Arg Pro Tyr Phe Arg Asp Pro Lys Ala Arg His Asn Gly Thr
                    195                 200                 205 tta tta ttc gct agt ata gat gcg cat aac gga gta gta gta tct cgt      672
Leu Leu Phe Ala Ser Ile Asp Ala His Asn Gly Val Val Val Ser Arg
210                 215                 220 aag gga gat tta gaa tct tta ggc tat tgc atg ata aag tgg tta gtt      720
Lys Gly Asp Leu Glu Ser Leu Gly Tyr Cys Met Ile Lys Trp Leu Val
225                 230                 235                 240 ggt agg cta cct tgg gag ggt tat gaa aaa gat cca gat tct gtg caa      768
Gly Arg Leu Pro Trp Glu Gly Tyr Glu Lys Asp Pro Asp Ser Val Gln
            245                 250                 255 aat atg aaa gaa aag ttt ata gag aat ata act aag aaa tat gta atc      816
Asn Met Lys Glu Lys Phe Ile Glu Asn Ile Thr Lys Lys Tyr Val Ile
                260                 265                 270 gaa aag gat att gat ata ata tac aat tat ata aaa aca gtt tca tca      864
Glu Lys Asp Ile Asp Ile Ile Tyr Asn Tyr Ile Lys Thr Val Ser Ser
                    275                 280                 285 ctg gat tat tca gaa aac cca gat tat gac cat tta aaa aaa atg ttt      912
Leu Asp Tyr Ser Glu Asn Pro Asp Tyr Asp His Leu Lys Lys Met Phe
290                 295                 300 tta taa                                                               918
Leu
305

<210> SEQ ID NO 108
<211> LENGTH: 305
<212> TYPE: PRT
<213> ORGANISM: Canarypox virus (ATCC VR-111)

<400> SEQUENCE: 108

Met Ala Leu Ile Asn Lys Lys Val Leu Pro Leu Pro Ser Gly Thr Val
1               5                   10                  15

Leu Thr Asp Leu Ala Lys Arg Arg Trp Val Leu Glu Lys Gln Ile Gly
            20                  25                  30

Cys Gly Gly Phe Gly Leu Val Tyr Asp Val Tyr Pro Glu Asn Asp Asn
        35                  40                  45

Thr Asn Met Arg Tyr Ile Ala Lys Leu Glu His Lys Asp Ser Gly Gly
    50                  55                  60

Leu Phe Cys Glu Ile Asn Phe Tyr Ile Arg Val Met Arg Asn Asn Tyr
65                  70                  75                  80

Phe Val Asp Glu Trp Lys Lys Asn Asn Leu Ile Ser His Leu Gly Ile
                85                  90                  95
```

```
Pro Lys Tyr His Gly Ser Gly Ile Ser Met Tyr Asn Gly Lys Glu Tyr
            100             105             110

Arg Phe Leu Ile Ile Glu Lys Leu Gly Ser Asp Ile His Arg Leu Leu
            115             120             125

Val Asp Arg Lys Lys Phe Asn Ile Ser Gly Val Lys Thr Leu Ala Thr
130             135             140

Asn Ile Leu Thr Ile Leu Glu Phe Ile His Asp Lys Gly Tyr Ser His
145             150             155             160

Gly Asp Ile Lys Ser Glu Asn Ile Leu Leu Gly Leu Arg Asp Asn Arg
                165             170             175

Ile Tyr Leu Val Asp Tyr Gly Leu Ser Ala Lys Phe Leu Gln Gly Lys
            180             185             190

Glu His Arg Pro Tyr Phe Arg Asp Pro Lys Ala Arg His Asn Gly Thr
        195             200             205

Leu Leu Phe Ala Ser Ile Asp Ala His Asn Gly Val Val Val Ser Arg
            210             215             220

Lys Gly Asp Leu Glu Ser Leu Gly Tyr Cys Met Ile Lys Trp Leu Val
225             230             235             240

Gly Arg Leu Pro Trp Glu Gly Tyr Glu Lys Asp Pro Asp Ser Val Gln
                245             250             255

Asn Met Lys Glu Lys Phe Ile Glu Asn Ile Thr Lys Lys Tyr Val Ile
            260             265             270

Glu Lys Asp Ile Asp Ile Ile Tyr Asn Tyr Ile Lys Thr Val Ser Ser
        275             280             285

Leu Asp Tyr Ser Glu Asn Pro Asp Tyr Asp His Leu Lys Lys Met Phe
    290             295             300

Leu
305
```